(12) United States Patent
Banner et al.

(10) Patent No.: US 7,893,099 B2
(45) Date of Patent: Feb. 22, 2011

(54) CYCLOPENTANE DERIVATIVES

(75) Inventors: David Banner, Basel (CH); Simona M. Ceccarelli, Basel (CH); Uwe Grether, Efringen-Kirchen (DE); Wolfgang Haap, Loerrach (DE); Hans Hilpert, Muenchenstein (CH); Holger Kuehne, Loerrach (DE); Harald Mauser, Schliengen (DE); Jean-Marc Plancher, Hagenthal-le-Bas (FR); Ruben Alvarez Sanchez, Rosenau (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/791,914

(22) Filed: Jun. 2, 2010

(65) Prior Publication Data

US 2010/0317647 A1 Dec. 16, 2010

(30) Foreign Application Priority Data

Jun. 11, 2009 (EP) .................................. 09162510

(51) Int. Cl.
| | |
|---|---|
| A61K 31/415 | (2006.01) |
| A61K 31/5375 | (2006.01) |
| A61K 31/54 | (2006.01) |
| A61K 31/495 | (2006.01) |
| A61K 31/50 | (2006.01) |
| A61K 31/40 | (2006.01) |
| A61K 31/435 | (2006.01) |
| C07D 231/10 | (2006.01) |
| C07D 265/30 | (2006.01) |
| C07D 279/12 | (2006.01) |
| C07D 205/00 | (2006.01) |
| C07D 211/00 | (2006.01) |
| C07D 213/00 | (2006.01) |
| C07C 255/01 | (2006.01) |

(52) U.S. Cl. ............... 514/406; 514/252.12; 514/222.2; 514/408; 514/247; 514/231.2; 514/277; 558/303; 558/304; 558/307; 548/377.1; 548/950; 548/400; 546/184; 546/1; 544/392; 544/59; 544/224; 544/106

(58) Field of Classification Search ............... 514/231.2, 514/247, 252.12, 222.2, 408, 277, 406; 544/106, 544/224, 392, 59; 546/184, 1; 548/950, 548/400, 377.1; 558/303, 304, 307
See application file for complete search history.

(56) References Cited

FOREIGN PATENT DOCUMENTS

WO 2004000825 12/2003

OTHER PUBLICATIONS

Crane, Sheldon N. β-Substituted Cyclohexanecarboxamide: A Nonpeptidic Framework for the Design of Potent Inhibitors of Cathepsin K. J. Med. Chem. 2006, 49, 1066-1079.*

Aikawa et al., Circulation (2009), pp. 1785-1794 (Plus Supplemental Information pp. 1-9).
Bromme et al., Current Protocols in Protein Science (2000) pp. 21.2.1-21.2.14.
Burns, et al., Cardiovascular Research (2004) vol. 62 pp. 610-620.
Cheng et al., American Journal of Pathology (2004) pp. 243-251.
deNooijer et al., Arterioscler. Thromb. Biol. (2008) pp. 188-194.
Driessen et al., The Journal of Cell Biology, vol. 147 (1999) pp. 775-790.
Funkelstein et al., J. Biol. Chem. (2008) vol. 283, No. 51, pp. 35652-35659.
Hsing et al., Immunological Reviews (2005) vol. 207, pp. 229-241.
Kitamoto et al., Circulation (2007) pp. 2065-2075.
Liu et al., Atherosclerosis, vol. 186 (2006) pp. 411-419.
Roberts et al, Drug News Perspective vol. 18(10) (2005) pp. 605-514.
Rodgers et al., Atherosclerosis Vascular Biol. (2006) pp. 851-856.
Rudensky et al, Lysosomal Cysteine Proteases Antigen Presentation (2006) pp. 82-95.
Sever et al, The Journal of Clinical Investigation (2007) pp. 2095-2104.
Shi et al., Circulation Research (2003) vol. 92 pp. 493-500.
Sukhova et al., J. Clin. Invest. vol. 102 No. 3 (1998) pp. 576-583.
Sukhova et al, J. Clin. Invest. vol. 111 (2003) pp. 897-906.
Wang et al, The Journal of Biological Chemistry vol. 281 (2006) pp. 6020-6029.
Williams et al., Pulmonary Pharm. & Therapeutics vol. 22 (2009) pp. 27-32.
Burden et al., Clinical Cancer Research vol. 15(19) (2009) pp. 6042-6051.
Llamas et al., Organic Letters vol. 8, No. 9, (2006) pp. 1795-1798.
Gauthier et al., Bioorganic & Medical Chem. Letters vol. 17, No. 17 (2007) pp. 4929-4933.

* cited by examiner

*Primary Examiner*—Golam M. M. Shameem
*Assistant Examiner*—Samantha L Shterengarts
(74) *Attorney, Agent, or Firm*—George W. Johnston; Patricia S. Rocha-Tramaloni; Gene J. Yao

(57) ABSTRACT

The invention relates to a compound of formula (I)

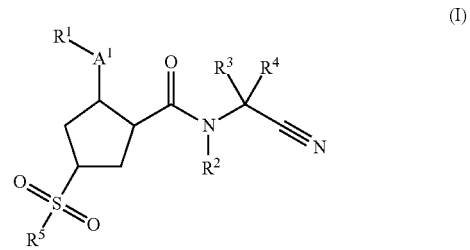

wherein $A^1$ and $R^1$ to $R^5$ are defined as in the description and in the claims. The compound of formula (I) can be used as a medicament.

19 Claims, No Drawings

CYCLOPENTANE DERIVATIVES

PRIORITY TO RELATED APPLICATION(S)

This application claims the benefit of European Patent Application No. 09162510.3, filed Jun. 11, 2009, which is hereby incorporated by reference in its entirety.

FIELD OF THE INVENTION

The present invention relates to compounds that are preferential inhibitors of the cysteine protease cathepsin, in particular of the cysteine protease cathepsin S or L.

SUMMARY OF THE INVENTION

The invention relates in particular to a compound of formula (I)

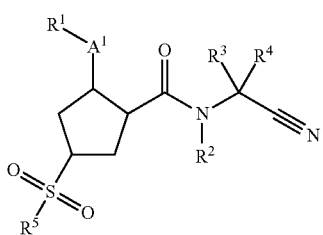

(I)

wherein
A$^1$ is selected from the group consisting of oxygen, carbonyl, —CH$_2$O—, —CH$_2$—, and —CONR$^{11}$— or is absent;
R$^1$ is selected from the group consisting of hydrogen, alkyl, haloalkyl, cycloalkyl, phenyl, halophenyl, alkoxybenzyl, carboxy, morpholinyl, alkylmorpholinyl, dioxothiomorpholinyl, 2-oxo-6-aza-spiro[3.3]heptanyl, piperidinyl, alkylpiperidinyl, hydroxypiperidinyl, halophenylpiperidinyl, piperazinyl, alkylpiperazinyl, azetidinyl, haloazetidinyl, hydroxyazetidinyl, alkoxyazetidinyl, 8-oxo-3-aza-bicyclo[3.2.1]octanyl, hydroxypiridazinyl, halopyrrolidinyl, formyl, pyridinyl, halopyridinyl, tetrahydropyranyl and thiopyranyl;
R$^2$ is hydrogen;
R$^3$ and R$^4$ are independently selected from hydrogen, alkyl or phenyl;
or R$^3$ and R$^4$ together with the carbon atom to which they are attached form cycloalkyl, alkylpiperidinyl or alkoxycarbonylpiperidinyl;
or R$^2$ and R$^3$ together with the nitrogen atom and carbon atom to which they are attached form pyrrolidinyl;
R$^5$ is selected from the group consisting of alkyl, cycloalkyl, cycloalkylalkyl, phenyl, substituted phenyl, benzyl, naphtyl, alkylpyridazinyl, pyridinyl, and halopyridinyl, wherein substituted phenyl is phenyl substituted with one or two substituents independently selected from the group consisting of alkyl, alkoxy, alkoxyalkoxy, halogen, haloalkyl, haloalkoxy, phenyl, halophenyl, halophenyloxy, alkylsulfonylphenyl, aminosulfonylphenyl, pyridinyl, alkylpyridinyl, halopyridinyl, alkoxypyridinyl, haloalkylpyridinyl, alkylsulfonylpyridinyl, alkylthiazolyl, piperidinyl, halopiperidinyl, hydroxypiperidinyl, 1H-pyrazolyl, alkyl-1H-pyrazolyl, alkyl-2H-pyrazolyl, hydroxyalkyl-1H-pyrazolyl, alkoxyalkyl-1H-pyrazolyl, alkoxycarbonylpyrazolyl, carboxyalkylpyrazolyl, aminocarbonylalkyl-1H-pyrazolyl, alkylaminocarbonylalkylpyrazolyl, oxetanylalkyl-1H-pyrazolyl, pyrimidinyl, alkylthiophenyl, pyridazinyl, alkyl-6-oxo-6H-pyridazinyl, alkylisoxazolyl, cycloalkylpiperazinyl, pyrazinyl, halopyrazinyl, haloazetidinyl, 2-oxo-6-aza-spiro[3.3]heptanyl, halopyrrolidinyl, alkylpiperazinyl, cycloalkylpiperazinyl, haloalkylpiperazinyl, carbonylpiperazinyl, alkylcarbonylpiperazinyl, oxetanyloxy and morpholinyl; and
R$^1$ is hydrogen or alkyl;

or a pharmaceutically acceptable salt thereof.

The invention also relates to a pharmaceutical composition comprising a compound as described above and a therapeutically inert carrier.

DETAILED DESCRIPTION OF THE INVENTION

The invention relates in particular to a compound of formula (I)

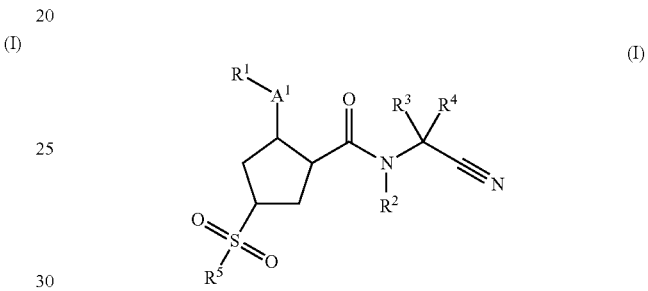

(I)

wherein
A$^1$ is selected from the group consisting of oxygen, carbonyl, —CH$_2$O—, —CH$_2$—, and —CONR$^{11}$— or is absent;
R$^1$ is selected from the group consisting of hydrogen, alkyl, haloalkyl, cycloalkyl, phenyl, halophenyl, alkoxybenzyl, carboxy, morpholinyl, alkylmorpholinyl, dioxothiomorpholinyl, 2-oxo-6-aza-spiro[3.3]heptanyl, piperidinyl, alkylpiperidinyl, hydroxypiperidinyl, halophenylpiperidinyl, piperazinyl, alkylpiperazinyl, azetidinyl, haloazetidinyl, hydroxyazetidinyl, alkoxyazetidinyl, 8-oxo-3-aza-bicyclo[3.2.1]octanyl, hydroxypiridazinyl, halopyrrolidinyl, formyl, pyridinyl, halopyridinyl, tetrahydropyranyl and thiopyranyl;
R$^2$ is hydrogen;
R$^3$ and R$^4$ are independently selected from hydrogen, alkyl or phenyl;
or R$^3$ and R$^4$ together with the carbon atom to which they are attached form cycloalkyl, alkylpiperidinyl or alkoxycarbonylpiperidinyl;
or R$^2$ and R$^3$ together with the nitrogen atom and carbon atom to which they are attached form pyrrolidinyl;
R$^5$ is selected from the group consisting of alkyl, cycloalkyl, cycloalkylalkyl, phenyl, substituted phenyl, benzyl, naphtyl, alkylpyridazinyl, pyridinyl, and halopyridinyl, wherein substituted phenyl is phenyl substituted with one or two substituents independently selected from the group consisting of alkyl, alkoxy, alkoxyalkoxy, halogen, haloalkyl, haloalkoxy, phenyl, halophenyl, halophenyloxy, alkylsulfonylphenyl, aminosulfonylphenyl, pyridinyl, alkylpyridinyl, halopyridinyl, alkoxypyridinyl, haloalkylpyridinyl, alkylsulfonylpyridinyl, alkylthiazolyl, piperidinyl, halopiperidinyl, hydroxypiperidinyl, 1H-pyrazolyl, alkyl-1H-pyrazolyl, alkyl-2H-pyrazolyl, hydroxyalkyl-1H-pyrazolyl, alkoxyalkyl-1H-pyrazolyl, alkoxycarbonylpyrazolyl, carboxyalkylpyrazolyl, aminocarbonylalkyl-1H-pyrazolyl, alkylaminocarbonylalkylpyrazolyl, oxetanylalkyl-1H-pyrazolyl, pyrimidinyl, alkylthiophenyl, pyridazinyl, alkyl-6-oxo-6H-pyridazinyl, alkylisoxazolyl, cycloalkylpiperazinyl, pyrazinyl, halopyrazinyl, haloazetidinyl, 2-oxo-6-aza-spiro[3.3]heptanyl, halopyrrolidinyl, alkylpiperazinyl, cycloalkylpiperazinyl, haloalkylpiperazinyl, carbonylpiperazinyl, alkylcarbonylpiperazinyl, oxetanyloxy and morpholinyl; and $R^{11}$ is hydrogen or alkyl;

or a pharmaceutically acceptable salt thereof.

The compounds of the invention are preferential inhibitors of the cysteine protease Cathepsin (Cat), in particular Cathepsin S or Cathepsin L and are therefore useful to treat metabolic diseases like diabetes, atherosclerosis, abdominal aortic aneurysm, peripheral arterial disease, cancer, reduction of cardiovascular events in chronic kidney disease and diabetic nephropathy. In addition, immune mediated diseases like rheumatoid arthritis, multiple sclerosis, sjorgen syndrome, lupus erythematosus, neuropathic pain, diabetes type I, asthma and allergy and skin related immune disease are suitable diseases to be treated with a cathepsin S inhibitor.

Objects of the present invention are the compounds of formula (I) and their aforementioned salts per se and their use as therapeutically active substances, a process for the manufacture of the said compounds, intermediates, pharmaceutical compositions, medicaments containing the said compounds, their pharmaceutically acceptable salts, the use of the said compounds and salts for the prophylaxis and/or therapy of illnesses, especially in the treatment or prophylaxis of diabetes, atherosclerosis, abdominal aortic aneurysm, peripheral arterial disease, cancer, reduction of cardiovascular events in chronic kidney disease and diabetic nephropathy, and the use of the said compounds and salts for the production of medicaments for the treatment or prophylaxis of diabetes, atherosclerosis, abdominal aortic aneurysm, peripheral arterial disease, cancer, reduction of cardiovascular events in chronic kidney disease and diabetic nephropathy.

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme 2001; Roberts 2005).

Cathepsin S is prominently expressed in antigen presenting cells like macrophages and dendritic cells and smooth muscle cells. (Hsing and Rudensky 2005; Rudensky and Beers 2006). While Cathepsin S is only weakly expressed in normal arterial tissue, strong upregulation is seen in atherosclerotic arteries (Liu et al. 2006; Sukhova et al. 1998).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice a significant reduction of acute plaque rupture events was reported. When chronic renal disease is introduced into CatS/In APO-E deficient mice a strong reduction of accelerated calcification is seen on top of the anti atherosclerotic activity in arteries and heart valves (Aikawa et al. 2009; de Nooijer et al. 2009; Rodgers et al. 2006; Sukhova et al. 2003). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly; Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells, resulting in reduced contribution of T cells to the chronic inflammation of the atherosclerotic tissue. Elevated inflammation results in further oxidative and proteolytic tissue damage and subsequently plaque destabilisation (Cheng et al. 2004; Driessen et al. 1999; Rudensky and Beers 2006).

The anti-inflammatory and anti-elastinolytic properties of a Cat S inhibitor make it also a prominent target for chronic obstructive pulmonary disease (Williams et al. 2009). Furthermore due to its extracellular functions in matrix degradation, inhibition of cathepsin S will impact neointima formation and angiogenesis (Burns-Kurtis et al. 2004; Cheng et al. 2004; Shi et al. 2003; Wang et al. 2006). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

Cathepsin L shows a broader expression profile than cathepsin S and there are also data which suggest a role of cathepsin L in atherosclerosis, e.g. LDLrec & Cat L deficient mice show a reduced atherosclerotic phenotype (Kitamoto et al. 2007). In addition, Cat L was suggested to be involved in metabolic syndrome as it controls adipogenesis and peripheral glucose tolerance. In renal disease Cathepsin L is described to regulate podocyte function by proteolytically processing dynamin and thereby proteinuria (Sever et al. 2007).

Tissue remodelling, extracellular matrix degradation, the generation of active neuropeptides and roles in antigen presentation in thymic epithelial cells are cellular activities described for Cathepsin L (Funkelstein et al. 2008; Rudensky and Beers 2006).

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl, propyl, isopropyl, isobutyl and tert.-butyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, cyclobutyl, cyclopentyl, cyclohexyl, cycloheptyl and cyclooctyl. Preferred cycloalkyl are cyclopropyl, cyclobutyl, cyclopentyl and cyclohexyl. Cyclopropyl and cyclobutyl are particularly preferred. Cyclopropyl is further preferred.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy, ethoxy, propoxy and isopropoxy.

The term "cycloalkyloxy", alone or in combination, signifies a group of the formula cycloalkyl-O— in which the term "cycloalkyl" has the previously given significance, such as cyclobutyloxy, cyclopentyloxy or cyclohexyloxy.

The term "phenyloxy", alone or in combination, signifies a phenyl-O— group.

The term "oxy", alone or in combination, signifies the —O— group.

The term "halogen" or "halo", alone or in combination, signifies fluorine, chlorine, bromine or iodine and preferably fluorine, chlorine or bromine, more preferably fluorine and chlorine.

The terms "haloalkyl", "halocycloalkyl" and "haloalkoxy", alone or in combination, denote an alkyl group, a cycloalkyl group and an alkoxy group substituted with at least one halogen, preferably substituted with one to five halogens. Fluoroalkyl is an alkyl group substituted with at least one fluorine atom, preferably substituted with one to five fluorine atoms. Preferred haloalkyl are trifluoromethyl, trifluoroethyland trifluoropropyl.

The term "carbonyl", alone or in combination, signifies the —C(O)— group.

The term "carboxy", alone or in combination, signifies the —COOH group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula (I) can also be present in the form of zwitterions. Particularly preferred pharmaceutically acceptable salts of compounds of formula (I) are the hydrochlorides, formiates, sulfates, phosphates and mesylates, in particular the hydrochlorides and formiates.

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

Preferred is a compound of formula (I) wherein
$A^1$ is selected from the group consisting of oxygen, carbonyl, —CH$_2$O—, and —CONR$^{11}$— or is absent;
$R^1$ is selected from the group consisting of hydrogen, alkyl, phenyl, halophenyl, carboxy, morpholinyl, alkylmorpholinyl, dioxothiomorpholinyl, 2-oxo-6-aza-spiro[3.3]heptanyl, piperidinyl, alkylpiperidinyl, hydroxypiperidinyl, piperazinyl, alkylpiperazinyl, azetidinyl, haloazetidinyl, hydroxyazetidinyl, alkoxyazetidinyl, 8-oxo-3-aza-bicyclo[3.2.1]octanyl, hydroxypiridazinyl and halopyrrolidinyl;
$R^2$ is hydrogen;
$R^3$ and $R^4$ are each independently selected from the group consisting of hydrogen, alkyl and phenyl;
or $R^3$ and $R^4$ together with the carbon atom to which they are attached form cycloalkyl or alkylpiperidinyl;
or $R^2$ and $R^3$ together with the nitrogen atom and carbon atom to which they are attached form pyrrolidinyl; and
$R^5$ is selected from the group consisting of alkyl, cycloalkyl, cycloalkylalkyl, phenyl, substituted phenyl, benzyl and naphtyl, wherein substituted phenyl is phenyl substituted with one or two substituents independently selected from the group consisting of alkyl, alkoxy, halogen, haloalkyl, haloalkoxy, halophenyl, halophenyloxy, alkylsulfonylphenyl, aminosulfonylphenyl, pyridinyl, alkylpyridinyl, halopyridinyl, alkoxypyridinyl, haloalkylpyridinyl, alkylsulfonylpyridinyl, alkylthiazolyl, piperidinyl, 1H-pyrazolyl, alkyl-1H-pyrazolyl, alkyl-2H-pyrayzolyl, pyrimidinyl, alkylthiophenyl, pyridazinyl, alkyl-6-oxo-6H-piridazinyl, alkylisoxazolyl, cycloalkylpiperazinyl, pyrazinyl, halopyrazinyl, haloazetidinyl, 2-oxo-6-aza-spiro[3.3]heptanyl, halopyrrolidinyl, alkylpiperazinyl, cycloalkylpiperazinyl, carbonylpiperazinyl and oxetanyloxy;

or a pharmaceutically acceptable salt thereof.

A compound of formula (I) wherein $A^1$ is selected from the group consisting of oxygen, carbonyl and —CH$_2$O— is preferred.

A compound of formula (I) wherein $A^1$ is oxygen is particularly preferred.

Further preferred is a compound of formula (I) wherein $R^1$ is selected from the group consisting of alkyl, halophenyl, morpholinyl and haloazetidinyl.

Particularly preferred is a compound of formula (I) wherein $R^1$ is selected from the group consisting of methyl, ethyl, chlorophenyl and difluoroazetidinyl.

In the definition of $R^1$, the groups morpholinyl, alkylmorpholinyl, dioxothiomorpholinyl, 2-oxo-6-aza-spiro[3.3]heptanyl, piperidinyl, alkyllpiperidinyl, hydroxypiperidinyl, piperazinyl, alkylpiperazinyl, azetidinyl, haloazetidinyl, hydroxyazetidinyl, alkoxyazetidinyl, 8-oxo-3-aza-bicyclo[3.2.1]octanyl, hydroxypiridazinyl and halopyrrolidinyl are preferably linked to $A^1$ by their nitrogen atom.

Furthermore, preferred is a compound of formula (I) wherein $R^2$ is hydrogen.

Preferred is a compound of formula (I) wherein $R^3$ and $R^4$ together with the carbon atom to which they are attached form cycloalkyl or alkylpiperidinyl.

Moreover, preferred is a compound of formula (I) wherein $R^3$ and $R^4$ together with the carbon atom to which they are attached form cyclopropyl or methylpiperidinyl.

A compound of formula (I) wherein $R^3$ and $R^4$ together with the carbon atom to which they are attached form cyclopropyl is particularly preferred.

Further, preferred is a compound of formula (I) wherein $R^5$ is phenyl substituted with one or two substituents independently selected from the group consisting of alkyl, halogen, haloalkyl, haloalkoxy, alkylpyridinyl, haloalkylpyridinyl, alkyl-1H-pyrazolyl and pyridazinyl.

Also preferred is a compound of formula (I) wherein $R^5$ is phenyl substituted with one or two substituents independently selected from the group consisting of methyl, chloro, trifluoromethyl, trifluoroethoxy, methylpyridinyl, trifluoromethylpyridinyl, methyl-1H-pyrazolyl and pyridazinyl.

A compound of formula (I) wherein $R^{11}$ is selected from the group consisting of methyl, ethyl and tert-butyl is further preferred.

The following compounds of formula (I) are particularly preferred:

(1R,2R,4R)-4-Benzenesulfonyl-2-(morpholine-4-carbonyl)-cyclopentanecarboxylic acid cyanomethyl-amide;
(1R,2R,4R)-4-Benzenesulfonyl-2-(morpholine-4-carbonyl)-cyclopentanecarboxylic acid (1-cyano-cyclopropyl)-amide;
(1R,2R,4R)-4-(2-Chloro-benzenesulfonyl)-2-(morpholine-4-carbonyl)-cyclopentanecarboxylic acid cyanomethyl-amide;
(1R,2R,4R)-2-(Morpholine-4-carbonyl)-4-(toluene-4-sulfonyl)-cyclopentanecarboxylic acid cyanomethyl-amide;
(1R,2R,4R)-2-(Morpholine-4-carbonyl)-4-(toluene-3-sulfonyl)-cyclopentanecarboxylic acid cyanomethyl-amide;
(1R,2R,4R)-4-(2,4-Difluoro-benzenesulfonyl)-2-(morpholine-4-carbonyl)-cyclopentanecarboxylic acid cyanomethyl-amide;
(1R,2R,4R)-4-(3-Chloro-4-fluoro-benzenesulfonyl)-2-(morpholine-4-carbonyl)-cyclopentanecarboxylic acid cyanomethyl-amide;
(1R,2R,4R)-4-(4-Chloro-2-methyl-benzenesulfonyl)-2-(morpholine-4-carbonyl)-cyclopentanecarboxylic acid cyanomethyl-amide;
(1R,2R,4R)-4-(2-Chloro-benzenesulfonyl)-2-(morpholine-4-carbonyl)-cyclopentanecarboxylic acid (1-cyano-cyclopropyl)-amide;
(1R,2R,4R)-4-Benzenesulfonyl-2-(1-cyano-cyclopropylcarbamoyl)-cyclopentanecarboxylic acid;
(1R,2R,4R)-4-Benzenesulfonyl-2-(2-oxa-6-aza-spiro[3.3]heptane-6-carbonyl)-cyclopentanecarboxylic acid (1-cyano-cyclopropyl)-amide;
(1R,2R,4R)-4-Benzenesulfonyl-2-(piperidine-1-carbonyl)-cyclopentanecarboxylic acid (1-cyano-cyclopropyl)-amide;
(1R,2R,4R)-4-Benzenesulfonyl-2-(4-hydroxy-piperidine-1-carbonyl)-cyclopentanecarboxylic acid (1-cyano-cyclopropyl)-amide;
(1R,2R,4R)-4-Benzenesulfonyl-2-(piperazine-1-carbonyl)-cyclopentanecarboxylic acid (1-cyano-cyclopropyl)-amide;
(1R,2R,4R)-4-Benzenesulfonyl-2-(3-hydroxy-azetidine-1-carbonyl)-cyclopentanecarboxylic acid (1-cyano-cyclopropyl)-amide;
(1R,2R,4R)-4-Benzenesulfonyl-2-((2S,6R)-2,6-dimethyl-morpholine-4-carbonyl)-cyclopentanecarboxylic acid (1-cyano-cyclopropyl)-amide;
(1R,2R,4R)-4-Benzenesulfonyl-2-((1R,5S)-8-oxa-3-aza-bicyclo[3.2.1]octane-3-carbonyl)-cyclopentanecarboxylic acid (1-cyano-cyclopropyl)-amide;
(1R,2R,4R)-4-Benzenesulfonyl-2-((1R,5S)-3-oxa-8-aza-bicyclo[3.2.1]octane-8-carbonyl)-cyclopentanecarboxylic acid (1-cyano-cyclopropyl)-amide;
(1R,2R,4R)-4-Benzenesulfonyl-2-(4-methyl-piperidine-1-carbonyl)-cyclopentanecarboxylic acid (1-cyano-cyclopropyl)-amide;
(1R,2R,4R)-4-Benzenesulfonyl-2-(1,1-dioxo-1-thiomorpholine-4-carbonyl)-cyclopentanecarboxylic acid (1-cyano-cyclopropyl)-amide;
(1R,2R,4R)-4-Benzenesulfonyl-2-(3-ethoxy-azetidine-1-carbonyl)-cyclopentanecarboxylic acid (1-cyano-cyclopropyl)-amide;
(1R,2R,4R)-4-Benzenesulfonyl-2-(3-methoxy-azetidine-1-carbonyl)-cyclopentanecarboxylic acid (1-cyano-cyclopropyl)-amide;
(1R,2R,4R)-4-Benzenesulfonyl-2-(pyrrolidine-1-carbonyl)-cyclopentanecarboxylic acid (1-cyano-cyclopropyl)-amide;
(1R,2R,4R)-2-(Azetidine-1-carbonyl)-4-benzenesulfonyl-cyclopentanecarboxylic acid (1-cyano-cyclopropyl)-amide;
(1R,2R,4R)-4-Benzenesulfonyl-cyclopentane-1,2-dicarboxylic acid 1-[(1-cyano-cyclopropyl)-amide]2-diethylamide;
(1R,2R,4R)-4-Benzenesulfonyl-2-(4-methyl-piperazine-1-carbonyl)-cyclopentanecarboxylic acid (1-cyano-cyclopropyl)-amide;
(1R,2R,4R)-4-Benzenesulfonyl-cyclopentane-1,2-dicarboxylic acid 1-[(1-cyano-cyclopropyl)-amide]2-dimethylamide;
(1R,2R,4S)-4-Benzenesulfonyl-cyclopentane-1,2-dicarboxylic acid 1-tert-butylamide 2-[(1-cyano-cyclopropyl)-amide];
(1R,2R,4S)-4-Benzenesulfonyl-cyclopentane-1,2-dicarboxylic acid 1-[(1-cyano-cyclopropyl)-amide]2-methylamide;
(1R,2R,4R)-4-[4-(5-Fluoro-pyridin-2-yl)-2-trifluoromethyl-benzenesulfonyl]-2-methoxy-cyclopentanecarboxylic acid (1-cyano-cyclopropyl)-amide;
(1S,2S,4S)-4-[4-(5-Fluoro-pyridin-2-yl)-2-trifluoromethyl-benzenesulfonyl]-2-methoxy-cyclopentanecarboxylic acid (1-cyano-cyclopropyl)-amide;
(1R,2R,4R)-4-(4-Chloro-2-methyl-benzenesulfonyl)-2-(morpholine-4-carbonyl)-cyclopentanecarboxylic acid (cyano-phenyl-methyl)-amide;
(1R,2R,4R)-4-(4-Chloro-2-methyl-benzenesulfonyl)-2-((2S,6R)-2,6-dimethyl-morpholine-4-carbonyl)-cyclopentanecarboxylic acid cyanomethyl-amide;
(1R,2R,4R)-4-(4-Chloro-2-methyl-benzenesulfonyl)-2-(4-methyl-piperazine-1-carbonyl)-cyclopentanecarboxylic acid cyanomethyl-amide;
(1R,2R,4R)-4-Benzenesulfonyl-2-(morpholine-4-carbonyl)-cyclopentanecarboxylic acid (cyano-dimethyl-methyl)-amide;
(1R,2R,4R)-4-Benzenesulfonyl-2-(morpholine-4-carbonyl)-cyclopentanecarboxylic acid (1-cyano-cyclobutyl)-amide;
(1R,2R,4R)-2-(Morpholine-4-carbonyl)-4-(naphthalene-1-sulfonyl)-cyclopentanecarboxylic acid cyanomethyl-amide;
(1R,2R,4R)-2-(Morpholine-4-carbonyl)-4-(2-trifluoroethyl-benzenesulfonyl)-cyclopentanecarboxylic acid cyanomethyl-amide;
(1R,2R,4R)-2-(Morpholine-4-carbonyl)-4-phenylmethanesulfonyl-cyclopentanecarboxylic acid cyanomethyl-amide;
(1R,2R,4R)-4-(2-Methyl-propane-1-sulfonyl)-2-(morpholine-4-carbonyl)-cyclopentanecarboxylic acid cyanomethyl-amide;
(1R,2R,4R)-4-Cyclopropylmethanesulfonyl-2-(morpholine-4-carbonyl)-cyclopentanecarboxylic acid cyanomethyl-amide;

(1R,2R,4R)-2-Methoxy-4-(4-pyridin-2-yl-2-trifluoromethyl-benzenesulfonyl)-cyclopentanecarboxylic acid (1-cyano-cyclopropyl)-amide;

(1S,2S,4S)-2-Methoxy-4-(4-pyridin-2-yl-2-trifluoromethyl-benzenesulfonyl)-cyclopentanecarboxylic acid (1-cyano-cyclopropyl)-amide;

(1R,2R,4S)-4-Benzenesulfonyl-cyclopentane-1,2-dicarboxylic acid 1-[(1-cyano-cyclopropyl)-amide]2-[(4-fluoro-phenyl)-amide];

3-(2-Chloro-benzenesulfonyl)-cyclopentanecarboxylic acid cyanomethyl-amide;

(S)-1-[(1R,2R,4S)-4-(4-Chloro-2-methyl-benzenesulfonyl)-2-(morpholine-4-carbonyl)-cyclopentanecarbonyl]-pyrrolidine-2-carbonitrile;

(1R,2R,4R)-4-(4-Chloro-2-methyl-benzenesulfonyl)-2-(morpholine-4-carbonyl)-cyclopentanecarboxylic acid (4-cyano-1-methyl-piperidin-4-yl)-amide;

(1R,2R,4R)-2-Methoxy-4-(2-trifluoromethyl-benzenesulfonyl)-cyclopentanecarboxylic acid (1-cyano-cyclopropyl)-amide;

(1S,2S,4S)-2-Methoxy-4-(2-trifluoromethyl-benzenesulfonyl)-cyclopentanecarboxylic acid (1-cyano-cyclopropyl)-amide;

(1R,2R,4R)-2-Methoxy-4-(2-trifluoromethyl-benzenesulfonyl)-cyclopentanecarboxylic acid cyanomethyl-amide;

(1S,2S,4S)-2-Methoxy-4-(2-trifluoromethyl-benzenesulfonyl)-cyclopentanecarboxylic acid cyanomethyl-amide;

(1R,2R,4R)-4-(2-Chloro-benzenesulfonyl)-2-hydroxy-cyclopentanecarboxylic acid (1-cyano-cyclopropyl)-amide;

(1S,2S,4S)-4-(2-Chloro-benzenesulfonyl)-2-hydroxy-cyclopentanecarboxylic acid (1-cyano-cyclopropyl)-amide;

(1R,2R,4R)-4-(2-Chloro-benzenesulfonyl)-2-hydroxy-cyclopentanecarboxylic acid cyanomethyl-amide;

(1S,2S,4S)-4-(2-Chloro-benzenesulfonyl)-2-hydroxy-cyclopentanecarboxylic acid cyanomethyl-amide;

(1R,2R,4R)-4-(2,4-Dichloro-benzenesulfonyl)-2-methoxy-cyclopentanecarboxylic acid (1-cyano-cyclopropyl)-amide;

(1S,2S,4S)-4-(2,4-Dichloro-benzenesulfonyl)-2-methoxy-cyclopentanecarboxylic acid (1-cyano-cyclopropyl)-amide;

(1R,2R,4R)-4-(2,4-Dichloro-benzenesulfonyl)-2-methoxy-cyclopentanecarboxylic acid cyanomethyl-amide;

(1S,2S,4S)-4-(2,4-Dichloro-benzenesulfonyl)-2-methoxy-cyclopentanecarboxylic acid cyanomethyl-amide;

(1S,2S,4R)-4-(2-Chloro-benzenesulfonyl)-2-hydroxy-cyclopentanecarboxylic acid (1-cyano-cyclopropyl)-amide;

(1R,2R,4S)-4-(2-Chloro-benzenesulfonyl)-2-hydroxy-cyclopentanecarboxylic acid (1-cyano-cyclopropyl)-amide;

(1S,2S,4R)-4-(2-Chloro-benzenesulfonyl)-2-hydroxy-cyclopentanecarboxylic acid cyanomethyl-amide;

(1R,2R,4S)-4-(2-Chloro-benzenesulfonyl)-2-hydroxy-cyclopentanecarboxylic acid cyanomethyl-amide;

(1R,2R,4R)-2-Propoxy-4-(2-trifluoromethyl-benzenesulfonyl)-cyclopentanecarboxylic acid (1-cyano-cyclopropyl)-amide;

(1S,2S,4S)-2-Propoxy-4-(2-trifluoromethyl-benzenesulfonyl)-cyclopentanecarboxylic acid (1-cyano-cyclopropyl)-amide;

(1R,2R,4R)-2-Propoxy-4-(2-trifluoromethyl-benzenesulfonyl)-cyclopentanecarboxylic acid cyanomethyl-amide;

(1S,2S,4S)-2-Propoxy-4-(2-trifluoromethyl-benzenesulfonyl)-cyclopentanecarboxylic acid cyanomethyl-amide;

(1R,2R,4R)-4-(2-Chloro-4-fluoro-benzenesulfonyl)-2-methoxy-cyclopentanecarboxylic acid (1-cyano-cyclopropyl)-amide;

(1S,2S,4S)-4-(2-Chloro-4-fluoro-benzenesulfonyl)-2-methoxy-cyclopentanecarboxylic acid (1-cyano-cyclopropyl)-amide;

(1R,2R,4R)-4-[2-Chloro-4-(4-fluoro-phenoxy)-benzenesulfonyl]-2-methoxy-cyclopentanecarboxylic acid (1-cyano-cyclopropyl)-amide;

(1S,2S,4S)-4-[2-Chloro-4-(4-fluoro-phenoxy)-benzenesulfonyl]-2-methoxy-cyclopentanecarboxylic acid (1-cyano-cyclopropyl)-amide;

(1R,2R,4R)-4-(4-Bromo-2-trifluoromethyl-benzenesulfonyl)-2-methoxy-cyclopentanecarboxylic acid (1-cyano-cyclopropyl)-amide;

(1S,2S,4S)-4-(4-Bromo-2-trifluoromethyl-benzenesulfonyl)-2-methoxy-cyclopentanecarboxylic acid (1-cyano-cyclopropyl)-amide;

(1R,2R,4R)-4-(2-Chloro-4-pyrazol-1-yl-benzenesulfonyl)-2-methoxy-cyclopentanecarboxylic acid (1-cyano-cyclopropyl)-amide;

(1S,2S,4S)-4-(2-Chloro-4-pyrazol-1-yl-benzenesulfonyl)-2-methoxy-cyclopentanecarboxylic acid (1-cyano-cyclopropyl)-amide;

(1R,2R,4R)-4-[2-Chloro-4-((R/S)-2,2,2-trifluoro-1-methylethoxy)-benzenesulfonyl]-2-methoxy-cyclopentanecarboxylic acid (1-cyano-cyclopropyl)-amide;

(1S,2S,4S)-4-[2-Chloro-4-((R/S)-2,2,2-trifluoro-1-methylethoxy)-benzenesulfonyl]-2-methoxy-cyclopentanecarboxylic acid (1-cyano-cyclopropyl)-amide;

(1R,2R,4R)-2-Methoxy-4-[4-(4-methyl-thiazol-2-yl)-2-trifluoromethyl-benzenesulfonyl]-cyclopentanecarboxylic acid (1-cyano-cyclopropyl)-amide;

(1S,2S,4S)-2-Methoxy-4-[4-(4-methyl-thiazol-2-yl)-2-trifluoromethyl-benzenesulfonyl]-cyclopentanecarboxylic acid (1-cyano-cyclopropyl)-amide;

(1R,2R,4R)-4-(2',4'-Difluoro-3-trifluoromethyl-biphenyl-4-sulfonyl)-2-methoxy-cyclopentanecarboxylic acid (1-cyano-cyclopropyl)-amide;

(1S,2S,4S)-4-(2',4'-Difluoro-3-trifluoromethyl-biphenyl-4-sulfonyl)-2-methoxy-cyclopentanecarboxylic acid (1-cyano-cyclopropyl)-amide;

(1R,2R,4R)-4-(4'-Fluoro-3-trifluoromethyl-biphenyl-4-sulfonyl)-2-methoxy-cyclopentanecarboxylic acid (1-cyano-cyclopropyl)-amide;

(1S,2S,4S)-4-(4'-Fluoro-3-trifluoromethyl-biphenyl-4-sulfonyl)-2-methoxy-cyclopentanecarboxylic acid (1-cyano-cyclopropyl)-amide;

(1R,2R,4R)-4-(2-Chloro-4-piperidin-1-yl-benzenesulfonyl)-2-methoxy-cyclopentanecarboxylic acid (1-cyano-cyclopropyl)-amide;

(1S,2S,4S)-4-(2-Chloro-4-piperidin-1-yl-benzenesulfonyl)-2-methoxy-cyclopentanecarboxylic acid (1-cyano-cyclopropyl)-amide;

(1R,2R,4R)-4-[2-Chloro-4-(2,2,2-trifluoro-ethoxy)-benzenesulfonyl]-2-methoxy-cyclopentanecarboxylic acid (1-cyano-cyclopropyl)-amide;

(1S,2S,4S)-4-[2-Chloro-4-(2,2,2-trifluoro-ethoxy)-benzenesulfonyl]-2-methoxy-cyclopentanecarboxylic acid (1-cyano-cyclopropyl)-amide;

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-4-[4-(2,5-Dimethyl-2H-pyrazol-3-yl)-2-trifluoromethyl-benzenesulfonyl]-2-methoxy-cyclopentanecarboxylic acid (1-cyano-cyclopropyl)-amide;

(1S,2S,4S)-4-[4-(2,5-Dimethyl-2H-pyrazol-3-yl)-2-trifluoromethyl-benzenesulfonyl]-2-methoxy-cyclopentanecarboxylic acid (1-cyano-cyclopropyl)-amide;

(1R,2R,4S)-4-(2-Chloro-benzenesulfonyl)-2-(4-chloro-phenoxymethyl)-cyclopentanecarboxylic acid cyanomethyl-amide;

(1R,2R,4R)-4-(2-Chloro-benzenesulfonyl)-2-(4-chloro-phenoxymethyl)-cyclopentanecarboxylic acid cyanomethyl-amide;

(1R,2R,4S)-4-(2-Chloro-benzenesulfonyl)-2-(4-chloro-phenoxymethyl)-cyclopentanecarboxylic acid (1-cyano-cyclopropyl)-amide;

(1R,2R,4R)-4-(2-Chloro-benzenesulfonyl)-2-(4-chloro-phenoxymethyl)-cyclopentanecarboxylic acid (1-cyano-cyclopropyl)-amide;

(1R,2R,4R)-2-Methoxy-4-[4-(1-methyl-1H-pyrazol-5-yl)-2-trifluoromethyl-benzenesulfonyl]-cyclopentanecarboxylic acid (1-cyano-cyclopropyl)-amide;

(1S,2S,4S)-2-Methoxy-4-[4-(1-methyl-1H-pyrazol-5-yl)-2-trifluoromethyl-benzenesulfonyl]-cyclopentanecarboxylic acid (1-cyano-cyclopropyl)-amide;

(1R,2R,4R)-2-Methoxy-4-[4-(1H-pyrazol-3-yl)-2-trifluoromethyl-benzenesulfonyl]-cyclopentanecarboxylic acid (1-cyano-cyclopropyl)-amide;

(1S,2S,4S)-2-Methoxy-4-[4-(1H-pyrazol-3-yl)-2-trifluoromethyl-benzenesulfonyl]-cyclopentanecarboxylic acid (1-cyano-cyclopropyl)-amide;

(1R,2R,4R)-4-(3',4'-Difluoro-3-trifluoromethyl-biphenyl-4-sulfonyl)-2-methoxy-cyclopentanecarboxylic acid (1-cyano-cyclopropyl)-amide;

(1S,2S,4S)-4-(3',4'-Difluoro-3-trifluoromethyl-biphenyl-4-sulfonyl)-2-methoxy-cyclopentanecarboxylic acid (1-cyano-cyclopropyl)-amide;

(1R,2R,4R)-4-(4'-Methanesulfonyl-3-trifluoromethyl-biphenyl-4-sulfonyl)-2-methoxy-cyclopentanecarboxylic acid (1-cyano-cyclopropyl)-amide;

(1S,2S,4S)-4-(4'-Methanesulfonyl-3-trifluoromethyl-biphenyl-4-sulfonyl)-2-methoxy-cyclopentanecarboxylic acid (1-cyano-cyclopropyl)-amide;

(1R,2R,4R)-2-Methoxy-4-(4'-sulfamoyl-3-trifluoromethyl-biphenyl-4-sulfonyl)-cyclopentanecarboxylic acid (1-cyano-cyclopropyl)-amide;

(1S,2S,4S)-2-Methoxy-4-(4'-sulfamoyl-3-trifluoromethyl-biphenyl-4-sulfonyl)-cyclopentanecarboxylic acid (1-cyano-cyclopropyl)-amide;

(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Methoxy-4-[4-(6-methoxy-pyridin-3-yl)-2-trifluoromethyl-benzenesulfonyl]-cyclopentanecarboxylic acid (1-cyano-cyclopropyl)-amide;

(1S,2S,4S)-2-Methoxy-4-[4-(6-methoxy-pyridin-3-yl)-2-trifluoromethyl-benzenesulfonyl]-cyclopentanecarboxylic acid (1-cyano-cyclopropyl)-amide;

(1R,3R-3-(2-Chloro-4-fluoro-benzenesulfonyl)-cyclopentanecarboxylic acid cyanomethyl-amide;

(1S,3S)-3-(2-Chloro-4-fluoro-benzenesulfonyl)-cyclopentanecarboxylic acid cyanomethyl-amide;

(1R,3R)-3-[2-Chloro-4-((R/S)-2,2,2-trifluoro-1-methyl-ethoxy)-benzenesulfonyl]-cyclopentanecarboxylic acid cyanomethyl-amide;

(1S,3S)-3-[2-Chloro-4-((R/S)-2,2,2-trifluoro-1-methyl-ethoxy)-benzenesulfonyl]-cyclopentanecarboxylic acid cyanomethyl-amide;

(1R,2R,4R)-2-Methoxy-4-[4-(6-methyl-pyridin-3-yl)-2-trifluoromethyl-benzenesulfonyl]-cyclopentanecarboxylic acid (1-cyano-cyclopropyl)-amide;

(1S,2S,4S)-2-Methoxy-4-[4-(6-methyl-pyridin-3-yl)-2-trifluoromethyl-benzenesulfonyl]-cyclopentanecarboxylic acid (1-cyano-cyclopropyl)-amide;

(1R,2R,4R)-2-Methoxy-4-(4-pyrimidin-5-yl-2-trifluoromethyl-benzenesulfonyl)-cyclopentanecarboxylic acid (1-cyano-cyclopropyl)-amide;

(1S,2S,4S)-2-Methoxy-4-(4-pyrimidin-5-yl-2-trifluoromethyl-benzenesulfonyl)-cyclopentanecarboxylic acid (1-cyano-cyclopropyl)-amide;

(1R,2R,4R)-4-[4-(5-Methanesulfonyl-pyridin-3-yl)-2-trifluoromethyl-benzenesulfonyl]-2-methoxy-cyclopentanecarboxylic acid (1-cyano-cyclopropyl)-amide;

(1S,2S,4S)-4-[4-(5-Methanesulfonyl-pyridin-3-yl)-2-trifluoromethyl-benzenesulfonyl]-2-methoxy-cyclopentanecarboxylic acid (1-cyano-cyclopropyl)-amide;

(1R,2R,4R)-4-[4-(5-Fluoro-pyridin-3-yl)-2-trifluoromethyl-benzenesulfonyl]-2-methoxy-cyclopentanecarboxylic acid (1-cyano-cyclopropyl)-amide;

(1S,2S,4S)-4-[4-(5-Fluoro-pyridin-3-yl)-2-trifluoromethyl-benzenesulfonyl]-2-methoxy-cyclopentanecarboxylic acid (1-cyano-cyclopropyl)-amide;

(1R,2R,4R)-2-Methoxy-4-[4-(5-methyl-pyridin-3-yl)-2-trifluoromethyl-benzenesulfonyl]-cyclopentanecarboxylic acid (1-cyano-cyclopropyl)-amide;

(1S,2S,4S)-2-Methoxy-4-[4-(5-methyl-pyridin-3-yl)-2-trifluoromethyl-benzenesulfonyl]-cyclopentanecarboxylic acid (1-cyano-cyclopropyl)-amide;

(1R,2R,4R)-2-Methoxy-4-[4-(5-methoxy-pyridin-3-yl)-2-trifluoromethyl-benzenesulfonyl]-cyclopentanecarboxylic acid (1-cyano-cyclopropyl)-amide;

(1S,2S,4S)-2-Methoxy-4-[4-(5-methoxy-pyridin-3-yl)-2-trifluoromethyl-benzenesulfonyl]-cyclopentanecarboxylic acid (1-cyano-cyclopropyl)-amide;

(1R,2R,4R)-4-[4-(2,5-Dimethyl-thiophen-3-yl)-2-trifluoromethyl-benzenesulfonyl]-2-methoxy-cyclopentanecarboxylic acid (1-cyano-cyclopropyl)-amide;

(1S,2S,4S)-4-[4-(2,5-Dimethyl-thiophen-3-yl)-2-trifluoromethyl-benzenesulfonyl]-2-methoxy-cyclopentanecarboxylic acid (1-cyano-cyclopropyl)-amide;

(1R,2R,4R)-4-[2-Chloro-4-(3-methyl-6-oxo-6H-pyridazin-1-yl)-benzenesulfonyl]-2-methoxy-cyclopentanecarboxylic acid (1-cyano-cyclopropyl)-amide;

(1S,2S,4S)-4-[2-Chloro-4-(3-methyl-6-oxo-6H-pyridazin-1-yl)-benzenesulfonyl]-2-methoxy-cyclopentanecarboxylic acid (1-cyano-cyclopropyl)-amide;

(1R,2R,4R)-4-(2-Chloro-4-methoxy-benzenesulfonyl)-2-methoxy-cyclopentanecarboxylic acid (1-cyano-cyclopropyl)-amide;

(1S,2S,4S)-4-(2-Chloro-4-methoxy-benzenesulfonyl)-2-methoxy-cyclopentanecarboxylic acid (1-cyano-cyclopropyl)-amide;

(1R,2R,4R)-4-[4-(5-Chloro-pyridin-3-yl)-2-trifluoromethyl-benzenesulfonyl]-2-methoxy-cyclopentanecarboxylic acid (1-cyano-cyclopropyl)-amide;

(1S,2S,4S)-4-[4-(5-Chloro-pyridin-3-yl)-2-trifluoromethyl-benzenesulfonyl]-2-methoxy-cyclopentanecarboxylic acid (1-cyano-cyclopropyl)-amide;

(1R,2R,4R)-4-[4-(3,5-Dimethyl-isoxazol-4-yl)-2-trifluoromethyl-benzenesulfonyl]-2-methoxy-cyclopentanecarboxylic acid (1-cyano-cyclopropyl)-amide;

(1S,2S,4S)-4-[4-(3,5-Dimethyl-isoxazol-4-yl)-2-trifluoromethyl-benzenesulfonyl]-2-methoxy-cyclopentanecarboxylic acid (1-cyano-cyclopropyl)-amide;

(1R,3R)-3-(2-Chloro-4-fluoro-benzenesulfonyl)-cyclopentanecarboxylic acid (1-cyano-cyclopropyl)-amide;
(1S,3S)-3-(2-Chloro-4-fluoro-benzenesulfonyl)-cyclopentanecarboxylic acid (1-cyano-cyclopropyl)-amide;
(1R,3R)-3-[2-Chloro-4-((R/S)-2,2,2-trifluoro-1-methylethoxy)-benzenesulfonyl]-cyclopentanecarboxylic acid (1-cyano-cyclopropyl)-amide;
(1S,3S)-3-[2-Chloro-4-((R/S)-2,2,2-trifluoro-1-methylethoxy)-benzenesulfonyl]-cyclopentanecarboxylic acid (1-cyano-cyclopropyl)-amide;
(1R,3R)-3-(2-Chloro-4-morpholin-4-yl-benzenesulfonyl)-cyclopentanecarboxylic acid (1-cyano-cyclopropyl)-amide;
(1S,3S)-3-(2-Chloro-4-morpholin-4-yl-benzenesulfonyl)-cyclopentanecarboxylic acid (1-cyano-cyclopropyl)-amide;
(1R,3R)-3-[2-Chloro-4-(2-oxa-6-aza-spiro[3.3]hept-6-yl)-benzenesulfonyl]-cyclopentanecarboxylic acid (1-cyano-cyclopropyl)-amide;
(1S,3S)-3-[2-Chloro-4-(2-oxa-6-aza-spiro[3.3]hept-6-yl)-benzenesulfonyl]-cyclopentanecarboxylic acid (1-cyano-cyclopropyl)-amide;
(1R,3R)-3-[2-Chloro-4-(3,3-difluoro-pyrrolidin-1-yl)-benzenesulfonyl]-cyclopentanecarboxylic acid (1-cyano-cyclopropyl)-amide;
(1S,3S)-3-[2-Chloro-4-(3,3-difluoro-pyrrolidin-1-yl)-benzenesulfonyl]-cyclopentanecarboxylic acid (1-cyano-cyclopropyl)-amide;
(1R,3R)-3-[2-Chloro-4-(4-ethyl-piperazin-1-yl)-benzenesulfonyl]-cyclopentanecarboxylic acid (1-cyano-cyclopropyl)-amide;
(1S,3S)-3-[2-Chloro-4-(4-ethyl-piperazin-1-yl)-benzenesulfonyl]-cyclopentanecarboxylic acid (1-cyano-cyclopropyl)-amide;
(1R,3R)-3-[2-Chloro-4-(2,2,2-trifluoro-ethoxy)-benzenesulfonyl]-cyclopentanecarboxylic acid (1-cyano-cyclopropyl)-amide;
(1S,3S)-3-[2-Chloro-4-(2,2,2-trifluoro-ethoxy)-benzenesulfonyl]-cyclopentanecarboxylic acid (1-cyano-cyclopropyl)-amide;
(1R,3S)-3-[2-Chloro-4-(2,2,2-trifluoro-ethoxy)-benzenesulfonyl]-cyclopentanecarboxylic acid (1-cyano-cyclopropyl)-amide;
(1S,3R)-3-[2-Chloro-4-(2,2,2-trifluoro-ethoxy)-benzenesulfonyl]-cyclopentanecarboxylic acid (1-cyano-cyclopropyl)-amide;
(1R,3R)-3-(2-Chloro-4-pyrazol-1-yl-benzenesulfonyl)-cyclopentanecarboxylic acid (1-cyano-cyclopropyl)-amide;
(1S,3S)-3-(2-Chloro-4-pyrazol-1-yl-benzenesulfonyl)-cyclopentanecarboxylic acid (1-cyano-cyclopropyl)-amide;
(1R,3S)-3-(2-Chloro-4-pyrazol-1-yl-benzenesulfonyl)-cyclopentanecarboxylic acid (1-cyano-cyclopropyl)-amide;
(1S,3R)-3-(2-Chloro-4-pyrazol-1-yl-benzenesulfonyl)-cyclopentanecarboxylic acid (1-cyano-cyclopropyl)-amide;
(1R,3R)-3-[2-Chloro-4-(4-cyclopropyl-piperazin-1-yl)-benzenesulfonyl]-cyclopentanecarboxylic acid (1-cyano-cyclopropyl)-amide;
(1S,3S)-3-[2-Chloro-4-(4-cyclopropyl-piperazin-1-yl)-benzenesulfonyl]-cyclopentanecarboxylic acid (1-cyano-cyclopropyl)-amide;
(1R,2R,4S)-4-(2-Chloro-benzenesulfonyl)-2-methoxymethyl-cyclopentanecarboxylic acid cyanomethyl-amide;
(1R,2R,4R)-4-(2-Chloro-benzenesulfonyl)-2-methoxymethyl-cyclopentanecarboxylic acid cyanomethylamide;
(1R,2R,4S)-4-(2-Chloro-benzenesulfonyl)-2-methoxymethyl-cyclopentanecarboxylic acid (1-cyano-cyclopropyl)-amide;
(1R,2R,4R)-4-(2-Chloro-benzenesulfonyl)-2-methoxymethyl-cyclopentanecarboxylic acid (1-cyano-cyclopropyl)-amide;
(1R,2R,4S)-4-(2-Chloro-benzenesulfonyl)-2-(6-hydroxy-pyridazin-3-yloxymethyl)-cyclopentanecarboxylic acid cyanomethylamide;
(1R,2R,4S)-4-(2-Chloro-benzenesulfonyl)-2-(6-hydroxy-pyridazin-3-yloxymethyl)-cyclopentanecarboxylic acid cyanomethylamide;
(1R,2R,4S)-4-(2-Chloro-benzenesulfonyl)-2-(6-hydroxy-pyridazin-3-yloxymethyl)-cyclopentanecarboxylic acid (1-cyano-cyclopropyl)-amide;
(1R,2R,4R)-4-(2-Chloro-benzenesulfonyl)-2-(6-hydroxy-pyridazin-3-yloxymethyl)-cyclopentanecarboxylic acid (1-cyano-cyclopropyl)-amide;
(1R,2R,4R)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;
(1S,2S,4S)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;
(1R,2R,4R)-2-Methoxy-4-(4-pyridazin-4-yl-2-trifluoromethyl-benzenesulfonyl)-cyclopentanecarboxylic acid (1-cyano-cyclopropyl)-amide;
(1S,2S,4S)-2-Methoxy-4-(4-pyridazin-4-yl-2-trifluoromethyl-benzenesulfonyl)-cyclopentanecarboxylic acid (1-cyano-cyclopropyl)-amide;
(1R,2R,4R)-2-Methoxy-4-(4-pyrazin-2-yl-2-trifluoromethyl-benzenesulfonyl)-cyclopentanecarboxylic acid (1-cyano-cyclopropyl)-amide;
(1S,2S,4S)-2-Methoxy-4-(4-pyrazin-2-yl-2-trifluoromethyl-benzenesulfonyl)-cyclopentanecarboxylic acid (1-cyano-cyclopropyl)-amide;
(1R,2R,4R)-4-(4-Bromo-2-trifluoromethyl-benzenesulfonyl)-2-isopropoxy-cyclopentanecarboxylic acid (1-cyano-cyclopropyl)-amide;
(1S,2S,4S)-4-(4-Bromo-2-trifluoromethyl-benzenesulfonyl)-2-isopropoxy-cyclopentanecarboxylic acid (1-cyano-cyclopropyl)-amide;
(1R,2R,4S)-4-(4-Bromo-2-trifluoromethyl-benzenesulfonyl)-2-ethoxy-cyclopentanecarboxylic acid (1-cyano-cyclopropyl)-amide;
(1S,2S,4R)-4-(4-Bromo-2-trifluoromethyl-benzenesulfonyl)-2-ethoxy-cyclopentanecarboxylic acid (1-cyano-cyclopropyl)-amide;
(1R,2R,4R)-2-Ethoxy-4-[4-(2-methyl-pyridin-4-yl)-2-trifluoromethyl-benzenesulfonyl]-cyclopentanecarboxylic acid (1-cyano-cyclopropyl)-amide;
(1S,2S,4S)-2-Ethoxy-4-[4-(2-methyl-pyridin-4-yl)-2-trifluoromethyl-benzenesulfonyl]-cyclopentanecarboxylic acid (1-cyano-cyclopropyl)-amide;
(1R,2R,4R)-4-[4-(3,5-Dimethyl-isoxazol-4-yl)-2-trifluoromethyl-benzenesulfonyl]-2-ethoxy-cyclopentanecarboxylic acid (1-cyano-cyclopropyl)-amide;
(1S,2S,4S)-4-[4-(3,5-Dimethyl-isoxazol-4-yl)-2-trifluoromethyl-benzenesulfonyl]-2-ethoxy-cyclopentanecarboxylic acid (1-cyano-cyclopropyl)-amide;
(1R,2R,4R)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;
(1S,2S,4S)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;
(1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide;

(1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide;

(1R,2R,4R)-4-(2-Chloro-4-fluoro-benzenesulfonyl)-2-(3,3-difluoro-azetidine-1-carbonyl)-cyclopentanecarboxylic acid (1-cyano-cyclopropyl)-amide;

(1R,2R,4R)-2-(3,3-Difluoro-azetidine-1-carbonyl)-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-(3,3-Difluoro-azetidine-1-carbonyl)-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-4-[4-(2-Chloro-pyridin-4-yl)-2-trifluoromethyl-benzenesulfonyl]-2-(3,3-difluoro-azetidine-1-carbonyl)-cyclopentanecarboxylic acid (1-cyano-cyclopropyl)-amide;

(1R,2R,4R)-4-[4-(6-Chloro-pyrazin-2-yl)-2-trifluoromethyl-benzenesulfonyl]-2-(3,3-difluoro-azetidine-1-carbonyl)-cyclopentanecarboxylic acid (1-cyano-cyclopropyl)-amide;

(1R,2R,4R)-2-(3,3-Difluoro-azetidine-1-carbonyl)-4-[4-(2-methyl-2H-pyrazol-3-yl)-2-trifluoromethyl-benzenesulfonyl]-cyclopentanecarboxylic acid (1-cyano-cyclopropyl)-amide;

(1R,2R,4R)-4-(4-Cyclopropyl-2-trifluoromethyl-benzenesulfonyl)-2-(3,3-difluoro-azetidine-1-carbonyl)-cyclopentanecarboxylic acid (1-cyano-cyclopropyl)-amide;

(1R,2R,4R)-4-[4-(5'-Chloro-[2,2']bipyrazinyl-6-yl)-2-trifluoromethyl-benzenesulfonyl]-2-(3,3-difluoro-azetidine-1-carbonyl)-cyclopentanecarboxylic acid (1-cyano-cyclopropyl)-amide;

2-(3,3-Difluoro-azetidine-1-carbonyl)-4-[4-(oxetan-3-yloxy)-2-trifluoromethyl-benzenesulfonyl]-cyclopentanecarboxylic acid (1-cyano-cyclopropyl)-amide;

2-(3,3-Difluoro-azetidine-1-carbonyl)-4-(4-pyrazol-1-yl-2-trifluoromethyl-benzenesulfonyl)-cyclopentanecarboxylic acid (1-cyano-cyclopropyl)-amide;

(1R,2R,4R)-4-[4-(4-Cyclopropyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide;

(1R,2R,4R)-4-[4-(4-tert-Butyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide;

4-[4-(4-Acetyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide;

2-(3,3-Difluoro-azetidine-1-carbonyl)-4-[4-(3,3-difluoro-pyrrolidin-1-yl)-2-trifluoromethyl-benzenesulfonyl]-cyclopentanecarboxylic acid (1-cyano-cyclopropyl)-amide;

(1R,2R,4R)-2-(3,3-Difluoro-azetidine-1-carbonyl)-4-[4-(2-oxa-6-aza-spiro[3.3]hept-6-yl)-2-trifluoromethyl-benzenesulfonyl]-cyclopentanecarboxylic acid (1-cyano-cyclopropyl)-amide;

(1R,2R,4R)-4-[2-Chloro-4-(2,2,2-trifluoro-ethoxy)-benzenesulfonyl]-2-(3,3-difluoro-azetidine-1-carbonyl)-cyclopentanecarboxylic acid (1-cyano-cyclopropyl)-amide;

(1R,2R,4R)-4-[2-Chloro-4-((S)-2,2,2-trifluoro-1-methyl-ethoxy)-benzenesulfonyl]-2-(3,3-difluoro-azetidine-1-carbonyl)-cyclopentanecarboxylic acid (1-cyano-cyclopropyl)-amide;

(1R,2R,4R)-4-[2-Chloro-4-(3,3-difluoro-azetidin-1-yl)-benzenesulfonyl]-2-(3,3-difluoro-azetidine-1-carbonyl)-cyclopentanecarboxylic acid (1-cyano-cyclopropyl)-amide;

(1R,2R,4R)-4-(4-Bromo-2-trifluoromethyl-benzenesulfonyl)-2-methoxy-cyclopentanecarboxylic acid (1-cyano-cyclopropyl)-amide;

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Isopropoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Isopropoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-4-[4-(3,5-Dimethyl-isoxazol-4-yl)-2-trifluoromethyl-benzenesulfonyl]-2-isopropoxy-cyclopentanecarboxylic acid (1-cyano-cyclopropyl)-amide;

(1S,2S,4S)-4-[4-(3,5-Dimethyl-isoxazol-4-yl)-2-trifluoromethyl-benzenesulfonyl]-2-isopropoxy-cyclopentanecarboxylic acid (1-cyano-cyclopropyl)-amide;

(1R,2R,4R)-2-Isopropoxy-4-[4-(1-methyl-1H-pyrazol-4-yl)-2-trifluoromethyl-benzenesulfonyl]-cyclopentanecarboxylic acid (1-cyano-cyclopropyl)-amide; and (1S,2S,4S)-2-Isopropoxy-4-[4-(1-methyl-1H-pyrazol-4-yl)-2-trifluoromethyl-benzenesulfonyl]-cyclopentanecarboxylic acid (1-cyano-cyclopropyl)-amide; or salts thereof.

The following compounds of formula (I) are also particularly preferred:

(1R,2R,4R)-4-(2-Chloro-benzenesulfonyl)-2-(morpholine-4-carbonyl)-cyclopentanecarboxylic acid (1-cyano-cyclopropyl)-amide;

(1R,2R,4R)-4-(4-Chloro-2-methyl-benzenesulfonyl)-2-(morpholine-4-carbonyl)-cyclopentanecarboxylic acid (4-cyano-1-methyl-piperidin-4-yl)-amide;

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4S)-4-(2-Chloro-benzenesulfonyl)-2-(4-chloro-phenoxymethyl)-cyclopentanecarboxylic acid (1-cyano-cyclopropyl)-amide;

(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;

(1S,2S,4S)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;

(1R,2R,4R)-2-Methoxy-4-(4-pyridazin-4-yl-2-trifluoromethyl-benzenesulfonyl)-cyclopentanecarboxylic acid (1-cyano-cyclopropyl)-amide;

(1S,2S,4S)-2-Methoxy-4-(4-pyridazin-4-yl-2-trifluoromethyl-benzenesulfonyl)-cyclopentanecarboxylic acid (1-cyano-cyclopropyl)-amide;

(1R,2R,4R)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-(3,3-Difluoro-azetidine-1-carbonyl)-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-(3,3-Difluoro-azetidine-1-carbonyl)-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-4-[2-Chloro-4-(2,2,2-trifluoro-ethoxy)-benzenesulfonyl]-2-(3,3-difluoro-azetidine-1-carbonyl)-cyclopentanecarboxylic acid (1-cyano-cyclopropyl)-amide;

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide; and (1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;

or salts thereof.

The following compounds of formula (I) are further particularly preferred:

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;

(1S,2S,4S)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;

(1R,2R,4R)-2-Methoxy-4-(4-pyridazin-4-yl-2-trifluoromethyl-benzenesulfonyl)-cyclopentanecarboxylic acid (1-cyano-cyclopropyl)-amide;

(1S,2S,4S)-2-Methoxy-4-(4-pyridazin-4-yl-2-trifluoromethyl-benzenesulfonyl)-cyclopentanecarboxylic acid (1-cyano-cyclopropyl)-amide;

(1R,2R,4R)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide; and (1S,2S,4S)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;

or salts thereof.

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide or a salt thereof is a particularly preferred compound of formula (I).

Also preferred are the compounds of formula (I) selected from (1R,2R,4S)-4-(2-Chloro-4-fluoro-benzenesulfonyl)-2-(4-fluoro-phenoxymethyl)-cyclopentanecarboxylic acid cyanomethyl-amide;

(1R,2R,4R)-4-(2-Chloro-4-fluoro-benzenesulfonyl)-2-(4-fluoro-phenoxymethyl)-cyclopentanecarboxylic acid cyanomethyl-amide;

(1R,2R,4S)-4-(2-Chloro-4-fluoro-benzenesulfonyl)-2-(4-fluoro-phenoxymethyl)-cyclopentanecarboxylic acid (1-cyano-cyclopropyl)-amide;

(1R,2R,4R)-4-(2-Chloro-4-fluoro-benzenesulfonyl)-2-(4-fluoro-phenoxymethyl)-cyclopentanecarboxylic acid (1-cyano-cyclopropyl)-amide;

(1R,2R,4S)-4-[2-Chloro-4-(4-ethyl-piperazin-1-yl)-benzenesulfonyl]-2-(4-fluoro-phenoxymethyl)-cyclopentanecarboxylic acid cyanomethyl-amide;

(1R,2R,4R)-4-(2-Chloro-benzenesulfonyl)-2-[4-(4-fluoro-phenyl)-piperidin-1-ylmethyl]-cyclopentanecarboxylic acid (1-cyano-cyclopropyl)-amide;

(1R,2R,4R)-4-[2-Chloro-4-(4-methyl-pyrazol-1-yl)-benzenesulfonyl]-2-methoxy-cyclopentanecarboxylic acid (1-cyano-cyclopropyl)-amide;

(1S,2S,4S)-4-[2-Chloro-4-(4-methyl-pyrazol-1-yl)-benzenesulfonyl]-2-methoxy-cyclopentanecarboxylic acid (1-cyano-cyclopropyl)-amide;

(1R,2R,4R)-4-(2-Chlorophenylsulfonyl)-N-(1-cyanocyclopropyl)-2-(4-methylbenzyloxy)cyclopentanecarboxamide;

(1S,2S,4S)-4-(2-Chlorophenylsulfonyl)-N-(1-cyanocyclopropyl)-2-(4-methylbenzyloxy)cyclopentanecarboxamide;

(1R,2R,4R)-2-(4-Chloro-2-(trifluoromethyl)benzyloxy)-4-(2-chlorophenylsulfonyl)-N-(1-cyanocyclopropyl)cyclopentanecarboxamide;

(1S,2S,4S)-2-(4-Chloro-2-(trifluoromethyl)benzyloxy)-4-(2-chlorophenylsulfonyl)-N-(1-cyanocyclopropyl)cyclopentanecarboxamide;

Formic acid (1R,2R,4S)-4-(4-bromo-2-trifluoromethyl-benzenesulfonyl)-2-(1-cyano-cyclopropylcarbamoyl)-cyclopentylmethyl ester;

(1R,2R,4S)-4-(2-Chloro-4-fluoro-benzenesulfonyl)-2-(4-methoxy-benzyloxymethyl)-cyclopentanecarboxylic acid (1-cyano-cyclopropyl)-amide;

(1R,2R,4R)-2-(4-Bromo-benzyloxy)-4-(2-chloro-benzenesulfonyl)-cyclopentanecarboxylic acid (1-cyano-cyclopropyl)-amide;

(1S,2S,4S)-2-(4-Bromo-benzyloxy)-4-(2-chloro-benzenesulfonyl)-cyclopentanecarboxylic acid (1-cyano-cyclopropyl)-amide;

(1R,2R,4S)-4-(2-Chloro-4-fluoro-benzenesulfonyl)-2-hydroxymethyl-cyclopentanecarboxylic acid (1-cyano-cyclopropyl)-amide;

(1R,2R,4S)-4-(2-Chloro-4-fluoro-benzenesulfonyl)-2-isopropoxymethyl-cyclopentanecarboxylic acid (1-cyano-cyclopropyl)-amide;

(1R,2R,4R)-4-(2-Chloro-4-fluoro-benzenesulfonyl)-2-fluoromethyl-cyclopentanecarboxylic acid (1-cyano-cyclopropyl)-amide;

(1R,2R,4R)-4-[2-Chloro-4-(4-methyl-piperazin-1-yl)-benzenesulfonyl]-2-(3,3-difluoro-azetidine-1-carbonyl)-cyclopentanecarboxylic acid (1-cyano-cyclopropyl)-amide;

(1R,2R,4R)-4-[2-Chloro-4-(4-cyclopropyl-piperazin-1-yl)-benzenesulfonyl]-2-(3,3-difluoro-azetidine-1-carbonyl)-cyclopentanecarboxylic acid (1-cyano-cyclopropyl)-amide;

(1R,2R,4R)-4-[4-(4-tert!-Butyl-piperazin-1-yl)-2-chloro-benzenesulfonyl]-2-(3,3-difluoro-azetidine-1-carbonyl)-cyclopentanecarboxylic acid (1-cyano-cyclopropyl)-amide;

(1R,2R,4R)-2-Methoxy-4-[4-(4-methyl-piperazin-1-yl)-2-trifluoromethyl-benzenesulfonyl]-cyclopentanecarboxylic acid (1-cyano-cyclopropyl)-amide;

(1S,2S,4S)-2-Methoxy-4-[4-(4-methyl-piperazin-1-yl)-2-trifluoromethyl-benzenesulfonyl]-cyclopentanecarboxylic acid (1-cyano-cyclopropyl)-amide;

(1R,2R,4S)-4-(2-Chloro-4-fluoro-benzenesulfonyl)-2-(6-chloro-pyridin-3-yloxymethyl)-cyclopentanecarboxylic acid (1-cyano-cyclopropyl)-amide;

(1R,2R,4S)-4-(2-Chloro-4-fluoro-benzenesulfonyl)-2-(pyridin-4-yloxymethyl)-cyclopentanecarboxylic acid (1-cyano-cyclopropyl)-amide;

(1R,2R,4S)-4-(2-Chloro-4-fluoro-benzenesulfonyl)-2-phenoxymethyl-cyclopentanecarboxylic acid (1-cyano-cyclopropyl)-amide;

(1R,2R,4S)-4-(2-Chloro-4-fluoro-benzenesulfonyl)-2-(pyridin-3-yloxymethyl)-cyclopentanecarboxylic acid (1-cyano-cyclopropyl)-amide;

(1R,2R,4R)-4-[4-(4-Acetyl-piperazin-1-yl)-2-chloro-benzenesulfonyl]-2-(3,3-difluoro-azetidine-1-carbonyl)-cyclopentanecarboxylic acid (1-cyano-cyclopropyl)-amide;

(1R,2R,4R)-4-(2-Chloro-4-pyrazol-1-yl-benzenesulfonyl)-2-(3,3-difluoro-azetidine-1-carbonyl)-cyclopentanecarboxylic acid (1-cyano-cyclopropyl)-amide;

(1R,2R,4R)-4-[2-Chloro-4-(2-methoxy-ethoxy)-benzenesulfonyl]-2-(3,3-difluoro-azetidine-1-carbonyl)-cyclopentanecarboxylic acid (1-cyano-cyclopropyl)-amide;

(1R,2R,4R)-4-(4-Bromo-2-trifluoromethyl-benzenesulfonyl)-2-(tetrahydro-pyran-4-yloxy)-cyclopentanecarboxylic acid (1-cyano-cyclopropyl)-amide;

(1S,2S,4S)-4-(4-Bromo-2-trifluoromethyl-benzenesulfonyl)-2-(tetrahydro-pyran-4-yloxy)-cyclopentanecarboxylic acid (1-cyano-cyclopropyl)-amide;

(1R,2R,4R)-4-{4-[1-(2-Hydroxy-ethyl)-1H-pyrazol-4-yl]-2-trifluoromethyl-benzenesulfonyl}-2-methoxy-cyclopentanecarboxylic acid (1-cyano-cyclopropyl)-amide;

(1S,2S,4S)-4-{4-[1-(2-Hydroxy-ethyl)-1H-pyrazol-4-yl]-2-trifluoromethyl-benzenesulfonyl}-2-methoxy-cyclopentanecarboxylic acid (1-cyano-cyclopropyl)-amide;

(1R,2R,4R)-2-Methoxy-4-(3-trifluoromethyl-biphenyl-4-sulfonyl)-cyclopentanecarboxylic acid (1-cyano-cyclopropyl)-amide;

(1S,2S,4S)-2-Methoxy-4-(3-trifluoromethyl-biphenyl-4-sulfonyl)-cyclopentanecarboxylic acid (1-cyano-cyclopropyl)-amide;

(1R,2R,4R)-2-Methoxy-4-{4-[1-(2-methoxy-ethyl)-1H-pyrazol-4-yl]-2-trifluoromethyl-benzenesulfonyl}-cyclopentanecarboxylic acid (1-cyano-cyclopropyl)-amide;

(1S,2S,4S)-2-Methoxy-4-{4-[1-(2-methoxy-ethyl)-1H-pyrazol-4-yl]-2-trifluoromethyl-benzenesulfonyl}-cyclopentanecarboxylic acid (1-cyano-cyclopropyl)-amide;

(1R,2R,4R)-4-[4-(1-Methyl-1H-pyrazol-4-yl)-2-trifluoromethyl-benzenesulfonyl]-2-(tetrahydro-pyran-4-yloxy)-cyclopentanecarboxylic acid (1-cyano-cyclopropyl)-amide;

(1S,2S,4S)-4-[4-(1-Methyl-1H-pyrazol-4-yl)-2-trifluoromethyl-benzenesulfonyl]-2-(tetrahydro-pyran-4-yloxy)-cyclopentanecarboxylic acid (1-cyano-cyclopropyl)-amide;

(1R,2R,4R)-4-[4-(2-Methyl-pyridin-4-yl)-2-trifluoromethyl-benzenesulfonyl]-2-(tetrahydro-pyran-4-yloxy)-cyclopentanecarboxylic acid (1-cyano-cyclopropyl)-amide;

(1S,2S,4S)-4-[4-(2-Methyl-pyridin-4-yl)-2-trifluoromethyl-benzenesulfonyl]-2-(tetrahydro-pyran-4-yloxy)-cyclopentanecarboxylic acid (1-cyano-cyclopropyl)-amide;

(1R,2R,4R)-2-(Tetrahydro-pyran-4-yloxy)-4-(2-trifluoromethyl-benzenesulfonyl)-cyclopentanecarboxylic acid (1-cyano-cyclopropyl)-amide;

(1S,2S,4S)-2-(Tetrahydro-pyran-4-yloxy)-4-(2-trifluoromethyl-benzenesulfonyl)-cyclopentanecarboxylic acid (1-cyano-cyclopropyl)-amide;

(1R,2R,4R)-2-Methoxy-4-(4-morpholin-4-yl-2-trifluoromethyl-benzenesulfonyl)-cyclopentanecarboxylic acid (1-cyano-cyclopropyl)-amide;

(1S,2S,4S)-2-Methoxy-4-(4-morpholin-4-yl-2-trifluoromethyl-benzenesulfonyl)-cyclopentanecarboxylic acid (1-cyano-cyclopropyl)-amide;

(1R,2R,4R)-4-[4-(4-Isopropyl-piperazin-1-yl)-2-trifluoromethyl-benzenesulfonyl]-2-methoxy-cyclopentanecarboxylic acid (1-cyano-cyclopropyl)-amide;

(1S,2S,4S)-4-[4-(4-Isopropyl-piperazin-1-yl)-2-trifluoromethyl-benzenesulfonyl]-2-methoxy-cyclopentanecarboxylic acid (1-cyano-cyclopropyl)-amide;

(1R,2R,4R)-4-[4-(4,4-Difluoro-piperidin-1-yl)-2-trifluoromethyl-benzenesulfonyl]-2-methoxy-cyclopentanecarboxylic acid (1-cyano-cyclopropyl)-amide;

(1S,2S,4S)-4-[4-(4,4-Difluoro-piperidin-1-yl)-2-trifluoromethyl-benzenesulfonyl]-2-methoxy-cyclopentanecarboxylic acid (1-cyano-cyclopropyl)-amide;

(4-{4-[(1R,3R,4R)-3-(1-Cyano-cyclopropylcarbamoyl)-4-methoxy-cyclopentanesulfonyl]-3-trifluoromethyl-phenyl}-pyrazol-1-yl)-acetic acid methyl ester;

(4-{4-[(1S,3S,4S)-3-(1-Cyano-cyclopropylcarbamoyl)-4-methoxy-cyclopentanesulfonyl]-3-trifluoromethyl-phenyl}-pyrazol-1-yl)-acetic acid methyl ester;

(1R,2R,4R)-4-(2-Chlorophenylsulfonyl)-N-(1-cyanocyclopropyl)-2-(2,4-dichloro-5-fluorobenzyloxy)cyclopentanecarboxamide;

(1S,2S,4S)-4-(2-Chlorophenylsulfonyl)-N-(1-cyanocyclopropyl)-2-(2,4-dichloro-5-fluorobenzyloxy)cyclopentanecarboxamide;

(1R,2R,4R)-4-(4-Bromo-2-trifluoromethyl-benzenesulfonyl)-2-[(tetrahydro-1,1-dioxo-2H-thiopyran-4-yl)oxy]-cyclopentanecarboxylic acid (1-cyano-cyclopropyl)-amide;

(1S,2S,4S)-4-(4-Bromo-2-trifluoromethyl-benzenesulfonyl)-2-[(tetrahydro-1,1-dioxo-2H-thiopyran-4-yl)oxy]-cyclopentanecarboxylic acid (1-cyano-cyclopropyl)-amide;

(1R,2R,4R)-4-(4-Bromo-2-trifluoromethyl-benzenesulfonyl)-2-cyclobutoxy-cyclopentanecarboxylic acid (1-cyano-cyclopropyl)-amide;

(1S,2S,4S)-4-(4-Bromo-2-trifluoromethyl-benzenesulfonyl)-2-cyclobutoxy-cyclopentanecarboxylic acid (1-cyano-cyclopropyl)-amide;

(1R,2R,4R)-2-[(tetrahydro-1,1-dioxo-2H-thiopyran-4-yl)oxy]-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-[(tetrahydro-1,1-dioxo-2H-thiopyran-4-yl)oxy]-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-[(tetrahydro-1,1-dioxo-2H-thiopyran-4-yl)oxy]-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-[(tetrahydro-1,1-dioxo-2H-thiopyran-4-yl)oxy]-4-[4-(1-methyl-1H-pyrazol-4-yl)-2-trifluoromethyl-benzenesulfonyl]-cyclopentanecarboxylic acid (1-cyano-cyclopropyl)-amide;

(4-{4-[(1R,3R,4R)-3-(1-Cyano-cyclopropylcarbamoyl)-4-methoxy-cyclopentanesulfonyl]-3-trifluoromethyl-phenyl}-pyrazol-1-yl)-acetic acid;

(4-{4-[(1S,3S,4S)-3-(1-Cyano-cyclopropylcarbamoyl)-4-methoxy-cyclopentanesulfonyl]-3-trifluoromethyl-phenyl}-pyrazol-1-yl)-acetic acid;

(1R,2R,4R)-4-(2-Chloro-4-fluoro-benzenesulfonyl)-2-(3,3-difluoro-pyrrolidine-1-carbonyl)-cyclopentanecarboxylic acid (1-cyano-cyclopropyl)-amide;

(1R,2R,4R)-4-(4-Bromo-2-chloro-benzenesulfonyl)-2-(3,3-difluoro-pyrrolidine-1-carbonyl)-cyclopentanecarboxylic acid (1-cyano-cyclopropyl)-amide;

(1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide;

(1R,2R,4R)-4-[2-Chloro-4-(2,2,2-trifluoro-ethoxy)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-((S)-2,2,2-trifluoro-1-methyl-ethoxy)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-(4-cyclopropyl-piperazin-1-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[4-(4-tert-Butyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide;

(1R,2R,4R)-2-Methoxy-4-{4-[4-(2,2,2-trifluoro-ethyl)-piperazin-1-yl]-2-trifluoromethyl-benzenesulfonyl}-cyclopentanecarboxylic acid (1-cyano-cyclopropyl)-amide;

(1S,2S,4S)-2-Methoxy-4-{4-[4-(2,2,2-trifluoro-ethyl)-piperazin-1-yl]-2-trifluoromethyl-benzenesulfonyl}-cyclopentanecarboxylic acid (1-cyano-cyclopropyl)-amide;

(1R,2R,4R)-4-[4-(1-Carbamoylmethyl-1H-pyrazol-4-yl)-2-trifluoromethyl-benzenesulfonyl]-2-methoxy-cyclopentanecarboxylic acid (1-cyano-cyclopropyl)-amide;

(1S,2S,4S)-4-[4-(1-Carbamoylmethyl-1H-pyrazol-4-yl)-2-trifluoromethyl-benzenesulfonyl]-2-methoxy-cyclopentanecarboxylic acid (1-cyano-cyclopropyl)-amide;

(1R,2R,4R)-4-(4-Bromo-2-trifluoromethyl-benzenesulfonyl)-2-cyclopentyloxy-cyclopentanecarboxylic acid (1-cyano-cyclopropyl)-amide;

(1S,2S,4S)-4-(4-Bromo-2-trifluoromethyl-benzenesulfonyl)-2-cyclopentyloxy-cyclopentanecarboxylic acid (1-cyano-cyclopropyl)-amide;

(1R,2R,4R)-4-[2-Chloro-4-(2-methyl-2H-pyrazol-3-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-(1-methyl-1H-pyrazol-4-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-(2-methyl-pyridin-4-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-(2-chloro-pyridin-4-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-(2-Chloro-4-methyl-benzenesulfonyl)-2-(3,3-difluoro-pyrrolidine-1-carbonyl)-cyclopentanecarboxylic acid (1-cyano-cyclopropyl)-amide;

(1R,2R,4R)-2-(3,3-Difluoro-pyrrolidine-1-carbonyl)-4-[3-(2-methyl-2H-pyrazol-3-yl)-benzenesulfonyl]-cyclopentanecarboxylic acid (1-cyano-cyclopropyl)-amide;

(1R,2R,4R)-2-(3,3-Difluoro-pyrrolidine-1-carbonyl)-4-[3-(1-methyl-1H-pyrazol-4-yl)-benzenesulfonyl]-cyclopentanecarboxylic acid (1-cyano-cyclopropyl)-amide;

(1R,2R,4R)-2-(3,3-Difluoro-pyrrolidine-1-carbonyl)-4-[3-(2-methyl-pyridin-4-yl)-benzenesulfonyl]-cyclopentanecarboxylic acid (1-cyano-cyclopropyl)-amide;

(1R,2R,4R)-4-[3-(2-Chloro-pyridin-4-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-2-(3,3-Difluoro-pyrrolidine-1-carbonyl)-4-(toluene-3-sulfonyl)-cyclopentanecarboxylic acid (1-cyano-cyclopropyl)-amide;

(1R,2R,4R)-4-[4-(3,3-Difluoro-azetidin-1-yl)-2-trifluoromethyl-benzenesulfonyl]-2-methoxy-cyclopentanecarboxylic acid (1-cyano-cyclopropyl)-amide;

(1S,2S,4S)-4-[4-(3,3-Difluoro-azetidin-1-yl)-2-trifluoromethyl-benzenesulfonyl]-2-methoxy-cyclopentanecarboxylic acid (1-cyano-cyclopropyl)-amide;

(1R,2R,4R)-4-[4-(4-Hydroxy-piperidin-1-yl)-2-trifluoromethyl-benzenesulfonyl]-2-methoxy-cyclopentanecarboxylic acid (1-cyano-cyclopropyl)-amide;

(1S,2S,4S)-4-[4-(4-Hydroxy-piperidin-1-yl)-2-trifluoromethyl-benzenesulfonyl]-2-methoxy-cyclopentanecarboxylic acid (1-cyano-cyclopropyl)-amide;

(1R,2R,4R)-4-[4-(4-Acetyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide;

(1R,2R,4S)-4-[4-(4-Acetyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide;

(1R,2R,4R)-2-Cyclobutoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Cyclobutoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Cyclobutoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Cyclobutoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-Cyclopentyloxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Cyclopentyloxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Cyclopentyloxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Cyclopentyloxy-4-[4-(1-methyl-1H -pyrazol-4-yl)-2-trifluoromethyl-benzenesulfonyl]-cyclopentanecarboxylic acid (1-cyano-cyclopropyl)-amide;

(1R,2R,4R)-2-Methoxy-4-{4-[1-(3-methyl-oxetan-3-ylmethyl)-1H-pyrazol-4-yl]-2-trifluoromethyl-benzenesulfonyl}-cyclopentanecarboxylic acid (1-cyano-cyclopropyl)-amide;

(1S,2S,4S)-2-Methoxy-4-{4-[1-(3-methyl-oxetan-3-ylmethyl)-1H-pyrazol-4-yl]-2-trifluoromethyl-benzenesulfonyl}-cyclopentanecarboxylic acid (1-cyano-cyclopropyl)-amide;

(1R,2R,4R)-4-[4-(4-Cyclopropyl-piperazin-1-yl)-2-trifluoromethyl-benzenesulfonyl]-2-methoxy-cyclopentanecarboxylic acid (1-cyano-cyclopropyl)-amide;

(1S,2S,4S)-4-[4-(4-Cyclopropyl-piperazin-1-yl)-2-trifluoromethyl-benzenesulfonyl]-2-methoxy-cyclopentanecarboxylic acid (1-cyano-cyclopropyl)-amide;

(1R,2R,4R) and (1S,2S,4S)-2-Methoxy-4-[4-(1-methylcarbamoylmethyl-1H-pyrazol-4-yl)-2-trifluoromethyl-benzenesulfonyl]-cyclopentanecarboxylic acid (1-cyano-cyclopropyl)-amide;

(1R,2R,4R)-4-[4-(4-Acetyl-piperazin-1-yl)-2-trifluoromethyl-benzenesulfonyl]-2-methoxy-cyclopentanecarboxylic acid (1-cyano-cyclopropyl)-amide;

(1S,2S,4S)-4-[4-(4-Acetyl-piperazin-1-yl)-2-trifluoromethyl-benzenesulfonyl]-2-methoxy-cyclopentanecarboxylic acid (1-cyano-cyclopropyl)-amide;

(1R,2R,4R)-4-[4-(1-Dimethylcarbamoylmethyl-1H-pyrazol-4-yl)-2-trifluoromethyl-benzenesulfonyl]-2-methoxy-cyclopentanecarboxylic acid (1-cyano-cyclopropyl)-amide;

(1S,2S,4S)-4-[4-(1-Dimethylcarbamoylmethyl-1H-pyrazol-4-yl)-2-trifluoromethyl-benzenesulfonyl]-2-methoxy-cyclopentanecarboxylic acid (1-cyano-cyclopropyl)-amide;

(1R,2R,4R)-2-[(tetrahydro-1,1-dioxo-2H-thiopyran-4-yl)oxy]-4-(2-trifluoromethyl-benzenesulfonyl)-cyclopentanecarboxylic acid (1-cyano-cyclopropyl)-amide;

(1S,2S,4S)-2-[(tetrahydro-1,1-dioxo-2H-thiopyran-4-yl)oxy]-4-(2-trifluoromethyl-benzenesulfonyl)-cyclopentanecarboxylic acid (1-cyano-cyclopropyl)-amide;

(1R,2R,4R)-2-Cyclobutoxy-4-(2-trifluoromethyl-benzenesulfonyl)-cyclopentanecarboxylic acid (1-cyano-cyclopropyl)-amide;

(1S,2S,4S)-2-Cyclobutoxy-4-(2-trifluoromethyl-benzenesulfonyl)-cyclopentanecarboxylic acid (1-cyano-cyclopropyl)-amide;

(1R,2R,4R)-2-Cyclopentyloxy-4-(2-trifluoromethyl-benzenesulfonyl)-cyclopentanecarboxylic acid (1-cyano-cyclopropyl)-amide;

(1S,2S,4S)-2-Cyclopentyloxy-4-(2-trifluoromethyl-benzenesulfonyl)-cyclopentanecarboxylic acid (1-cyano-cyclopropyl)-amide;

(1R,2R,4R)-4-(2-Chloro-benzenesulfonyl)-2-(4-chloro-benzyloxy)-cyclopentanecarboxylic acid (1-cyano-cyclopropyl)-amide;

(1S,2S,4S)-4-(2-Chloro-benzenesulfonyl)-2-(4-chloro-benzyloxy)-cyclopentanecarboxylic acid (1-cyano-cyclopropyl)-amide;

(1R,2R,4R)-4-[4-(1-Ethylcarbamoylmethyl-1H-pyrazol-4-yl)-2-trifluoromethyl-benzenesulfonyl]-2-methoxy-cyclopentanecarboxylic acid (1-cyano-cyclopropyl)-amide;

(1S,2S,4S)-4-[4-(1-Ethylcarbamoylmethyl-1H-pyrazol-4-yl)-2-trifluoromethyl-benzenesulfonyl]-2-methoxy-cyclopentanecarboxylic acid (1-cyano-cyclopropyl)-amide;

(1R,2R)-2-(3,3-Difluoro-pyrrolidine-1-carbonyl)-4-(6-methyl-pyridazine-3-sulfonyl)-cyclopentanecarboxylic acid (1-cyano-cyclopropyl)-amide;

(1R,2R,4R)-4-(5-Chloro-pyridine-2-sulfonyl)-2-(3,3-difluoro-pyrrolidine-1-carbonyl)-cyclopentanecarboxylic acid (1-cyano-cyclopropyl)-amide;

(1R,2R,4S)-4-(5-Chloro-pyridine-2-sulfonyl)-2-(3,3-difluoro-pyrrolidine-1-carbonyl)-cyclopentanecarboxylic acid (1-cyano-cyclopropyl)-amide;

(1R,2R,4R)-2-(3,3-Difluoro-pyrrolidine-1-carbonyl)-4-(pyridine-2-sulfonyl)-cyclopentanecarboxylic acid (1-cyano-cyclopropyl)-amide;

(1R,2R,4S)-2-(3,3-Difluoro-pyrrolidine-1-carbonyl)-4-(pyridine-2-sulfonyl)-cyclopentanecarboxylic acid (1-cyano-cyclopropyl)-amide;

(1R,2R,4R)-2-Cyclopentyloxy-4-[4-(4-isopropyl-piperazin-1-yl)-2-trifluoromethyl-benzenesulfonyl]-cyclopentanecarboxylic acid (1-cyano-cyclopropyl)-amide;

(1S,2S,4S)-2-Cyclopentyloxy-4-[4-(4-isopropyl-piperazin-1-yl)-2-trifluoromethyl-benzenesulfonyl]-cyclopentanecarboxylic acid (1-cyano-cyclopropyl)-amide;

(1R,2R,4R)-2-Cyclopentyloxy-4-{4-[4-(2,2,2-trifluoro-ethyl)-piperazin-1-yl]-2-trifluoromethyl-benzenesulfonyl}-cyclopentanecarboxylic acid (1-cyano-cyclopropyl)-amide;

(1S,2S,4S)-2-Cyclopentyloxy-4-{4-[4-(2,2,2-trifluoro-ethyl)-piperazin-1-yl]-2-trifluoromethyl-benzenesulfonyl}-cyclopentanecarboxylic acid (1-cyano-cyclopropyl)-amide;

(1R,2R,4R)-2-Phenoxy-4-(2-trifluoromethyl-benzenesulfonyl)-cyclopentanecarboxylic acid (1-cyano-cyclopropyl)-amide;

(1S,2S,4S)-2-Phenoxy-4-(2-trifluoromethyl-benzenesulfonyl)-cyclopentanecarboxylic acid (1-cyano-cyclopropyl)-amide;

(1R,2R,4R)-2-(4-Chloro-benzyloxy)-4-(2-trifluoromethyl-benzenesulfonyl)-cyclopentanecarboxylic acid (1-cyano-cyclopropyl)-amide;

(1S,2S,4S)-2-(4-Chloro-benzyloxy)-4-(2-trifluoromethyl-benzenesulfonyl)-cyclopentanecarboxylic acid (1-cyano-cyclopropyl)-amide;

(1R,2R,4R)-2-(4-Chloro-benzyloxy)-4-(2,4-dichloro-benzenesulfonyl)-cyclopentanecarboxylic acid (1-cyano-cyclopropyl)-amide;

(1S,2S,4S)-2-(4-Chloro-benzyloxy)-4-(2,4-dichloro-benzenesulfonyl)-cyclopentanecarboxylic acid (1-cyano-cyclopropyl)-amide;

(1R,2R,4R)-2-(4-Chloro-benzyloxy)-4-(2,4-dichloro-benzenesulfonyl)-cyclopentanecarboxylic acid (4-cyano-1-methyl-piperidin-4-yl)-amide;

(1S,2S,4S)-2-(4-Chloro-benzyloxy)-4-(2,4-dichloro-benzenesulfonyl)-cyclopentanecarboxylic acid (4-cyano-1-methyl-piperidin-4-yl)-amide;

(1R,2R,4R)-2-(4-Chloro-benzyloxy)-4-(2-trifluoromethyl-benzenesulfonyl)-cyclopentanecarboxylic acid (4-cyano-1-methyl-piperidin-4-yl)-amide;

(1S,2S,4S)-2-(4-Chloro-benzyloxy)-4-(2-trifluoromethyl-benzenesulfonyl)-cyclopentanecarboxylic acid (4-cyano-1-methyl-piperidin-4-yl)-amide;

(1R,2R,4R)-2-Methoxy-4-[4-(1-methyl-1H-pyrazol-4-yl)-2-trifluoromethyl-benzenesulfonyl]-cyclopentanecarboxylic acid (4-cyano-1-methyl-piperidin-4-yl)-amide;

(1S,2S,4S)-2-Methoxy-4-[4-(1-methyl-1H-pyrazol-4-yl)-2-trifluoromethyl-benzenesulfonyl]-cyclopentanecarboxylic acid (4-cyano-1-methyl-piperidin-4-yl)-amide;

4-Cyano-4-({(1R,2R,4R)-2-methoxy-4-[4-(1-methyl-1H-pyrazol-4-yl)-2-trifluoromethyl-benzenesulfonyl]-cyclopentanecarbonyl}-amino)-piperidine-1-carboxylic acid ethyl ester;

4-Cyano-4-({(1S,2S,4S)-2-methoxy-4-[4-(1-methyl-1H-pyrazol-4-yl)-2-trifluoromethyl-benzenesulfonyl]-cyclopentanecarbonyl}-amino)-piperidine-1-carboxylic acid ethyl ester;

(1R,2R,4R)-2-Methoxy-4-[4-(1-methyl-1H-pyrazol-4-yl)-2-trifluoromethyl-benzenesulfonyl]-cyclopentanecarboxylic acid (4-cyano-1-ethyl-piperidin-4-yl)-amide;

(1S,2S,4S)-2-Methoxy-4-[4-(1-methyl-1H-pyrazol-4-yl)-2-trifluoromethyl-benzenesulfonyl]-cyclopentanecarboxylic acid (4-cyano-1-ethyl-piperidin-4-yl)-amide;

(1R,2R,4R)-2-(4-Chloro-benzyloxy)-4-(2-trifluoromethyl-benzenesulfonyl)-cyclopentanecarboxylic acid (4-cyano-1-ethyl-piperidin-4-yl)-amide;

(1S,2S,4S)-2-(4-Chloro-benzyloxy)-4-(2-trifluoromethyl-benzenesulfonyl)-cyclopentanecarboxylic acid (4-cyano-1-ethyl-piperidin-4-yl)-amide;

(1R,2R,4R)-2-(4-Chloro-benzyloxy)-4-(2,4-dichloro-benzenesulfonyl)-cyclopentanecarboxylic acid (4-cyano-1-ethyl-piperidin-4-yl)-amide;

(1S,2S,4S)-2-(4-Chloro-benzyloxy)-4-(2,4-dichloro-benzenesulfonyl)-cyclopentanecarboxylic acid (4-cyano-1-ethyl-piperidin-4-yl)-amide;

4-{[(1R,2R,4R)-2-(4-Chloro-benzyloxy)-4-(2-trifluoromethyl-benzenesulfonye-cyclopentanecarbonyl]-amino}-4-cyano-piperidine-1-carboxylic acid ethyl ester;

4-{[(1S,2S,4S)-2-(4-Chloro-benzyloxy)-4-(2-trifluoromethyl-benzenesulfonyl)-cyclopentanecarbonyl]-amino}-4-cyano-piperidine-1-carboxylic acid ethyl ester;

4-{[(1R,2R,4R)-2-(4-Chloro-benzyloxy)-4-(2,4-dichloro-benzenesulfonyl)-cyclopentanecarbonyl]-amino}-4-cyano-piperidine-1-carboxylic acid ethyl ester;

4-{[(1S,2S,4S)-2-(4-Chloro-benzyloxy)-4-(2,4-dichloro-benzenesulfonyl)-cyclopentanecarbonyl]-amino}-4-cyano-piperidine-1-carboxylic acid ethyl ester;

(1R,2R,4R)-4-(2-Chloro-benzenesulfonyl)-2-(4-chloro-phenoxy)-cyclopentanecarboxylic acid (1-cyano-cyclopropyl)-amide (1S,2S,4S)-4-(2-Chloro-benzenesulfonyl)-2-(4-chloro-phenoxy)-cyclopentanecarboxylic acid (1-cyano-cyclopropyl)-amide;

(1R,2R,4R)-2-(2-(4-chlorophenyl)propan-2-yloxy)-4-(2-chlorophenylsulfonyl)-N-(1-cyanocyclopropyl)cyclopentanecarboxamide;

(1S,2S,4S)-2-(2-(4-chlorophenyl)propan-2-yloxy)-4-(2-chlorophenylsulfonyl)-N-(1-cyanocyclopropyl)cyclopentanecarboxamide;

(1R,2R,4R)-4-(2-chlorophenylsulfonyl)-N-(1-cyanocyclopropyl)-2-(2-p-tolylpropan-2-yloxy)cyclopentanecarboxamide;

(1S,2S,4S)-4-(2-chlorophenylsulfonyl)-N-(1-cyanocyclopropyl)-2-(2-p-tolylpropan-2-yloxy)cyclopentanecarboxamide;

(1S,2S,4S)-2-Methoxy-4-[4-(4-methoxymethyl-[1,2,3]triazol-1-yl)-2-trifluoromethyl-benzenesulfonyl]-cyclopentanecarboxylic acid (1-cyano-cyclopropyl)-amide;

(1R,2R,4R)-2-Methoxy-4-[4-(4-methoxymethyl-[1,2,3]triazol-1-yl)-2-trifluoromethyl-benzenesulfonyl]-cyclopentanecarboxylic acid (1-cyano-cyclopropyl)-amide;

(1R,2R,4R)-4-(2-chlorophenylsulfonyl)-N-(1-cyanocyclopropyl)-2-(4-(trifluoromethyl)benzyloxy)cyclopentanecarboxamide;

(1S,2S,4S)-4-(2-chlorophenylsulfonyl)-N-(1-cyanocyclopropyl)-2-(4-(trifluoromethyl)benzyloxy)cyclopentanecarboxamide;

(1R,2R,4R)-4-(2-Chloro-benzenesulfonyl)-2-(4-chloro-2-methanesulfonyl-benzyloxy)-cyclopentanecarboxylic acid (1-cyano-cyclopropyl)-amide;

(1S,2S,4S)-4-(2-Chloro-benzenesulfonyl)-2-(4-chloro-2-methanesulfonyl-benzyloxy)-cyclopentanecarboxylic acid (1-cyano-cyclopropyl)-amide;

(1R,2R,4R)-4-(2-Chloro-benzenesulfonyl)-2-(4-chloro-3-fluoro-benzyloxy)-cyclopentanecarboxylic acid (1-cyano-cyclopropyl)-amide;

(1S,2S,4S)-4-(2-Chloro-benzenesulfonyl)-2-(4-chloro-3-fluoro-benzyloxy)-cyclopentanecarboxylic acid (1-cyano-cyclopropyl)-amide;

(1R,2R,4R)-4-(2-Chloro-benzenesulfonyl)-2-(3,4-dichloro-benzyloxy)-cyclopentanecarboxylic acid (1-cyano-cyclopropyl)-amide;

(1S,2S,4S)-4-(2-Chloro-benzenesulfonyl)-2-(3,4-dichloro-benzyloxy)-cyclopentanecarboxylic acid (1-cyano-cyclopropyl)-amide;

(1R,2R,4R)-4-(2-Chloro-benzenesulfonyl)-2-(4-chloro-2,6-difluoro-benzyloxy)-cyclopentanecarboxylic acid (1-cyano-cyclopropyl)-amide;

(1S,2S,4S)-4-(2-Chloro-benzenesulfonyl)-2-(4-chloro-2,6-difluoro-benzyloxy)-cyclopentanecarboxylic acid (1-cyano-cyclopropyl)-amide;

(1R,2R,4R)-4-(2-Chloro-benzenesulfonyl)-2-(4-chloro-2-fluoro-benzyloxy)-cyclopentanecarboxylic acid (1-cyano-cyclopropyl)-amide;

(1S,2S,4S)-4-(2-Chloro-benzenesulfonyl)-2-(4-chloro-2-fluoro-benzyloxy)-cyclopentanecarboxylic acid (1-cyano-cyclopropyl)-amide;

(1S,2S,4S)-4-{4-[4-(2-Hydroxy-ethyl)-[1,2,3]triazol-1-yl]-2-trifluoromethyl-benzenesulfonyl}-2-methoxy-cyclopentanecarboxylic acid (1-cyano-cyclopropyl)-amide; and (1R,2R,4R)-4-{4-[4-(2-Hydroxy-ethyl)-[1,2,3]triazol-1-yl]-2-trifluoromethyl-benzenesulfonyl}-2-methoxy-cyclopentanecarboxylic acid (1-cyano-cyclopropyl)-amide.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art. Unless otherwise specified, $A^1$ and $R^1$-$R^5$ have the same meaning as defined above.

The following abbreviations are used in the present text:

BOP=Benzotriazol-1-yloxytris(dimethylamino)phosphonium hexafluorophosphate

BOP-Cl=Bis(2-oxo-3-oxazolidinyl)phosphinic chloride

DCC=N,N'-Dicyclohexylcarbodiimide

DCM=Dichloromethane

DIC=N,N'-Diisopropylcarbodiimide

DIPEA=Diisopropylethyl amine

DMAP=N,N-Dimethylpyridine

DMF=N,N-Dimethylformamide

DMS=Dimethyl sulfide

EDCI=1-(3-Dimethylaminopropyl)-3-ethylcarbodiimide hydrochloride

EDTA=ethylenediaminetetraacetic acid

EtOAc=Ethyl acetate

HATU=O-(7-Azabenzotriazol-1-yl)-1,1,3,3-tetramethyluronium hexafluorophosphate

HOBT=1-Hydroxybenzotriazol

LiHMDS=Lithium bis(trimethylsilyl)amide mCPBA=Meta-chloroperbenzoic acid

MeOH=Methanol

MsCl=Methanesulfonyl chloride

NosCl=3-Nitrobenzenesulfonyl chloride pTsOH=p-Toluenesulfonic acid

PyBop=(Benzotriazol-1-yloxy)tripyrrolidinophosphonium hexafluorophosphate

RT=Room temperature

TBAF=Tetrabutylammonium fluoride

TBTU=2-(1H-Benzotriazole-1-yl)-1,1,3,3-tetramethyluronium tetrafluoroborate

TEA=Triethylamine

THF=Tetrahydrofuran
TsCl=Para-toluenesulfonyl chloride.

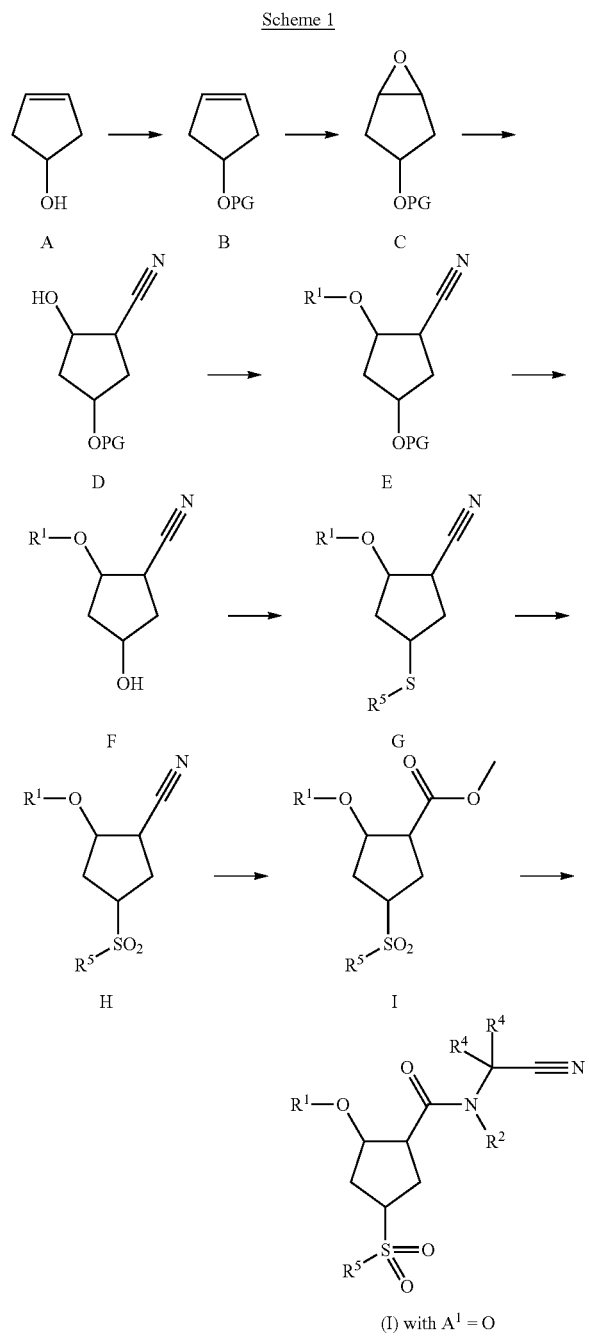

Scheme 1

In more detail, the compounds of formula (I) with A¹=O can be prepared as outlined in scheme 1. The hydroxyl function of cyclopent-3-enol A can be protected with a suitable protecting group using standard methods to obtain compound B. For example, such a protection can be achieved by O-silylation, using reagents such as tert.-butyldimethylsilyl chloride or tert.-butyldiphenyl chloride in the presence of a base such as imidazole. Epoxidation of a compound B can be performed preferably with mCPBA in a non-polar solvent such as cyclohexane and the resulting diastereomeric epoxides C can be separated using chromatographic methods.

Compounds of type D are obtained from C by epoxide-ring-opening with a cyanide-nucleophile using a suitable reagent such as diethyl aluminum cyanide. Reaction of D with a primary alkyl halide (preferably primary alkyl iodide) in presence of silver oxide results in the formation of type E compounds that can subsequently be de-protected using standard methods. If O-silylation has been used as a protection strategy before, fluoride reagents such as HF-pyridine or TBAF/HOAc can be used in the de-protection step. For the conversion of the resulting alcohols F into thioether compounds G, the hydroxyl function of compounds F is first converted into a leaving group and this intermediate is then reacted with an appropriate thiol. The conversion of the hydroxyl function into a leaving group can for example be accomplished by reaction with an appropriate sulfonylchloride or sulfonic acid anhydride such as MsCl, NosCl, TsCl or triflic anhydride in presence of a base, whereas the subsequent reaction with a suitable thiol can be performed in presence of a base such as NaH, LiHMDS, TEA or DIPEA. Oxidation of the obtained thioether can be accomplished with an appropriate oxidizing agent such as $H_2O_2$, Oxone or mCPBA to yield compounds H. Pinner reaction can be used to convert nitrile compounds H into the corresponding ester derivatives I. Cleavage of the ester using bases such as LiOH, NaOH or KOH followed by amide coupling with the appropriate α-aminonitrile derivative delivers the desired compounds (I). The amide coupling step can be performed using standard methods, employing coupling reagents such as BOP-Cl, TBTU, BOP, PyBop, HATU, EDCI/HOBT, DIC/HOBT or DCC/HOBT or employing alkyl-chloroformates such as ethyl chloroformate or iso-butyl chloroformate to form the mixed anhydride prior to the reaction with the amine derivative.

Scheme 2

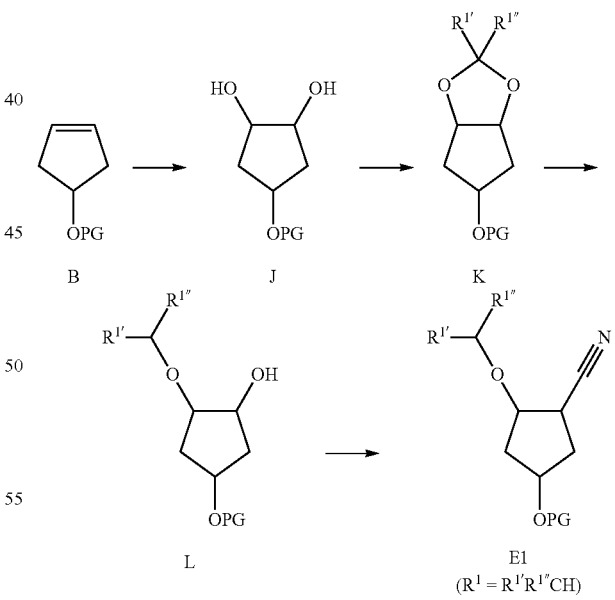

An alternative approach to compounds of formula (I) where A¹=O is outlined in scheme 2. Compound B can be di-hydroxylated to obtain compound J which is converted into compounds of type K by the reaction with an appropriate carbonyl compound or its dialkyl acetal in presence of catalytic amounts of an acid such as pTsOH. The di-hydroxylation step can preferably be performed using an oxidant such as trimethylamine oxide in the presence of a catalytic amount of osmium tetroxide. Reductive ketal-opening, using reagents such as Et$_3$SiH/TiCl$_4$ or BH$_3$-DMS/BF$_3$-OEt$_2$, provides compounds of type L. Conversion of the hydroxyl function of compounds L into a leaving group using a sulfonic acid derivative such as triflic anhydride, followed by reaction with a cyanide reagent such as tetrabutyl ammonium cyanide, delivers compounds of type E1 which can be converted to the compounds of formula (I) according to scheme 1.

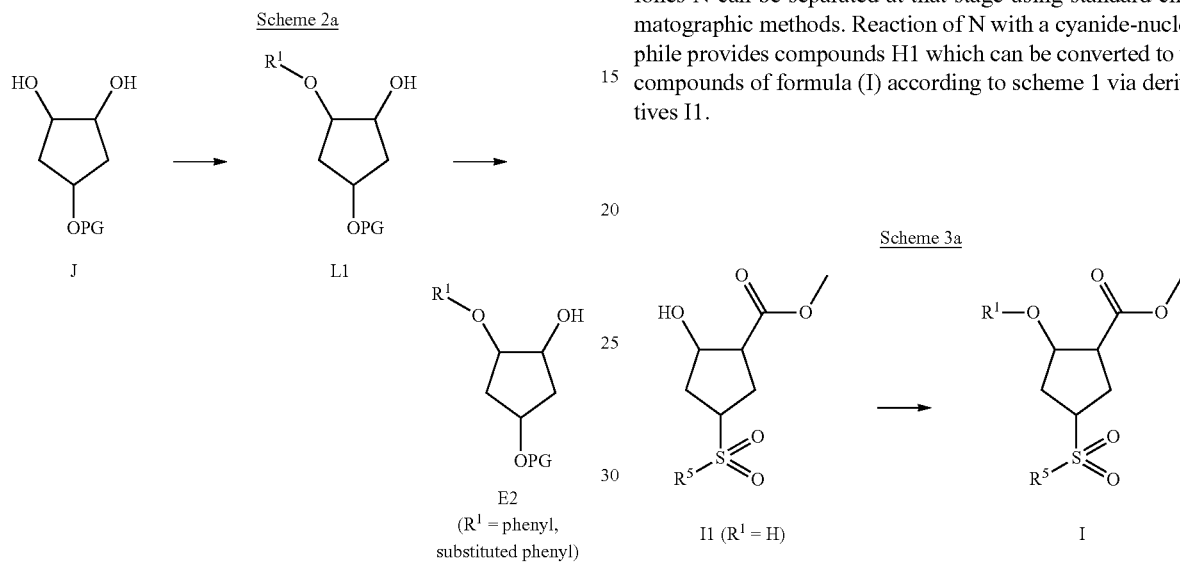

Formula (I) compounds where A$^1$=O and R$^1$ is phenyl or substituted phenyl can be synthesized as outlined in scheme 2a. Aryloxy compounds L1 can be obtained by reaction of dihydroxy compound J with triarylbismuth diacetate or triarylbismuth bis(trifluoroacetate) in presence of a copper catalyst. Conversion of compounds L1 into type E2 compounds and further manipulation into formula (I) compounds can be achieved according to scheme 2 and 1.

For the preparation of the compounds of formula (I) with A$^1$=O and R$^1$=H a possible synthesis is outlined in Scheme 3. Conversion of the hydroxyl function of cyclopent-3-enol A into a leaving group using a sulfonylchloride or sulfonic acid anhydride such as MsCl, NosCl, TsCl or triflic anhydride in presence of a base such as pyridine and subsequent reaction of this intermediate with the appropriate thiol in presence of a base such as NaH delivers compounds of type M. Oxidation of type M compounds with a suitable oxidizing agent such as mCPBA yields epoxy-sulfones N. Diastereomeric epoxy-sulfones N can be separated at that stage using standard chromatographic methods. Reaction of N with a cyanide-nucleophile provides compounds H1 which can be converted to the compounds of formula (I) according to scheme 1 via derivatives I1.

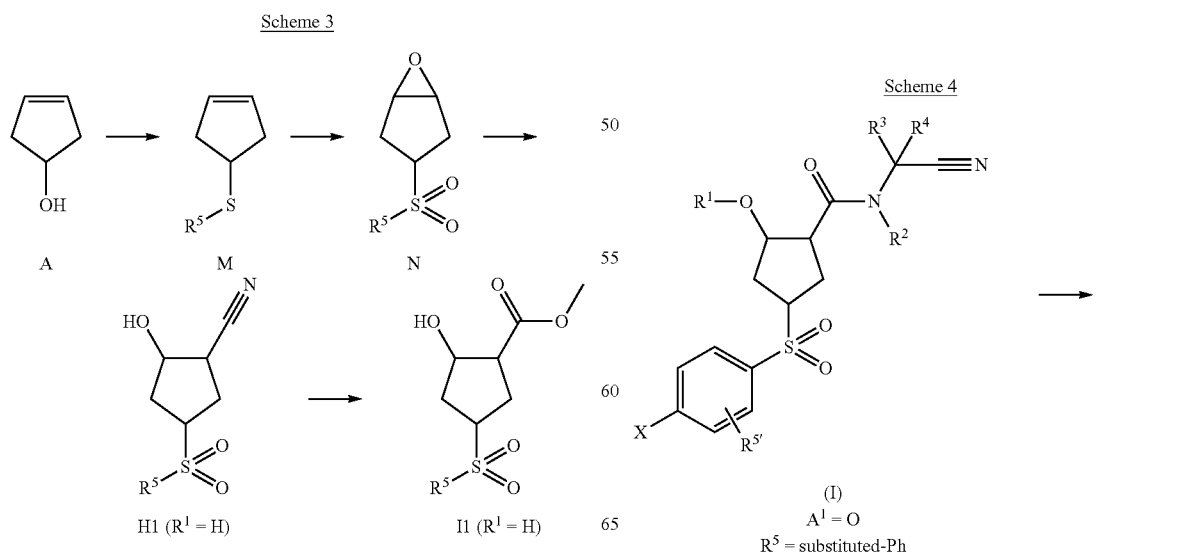

According to scheme 3a, hydroxyl esters I1 can also be used to prepare formula (I) compounds with A$^1$=O and were R$^1$ is not hydrogen. R$^1$ substituents can be introduced either by reaction of I1 with a primary alkyl halide in presence of silver oxide or by reaction of I1 with a trichloroacetimidate derivative in presence of a catalytic amount of an acid such as trifluoro-methanesulfonic acid.

-continued

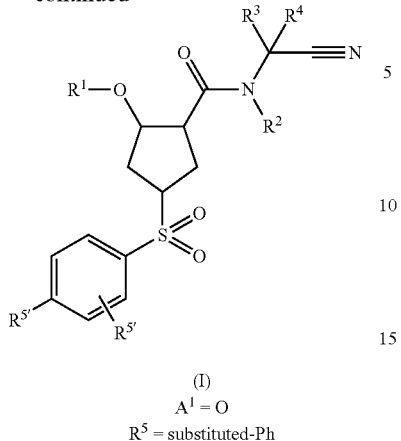

(I)
A¹ = O
R⁵ = substituted-Ph

The compounds of formula (I) with A¹=O and R⁵=substituted-phenyl can be further modified as outlined in scheme 4, if the phenyl substituent X is a halogen atom. R⁵" is alkoxy, haloalkoxy, halophenyl, halophenyloxy, alkylsulfonylphenyl, aminosulfonylphenyl, pyridinyl, alkylpyridinyl, halopyridinyl, alkoxypyridinyl, haloalkylpyridinyl, triazolyl, alkylsulfonylpyridinyl, alkylthiazolyl, piperidinyl, 1H-pyrazolyl, alkyl-1H-pyrazolyl, alkyl-2H-pyrayzolyl, pyrimidinyl, alkylthiophenyl, pyridazinyl, alkyl-6-oxo-6H-piridazinyl, alkylisoxazolyl, cycloalkylpiperazinyl, pyrazinyl, halopyrazinyl, haloazetidinyl, 2-oxo-6-aza-spiro[3.3]heptanyl, halopyrrolidinyl, alkylpiperazinyl, cycloalkylpiperazinyl, carbonylpiperazinyl or oxetanyloxy. R⁵' is halogen, alkyl, haloalkyl, alkoxy. Introduction of residues R⁵" can for example be achieved using palladium catalyzed coupling reactions.

Reagents for these coupling reactions include boronic acid derivatives in presence of a base such as KOAc or Na₂CO₃ and tin organic compounds in combination with catalysts such as [1,1'-bis(diphenylphosphino)ferrocene]palladium(II) chloride 1:1 complex with dichloromethane or tetrakis(triphenylphosphine)palladium(0). Introduction of residues R⁵" can for example also be achieved by nucleophilic substitution reactions employing oxygen- or nitrogen-nucleophiles such as phenols, alcohols, amines or heterocylic amines optionally in presence of a base.

Scheme 4a

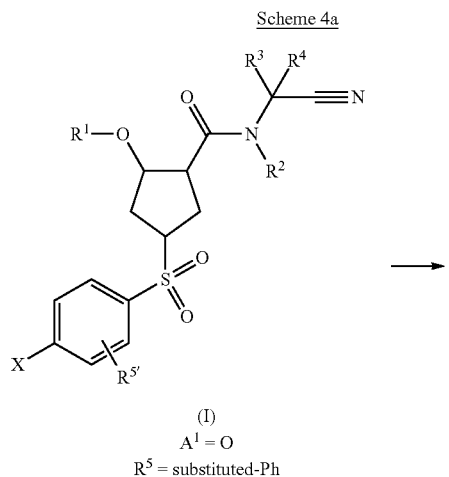

(I)
A¹ = O
R⁵ = substituted-Ph

-continued

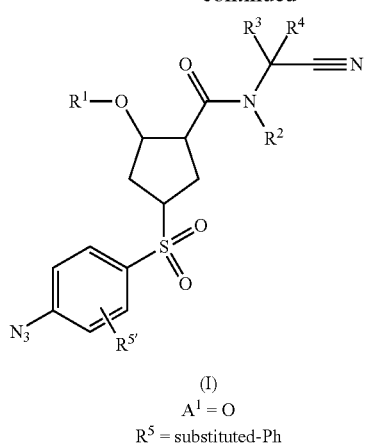

(I)
A¹ = O
R⁵ = substituted-Ph

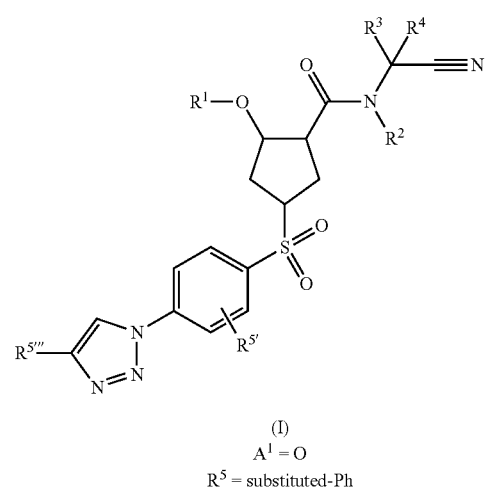

(I)
A¹ = O
R⁵ = substituted-Ph

To introduce triazoles as R⁵" residues, a two step procedure can be applied as outlined in scheme 4a. An azide anion is used in the nucleophilic substitution step and the resulting azido compound can be converted to the triazolo derivative by reaction with an alkine derivative in presence of a copper catalyst.

Scheme 5

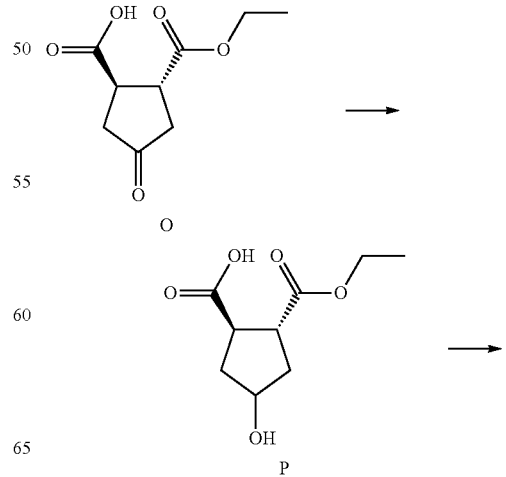

P

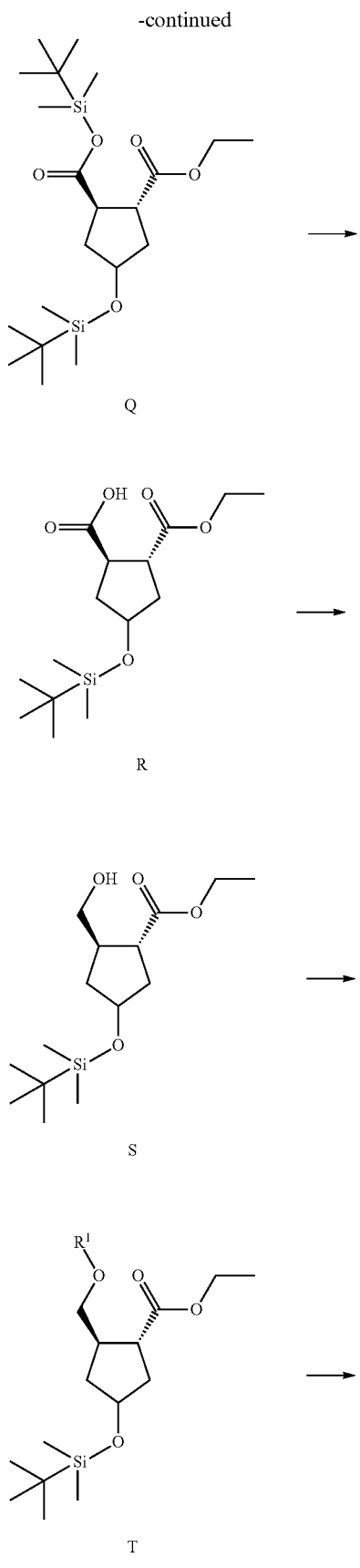
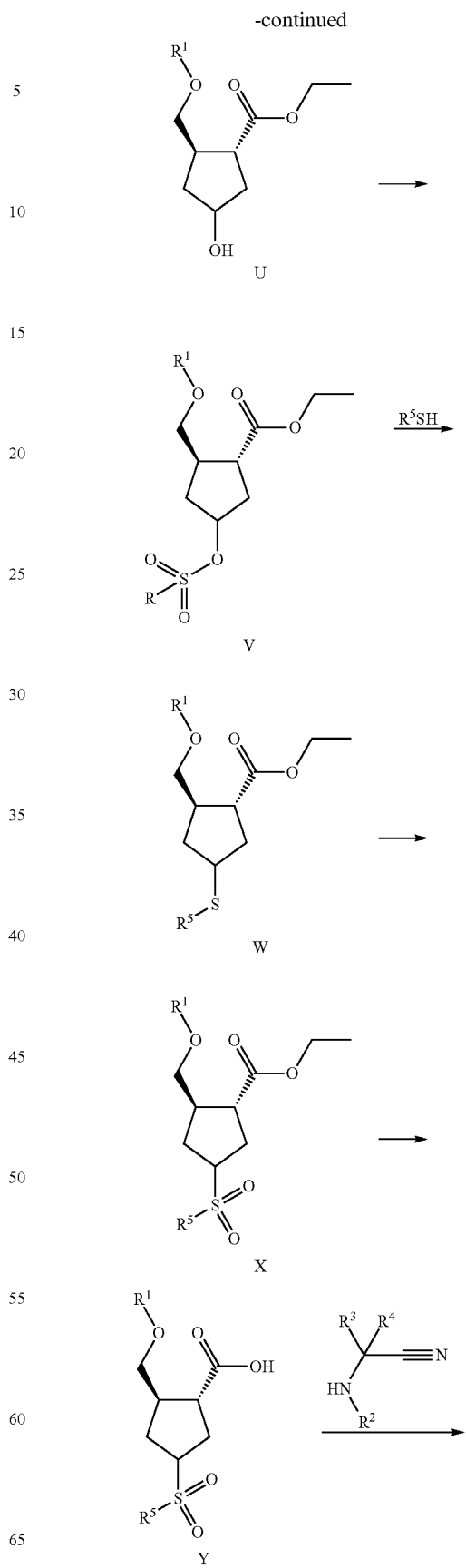

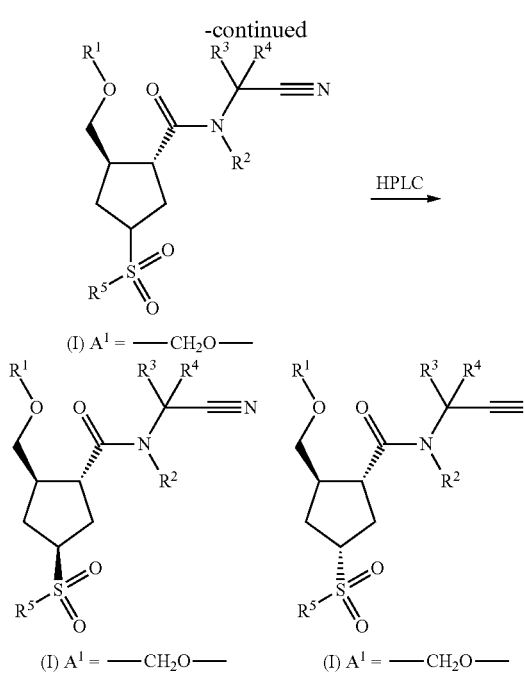

(I) A¹ = —CH₂O—

(I) A¹ = —CH₂O—    (I) A¹ = —CH₂O—

R = methyl, ethyl or t-Bu. R' = methyl, CF₃, p-methyl-phenyl or p-nitro-phenyl.

The compounds of formula (I) with A¹=—CH₂O— can be prepared as outlined in scheme 5 starting from (1R,2R)-4-oxo-cyclopentane-1,2-dicarboxylic acid monoethyl ester O. Compound O can be subjected to a suitable reducing agent such as sodium borohydride to obtain alcohol P which can be converted into the silylether R in a two step procedure. This two step process is employing simultaneous silylether and silylester formation using tert.-butyldimethylsilyl chloride in presence of imidazole to obtain compound Q with subsequent hydrolysis of the silylester using a base such as $K_2CO_3$. Conversion of acid R into alcohol S can be achieved using reducing agents such as $BH_3$-THF preferably at low temperature. Reaction of S with a primary alkyl halide (preferably primary alkyl iodide) in presence of silver oxide results in the formation of type T compounds. Alternatively, compounds S can be reacted with a phenol derivative (or a corresponding heteroaromatic compound) under Mitsunobu conditions to obtain type T compounds. Silylether cleavage to obtain alcohols U can be accomplished using a fluoride reagent such as HF-pyridine. For the conversion of the resulting alcohols U into thioether compounds W, the hydroxyl function of compounds U is first converted into a methane sulfonate by reaction with methanesulfonyl chloride in presence of TEA and this intermediate V is then reacted with an appropriate thiol in presence of a base such as NaH, LiHMDS, TEA or DIPEA. Oxidation of the obtained thioether can be accomplished with an appropriate oxidizing agent such as $H_2O_2$, Oxone or mCPBA to yield compounds X. Saponification of the ester function of compounds X using bases such as LiOH, NaOH or KOH followed by amide coupling of the acids Y with the appropriate α-aminonitrile derivative delivers the desired compounds of formula (I). The amide coupling step can be performed using standard methods, employing coupling reagents such as BOP-Cl, TBTU, BOP, PyBop, HATU, EDCI/HOBT, DIC/HOBT or DCC/HOBT or employing alkyl-chloroformates such as ethyl chloroformate or iso-butyl chloroformate to form the mixed anhydride prior to the reaction with the amine derivative. Epimeric compounds (1) with A¹=—CH₂O— can be separated by standard chromatographic methods such as HPLC. If R⁵=substituted-phenyl, further modification is possible in analogy to the process described for scheme 4.

Scheme 6

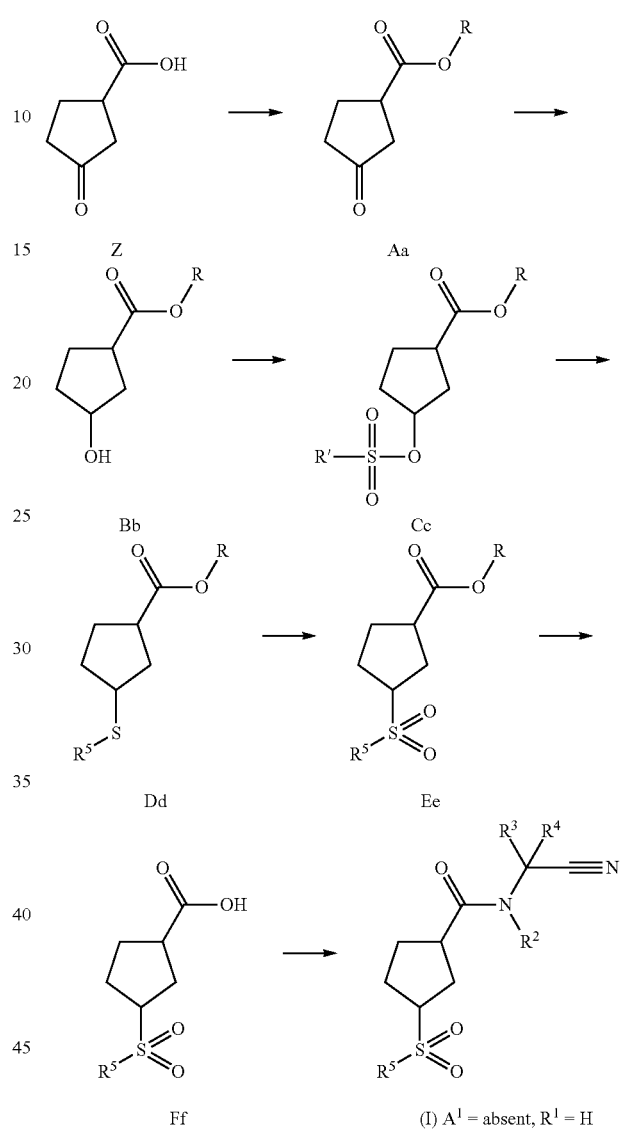

R = R' as defined above.

A possible preparation of the compounds of formula (I) with R¹=H and where A¹ is absent is outlined in scheme 6. 3-oxo-cyclopentanecarboxylic acid Z can be converted into the corresponding carboxylic acid esters Aa by standard methods. For example, to obtain the tert.-butyl ester Aa, suitable conditions are the reaction with tert.-butanol in presence of an appropriate coupling reagent such as DCC/DMAP. Reaction of Aa with a reducing agent such as sodium borohydride preferably at low temperature results in the formation of hydroxyl compounds Bb. Conversion of compounds Bb into compounds of type Ee can be achieved in analogy to the described conversion of compounds F to H (scheme 1). Cleavage of the ester to obtain type Ff compounds can be accomplished with reagents such as LiOH, NaOH or KOH, or in case of a tert.-butyl ester under acidic conditions with reagents such as trifluoroacetic acid. Type Ff acids can be converted to the corresponding compounds of formula (I) in a final amide coupling step with a suitable α-aminonitrile in analogy to the processes described for scheme 1 or 5.

Scheme 7

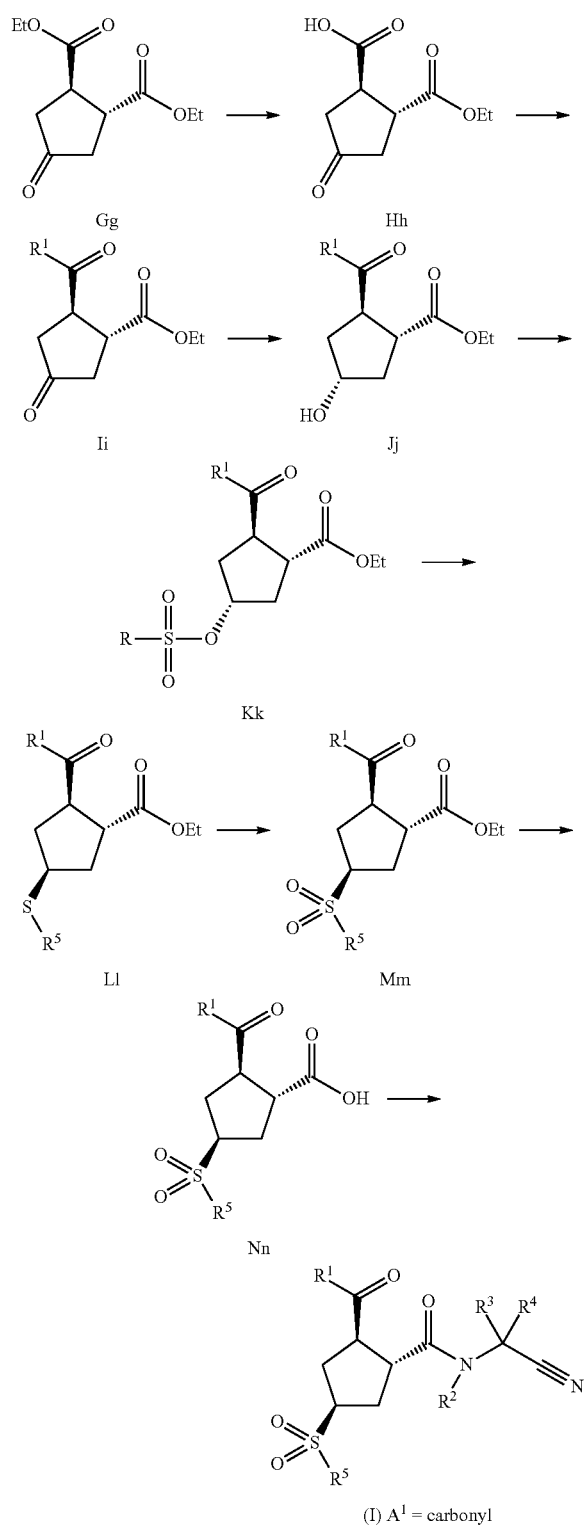

R = R' as defined above.

A general method to prepare the compounds of formula (I) with A¹=carbonyl is outlined in scheme 7. (1R,2R)-4-Oxo-cyclopentane-1,2-dicarboxylic acid monoethyl ester Hh can be prepared starting from the racemic diethyl ester Gg (synthesized according to a procedure described in Synthesis 2003, 1, 136) by enzymatic enantioselective monoester hydrolysis. Suitable enzymes for the enantioselective monohydrolysis of diester Gg are hydrolases such as lipases, esterases, cholesterases, proteases, acylases and the like. A suitable enzyme turned out to be lipase from *Candida antarctica*, form B, a commercial preparation of which is CALB L (a liquid enzyme formulation from Novozymes, Bagsvaerd, Denmark). The enantioselective hydrolysis is carried out by contacting a suitable enzyme with the diester substrate Gg emulsified in an aqueous buffer by vigorous stirring for a time period during which the enantiomeric excess of the formed acid Hh stays above 95% (<50% conversion). Suitable buffers are the conventional buffers commonly used in biochemistry in the range of pH 5-9, preferably 6-8. In the course of the reaction, the pH of the reaction mixture is kept constant at the selected value by the addition of a base, preferentially NaOH or KOH-solution. Additives, such as salts, solvents (water-miscible or -immiscible), polyhydric alcohols or PEG may enhance activity and/or enantioselectivity. In the case of *C. antarctica* lipase B, the use of magnesium acetate (e.g. 50 mM) and a comparatively low pH of pH 6.2 is benificial for the enantioselectivity. The enzymes might be applied at a lower temperature (0-25° C.) in order to enhance the enantioselectivity. As an alternative, the enzymes may be used in immobilized form. Reaction of acid Hh with appropriate secondary or primary amines using standard coupling conditions employing coupling reagents such as BOP-Cl, TBTU, BOP, PyBop, HATU, EDCI/HOBT, DIC/HOBT or DCC/HOBT, results in the formation of type Ii compounds. The conversion of ketone derivatives Ii into alcohols Jj can be accomplished by an enzymatic reduction using enzymes such as ketoreductase KRED-NADP-131 from Codexis (Jülich Chiral solutions GMBH, A Codexis company, Prof. Rehm Str. 1, 52428 Jülich, Germany). Conversion of Jj compounds into the corresponding compounds of formula (I) can be achieved in analogy to the processes described for scheme 1 or 5.

Scheme 8

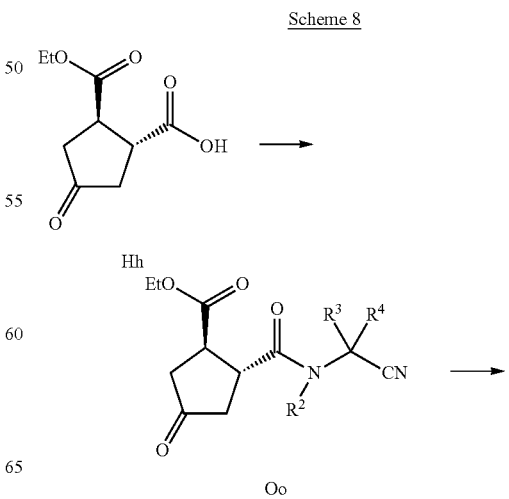

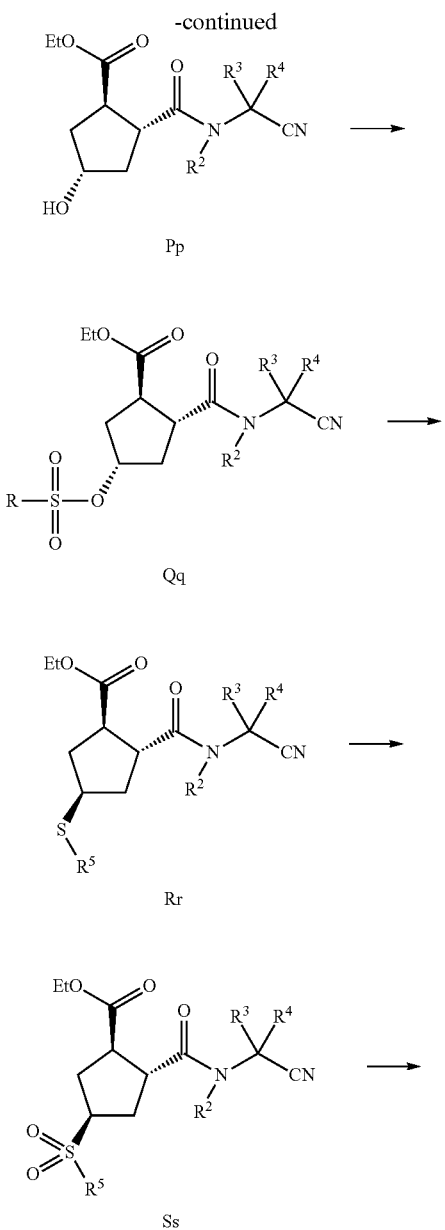

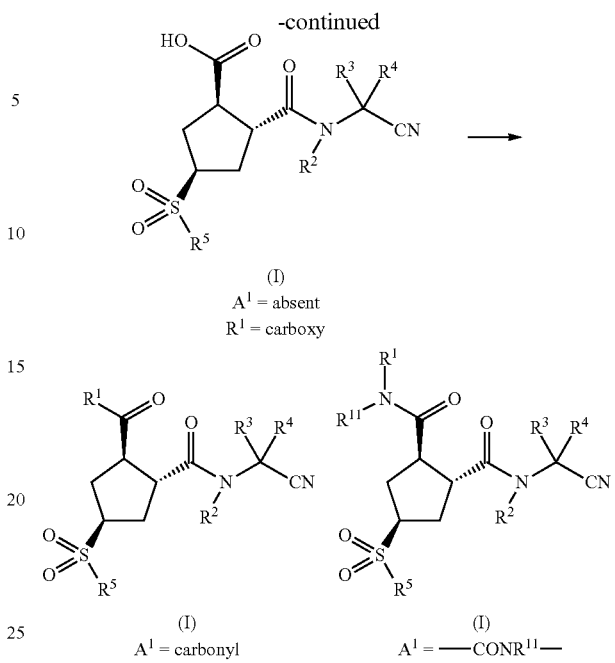

An alternative approach to the compounds of formula (I) with $A^1$=carbonyl or to the compounds of formula (I) with $A^1$=—$CONR^{11}$— is outlined in scheme 8. (1R,2R)-4-oxo-cyclopentane-1,2-dicarboxylic acid monoethyl ester Hh can be reacted with suitable α-aminonitrile derivatives using standard amide coupling conditions to obtain type Oo compounds. Reaction of ketones Oo with reducing agents such as sodium borohydride preferably at low temperature delivers alcohols Pp. The conversion into derivatives Ss requires transformation of the hydroxyl function of Pp into a leaving group, reaction with a suitable thiol and subsequent oxidation of the thioethers Rr to the corresponding sulfones Ss. This reaction sequence can be performed in analogy to the similar processes that are described for scheme 1 or 5. Derivatives Ss can be reacted with reagents such as LiOH, NaOH or KOH to obtain compounds of formula (I) with $R^1$=carboxy and $A^1$ is absent. These acids can be further modified by reaction with an appropriate secondary or primary amine using standard coupling conditions employing coupling reagents such as BOP-Cl, TBTU, BOP, PyBop, HATU, EDCI/HOBT, DIC/HOBT or DCC/HOBT to obtain compounds of formula (I) with $A^1$=carbonyl or $A^1$=—$CONR^{11}$-. If $R^5$=substituted-phenyl, further modification is possible in analogy to the process described for scheme 4.

Scheme 9

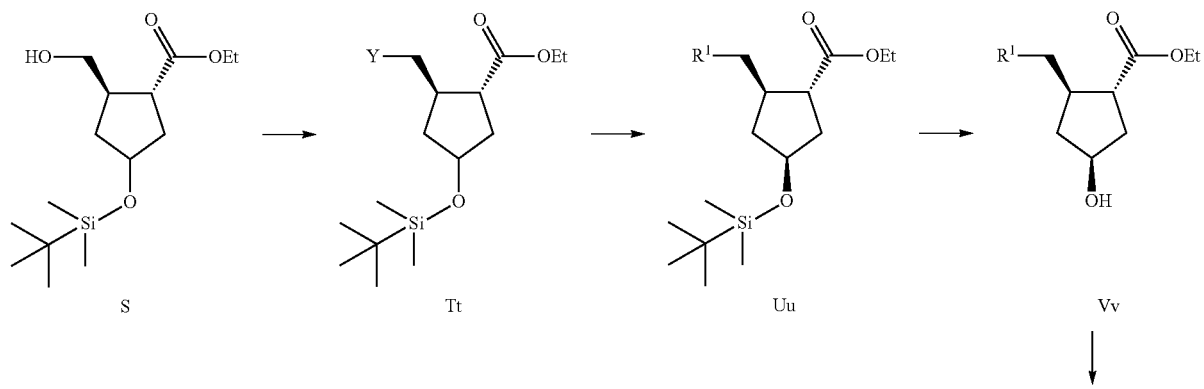

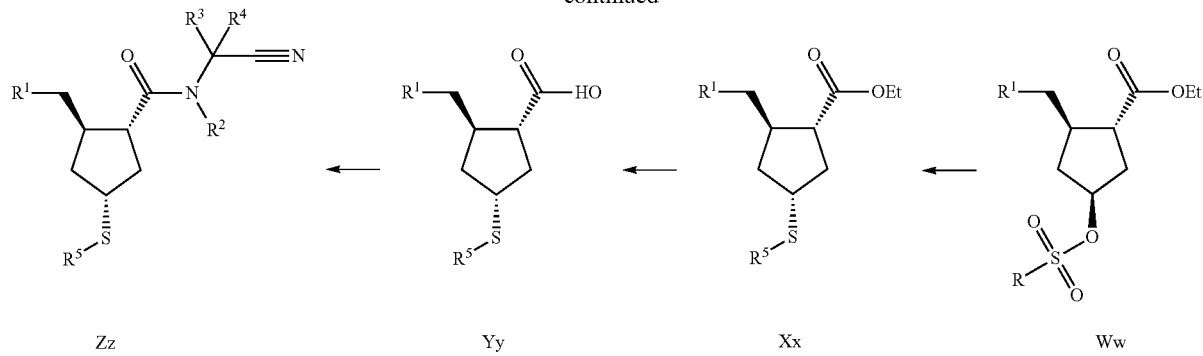

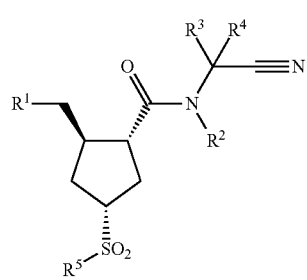

(I)
A¹ = CH₂

R = R' as defined above.

An alternative approach to the compounds of formula (I) with $A^1$=—$CH_2$— is outlined in scheme 9. After the conversion of the primary alcohol S into an halogen or pseudohalogen (noted Y on the scheme above) e.g. mesylate using standart conditions, this pseudohalogen can be diplaced by a nucleophile such as amine of alcohol. Optionally, the initial mixture of diastereomer can be separated using either standart flash chromatography or HPLC using chiral stationary phase. Compounds Uu are then converted into compounds of formula (I) using the sequence outlined in Scheme 5.

If $R^5$=substituted-phenyl, further modification is possible in analogy to the process described for scheme 4.

Scheme 10

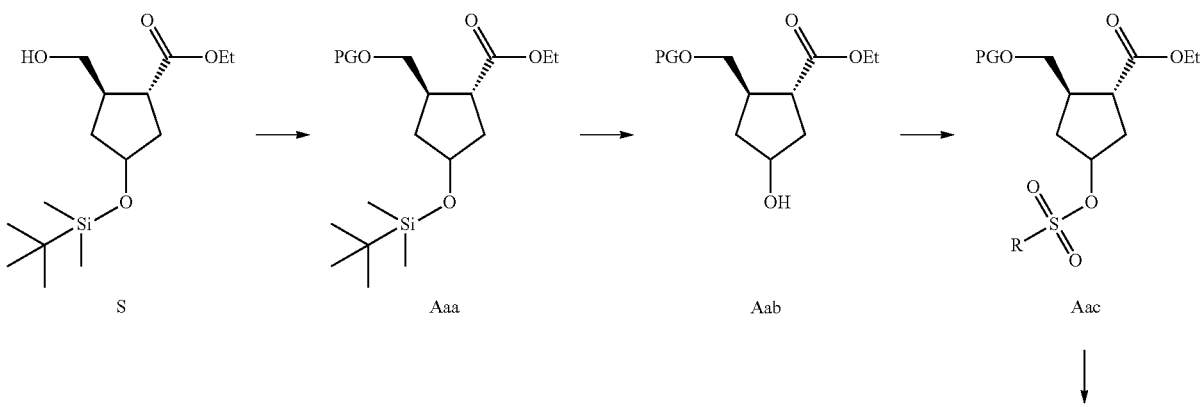

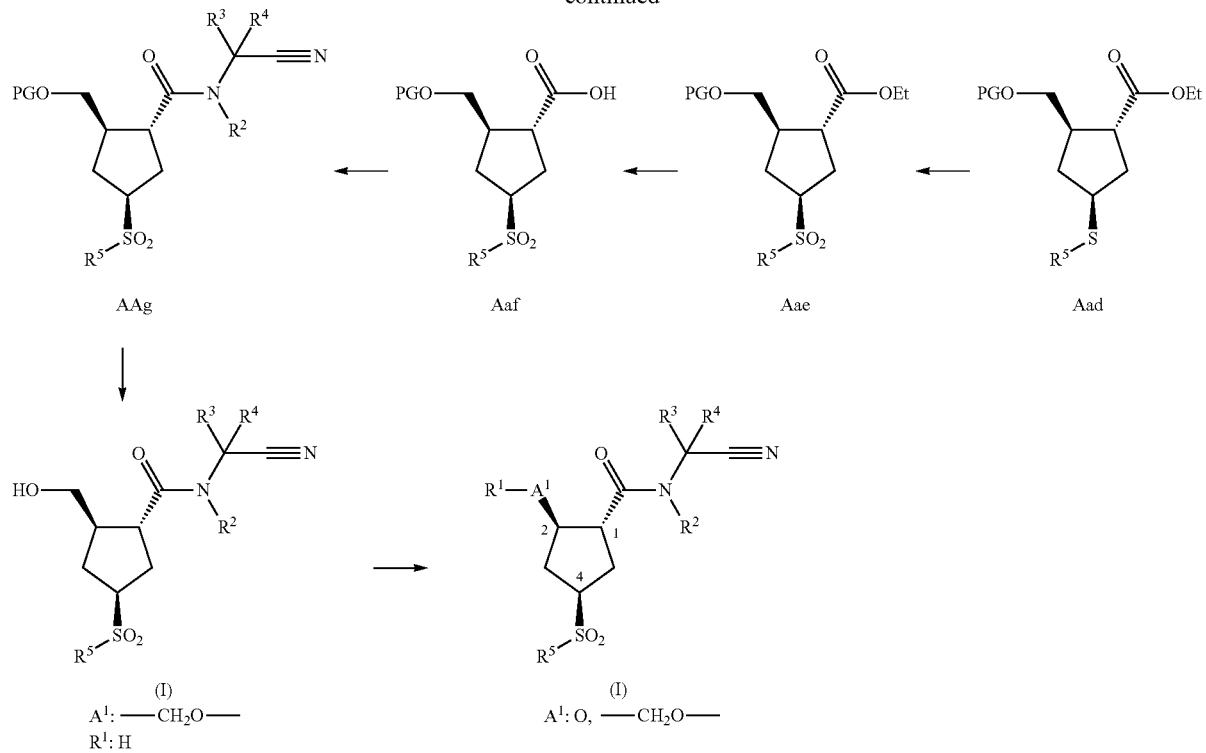

An alternative approach to the compounds of formula (I) with $A^1$=O or —$CH_2$— is outlined in scheme 10. This approach is allowing a late stage derivatization of $R^1$-$A^1$, favorable for exploring the structure-activity relationship of this region. The primary alcohol S is protected by a suitable protecting group exemplified but not limited by the use of trityl using standart conditions (cf. Protectective groups in organic synthesis, $3^{rd}$ edition; T. W. Greene & P. G. M. Wuts; Wiley Interscience Editions). Sustituants on positions 1 and 4 are then further manipulated according the description outlined in scheme 5 to obtain compound AAg. The diastereomeric mixture can be separated in the course of the synthesis either by using flash chromatography or HPLC with chiral stationary phase. Cleavage of the protecting group is releasing the primary alcohol. This alcohol can be converted to halogen using methods known by those skilled in the Art e.g. reaction with a mixture of perfluoro-1-butanesulfonyl fluoride and triethylamine.trishydrofluoride salt is leading to the fluoro derivative. Alternatively, reductive etherification using exemplified but not limited by the use of anhydrous iron(III) chloride and triethylsilane with the appropriate ketone can be use to produce compounds with $A^1$: —$CH_2O$— and $R^1$=aliphatic residue. In addition, when $A^1$: —$CH_2O$— and $R^1$=aromatic or heteroaromatic residue, the Mitsunobu reaction is the method of choose.

If $R^5$=substituted-phenyl, further modification is possible in analogy to the process described for scheme 4.

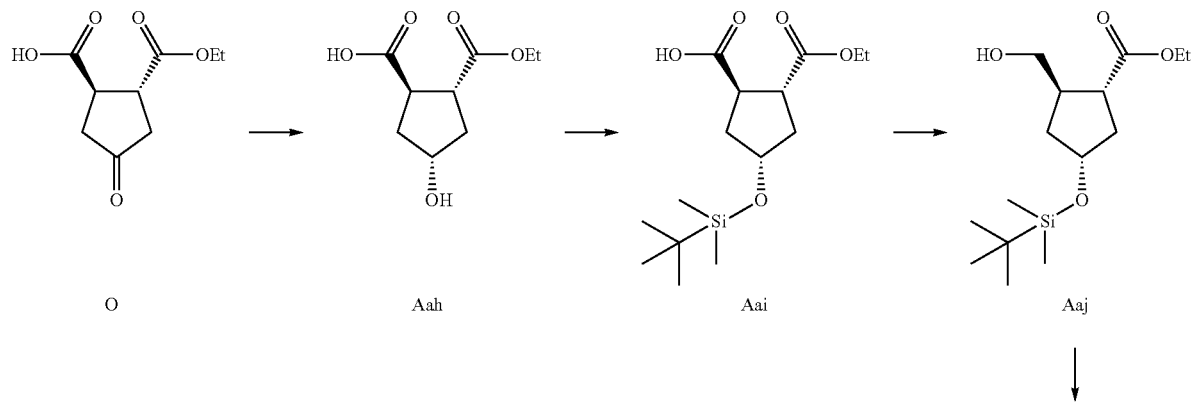

-continued

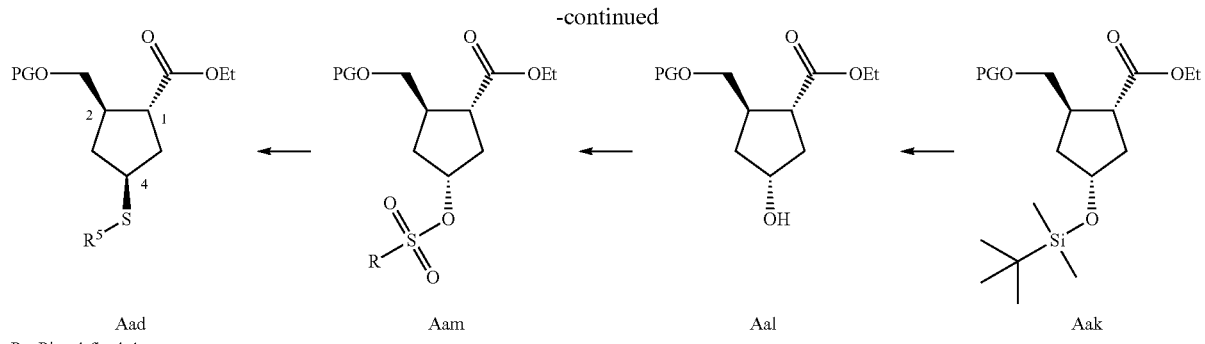

Aad    Aam    Aal    Aak

R = R' as defined above.

An alternative approach allowing a diastereo- and enantio-selective synthesis of compound Aad is outlined in scheme 11. The ketone O can be reduced diastereoselectively by the use of an enzyme. Suitable enzymes for the diastereoslective reduction of the ketone O are reductases. A suitable enzyme turned out to be the commercial preparation KRED (from Codexis). The diastereoslective reduction is carried out by contacting a suitable enzyme with the ketone substrate O emulsified in an aqueous buffer by vigorous stirring for a time period during which the diastereomeric pourcentage of the formed alcohol Aah stays above 90%. Suitable buffers are the conventional buffers commonly used in biochemistry in the range of pH 5-9, preferably 6-8. As an alternative, the enzymes may be used in immobilized form.

After the introduction of a sily protective group on both the alcohol and the acid, following by a chemoselective cleavage to the carboxylate protective group in basic conditions, the free acid is reduced to the primary alcohol Aaj. This primary alcohol is then protected with a suitable protecting group exemplified but not limited by the use of p-methoxy-benzyl using standart conditions (cf. Protectective groups in organic synthesis, 3$^{rd}$ edition; T. W. Greene & P. G. M. Wuts; Wiley Interscience Editions). Compound Aak can be sequentially transformed into Aad using the sequence already described in scheme 5.

The invention also relates to a process for the preparation of a compound of formula (I) comprising one of the following steps:

(a) the reaction of a compound of formula (II)

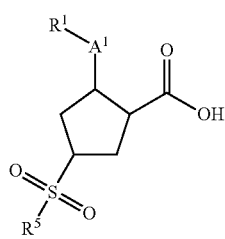

(II)

in the presence of a compound of formula (III)

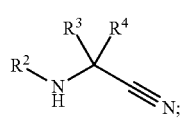

(III)

(b) the reaction of a compound of formula (IV)

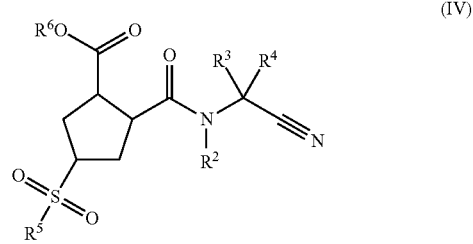

(IV)

in the presence of a base; or (c) the reaction of a compound of formula (V)

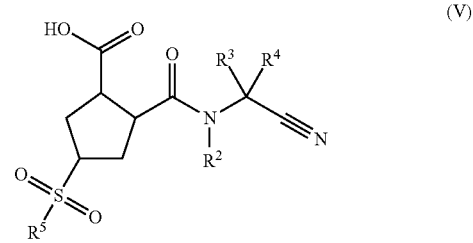

(V)

in the presence of $R^{11}NH_2$ or $R'R^{11}NH$ and a acoupling agent or an activating agent; wherein $R^{11}$, $R^1$ to $R^5$ and $A^1$ are as defined above and wherein $R^6$ is alkyl. Step (a) can be accomplished by activating a compound of formula (II) prior to the reaction in the presence of a compound of formula (III) with agents such as BOP-Cl, TBTU, BOP, PyBop, HATU, EDCI/HOBT, DIC/HOBT or DCC/HOBT or employing alkyl-chloroformates such as ethyl chloroformate or iso-butyl chloroformate as activating agents. The reaction is preferably carried out in an inert solvent such as acetonitrile or DMF in presence of a base such as TEA or DIPEA at a temperature between –20° C. and 50° C. Preferably the reaction is carried out using EDCI/HOBT or HATU as an activating agent in presence of DIPEA in DMF as a solvent at RT. In step (b), $R^6$ is preferably methyl or ethyl, more preferably ethyl. The base is for example LiOH, NaOH or KOH. The reaction can be carried out in water as a solvent or in solvent mixtures containing water and solvents such as methanol, THF or dioxane. The Temperature is preferably between 0° C. and 100° C. Preferably, LiOH is used in a solvent mixture of methanol, THF and water at RT.

In step (c), the coupling reagent can be BOP-Cl, TBTU, BOP, PyBop, HATU, EDCI/HOBT, DIC/HOBT or DCC/

HOBT. Alkyl-chloroformates such as ethyl chloroformate or iso-butyl chloroformate are preferred activating agents. The reaction is preferably carried out in an inert solvent such as acetonitrile or DMF in presence of a base such as TEA or DIPEA. The temperature is preferably between −20° C. and 50° C. Preferably the reaction is carried out using EDCI/HOBT or HATU as an activating agent in presence of DIPEA in DMF as a solvent at RT.

A compound of formula (I) for use as a therapeutically active substance is also an object of the invention.

A further object of the invention is a pharmaceutical composition comprising a compound of formula (I) and a therapeutically inert carrier.

The invention also relates to the use of a compound of formula (I) for the preparation of medicaments for the treatment or prophylaxis of diabetes, atherosclerosis, abdominal aortic aneurysm, peripheral arterial disease or diabetic nephropathy.

A compound of formula (I), when manufactured according to a process of the invention is also an object of the invention.

The invention is further concerned with a method for the treatment or prophylaxis of diabetes, atherosclerosis, abdominal aortic aneurysm, peripheral arterial disease or diabetic nephropathy, which method comprises administering an effective amount of a compound of formula (I).

The invention will now be illustrated by the following examples which have no limiting character.

EXAMPLES

Example 1

(1R,2R,4R)-4-Benzenesulfonyl-2-(morpholine-4-carbonyl)-cyclopentanecarboxylic acid cyanomethyl-amide

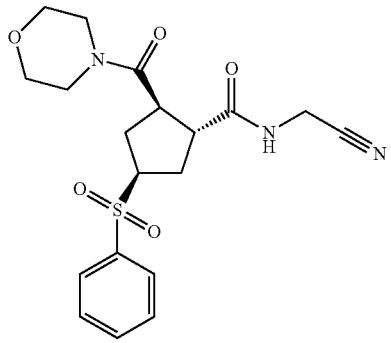

Step 1:
(1R,2R)-4-oxo-cyclopentane-1,2-dicarboxylic acid monoethyl ester 60.44 g of rac-trans-4-oxo-cyclopentane-1,2-dicarboxylic acid diethyl ester (prepared according to E. Lee-Ruff et al., J. Org. Chem. 59, 2114, 1994 or J. Mittendorf et al., Synthesis, 136, 2003) was emulsified under vigorous stirring in 1.16 L 5 mM 2-morpholinoethanesulfonic acid, 50 mM magnesium acetetate buffer pH 6.2. 1.94 ml CALB L (liquid enzyme formulation from Novozymes, Denmark) was added and the pH kept constant at 6.2 under vigorous stirring by the automated addition (pH-stat) of 1.0 M NaOH-solution. After reaching 45% conversion (ca. 42 h reaction time; enantiomeric excess of formed acid still >95% according to GC in process control) 1.0 L dichloromethane was added. The aqueous phase was washed with 3×1.5 L dichloromethane, set to pH 3.0 using 85% phosphoric acid and extracted with 4×1.0 L ethyl acetate. The combined ethyl acetate phases were dried over sodium sulfate, evaporated and dried under high vacuum overnight to give 24.40 g of the title compound as white crystals: MS: 199.1 (M−H); >99% GC; [α]589 (20° C.)=−101.2° (c 1.0; EtOH); chiral GC: 95% ee [BGB-176, 30 m×0.25 mm; H2; 100° C. to 200° C. with 2° C./min].

Step 2: (1R,2R)-2-(morpholine-4-carbonyl)-4-oxo-cyclopentanecarboxylic acid ethyl ester To a mixture of (1R,2R)-4-oxo-cyclopentane-1,2-dicarboxylic acid monoethyl ester (10.0 mmol) in tetrahydrofuran (25 ml) was subsequently added morpholine (11 mmol) triethylamine (70 mmol), 1-hydroxybenzotriazole hydrate (20 mmol) and 1-(3-dimethylaminopropyl)-3-ethylcarbodiimide hydrochloride (EDC, 20 mmol) and stirring was continued at 22° C. for 4 h. The mixture was partitioned between ethyl acetate and 1N aqueous HCl, the organic layer was washed with saturated aqueous $Na_2CO_3$, dried and evaporated to give the title compound as pale brown oil. MS: 270.3 (M+H)⁺.

Step 3: (1R,2R,4R)-4-hydroxy-2-(morpholine-4-carbonyl)-cyclopentanecarboxylic acid ethyl ester A mixture of 7.77 g of (1R,2R)-2-(morpholine-4-carbonyl)-4-oxo-cyclopentanecarboxylic acid ethyl ester in 148 ml of aqueous buffer (10 mM 2-(N-morpholino)ethanesulfonic acid; 0.5 M D-glucose [2.7 equ.]; 2 mM magnesium chloride) was adjusted to pH 6.5. Under stirring the reduction was started by the addition of the cofactor NADP (779 mg [0.03 equ.]), the cofactor regeneration enzyme-glucose dehydrogenase (77 mg GDH 102 [Codexis]) and the reductase (387 mg KRED-NADP-131 [Codexis]). During the 21 h reaction time the pH was maintained at pH 6.5 by the addition of 31.9 ml 1M NaOH. At this time point the reaction mixture was blended with the use-test previously carried out, in which 1.5 g (1R,2R)-2-(morpholine-4-carbonyl)-4-oxo-cyclopentanecarboxylic acid ethyl ester were reduced under exactly the described conditions. Under stirring the mixture was adjusted to pH 2.8, saturated with 43.6 g sodium chloride and stirred for at least 10 min. after the addition of 17 g filter aid—Dicalite—and 300 ml ethyl acetate. Subsequently the filter aid was removed and the filtrate was adjusted to pH 7.0 prior to extraction. The aqueous phase was extracted twice with 300 ml ethyl acetate. Treatment of the combined organic phases with sodium sulfate, evaporation and drying over night under a high vacuum yielded in 8.73 g of (1R,2R,4R)-4-hydroxy-2-(morpholine-4-carbonyl)-cyclopentanecarboxylic acid ethyl ester as a pale yellow oil. MS: 272.1 (M+H)⁺; chiral GC: ee 95.2% [BGB-176, 30 m; $H_2$; 2° C./min, 150° C. to 220° C.].

Step 4: (1R,2R,4R)-4-methanesulfonyloxy-2-(morpholine-4-carbonyl)-cyclopentanecarboxylic acid ethyl ester To a solution of (1R,2R,4R)-4-hydroxy-2-(morpholine-4-carbonyl)-cyclopentanecarboxylic acid ethyl ester (1.0 mmol) in dichloromethane (5 ml) was added at 5° C. triethylamine (2.2 mmol) and methanesulfonyl chloride (2.2 mmol) and stirring was continued for 1 h. The mixture was partitioned between 1 N aqueous HCl and ethyl acetate, the organic layer was dried, evaporated and chromatographed on silica using ethyl acetate to give (1R,2R,4R)-4-methanesulfonyloxy-2-(morpholine-4-carbonyl)-cyclopentanecarboxylic acid ethyl ester as a colorless oil. MS: 350.4 (M+H)+.

Step 5: (1R,2R,4S)-2-(morpholine-4-carbonyl)-4-phenylsulfanyl-cyclopentanecarboxylic acid ethyl ester To a solution of the thiophenol (0.41 mmol) in THF (4 ml) was added NaH (55% in oil, 0.41 mmol) at 22° C. and stirring was continued until gas evolution ceased. To the mixture was added a solution of (1R,2R,4R)-4-methanesulfonyloxy-2-(morpholine-4-carbonyl)-cyclopentanecarboxylic acid ethyl ester (0.28 mmol) in THF (4 ml) and stirring was continued at 50° C. until completion of the reaction. The mixture was partitioned between ethyl acetate and water, the organic layer was dried, evaporated and the residue chromatographed on silica using mixtures of cyclohexane and ethyl acetate to give the title compound as pale yellow oil. MS: 364.5 (M+H)+.

Step 6: (1R,2R,4S)-4-benzenesulfonyl-2-(morpholine-4-carbonyl)-cyclopentanecarboxylic acid ethyl ester To a solution of (1R,2R,4S)-2-(morpholine-4-carbonyl)-4-phenylsulfanyl-cyclopentanecarboxylic acid ethyl ester (0.1 mmol) in dichloromethane (1 ml) was added a solution of m-chloroperbenzoic acid (70%, 0.4 mmol) in dichloromethane (2 ml) and stirring was continued at 22° C. until completion of the reaction. The mixture was vigorously shaken with aqueous NaHSO₃, the organic layer was washed with aqueous Na₂CO₃ and water, the organic layer was dried, evaporated and the residue chromatographed on silica using mixtures of cyclohexane and ethyl acetate to give the title compound as a colorless oil. MS: 396.1 (M+H)+.

Step 7: (1R,2R,4S)-4-benzenesulfonyl-2-(morpholine-4-carbonyl)-cyclopentanecarboxylic acid To a solution of (1R,2R,4S)-4-benzenesulfonyl-2-(morpholine-4-carbonyl)-cyclopentanecarboxylic acid ethyl ester (1.35 mmol) in THF (10 ml) was added a solution of LiOH (3.0 mmol) in water (3 ml) and methanol (3 ml) and stirring was continued at 22° C. until completion of the reaction. The mixture was evaporated and the residue partitioned between ethyl acetate and hydrochloric acid (0.1 N). The organic layer was dried and evaporated to give the title compound as a colorless foam. MS: 368.1 (M+H)+.

Step 8: (1R,2R,4R)-4-Benzenesulfonyl-2-(morpholine-4-carbonyl)-cyclopentanecarboxylic acid cyanomethyl-amide A mixture of (1R,2R,4S)-4-benzenesulfonyl-2-(morpholine-4-carbonyl)-cyclopentanecarboxylic acid (0.1 mmol) and amino-acetonitrile hydrochloride (0.12 mmol) in dimethylformamide (0.5 ml) was subsequently treated with diisopropylethyl amine (0.5 mmol), 1-hydroxybenzotriazole hydrate (0.2 mmol) and 1-(3-dimethylaminopropyl)-3-ethyl-carbodiimide hydrochloride (EDC, 0.2 mmol) and stirring was continued at 22° C. overnight. The mixture was purified by preparative HPLC on a RP-18 column using a gradient of a mixture of acetonitrile and water to give (1R,2R,4R)-4-benzenesulfonyl-2-(morpholine-4-carbonyl)-cyclopentanecarboxylic acid cyanomethyl-amide as a white solid. MS: 406.5 (M+H)+.

Example 2

(1R,2R,4R)-4-Benzenesulfonyl-2-(morpholine-4-carbonyl)-cyclopentanecarboxylic acid (1-cyano-cyclopropyl)-amide

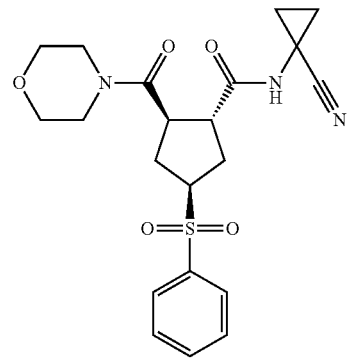

The title compound was prepared in analogy to example 1 using 1-amino-1-cyclopropanecarbonitrile hydrochloride instead of aminoacetonitrile hydrochloride in step 8. Colorless solid. MS: 432.4 (M+H)+.

Example 3

(1R,2R,4R)-4-(2-Chloro-benzenesulfonyl)-2-(morpholine-4-carbonyl)-cyclopentanecarboxylic acid cyanomethyl-amide

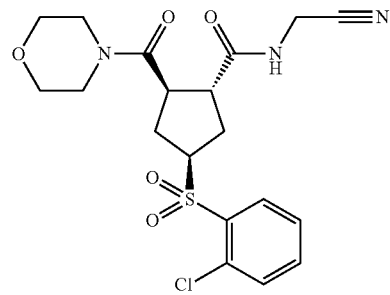

The title compound was prepared in analogy to example 1 using 2-chlorothiophenol instead of thiophenol in step 5. Colorless solid. MS: 440.1 (M+H)+.

Example 4

(1R,2R,4R)-2-(Morpholine-4-carbonyl)-4-(toluene-4-sulfonyl)-cyclopentanecarboxylic acid cyanomethyl-amide

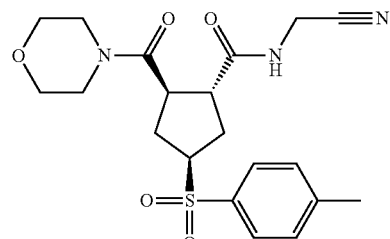

The title compound was prepared in analogy to example 1 using 4-methylbenzenethiol instead of thiophenol in step 5. Colorless oil. MS: 420.3 (M+H)+.

Example 5

(1R,2R,4R)-2-(Morpholine-4-carbonyl)-4-(toluene-3-sulfonyl)-cyclopentanecarboxylic acid cyanomethyl-amide

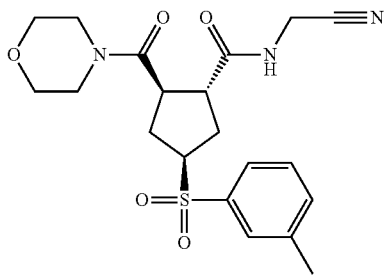

The title compound was prepared in analogy to example 1 using 3-methylbenzenethiol instead of thiophenol in step 5. Colorless oil. MS: 420.3 (M+H)⁺.

Example 6

(1R,2R,4R)-4-(2,4-Difluoro-benzenesulfonyl)-2-(morpholine-4-carbonyl)-cyclopentanecarboxylic acid cyanomethyl-amide

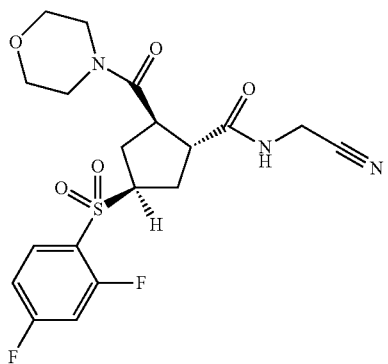

The title compound was prepared in analogy to example 1 using 2,4-difluorothiophenol instead of thiophenol in step 5. Colorless oil. MS: 442.4 (M+H)⁺.

Example 7

(1R,2R,4R)-4-(3-Chloro-4-fluoro-benzenesulfonyl)-2-(morpholine-4-carbonyl)-cyclopentanecarboxylic acid cyanomethyl-amide

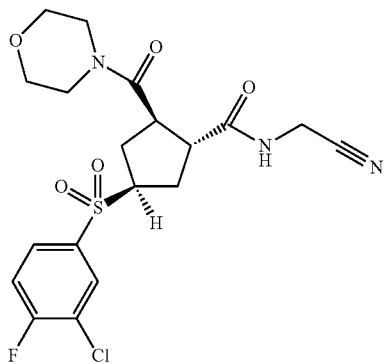

The title compound was prepared in analogy to example 1 using 3-chloro-4-fluorothiophenol instead of thiophenol in step 5. Colorless oil. MS: 458.1 (M+H)⁺.

Example 8

(1R,2R,4R)-4-(4-Chloro-2-methyl-benzenesulfonyl)-2-(morpholine-4-carbonyl)-cyclopentanecarboxylic acid cyanomethyl-amide

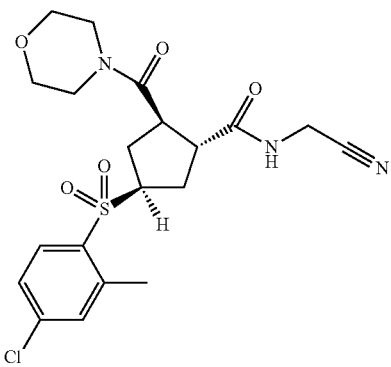

The title compound was prepared in analogy to example 1 using 4-chloro-2-methylthiophenol instead of thiophenol in step 5. Colorless solid. MS: 454.0 (M+H)⁺.

Example 9

(1R,2R,4R)-4-(2-Chloro-benzenesulfonyl)-2-(morpholine-4-carbonyl)-cyclopentanecarboxylic acid (1-cyano-cyclopropyl)-amide

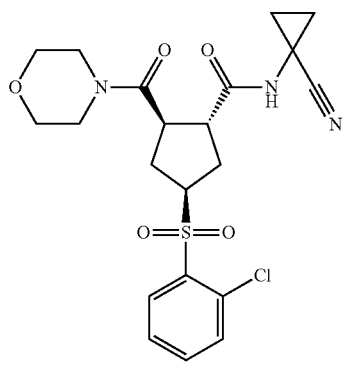

The title compound was prepared in analogy to example 3 using 1-amino-1-cyclopropanecarbonitrile hydrochloride instead of aminoacetonitrile hydrochloride in step 8. Colorless solid. MS: 466.2 (M+H)⁺.

Example 10

(1R,2R,4R)-4-Benzenesulfonyl-2-(1-cyano-cyclopropylcarbamoyl)-cyclopentanecarboxylic acid

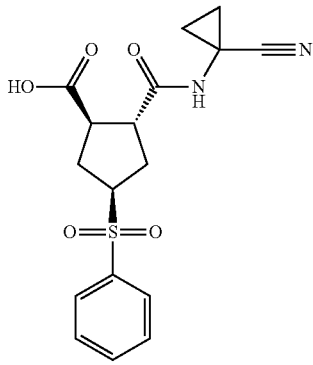

Step 1: (1R,2R)-2-(1-Cyano-cyclopropylcarbamoyl)-4-oxo-cyclopentanecarboxylic acid ethyl ester The reaction of (1R,2R)-4-oxo-cyclopentane-1,2-dicarboxylic acid monoethyl ester and 1-amino-cyclopropanecarbonitrile hydrochloride performed in analogy to example 1, step 8 yielded the title compound as a colorless solid. MS: 265.1 (M+H)$^+$.

Step 2: (1R,2R,4R) and (1R,2R,4S)-2-(1-Cyano-cyclopropylcarbamoyl)-4-hydroxy-cyclopentanecarboxylic acid ethyl ester To a solution of (1R,2R)-2-(1-cyano-cyclopropylcarbamoyl)-4-oxo-cyclopentanecarboxylic acid ethyl ester (0.38 mmol) in THF (2.0 ml) was added at −15° C. sodium borohydride (0.38 mmol) and stirring was continued for 4 h. The mixture was partitioned between 1N aqueous HCl and ethyl acetate, the organic layer was dried, evaporated and the residue chromatographed on silica using ethyl acetate to give (1R,2R)-2-(1-cyano-cyclopropylcarbamoyl)-4-hydroxy-cyclopentanecarboxylic acid ethyl ester as a 2:1 mixture of epimers as a colorless solid. MS: 267.0 (M+H)$^+$.

Step 3: (1R,2R,4R) and (1R,2R,4S)-2-(1-Cyano-cyclopropylcarbamoyl)-4-methanesulfonyloxy-cyclopentanecarboxylic acid ethyl ester The mixture of (1R,2R,4R) and (1R,2R,4S)-2-(1-cyano-cyclopropylcarbamoyl)-4-hydroxy-cyclopentanecarboxylic acid ethyl ester from step 2 was converted to the corresponding mesylate according to the procedure from example 1, step 4 to give (1R,2R)-2-(1-cyano-cyclopropylcarbamoyl)-4-methanesulfonyloxy-cyclopentanecarboxylic acid ethyl ester as a 2:1 mixture of epimers as a colorless solid. MS: 345.0 (M+H)$^+$.

Step 4: (1R,2R,4R)-2-(1-Cyano-cyclopropylcarbamoyl)-4-phenylsulfanyl-cyclopentanecarboxylic acid ethyl ester The reaction of the mixture of (1R,2R,4R) and (1R,2R,4S)-2-(1-cyano-cyclopropylcarbamoyl)-4-methanesulfonyloxy-cyclopentanecarboxylic acid ethyl ester from step 3 with thiophenol performed in analogy to example 1, step 5, yielded a crude material which was purified on silica using n-heptane/EtOAc (3:2) to give in the first fraction the desired (1R,2R,4R)-2-(1-cyano-cyclopropylcarbamoyl)-4-phenylsulfanyl-cyclopentanecarboxylic acid ethyl ester as a colorless oil. MS: 359.2 (M+H)$^+$.

Step 5: (1R,2R,4R)-4-Benzenesulfonyl-2-(1-cyano-cyclopropylcarbamoyl)-cyclopentanecarboxylic acid ethyl ester The oxidation of (1R,2R,4R)-2-(1-cyano-cyclopropylcarbamoyl)-4-phenylsulfanyl-cyclopentanecarboxylic acid ethyl ester was performed in analogy to example 1, step 6 and yielded (1R,2R,4R)-4-benzenesulfonyl-2-(1-cyano-cyclopropylcarbamoyl)-cyclopentanecarboxylic acid ethyl ester as a white solid. MS: 391.2 (M+H)$^+$.

Step 6: (1R,2R,4R)-4-Benzenesulfonyl-2-(1-cyano-cyclopropylcarbamoyl)-cyclopentanecarboxylic acid Hydrolysis of the ester of (1R,2R,4R)-4-benzenesulfonyl-2-(1-cyano-cyclopropylcarbamoyl)-cyclopentanecarboxylic acid ethyl ester was done in analogy to example 1, step 7 to yield the title acid as a white crystals. MS: 361.1 (M−H)$^−$.

Example 11

(1R,2R,4R)-4-Benzenesulfonyl-2-(2-oxa-6-aza-spiro[3.3]heptane-6-carbonyl)-cyclopentanecarboxylic acid (1-cyano-cyclopropyl)-amide

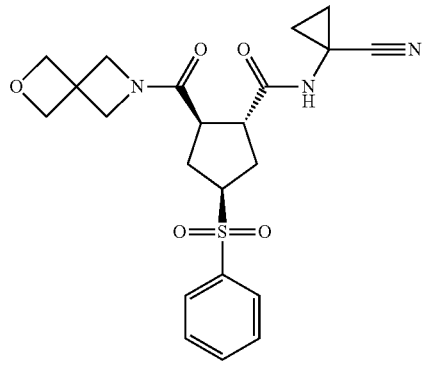

The title compound was prepared by reaction of (1R,2R,4R)-4-benzenesulfonyl-2-(1-cyano-cyclopropylcarbamoyl)-cyclopentanecarboxylic acid (example 10) with 2-oxa-6-aza-spiro[3.3]heptane (prepared according to G. Wuitschik et al., Angew. Chem., Int. Ed., 47, 4512, 2008) using a procedure as described in example 1, step 8. Colorless foam. MS: 444.3 (M+H)$^+$.

Example 12

(1R,2R,4R)-4-Benzenesulfonyl-2-(piperidine-1-carbonyl)-cyclopentanecarboxylic acid (1-cyano-cyclopropyl)-amide

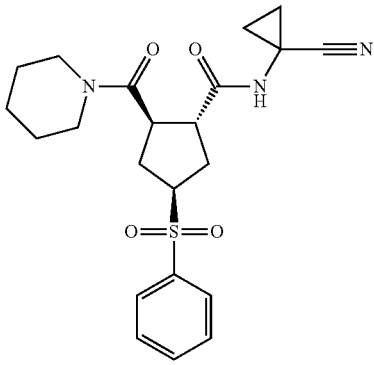

The title compound was prepared in analogy to example 11 using piperidine instead of 2-oxa-6-aza-spiro[3.3]heptan. Colorless solid. MS: 430.3 (M+H)$^+$.

Example 13

(1R,2R,4R)-4-Benzenesulfonyl-2-(4-hydroxy-piperidine-1-carbonyl)-cyclopentanecarboxylic acid (1-cyano-cyclopropyl)-amide

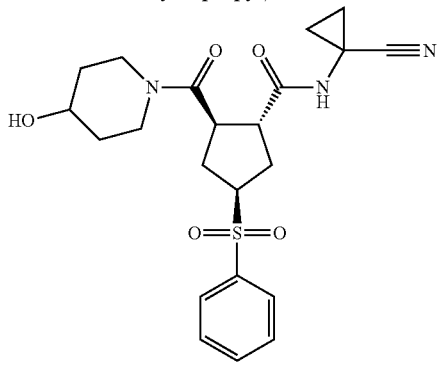

The title compound was prepared in analogy to example 11 using 4-hydroxy-piperidine instead of 2-oxa-6-aza-spiro[3.3]heptan. Colorless solid. MS: 446.2 (M+H)$^+$.

Example 14

(1R,2R,4R)-4-Benzenesulfonyl-2-(piperazine-1-carbonyl)-cyclopentanecarboxylic acid (1-cyano-cyclopropyl)-amide

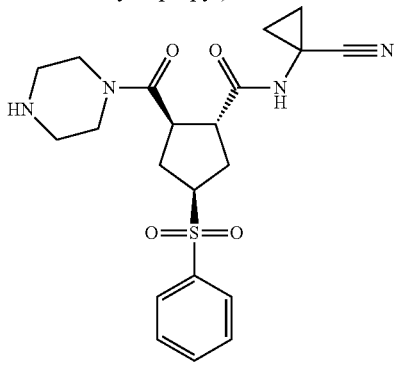

The title compound was prepared in analogy to example 11 using piperazine instead of 2-oxa-6-aza-spiro[3.3]heptan. Colorless solid. MS: 431.3 (M+H)$^+$.

Example 15

(1R,2R,4R)-4-Benzenesulfonyl-2-(3-hydroxy-azetidine-1-carbonyl)-cyclopentanecarboxylic acid (1-cyano-cyclopropyl)-amide

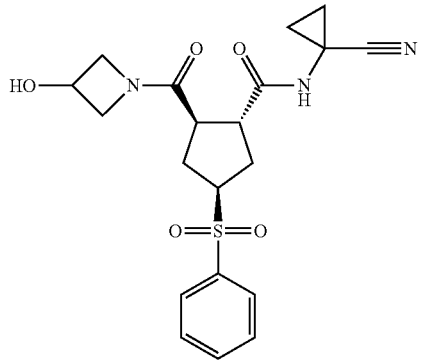

The title compound was prepared in analogy to example 11 using azetidine-3-ol instead of 2-oxa-6-aza-spiro[3.3]heptan. Colorless solid. MS: 418.3 (M+H)$^+$.

Example 16

(1R,2R,4R)-4-Benzenesulfonyl-2-((2S,6R)-2,6-dimethyl-morpholine-4-carbonyl)-cyclopentanecarboxylic acid (1-cyano-cyclopropyl)-amide

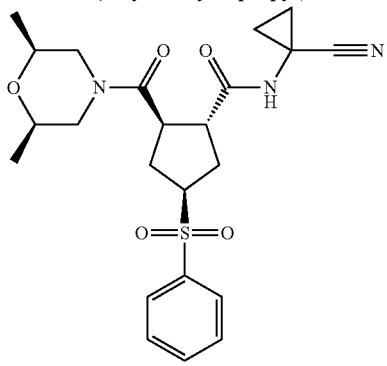

The title compound was prepared in analogy to example 11 using cis-2,6-dimethymorpholine instead of 2-oxa-6-aza-spiro[3.3]heptan. Colorless solid. MS: 460.4 (M+H)$^+$.

Example 17

(1R,2R,4R)-4-Benzenesulfonyl-2-((1R,5S)-8-oxa-3-aza-bicyclo[3.2.1]octane-3-carbonyl)-cyclopentanecarboxylic acid (1-cyano-cyclopropyl)-amide

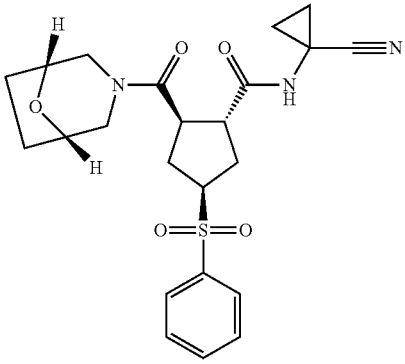

The title compound was prepared in analogy to example 11 using 8-oxa-3-azabicyclo[3.2.1]octane instead of 2-oxa-6-aza-spiro[3.3]heptan. Colorless solid. MS: 458.3 (M+H)$^+$.

Example 18

(1R,2R,4R)-4-Benzenesulfonyl-2-((1R,5S)-3-oxa-8-aza-bicyclo[3.2.1]octane-8-carbonyl)-cyclopentanecarboxylic acid (1-cyano-cyclopropyl)-amide

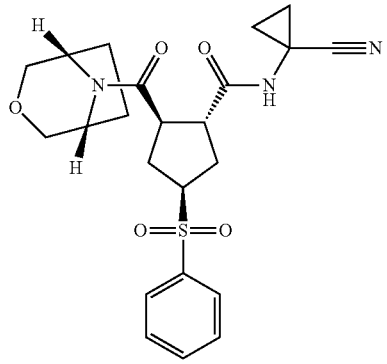

The title compound was prepared in analogy to example 11 using (1R,5S)-3-oxa-8-aza-bicyclo[3.2.1]octane (prepared according to S. Jolidon et al., int. patent application WO2006082001) instead of 2-oxa-6-aza-spiro[3.3]heptan. Colorless solid. MS: 458.3 (M+H)+.

Example 19

(1R,2R,4R)-4-Benzenesulfonyl-2-(4-methyl-piperidine-1-carbonyl)-cyclopentanecarboxylic acid (1-cyano-cyclopropyl)-amide

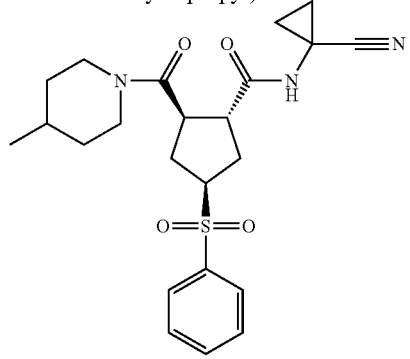

The title compound was prepared in analogy to example 11 using 4-methylpiperidine instead of 2-oxa-6-aza-spiro[3.3]heptan. Colorless solid. MS: 444.4 (M+H)+.

Example 20

(1R,2R,4R)-4-Benzenesulfonyl-2-(1,1-dioxo-1-thiomorpholine-4-carbonyl)-cyclopentanecarboxylic acid (1-cyano-cyclopropyl)-amide

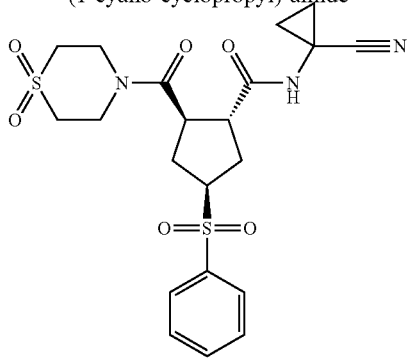

The title compound was prepared in analogy to example 11 using thiomorpholine-1,1-dioxide instead of 2-oxa-6-aza-spiro[3.3]heptan. Colorless solid. MS: 480.2 (M+H)+.

Example 21

(1R,2R,4R)-4-Benzenesulfonyl-2-(3-ethoxy-azetidine-1-carbonyl)-cyclopentanecarboxylic acid (1-cyano-cyclopropyl)-amide

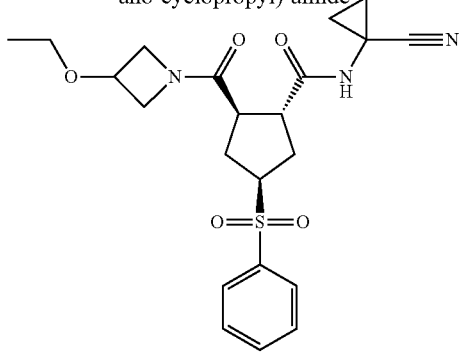

The title compound was prepared in analogy to example 11 using 3-ethoxy-azetidine instead of 2-oxa-6-aza-spiro[3.3]heptan. Colorless solid. MS: 446.2 (M+H)+.

Example 22

(1R,2R,4R)-4-Benzenesulfonyl-2-(3-methoxy-azetidine-1-carbonyl)-cyclopentanecarboxylic acid (1-cyano-cyclopropyl)-amide

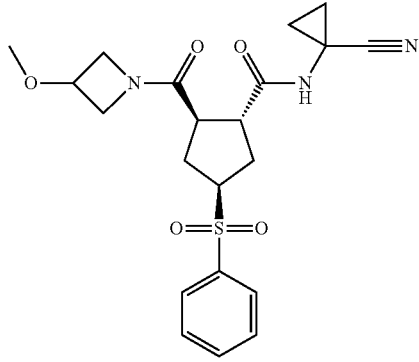

The title compound was prepared in analogy to example 11 using 3-methoxy-azetidine instead of 2-oxa-6-aza-spiro[3.3]heptan. Pale yellow solid. MS: 432.3 (M+H)+.

Example 23

(1R,2R,4R)-4-Benzenesulfonyl-2-(pyrrolidine-1-carbonyl)-cyclopentanecarboxylic acid (1-cyano-cyclopropyl)-amide

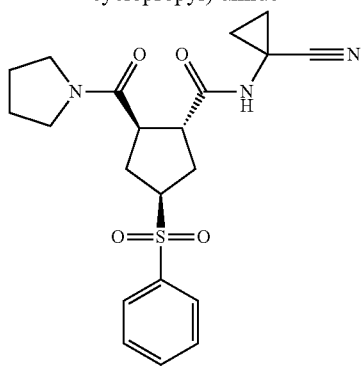

The title compound was prepared in analogy to example 11 using pyrrolidine instead of 2-oxa-6-aza-spiro[3.3]heptan. Colorless solid. MS: 416.2 (M+H)+.

Example 24

(1R,2R,4R)-2-(Azetidine-1-carbonyl)-4-benzenesulfonyl-cyclopentanecarboxylic acid (1-cyano-cyclopropyl)-amide

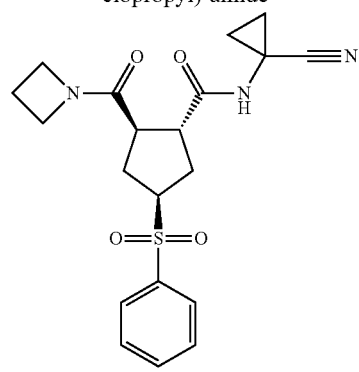

The title compound was prepared in analogy to example 11 using azetidine instead of 2-oxa-6-aza-spiro[3.3]heptan. Colorless solid. MS: 402.3 (M+H)+.

Example 25

(1R,2R,4R)-4-Benzenesulfonyl-cyclopentane-1,2-dicarboxylic acid 1-[(1-cyano-cyclopropyl)-amide]2-diethylamide

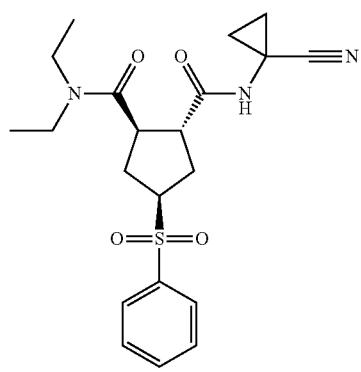

The title compound was prepared in analogy to example 11 using diethylamine instead of 2-oxa-6-aza-spiro[3.3]heptan. Colorless solid. MS: 418.3 (M+H)$^+$.

Example 26

(1R,2R,4R)-4-Benzenesulfonyl-2-(4-methyl-piperazine-1-carbonyl)-cyclopentanecarboxylic acid (1-cyano-cyclopropyl)-amide

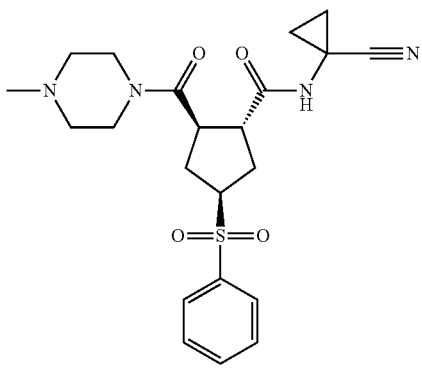

The title compound was prepared in analogy to example 11 using 1-methylpiperazine instead of 2-oxa-6-aza-spiro[3.3]heptan. Pale yellow solid. MS: 445.3 (M+H)$^+$.

Example 27

(1R,2R,4R)-4-Benzenesulfonyl-cyclopentane-1,2-dicarboxylic acid 1-[(1-cyano-cyclopropyl)-amide]2-dimethylamide

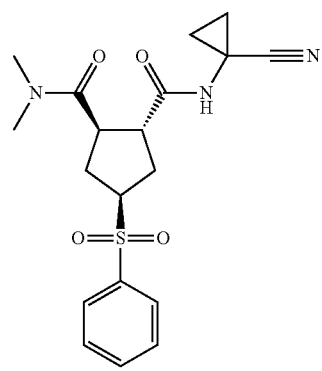

The title compound was prepared in analogy to example 11 using dimethylamine instead of 2-oxa-6-aza-spiro[3.3]heptan. Colorless solid. MS: 390.2 (M+H)$^+$.

Example 28

(1R,2R,4S)-4-Benzenesulfonyl-cyclopentane-1,2-dicarboxylic acid 1-tert-butylamide 2-[(1-cyano-cyclopropyl)-amide]

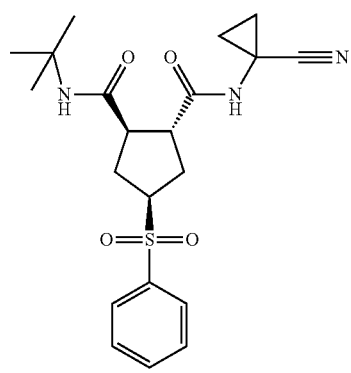

The title compound was prepared in analogy to example 11 using t-butylamine instead of 2-oxa-6-aza-spiro[3.3]heptan. White crystals. MS: 418.3 (M+H)$^+$.

Example 29

(1R,2R,4S)-4-Benzenesulfonyl-cyclopentane-1,2-dicarboxylic acid 1-[(1-cyano-cyclopropyl)-amide]2-methylamide

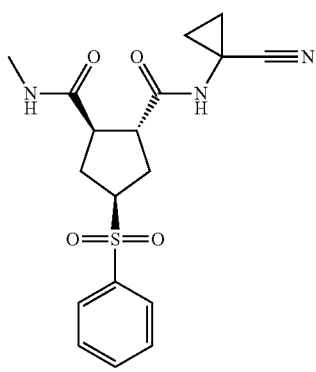

The title compound was prepared in analogy to example 11 using methylamine instead of 2-oxa-6-aza-spiro[3.3]heptan. White crystals. MS: 376.3 (M+H)⁺.

Example 30

(1R,2R,4R) and (1S,2S,4S)-4-[4-(5-Fluoro-pyridin-2-yl)-2-trifluoromethyl-benzenesulfonyl]-2-methoxy-cyclopentanecarboxylic acid (1-cyano-cyclopropyl)-amide

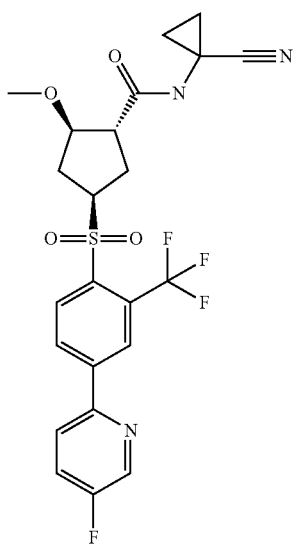

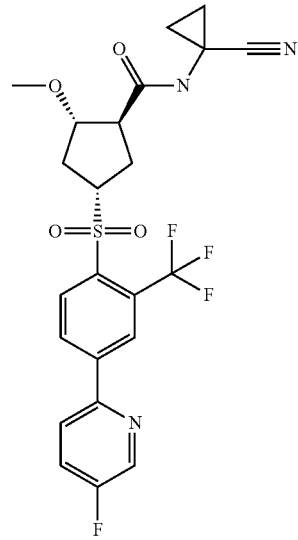

The title compound was prepared in analogy to example 109 using 2-bromo-5-fluoropyridine instead of 2-bromo-2-trifluoromethylpyridine. Light brown solid. MS (EI): 512.2 (M+H)⁺.

Example 31

(1R,2R,4R)-4-(4-Chloro-2-methyl-benzenesulfonyl)-2-(morpholine-4-carbonyl)-cyclopentanecarboxylic acid (cyano-phenyl-methyl)-amide

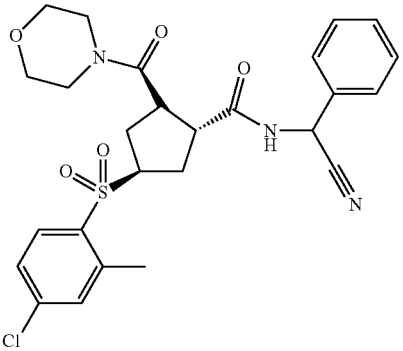

The title compound was prepared in analogy to example 8 using rac-amino-phenyl-acetonitrile instead of aminoacetonitrile hydrochloride in step 8. Pale yellow oil. MS: 530.3 (M+H)⁺.

Example 32

(1R,2R,4R)-4-(4-Chloro-2-methyl-benzenesulfonyl)-
2-((2S,6R)-2,6-dimethyl-morpholine-4-carbonyl)-
cyclopentanecarboxylic acid cyanomethyl-amide

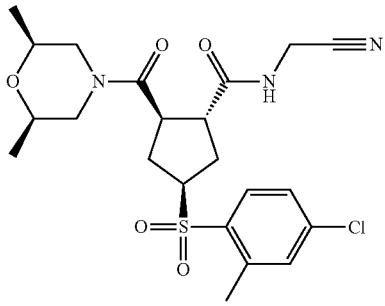

Step 1: (1R,2R)-2-(cyanomethyl-carbamoyl)-4-oxo-cyclopentanecarboxylic acid ethyl ester The reaction of (1R,2R)-4-oxo-cyclopentane-1,2-dicarboxylic acid monoethyl ester and aminoacetonitrile hydrochloride performed in analogy to example 1, step 8 yielded the title compound as a pale brown solid. MS: 237.3 (M–H)⁻.

Step 2: (1R,2R,4R) and (1R,2R,4S)-2-(Cyanomethyl-carbamoyl)-4-hydroxy-cyclopentanecarboxylic acid ethyl ester To a suspension of (1R,2R)-2-(cyanomethyl-carbamoyl)-4-oxo-cyclopentanecarboxylic acid ethyl ester (2.7 mmol) in THF (12 ml) was added DMF (1 ml), the solution was cooled to 0° C., sodium borohydride (3.3 mmol) was added and stirring was continued for 2 h. The mixture was partitioned between 1N aqueous HCl and ethyl acetate, the organic layer was dried, evaporated and the residue chromatographed on silica using dichloromethane/MeOH (97:3) to give in the first fraction (1R,2R,4R)-2-(cyanomethyl-carbamoyl)-4-hydroxy-cyclopentanecarboxylic acid ethyl ester as a white solid. MS: 241.4 (M+H)⁺. The second fraction contained the desired isomer,
(1R,2R,4S)-2-(cyanomethyl-carbamoyl)-4-hydroxy-cyclopentanecarboxylic acid ethyl ester as a white solid. MS: 241.4 (M+H)⁺.

Step 3: (1R,2R,4S)-2-(Cyanomethyl-carbamoyl)-4-methanesulfonyloxy-cyclopentanecarboxylic acid ethyl ester (1R,2R,4S)-2-(Cyanomethyl-carbamoyl)-4-hydroxy-cyclopentanecarboxylic acid ethyl ester (second fraction from step 2) was converted to the corresponding mesylate according to the procedure from example 1, step 4 to give (1R,2R,4S)-2-(cyanomethyl-carbamoyl)-4-methanesulfonyloxy-cyclopentanecarboxylic acid ethyl ester as a colorless solid. MS: 319.3 (M+H)⁺.

Step 4: (1R,2R,4R)-4-(4-Chloro-2-methyl-phenylsulfanyl)-2-(cyanomethyl-carbamoyl)-cyclopentanecarboxylic acid ethyl ester The reaction of (1R,2R,4S)-2-(cyanomethyl-carbamoyl)-4-methanesulfonyloxy-cyclopentanecarboxylic acid ethyl ester with 4-chloro-2-methyl-benzenethiol performed in analogy to example 1, step 5, yielded the title compound as a colorless solid. MS: 381.4 (M+H)⁺.

Step 5: (1R,2R,4R)-4-(4-Chloro-2-methyl-benzenesulfonyl)-2-(cyanomethyl-carbamoyl)-cyclopentanecarboxylic acid ethyl ester The oxidation of (1R,2R,4R)-4-(4-chloro-2-methyl-phenylsulfanyl)-2-(cyanomethyl-carbamoyl)-cyclopentanecarboxylic acid ethyl ester was performed in analogy to example 1, step 6 and yielded (1R,2R,4R)-4-(4-chloro-2-methyl-benzenesulfonyl)-2-(cyanomethyl-carbamoyl)-cyclopentanecarboxylic acid ethyl ester as a white solid. MS: 413.1 (M+H)⁺.

Step 6: (1R,2R,4R)-4-(4-Chloro-2-methyl-benzenesulfonyl)-2-(cyanomethyl-carbamoyl)-cyclopentanecarboxylic acid The hydrolysis of (1R,2R,4R)-4-(4-chloro-2-methyl-benzenesulfonyl)-2-(cyanomethyl-carbamoyl)-cyclopentanecarboxylic acid ethyl ester was done in analogy to example 1, step 7 to yield the title acid as a colorless foam. MS: 383.0 (M–H)⁻.

Step 7: (1R,2R,4R)-4-(4-Chloro-2-methyl-benzenesulfonyl)-2-((2S,6R)-2,6-dimethyl-morpholine-4-carbonyl)-cyclopentanecarboxylic acid cyanomethyl-amide The title compound was prepared in analogy to example 11 using cis-2,6-dimethymorpholine instead of 2-oxa-6-azaspiro[3.3]heptan and (1R,2R,4R)-4-(4-chloro-2-methyl-benzenesulfonyl)-2-(cyanomethyl-carbamoyl)-cyclopentanecarboxylic acid instead of (1R,2R,4R)-4-benzenesulfonyl-2-(1-cyano-cyclopropylcarbamoyl)-cyclopentanecarboxylic acid. Colorless oil. MS: 480.0 (M–H)⁻.

Example 33

(1R,2R,4R)-4-(4-Chloro-2-methyl-benzenesulfonyl)-
2-(4-methyl-piperazine-1-carbonyl)-cyclopentanecarboxylic acid cyanomethyl-amide

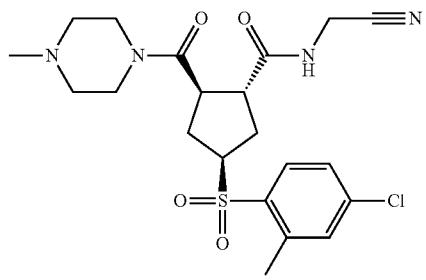

The title compound was prepared in analogy to example 32 using 1-methylpiperazine instead of cis-2,6-dimethymorpholine in step 7. Colorless oil. MS: 467.1 (M+H)⁺.

Example 34

(1R,2R,4R)-4-Benzenesulfonyl-2-(morpholine-4-carbonyl)-cyclopentanecarboxylic acid (cyano-dimethyl-methyl)-amide

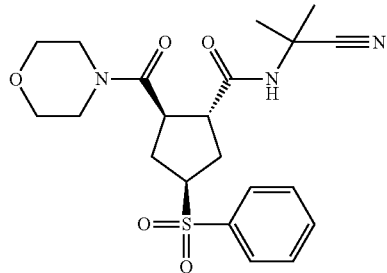

The title compound was prepared in analogy to example 1 using 2-amino-2-methyl-propionitrile hydrochloride instead of aminoacetonitrile hydrochloride in step 8. Colorless solid. MS: 434.3 (M+H)$^+$.

Example 35

(1R,2R,4R)-4-Benzenesulfonyl-2-(morpholine-4-carbonyl)-cyclopentanecarboxylic acid (1-cyano-cyclobutyl)-amide

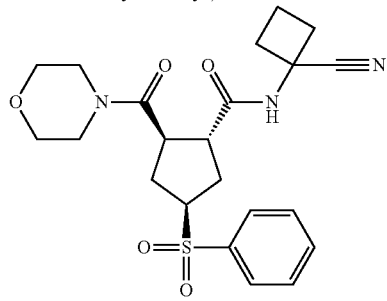

The title compound was prepared in analogy to example 1 using 1-aminocyclobutane-1-carbonitrile instead of aminoacetonitrile hydrochloride in step 8. Colorless oil. MS: 446.1 (M+H)$^+$.

Example 36

(1R,2R,4R)-2-(Morpholine-4-carbonyl)-4-(naphthalene-1-sulfonyl)-cyclopentanecarboxylic acid cyanomethyl-amide

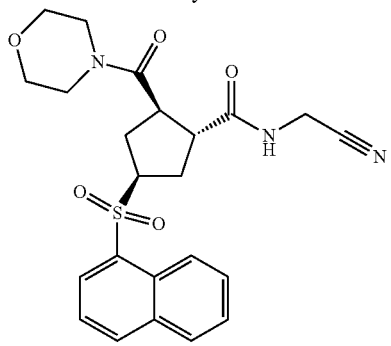

The title compound was prepared in analogy to example 1 using 1-naphthalenethiol instead of thiophenol in step 5. White solid. MS: 456.3 (M+H)$^+$.

Example 37

(1R,2R,4R)-2-(Morpholine-4-carbonyl)-4-(2-trifluoromethyl-benzenesulfonyl)-cyclopentanecarboxylic acid cyanomethyl-amide

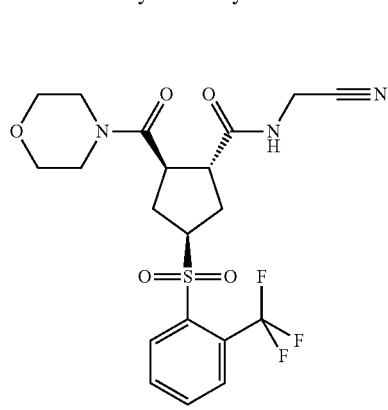

The title compound was prepared in analogy to example 1 using 2-(trifluoromethyl)thiophenol instead of thiophenol in step 5. Colorless foam. MS: 474.1 (M+H)$^+$.

Example 38

(1R,2R,4R)-2-(Morpholine-4-carbonyl)-4-phenylmethanesulfonyl-cyclopentanecarboxylic acid cyanomethyl-amide

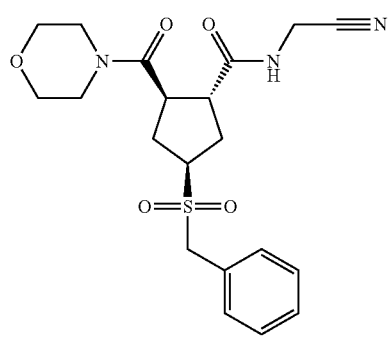

The title compound was prepared in analogy to example 1 using benzylmercaptane instead of thiophenol in step 5 in a modified procedure: To a suspension of (1R,2R,4R)-4-methanesulfonyloxy-2-(morpholine-4-carbonyl)-cyclopentanecarboxylic acid ethyl ester (0.14 mmol) in ethyl methyl ketone (0.8 ml) was added benzylmercaptane (0.19 mmol) and powdered K$_2$CO$_3$ (45 mg) and the mixture was heated to reflux temperature for 20 h. The suspension was filtered and the filtrate was chromatographed on silica using n-heptane/ ethyl acetate to give (1R,2R,4S)-4-benzylsulfanyl-2-(morpholine-4-carbonyl)-cyclopentanecarboxylic acid ethyl ester as a colorless oil. MS: 378.5 (M+H)$^+$.

The title compound was obtained from this intermediate according to example 1 as colorless oil. MS: 420.1 (M+H)$^+$.

Example 39

(1R,2R,4R)-4-(2-Methyl-propane-1-sulfonyl)-2-(morpholine-4-carbonyl)-cyclopentanecarboxylic acid cyanomethyl-amide

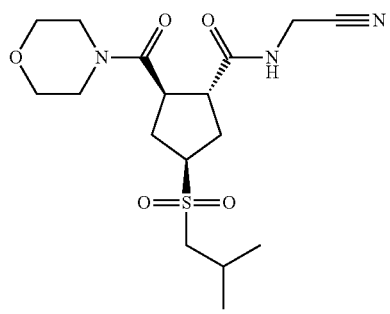

The title compound was prepared in analogy to example 38 using with 2-methyl-1-propanethiol instead of benzylmercaptane in step 5. Colorless oil. MS: 386.4 (M+H)+.

Example 40

(1R,2R,4R)-4-Cyclopropylmethanesulfonyl-2-(morpholine-4-carbonyl)-cyclopentanecarboxylic acid cyanomethyl-amide

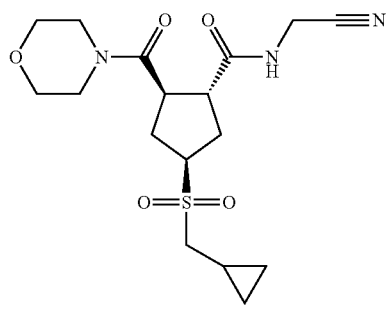

The title compound was prepared in analogy to example 38 using cyclopropylmethanethiol (prepared according to I. Kretzschmar et al., J. Phys. Chem. B, 106, 663, 2002) instead of benzylmercaptane in step 5. Colorless oil. MS: 384.1 (M+H)+.

Example 41

(1R,2R,4R) and (1S,2S,4S)-2-Methoxy-4-(4-pyridin-2-yl-2-trifluoromethyl-benzenesulfonyl)-cyclopentanecarboxylic acid (1-cyano-cyclopropyl)-amide

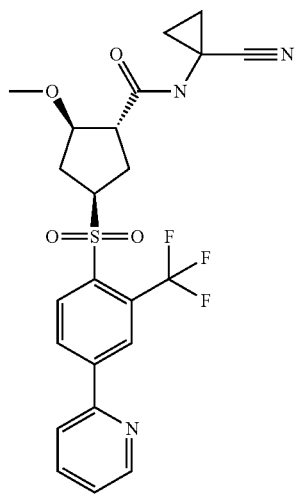

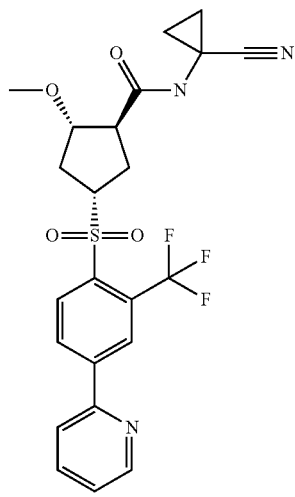

The title compound was prepared in analogy to example 109 using 2-bromopyridine instead of 2-bromo-2-trifluoromethylpyridine. White solid. MS (EI): 494.1 (M+H)+.

Example 42

(1R,2R,4S)-4-Benzenesulfonyl-cyclopentane-1,2-dicarboxylic acid 1-[(1-cyano-cyclopropyl)-amide]2-[(4-fluoro-phenyl)-amide]

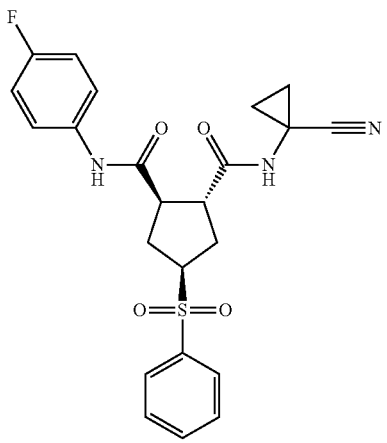

The title compound was prepared in analogy to example 11 using 4-fluoroaniline instead of 2-oxa-6-aza-spiro[3.3]heptan. Colorless solid. MS: 456.2 (M+H)$^+$.

Example 43

3-(2-Chloro-benzenesulfonyl)-cyclopentanecarboxylic acid cyanomethyl-amide

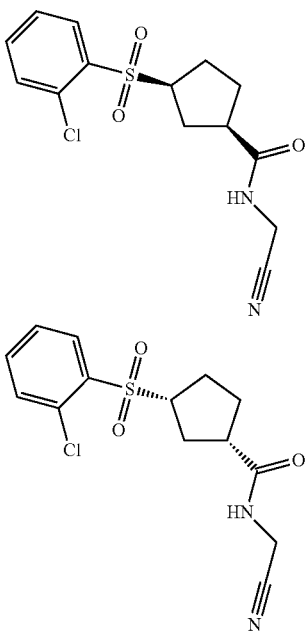

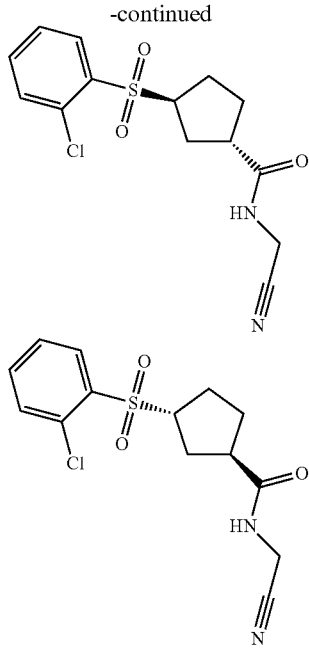

Step 1: 3-Hydroxy-cyclopentanecarboxylic acid methyl ester

A solution of 3-oxo-cyclopentanecarboxylic acid methyl ester (2.0 g, 1.0 eq) was dissolved in methanol (15 mL) and cooled to 0° C. NaBH4 (0.53 g) was added and the mixture was stirred at 0° C. for 30 min. The mixture was quenched with acetic acid (0.5 mL) and the methanol was evaporated. The residue was taken up in ethyl acetate, washed with water, dried and evaporated. Purification by flash chromatography on silica gel with a dichloromethane/ethyl acetate gradient yielded the title compound as mixture of the cis and trans isomers. Colorless liquid, 1.6 g, 78%.

Step 2: 3-Methanesulfonyloxy-cyclopentanecarboxylic acid methyl ester

A solution of 3-hydroxy-cyclopentanecarboxylic acid methyl ester (1.6 g, 1.0 eq, cis/trans-mixture from step 1) in dichloromethane (25 mL) was cooled to −20° C. and treated with triethylamine (1.4 g, 1.3 eq) and methansulfonyl chloride (1.5 g, 1.2 eq). The mixture was stirred at −20° C. for 20 min and then partitioned between water and dichloromethane. The organic phase was washed with brine, dried over sodium sulfate and evaporated. The title compound was obtained as a yellow liquid (2.4 g, 97%) and was used crude in the next step.

Step 3: 3-(2-Chloro-phenylsulfanyl)-cyclopentanecarboxylic acid methyl ester A solution of 2-chlorothiophenol (0.19 g, 1.5 eq) in THF (6.0 mL) was treated with NaH (60% dispersion in mineral oil, 0.05 g, 1.5 eq). The resulting solution was stirred at RT for 30 min. A solution of 3-methanesulfonyloxy-cyclopentanecarboxylic acid methyl ester (0.20 g, 1.0 eq) in THF (2.0 mL) was then added dropwise. The mixture was warmed at 50° C.

and stirred for 3 h. The mixture was partitioned between 1N sodium bicarbonate and ethyl acetate. The combined organic phases were dried over sodium sulfate and evaporated. The title compound was obtained as a colorless oil (0.24 g, 98%) and was used without further purification in the next step. MS (ESI): m/z=271.2 [M+H]⁺.

Step 4: 3-(2-Chloro-benzenesulfonyl)-cyclopentanecarboxylic acid methyl ester

A solution of 3-(2-chloro-phenylsulfanyl)-cyclopentanecarboxylic acid methyl ester (0.24 g, 1.0 eq) in dichloromethane (10 mL) was treated at 0° C. with a solution of MCPBA (1.1 g, 5.0 eq) in dichloromethane (7 mL), which was added dropwise. The mixture was stirred at 0° C. for 3 h, then treated with 20% sodium bisulfite and stirred at RT for 15 min. The mixture was filtered, washing with chloroform. The organic phase was washed with saturated sodium bicarbonate, dried over sodium sulfate and evaporated. The residue was purified by flash chromatography on silica gel with a heptane/ethyl acetate gradient, yielding the title compound as a colorless oil (0.25 g, 90%). MS (ESI): m/z=303.2 [M+H]⁺.

Step 5: 3-(2-Chloro-benzenesulfonyl)-cyclopentanecarboxylic acid

A solution of 3-(2-chloro-benzenesulfonyl)-cyclopentanecarboxylic acid methyl ester (0.25 g, 1.0 eq) in methanol (8.0 mL) was treated with 1N LiOH (1.6 mL, 2.0 eq). The mixture was stirred at RT for 3 h and then acidified to pH 4 with HCl 1N. The methanol was evaporated and the residue extracted with ethyl acetate. The organic phase was dried over sodium sulfate and evaporated. The title compound was obtained as a colorless oil (0.25 g, 100%) and was used crude. MS (ESI): m/z=287.3 [M−H]⁻.

Step 6: 3-(2-Chloro-benzenesulfonyl)-cyclopentanecarboxylic acid cyanomethyl-amide A solution of 3-(2-chloro-benzenesulfonyl)-cyclopentanecarboxylic acid (0.25 g, 1.0 eq) in DMF (4.0 mL) was treated with DIPEA (0.22 mL, 1.5 eq) and HATU (0.39 g, 1.2 eq). The mixture was stirred at RT for 15 min, then a solution of aminoacetonitrile hydrochloride (0.12 g, 1.5 eq) and DIPEA (0.22 mL, 1.5 eq) in DMF (1 mL) was added. The resulting solution was stirred at RT overnight and then purified by preparative HPLC. The title compound was obtained as a light yellow gum (0.10 g, 37%). MS (ESI): m/z=327.1 [M+H]⁺.

Example 44

(S)-1-[(1R,2R,4S)-4-(4-Chloro-2-methyl-benzene-sulfonyl)-2-(morpholine-4-carbonyl)-cyclopentanecarbonyl]-pyrrolidine-2-carbonitrile

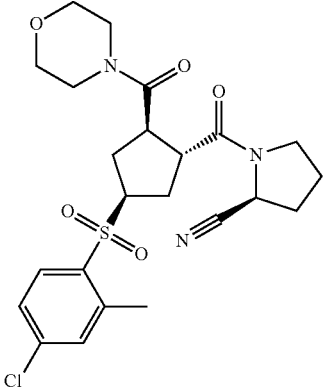

The title compound was prepared in analogy to example 8 using pyrrolidine-2-carbonitrile hydrochloride instead of aminoacetonitrile hydrochloride in step 8. MS: 494.2 (M+H)⁺.

Example 45

(1R,2R,4R)-4-(4-Chloro-2-methyl-benzenesulfonyl)-2-(morpholine-4-carbonyl)-cyclopentanecarboxylic acid (4-cyano-1-methyl-piperidin-4-yl)-amide formiate

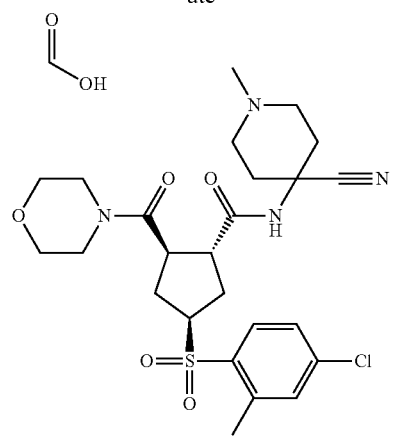

The title compound was prepared in analogy to example 8 using 4-amino-1-methyl-piperidine-4-carbonitrile (prepared according to Y. Bekkali et al., Bioorg. Med. Chem. Lett. 17, 2465, 2007) instead of aminoacetonitrile hydrochloride in step 8. Colorless oil. MS: 537.3 (M+H)⁺.

Example 46

(1R,2R,4R) and (1S,2S,4S)-2-Methoxy-4-(2-trifluoromethyl-benzenesulfonyl)-cyclopentanecarboxylic acid (1-cyano-cyclopropyl)-amide

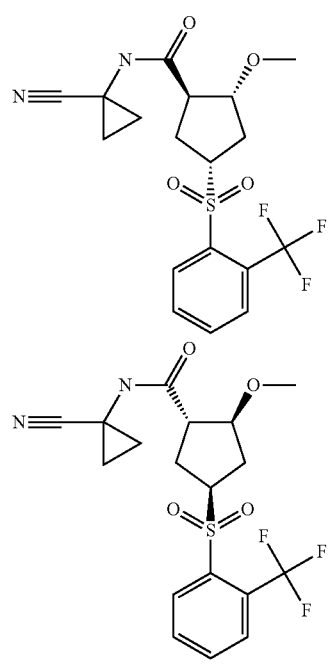

Step 1:
tert-Butyl-(cyclopent-3-enyloxy)-diphenyl-silane

To a solution of 3-cyclopentene-1-ol (10 g, 118.9 mmol) in DMF (100 ml) was added imidazole (16.2 g, 238 mmol) and the solution was cooled to 0° C. Then tert-butyldiphenylchlorosilane (36.7 ml, 142.7 mmol) was added slowly and the reaction mixture was stirred at room temperature overnight. The reaction mixture was diluted with water and extracted two times with heptane.

The combined organic layers were washed with water and brine, dried over $Na_2SO_4$ and evaporated. The crude material was purified by silica gel column chromatography (heptane/EtOAc 95:5) to obtain 35.27 g (109 mmol, 92%) of the title compound as colorless oily liquid. MS (EI): 323.3 $(M+H)^+$.

Step 2: tert-Butyl[(1R,3s,5S)-6-oxabicyclo[3.1.0]hex-3-yloxy]diphenylsilane and tert-butyl [(1R,3r,5S)-6-oxabicyclo[3.1.0]hex-3-yloxy]diphenylsilane tert-Butyl-(cyclopent-3-enyloxy)-diphenyl-silane (11.7 g, 36.3 mmol) was dissolved in cyclohexane (250 ml). The solution was cooled with an icebath and m-chloroperbenzoic acid (11.62 g, containing 70% mCPBA, 47.2 mmol) was added in 5 portions. After the addition was completed the icebath was removed and the mixture was allowed to stir at room temperature for 2 days. The white suspension was diluted with saturated $NaHCO_3$ solution and extracted 3 times with EtOAc. The combined organic layers were washed with saturated $NaHCO_3$ solution, dried over $Na_2SO_4$ and evaporated. The remaining light yellow liquid was purified by silica gel column chromatography (heptane/EtOAc 95:5) to obtain 7.624 g (23 mmol, 62%) of tert-butyl[(1R,3s,5S)-6-oxabicyclo[3.1.0]hex-3-yloxy]diphenylsilane as colorless oil (solidified after a while, MS (EI): 339.3 $(M+H)^+$) and 2.536 g (7 mmol, 21%) of tert-butyl[(1R,3r,5S)-6-oxabicyclo[3.1.0]hex-3-yloxy]diphenylsilane as colorless oil (MS (EI): 339.1 $(M+H)^+$).

Step 3: (1S,2R,4S) and (1R,2S,4R)-4-(tert-Butyl-diphenyl-silanyloxy)-2-hydroxy-cyclopentanecarbonitrile tert-Butyl[(1R,3s,5S)-6-oxabicyclo[3.1.0]hex-3-yloxy]diphenylsilane (11.80 g, 34.9 mmol) was dissolved in toluene (500 ml). At 0° C. diethyl-aluminium cyanide (36.6 ml, 36.6 mmol, 1M solution in toluene) was added dropwise and the reaction mixture was then stirred at room temperature overnight. Then NaF (36.6 g, 871 mmol) and water (23 ml) were added at 0° C. and the mixture was stirred for 1 h. After filtration and washing of the precipitate with EtOAc, the filtrate was dried over $Na_2SO_4$ and evaporated. The remaining yellow gum was purified by silica gel column chromatography (heptane/EtOAc 60:40) to obtain the title compound (12.534 g, 34 mmol, 98%) as yellow oil. MS (EI): 366.2 $(M+H)^+$.

Step 4: (1S,2R,4S) and (1R,2S,4R)-4-(tert-Butyl-diphenyl-silanyloxy)-2-methoxy-cyclopentanecarbonitrile A mixture of (1S,2R,4S) and (1R,2S,4R)-4-(tert-butyl-diphenyl-silanyloxy)-2-hydroxy-cyclopentanecarbonitrile (2 g, 5.47 mmol), methyliodide (15 ml; 246 mmol) and silver(I) oxide (2.54 g, 10.94 mmol) was stirred at room temperature overnight. The excess of methyliodide was removed under reduced pressure and the remaining residue was suspended in DCM and filtered through a pad of celite. The filtrate was evaporated and the remaining yellow gum was purified by silica gel column chromatography (heptane/EtOAc 90:10-80:20) to obtain 1.62 g (4 mmol, 78%) of the title compound as colorless gum. MS (EI): 380.2 $(M+H)^+$.

Step 5: (1S,2R,4S) and (1R,2S,4R)-4-Hydroxy-2-methoxy-cyclopentanecarbonitrile A solution of (1S,2R,4S) and (1R,2S,4R)-4-(tert-butyl-diphenyl-silanyloxy)-2-methoxy-cyclopentanecarbonitrile (3.86 g, 10.17 mmol) in THF (20 ml) was added to a solution of TBAF (20.3 ml, 20.3 mmol, 1M solution in THF) and acetic acid (1.2 ml, 20.9 mmol) in THF (50 ml) at 0° C. After the addition was completed, the icebath was removed and the light brown solution was allowed to stir at room temperature for 3.5 h. The solution was then diluted with water and extracted 3 times with EtOAc. The combined organic layers were washed with a mixture of brine and saturated $NaHCO_3$ solution, dried over $Na_2SO_4$ and evaporated. The remaining yellow oil was purified by silica gel chromatography (heptane/EtOAc 70:30-45:55) to obtain the title compound as yellow oil (1.29 g, 9 mmol, 90%). MS (EI): 200.3 $(M+OAc)^-$.

Step 6: Methanesulfonic acid (1S,3S,4R) and (1R,3R,4S)-3-cyano-4-methoxy-cyclopentyl ester To a solution of (1S,2R,4S) and (1R,2S,4R)-4-hydroxy-2-methoxy-cyclopentanecarbonitrile (1.28 g, 9.07 mmol) in DCM (45 ml) was added N-ethyl-N,N-diisopropyl amine (2.3 ml, 95% purity, 12.69 mmol) at 0° C. Then methanesulfonyl chloride (848 ml, 10.88 mmol) was added and the reaction mixture was stirred at 0-10° C. for 3 h. The solution was allowed to warm to rt, water was added and the mixture was extracted with DCM. The combined organic extracts were washed with water and brine, dried over $Na_2SO_4$ and evaporated. The title compound was obtained as orange brown oil (2.109 g) and was used in the next reaction step without further purification. MS (EI): 278.3 $(M+OAc)^-$.

Step 7: (1S,2R,4R) and (1R,2S,4S)-2-Methoxy-4-(2-trifluoromethyl-phenylsulfanyl)-cyclopentanecarbonitrile NaH (67 mg, 55% in oil, 1.4 mmol) was suspended in DMF at 0° C. Then 2-(trifluoromethyl)-thiophenol (205 ml, 1.55 mmol) was added slowly and the mixture was stirred for 1 h at 0° C. and for 20 min at rt. Then the reaction mixture was cooled again to 0° C. and a solution of methanesulfonic acid (1S,3S,4R) and (1R,3R,4S)-3-cyano-4-methoxy-cyclopentyl ester (170 mg, 0.78 mmol) in DMF (0.5 ml) was added dropwise. The reaction mixture was stirred for 2 h at 0° C. and for additional 4 h at rt. Then water was added and the mixture was extracted 3 times with EtOAc. The combined organic extracts were washed with brine, dried over $Na_2SO_4$ and evaporated. The remaining red oil was purified by silica gel chromatography (heptane/EtOAc 2:1) to obtain the title compound as colorless oil (168 mg, 72%). MS (EI): 360.2 $(M+OAc)^-$.

Step 8: (1S,2R,4R) and (1R,2S,4S)-2-Methoxy-4-(2-trifluoromethyl-benzenesulfonyl)-cyclopentanecarbonitrile (1S,2R,4R) and (1R,2S,4S)-2-Methoxy-4-(2-trifluoromethyl-phenylsulfanyl)-cyclopentanecarbonitrile (165 mg, 0.55 mmol) was dissolved in methanol (4 ml) and a solution of oxone (673 mg, 1.1 mmol) in water (4 ml) was added dropwise at 0° C. The reaction mixture was stirred at room temperature for 2 h. The mixture was then extracted 2 times with EtOAc and the combined organic extracts were washed with water and brine, dried over $Na_2SO_4$ and concentrated. The remaining title compound (178 mg, 97%,) was obtained as colorless oil and was used in the next reaction step without further purification. MS (EI): 392.2 (M+OAc)⁻.

Step 9: (1R,2R,4R) and (1S,2S,4S)-2-Methoxy-4-(2-trifluoromethyl-benzenesulfonyl)-cyclopentanecarboxylic acid methyl ester (1S,2R,4R) and (1R,2S,4S)-2-Methoxy-4-(2-trifluoromethyl-benzenesulfonyl)-cyclopentanecarbonitrile (100 mg, 0.3 mmol) was dissolved in a saturated solution of HCl in methanol (5 ml) at 0° C. and the reaction mixture was then stirred at room temperature for 17 h. Then half of the methanol volume was removed under reduced pressure, saturated $NaHCO_3$ solution was added and the mixture was extracted with EtOAc. The combined organic layers were washed with brine, dried over $Na_2SO_4$ and concentrated. The remaining brown oil was purified by silica gel chromatography (heptane/EtOAc 2:1) to obtain the title compound as colorless oil (67 mg, 61%). MS (EI): 367.1 (M+H)⁺.

Step 10: Lithium (1R,2R,4R) and (1S,2S,4S)-2-methoxy-4-(2-trifluoromethyl-benzenesulfonyl)-cyclopentanecarboxylate To a solution of (1R,2R,4R) and (1S,2S,4S)-2-methoxy-4-(2-trifluoromethyl-benzenesulfonyl)-cyclopentanecarboxylic acid methyl ester (67 mg, 0.18 mmol) in THF (2 ml) was added 1N LiOH (360 ml, 0.36 mmol) and the reaction mixture was heated to 40° C. for 6 h. Then the excess of LiOH was neutralized by addition of HCl and all volatiles were removed under reduced pressure. Residual water was removed from the remaining residue by azeotropic distillation with toluene to obtain a light brown solid (80 mg) containing the title compound. MS (EI): 351.2 (M−H)⁻.

Step 11: (1R,2R,4R) and (1S,2S,4S)-2-Methoxy-4-(2-trifluoromethyl-benzenesulfonyl)-cyclopentanecarboxylic acid (1-cyano-cyclopropyl)-amide Lithium (1R,2R,4R) and (1S,2S,4S)-2-methoxy-4-(2-trifluoromethyl-benzenesulfonyl)-cyclopentanecarboxylate obtained in step 10 (0.17 mmol) was dissolved in acetonitrile (3 ml) and N-(3-dimethylaminopropyl)-N'-ethylcarbodiimide hydrochloride (67 mg, 0.35 mmol), N-ethyl-N,N-diisopropyl amine (89 ml, 0.52 mmol) and 1-hydroxybenzotriazole (35 mg, 0.26 mmol) were added. Then 1-amino-1-cyclopropanecarbonitrile hydrochloride (25 mg, 0.21 mmol) was added and the reaction mixture was stirred at room temperature over night. All volatiles were removed under reduced pressure and the title compound was isolated from the remaining brown oil by silica gel chromatography (DCM/EtOAc 9:1) as a white solid (45 mg, 62%). MS (EI): 417.0 (M+H)⁺.

Example 47

(1R,2R,4R) and (1S,2S,4S)-2-Methoxy-4-(2-trifluoromethyl-benzenesulfonyl)-cyclopentanecarboxylic acid cyanomethyl-amide

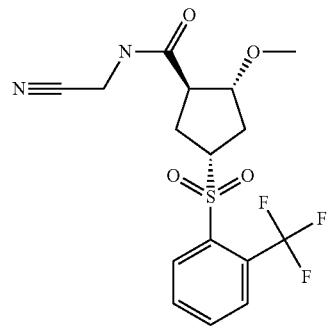

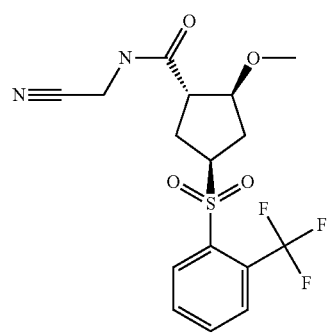

The title compound was prepared in analogy to example 46 using aminoacetonitrile hydrochloride instead of 1-amino-1-cyclopropanecarbonitrile hydrochloride in step 11. White solid. MS (EI): 389.4 (M−H)⁻.

Example 48

(1R,2R,4R) and (1S,2S,4S)-4-(2-Chloro-benzenesulfonyl)-2-hydroxy-cyclopentanecarboxylic acid (1-cyano-cyclopropyl)-amide

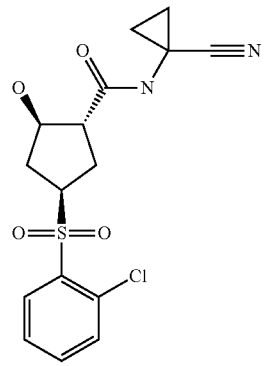

-continued

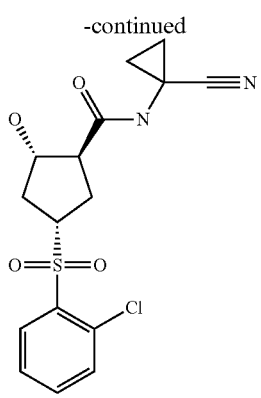

Step 1: Toluene-4-sulfonic acid cyclopent-3-enyl ester

Cyclopent-3-ene-1-ol (200 mg, 2.38 mmol) was dissolved in pyridine (2.5 ml) and p-toluenesulfonyl chloride (558 mg, 2.92 mmol) was added portionwise at 0° C. After the addition was completed the reaction mixture was stirred at 0° C. for 3 h and then kept in the fridge overnight. Then it was poured into to a mixture of ice and diluted HCl (pH ~5). The solid was filtered off, washed with diluted HCl and dried to obtain the title compound as off-white solid (447 mg, 79%). MS (EI): 256.2 (M+NH$_4$)$^+$.

Step 2: 1-Chloro-2-(cyclopent-3-enylsulfanyl)-benzene

NaH (316 mg, 55% in mineral oil, 7.24 mmol) was suspended in DMF (6 ml) and the suspension was cooled to 0° C. A solution of 2-chloro-thiophenol (880 ml, 97% purity, 7.55 mmol) in DMF (2 ml) was added dropwise. After stirring for 45 min at 0° C. a solution of toluene-4-sulfonic acid cyclopent-3-enyl ester (1500 mg, 6.29 mmol) in DMF (3 ml) was added dropwise and the reaction mixture was stirred at room temperature for 2 days. Water was added and the mixture was extracted 3 times with EtOAc. The combined organic layers were washed with water, saturated NaHCO$_3$ solution and brine, dried over Na$_2$OS$_4$ and evaporated. The remaining brown oil was purified by silica gel chromatography (heptane/EtOAc 100:0-99:1) to obtain the title compound (1.047 g, 79%) as colorless liquid.

Step 3: (1R,3r,5S)-3-[(2-Chlorophenyl)sulfonyl]-6-oxabicyclo[3.1.0]hexane and (1R,3s,5S)-3-[(2-chlorophenyl)sulfonyl]-6-oxabicyclo[3.1.0]hexane Chloro-2-(cyclopent-3-enylsulfanyl)-benzene (1 g, 4.75 mmol) was dissolved in DCM (32 ml) and the solution was cooled to 0° C. Then m-chloroperbenzoic acid (3.86 g, containing 70% mCPBA, 15.66 mmol) was added portionwise that the temperature of the reaction mixture was kept below 5° C. After the addition was completed, the white suspension was stirred at room temperature for 4 h. The reaction mixture was diluted with saturated NaHCO$_3$ solution and extracted 3 times with DCM. The combined organic layers were washed 4 times with saturated NaHCO$_3$ solution, dried over Na$_2$SO$_4$ and evaporated. The remaining white solid was purified by silica gel chromatography (heptane/EtOAc 80:20-40:60) to obtain (1R,3r,5S)-3-[(2-chlorophenyl)sulfonyl]-6-oxabicyclo[3.1.0]hexane (134 mg, 11%) as white solid and (1R,3s,5S)-3-[(2-chlorophenyl)sulfonyl]-6-oxabicyclo[3.1.0]hexane (970 mg, 79%) as white solid. MS (EI): 259.1 (M+H)$^+$.

Step 4: (1S,2R,4R) and (1R,2S,4S)-4-(2-Chloro-benzenesulfonyl)-2-hydroxy-cyclopentanecarbonitrile The title compound was prepared from (1R,3r,5S)-3-[(2-chlorophenyl)sulfonyl]-6-oxabicyclo[3.1.0]hexane in analogy to (1S,2R,4S) and (1R,2S,4R)-4-(tert-Butyl-diphenyl-silanyloxy)-2-hydroxy-cyclopentanecarbonitrile in example 46, step 3 and was obtained as white foam. MS (EI): 286.1 (M+H)$^+$.

Step 5: (1R,2R,4R) and (1S,2S,4S)-4-(2-Chloro-benzenesulfonyl)-2-hydroxy-cyclopentanecarboxylic acid methyl ester The title compound was prepared in analogy to (1R,2R,4R) and (1S,2S,4S)-2-methoxy-4-(2-trifluoromethyl-benzenesulfonyl)-cyclopentanecarboxylic acid methyl ester in example 46, step 9 and was obtained as colorless gum. MS (EI): 319.0 (M+H)$^+$.

Step 6: Lithium (1R,2R,4R) and (1S,2S,4S)-4-(2-chloro-benzenesulfonyl)-2-hydroxy-cyclopentanecarboxylate The title compound was prepared in analogy to lithium (1R,2R,4R) and (1S,2S,4S)-2-methoxy-4-(2-trifluoromethyl-benzenesulfonyl)-cyclopentanecarboxylate in example 46, step 10 and was obtained as off-white solid. MS (EI): 303.0 (M-H)$^-$.

Step 7: (1R,2R,4R) and (1S,2S,4S)-4-(2-Chloro-benzenesulfonyl)-2-hydroxy-cyclopentanecarboxylic acid (1-cyano-cyclopropyl)-amide The title compound was prepared in analogy to example 46, step 11 but using DMF instead of acetonitrile as solvent and was obtained as white foam. MS (EI): 369.1 (M+H)$^+$.

Example 49

(1R,2R,4R) and (1S,2S,4S)-4-(2-Chloro-benzene-sulfonyl)-2-hydroxy-cyclopentanecarboxylic acid cyanomethyl-amide

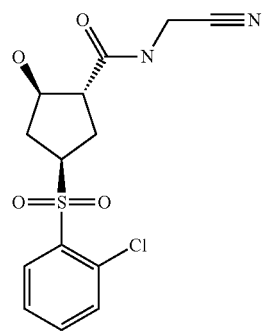

-continued

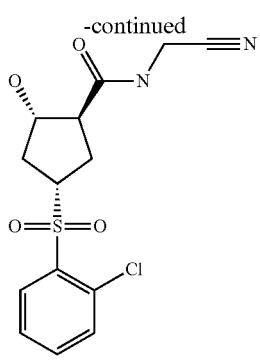

The title compound was prepared in analogy to example 48 using aminoacetonitrile hydrochloride instead of 1-amino-1-cyclopropanecarbonitrile hydrochloride in step 7. White foam. MS (EI): 343.2 (M+H)+.

Example 50

(1R,2R,4R) and (1S,2S,4S)-4-(2,4-Dichloro-benzenesulfonyl)-2-methoxy-cyclopentanecarboxylic acid (1-cyano-cyclopropyl)-amide

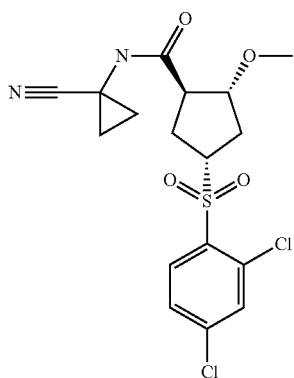

The title compound was prepared in analogy to example 46 using 2,4-dichloro-benzenethiol instead of 2-(trifluoromethyl)-thiophenol in step 7. White solid. MS (EI): 415.3 (M−H)−.

Example 51

(1R,2R,4R) and (1S,2S,4S)-4-(2,4-Dichloro-benzenesulfonyl)-2-methoxy-cyclopentanecarboxylic acid cyanomethyl-amide

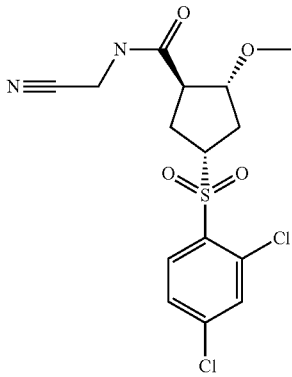

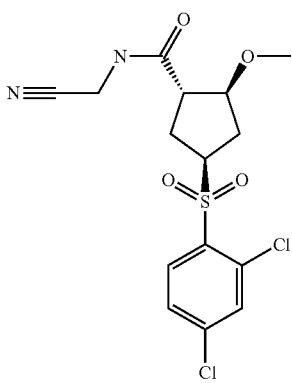

The title compound was prepared in analogy to example 47 using 2,4-dichloro-benzenethiol instead of 2-(trifluoromethyl)-thiophenol in step 7. White solid. MS (EI): 389.3 (M−H)−.

Example 52

(1S,2S,4R) and (1R,2R,4S)-4-(2-Chloro-benzenesulfonyl)-2-hydroxy-cyclopentanecarboxylic acid (1-cyano-cyclopropyl)-amide

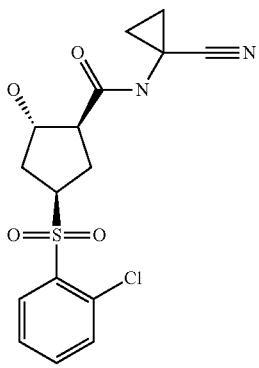

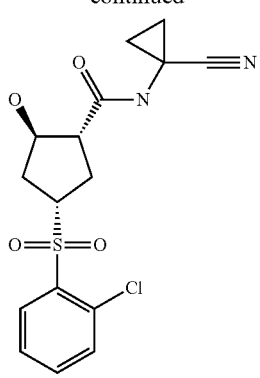

The title compound was prepared in analogy to example 48 using (1R,3s,5S)-3-[(2-chlorophenyl)sulfonyl]-6-oxabicyclo[3.1.0]hexane instead of (1R,3r,5S)-3-[(2-chlorophenyl)sulfonyl]-6-oxabicyclo[3.1.0]hexane in step 4. White solid. MS (EI): 369.1 (M+H)$^+$.

Example 53

(1S,2S,4R) and (1R,2R,4S)-4-(2-Chloro-benzenesulfonyl)-2-hydroxy-cyclopentanecarboxylic acid cyanomethyl-amide

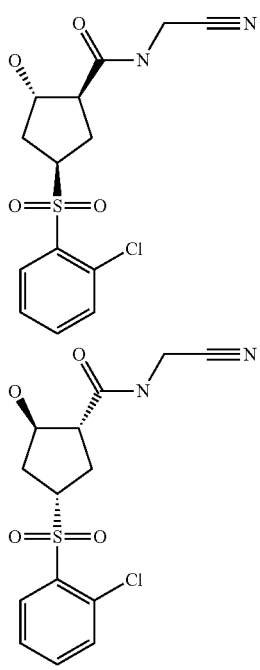

The title compound was prepared in analogy to example 49 using (1R,3s,5S)-3-[(2-chlorophenyl)sulfonyl]-6-oxabicyclo[3.1.0]hexane instead of (1R,3r,5S)-3-[(2-chlorophenyl)sulfonyl]-6-oxabicyclo[3.1.0]hexane in step 4. White solid. MS (EI): 343.2 (M+H)$^+$.

Example 54

(1R,2R,4R) and (1S,2S,4S)-2-Propoxy-4-(2-trifluoromethyl-benzenesulfonyl)-cyclopentanecarboxylic acid (1-cyano-cyclopropyl)-amide

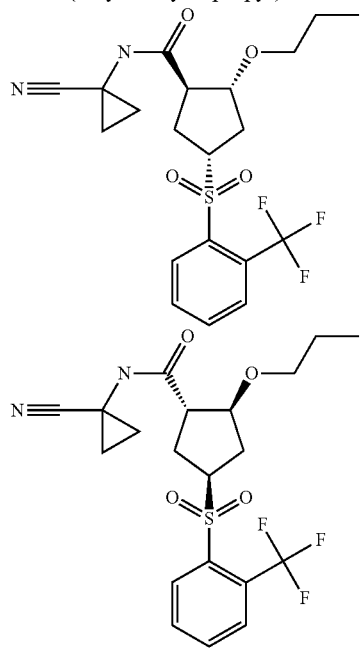

The title compound was prepared in analogy to example 46 using propyliodide instead of methyliodide in step 4. White solid. MS (EI): 443.3 (M–H)$^-$.

Example 55

(1R,2R,4R) and (1S,2S,4S)-2-Propoxy-4-(2-trifluoromethyl-benzenesulfonyl)-cyclopentanecarboxylic acid cyanomethyl-amide

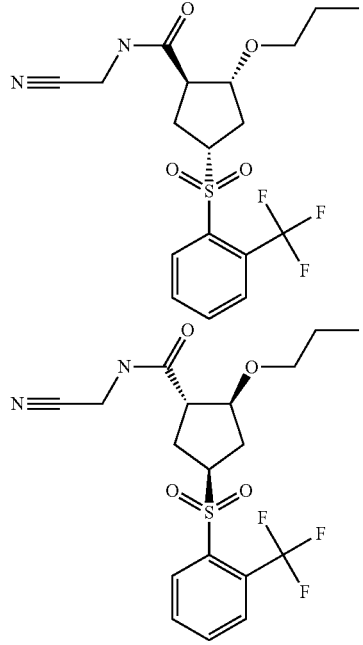

The title compound was prepared in analogy to example 47 using propyliodide instead of methyliodide in step 4. White solid. MS (EI): 417.3 (M–H)$^-$.

Example 56

(1R,2R,4R) and (1S,2S,4S)-4-(2-Chloro-4-fluoro-benzenesulfonyl)-2-methoxy-cyclopentanecarboxylic acid (1-cyano-cyclopropyl)-amide

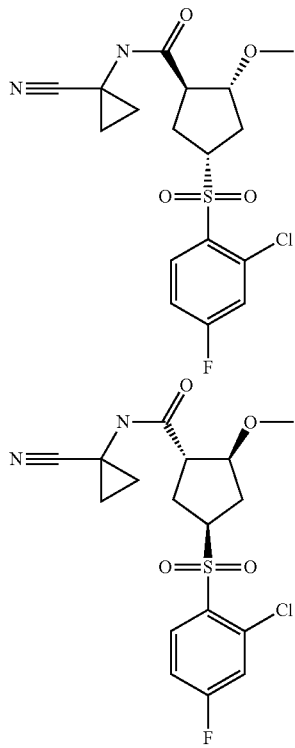

The title compound was prepared in analogy to example 46 using 2-chloro-4-fluoro-benzenethiol instead of 2-(trifluoromethyl)-thiophenol in step 7. White solid. MS (EI): 401.2 (M+H)$^+$.

Example 57

(1R,2R,4R) and (1S,2S,4S)-4-[2-Chloro-4-(4-fluoro-phenoxy)-benzenesulfonyl]-2-methoxy-cyclopentanecarboxylic acid (1-cyano-cyclopropyl)-amide

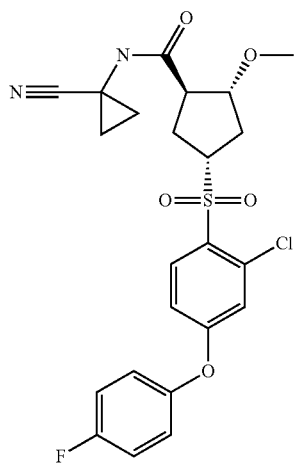

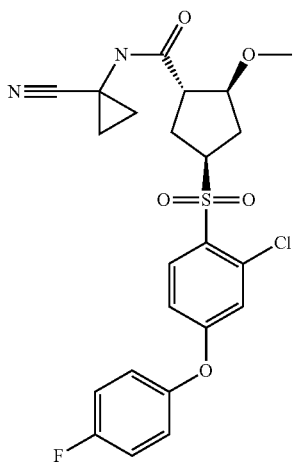

(1R,2R,4R) and (1S,2S,4S)-4-(2-Chloro-4-fluoro-benzenesulfonyl)-2-methoxy-cyclopentanecarboxylic acid (1-cyano-cyclopropyl)-amide (25 mg, 0.062 mmol, example 56) was dissolved in DMF (1.5 ml) and 4-fluorophenol (14 mg, 0.125 mmol) and Cs$_2$CO$_3$ (61 mg, 0.187 mmol) were added. The reaction mixture was stirred for 4 h at 50° C. Then water was added and the mixture was extracted with EtOAc. The combined extracts were washed with brine, dried over Na$_2$SO$_4$ and concentrated. The remaining residue was purified by silica gel chromatography (DCM/EtOAc 9:1) to obtain the title compound (21 mg, 63%) as white solid. MS (EI): 491.1 (M−H)$^-$.

Example 58

(1R,2R,4R) and (1S,2S,4S)-4-(4-Bromo-2-trifluoromethyl-benzenesulfonyl)-2-methoxy-cyclopentanecarboxylic acid (1-cyano-cyclopropyl)-amide

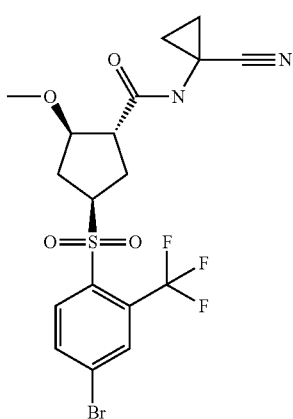

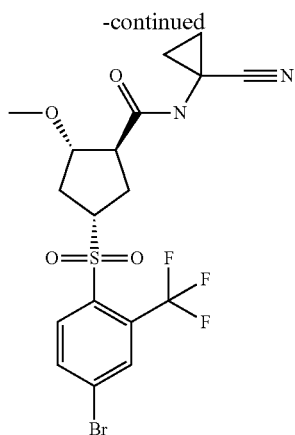

Step 1: 4-Bromo-2-trifluoromethyl-benzenethiol

To a mixture of 4-bromo-2-trifluoromethyl-benzene sulfonyl chloride (9.38 g, 29 mmol) in dioxane (45 mL) and water (10 mL) was added tris-(2-carboxyethyl)phosphine hydrochloride (34.4 g, 118 mmol) and the reaction mixture was refluxed for 5 h, then cooled down, and partitioned between water and dichloromethane. The aqueous layer was extracted with dichloromethane and combined organic layers were washed with water then dried over sodium sulfate and concentrated in vacuo to afford the title compound (7.00 g, 94%) as a colorless liquid. MS (EI): 254.9 (M−H)−.

Step 2: (1R,2R,4R) and (1S,2S,4S)-4-(4-Bromo-2-trifluoromethyl-benzenesulfonyl)-2-methoxy-cyclopentanecarboxylic acid (1-cyano-cyclopropyl)-amide The title compound was prepared in analogy to example 46 using 4-bromo-2-trifluoromethyl-benzenethiol (Intermediate 1, Example 58) instead of 2-(trifluoromethyl)-thiophenol in step 7 and HATU instead of EDCI/HOBt. Off-white solid. MS (EI): 495.1 (M+H)+.

Example 59

(1R,2R,4R) and (1S,2S,4S)-4-(2-Chloro-4-pyrazol-1-yl-benzenesulfonyl)-2-methoxy-cyclopentanecarboxylic acid (1-cyano-cyclopropyl)-amide

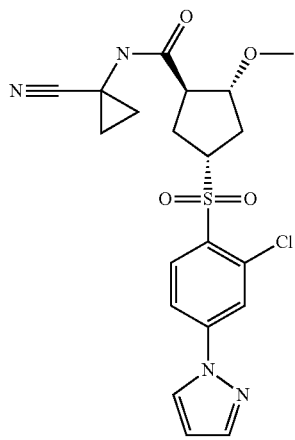

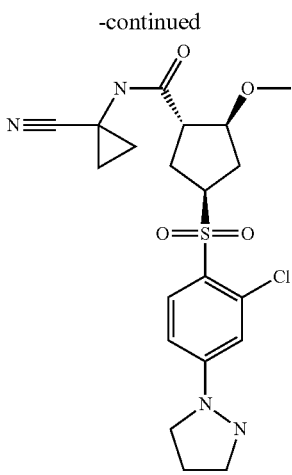

The title compound was prepared in analogy to example 57 using pyrazole instead of 4-fluorophenol. White solid. MS (EI): 449.1 (M+H)+.

Example 60

(1R,2R,4R) and (1S,2S,4S)-4-[2-Chloro-4-((R/S)-2,2,2-trifluoro-1-methyl-ethoxy)-benzenesulfonyl]-2-methoxy-cyclopentanecarboxylic acid (1-cyano-cyclopropyl)-amide

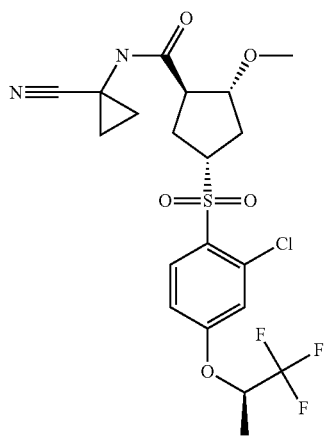

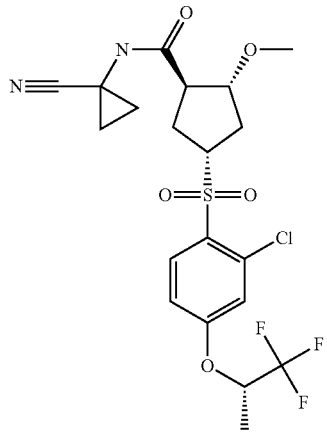

-continued

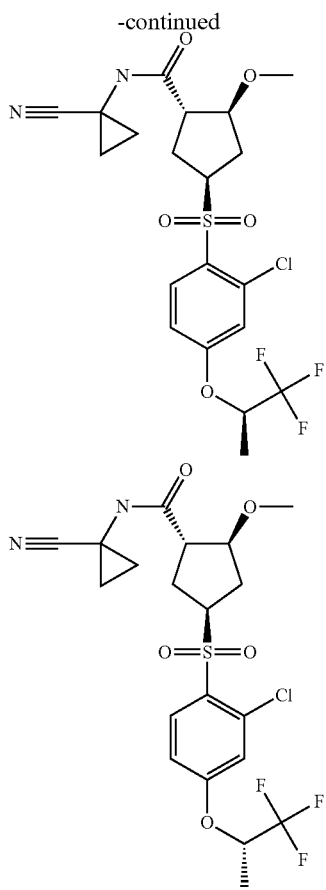

The title compound was prepared in analogy to example 57 using 1,1,1-trifluoroisopropanol instead of 4-fluorophenol. White solid. MS (EI): 493.1 (M–H)⁻.

Example 61

(1R,2R,4R) and (1S,2S,4S)-2-Methoxy-4-[4-(4-methyl-thiazol-2-yl)-2-trifluoromethyl-benzenesulfonyl]-cyclopentanecarboxylic acid (1-cyano-cyclopropyl)-amide

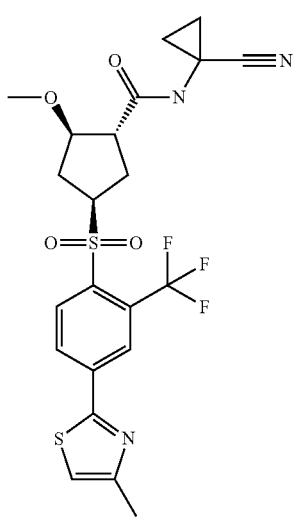

-continued

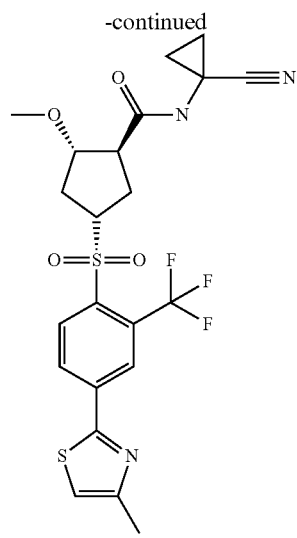

To a suspension of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide (40 mg, 0.0808 mmol, example 58) in dioxane (1.5 ml) was added a solution of 4-methyl-2-(tributylstannyl)-thiazole (38 mg, 0.0970 mmol) in dioxane (0.5 ml) and argon was bubbled through the resulting mixture for 10 minutes. Then LiCl (10 mg, 0.242 mmol) and tetrakis(triphenylphosphine)palladium (0) (5 mg, 0.00404 mmol) were added and the mixture was stirred at reflux for 3.5 h. The reaction mixture was allowed to cool to room temperature, diluted with DCM and filtered through a pad of silica gel. The filtrate was evaporated and the remaining light brown solid was purified by silica column chromatography (DCM/EtOAc 4:1) to obtain a white solid (15 mg) which was triturated with ether to obtain the title compound (9 mg, 22%) as a white solid.

Example 62

(1R,2R,4R) and (1S,2S,4S)-4-(2',4'-Difluoro-3-trifluoromethyl-biphenyl-4-sulfonyl)-2-methoxy-cyclopentanecarboxylic acid (1-cyano-cyclopropyl)-amide

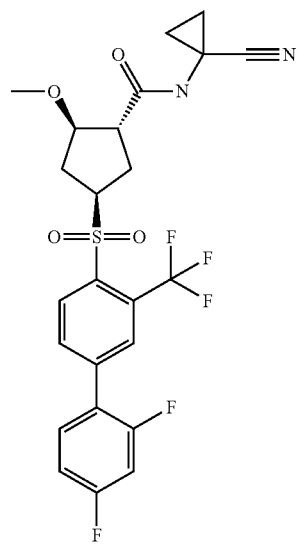

-continued

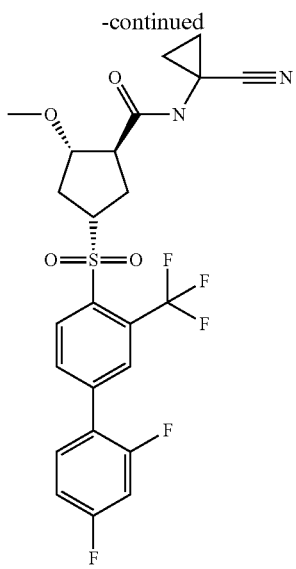

Argon was bubbled through a mixture of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide (30 mg, 0.0606 mmol, example 58), 2.4-difluorophenylboronic acid (11 mg, 0.0727 mmol) and $Na_2CO_3$ (17 mg, 0.1635 mmol) in DMF (1.5 ml) and water (81.8 ul) for 15 min. Then [1,1'-bis(diphenyl-phosphino)ferrocene]palladium(II) chloride 1:1 complex with DCM (5 mg, 0.00606 mmol) was added and the orange mixture was heated to 80° C. for 3 h. The mixture was then cooled to room temperature, poured onto a mixture of saturated NaHCO3 solution and ice and extracted 3 times with EtOAc. The combined extracts were washed with water and brine, dried over $Na_2SO_4$ and evaporated. The remaining brown solid was purified by silica gel chromatography (DCM/MeOH 98:2) to obtain the title compound (27 mg, 84%) as off-white solid. MS (EI): 529.2 $(M+H)^+$.

Example 63

(1R,2R,4R) and (1S,2S,4S)-4-(4'-Fluoro-3-trifluoromethyl-biphenyl-4-sulfonyl)-2-methoxy-cyclopentanecarboxylic acid (1-cyano-cyclopropyl)-amide

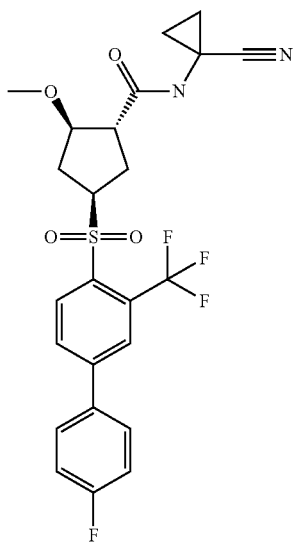

-continued

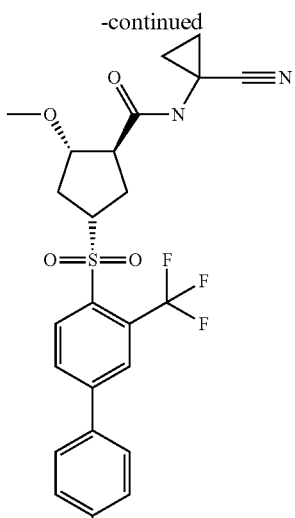

The title compound was prepared in analogy to example 62 using 4-fluorophenylboronic acid instead of 2.4-difluorophenylboronic acid. Off-white solid. MS (EI): 511.3 $(M+H)^+$.

Example 64

(1R,2R,4R) and (1S,2S,4S)-4-(2-Chloro-4-piperidin-1-yl-benzenesulfonyl)-2-methoxy-cyclopentanecarboxylic acid (1-cyano-cyclopropyl)-amide

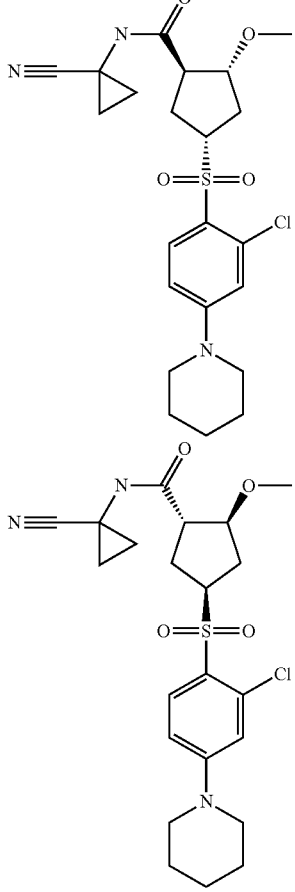

The title compound was prepared in analogy to example 57 using piperidine instead of 4-fluorophenol. White solid. MS (EI): 466.2 $(M+H)^+$.

Example 65

(1R,2R,4R) and (1S,2S,4S)-4-[2-Chloro-4-(2,2,2-trifluoro-ethoxy)-benzenesulfonyl]-2-methoxy-cyclopentanecarboxylic acid (1-cyano-cyclopropyl)-amide

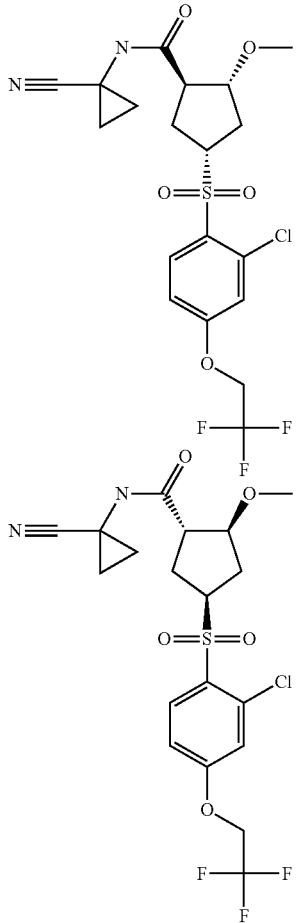

The title compound was prepared in analogy to example 57 using 2,2,2-trifluoroethanol instead of 4-fluorophenol. White solid. MS (EI): 479.1 (M−H)⁻.

Example 66

(1R,2R,4R) and (1S,2S,4S)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide

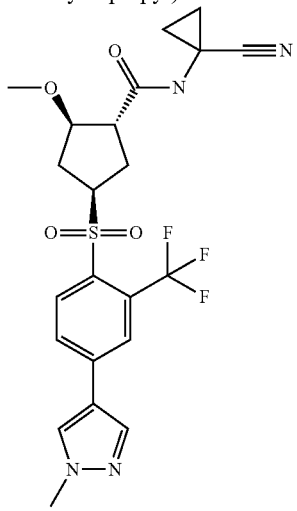

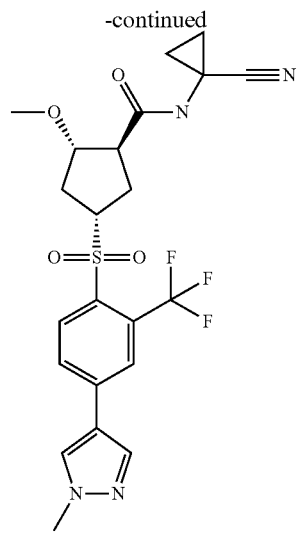

The title compound was prepared in analogy to example 62 using 1-methyl-4-(4.4.5.5-tetramethyl-1.3.2-dioxaborolan)-1H-pyrazole instead of 2.4-difluorophenylboronic acid. Light brown solid. MS (EI): 497.3 (M+H)⁺.

Example 67

(1R,2R,4R) and (1S,2S,4S)-4-[4-(2,5-Dimethyl-2H-pyrazol-3-yl)-2-trifluoromethyl-benzenesulfonyl]-2-methoxy-cyclopentanecarboxylic acid (1-cyano-cyclopropyl)-amide

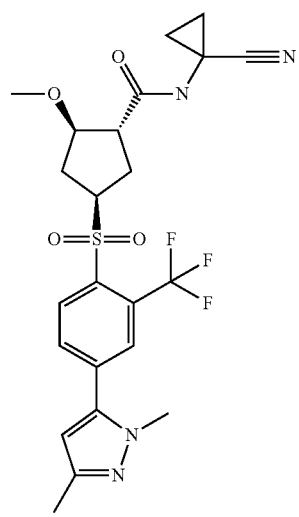

93

-continued

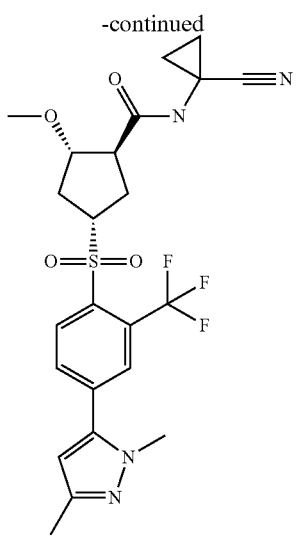

The title compound was prepared in analogy to example 62 using 1.3-dimethyl-5-(4.4.5.5-tetramethyl-1.3.2-dioxaborolan-2-yl-)-1H-pyrazole instead of 2.4-difluorophenylboronic acid. White foam. MS (EI): 511.3 (M+H)⁺.

Example 68 and Example 69

(1R,2R,4S)-4-(2-Chloro-benzenesulfonyl)-2-(4-chloro-phenoxymethyl)-cyclopentanecarboxylic acid cyanomethyl-amide and (1R,2R,4R)-4-(2-Chloro-benzenesulfonyl)-2-(4-chloro-phenoxymethyl)-cyclopentanecarboxylic acid cyanomethyl-amide

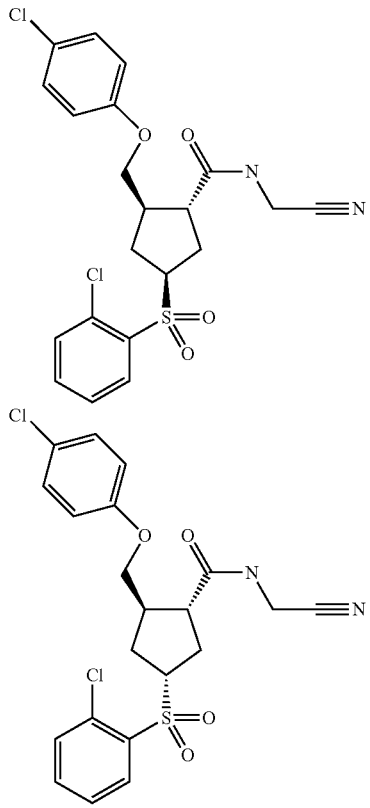

94

Step 1:
(1R,2R)-4-Hydroxy-cyclopentane-1,2-dicarboxylic acid monoethyl ester (epimeric mixture)

To a cold (ice bath solution of (1R,2R)-4-Oxo-cyclopentane-1,2-dicarboxylic acid monoethyl ester (3.0 g) in tetrahydrofuran (30 mL) was added sodium borohydride (737 mg) in several portions over 5.5 h. After 6.5 h, hydrochloric acid (1N, 40 mL) then sodium chloride (8 g) were added to the reaction mixture. After 30 min, the reaction mixture was extracted with ethyl acetate. The organic layers were dried over sodium sulfate and concentrated in vacuo to afford the title compound (3.2 g, 95%) as colorless oil, used in the next step without further purification. MS (EI): 201.2 (M−H)⁻.

Step 2: (1R,2R)-4-(tert-Butyl-dimethyl-silanyloxy)-cyclopentane-1,2-dicarboxylic acid 1-ethyl ester 2-(tert-Butyl-dimethyl-silanyl) ester (epimeric mixture)

To a solution (1R,2R)-4-Hydroxy-cyclopentane-1,2-dicarboxylic acid monoethyl ester (epimeric mixture, 3.14 g) in dimethylformamide (6 mL) was sequentially imidazole (5.29 g), tert-Butyl-dimethyl-silanylchloride (5.42 g) and dimethylformamide (2 mL). After 40 h at room temperature, the reaction mixture was diluted with ethyl acetate and washed sequentially with a saturated aqueous solution of ammonium chloride, a saturated aqueous solution of sodium hydrogenocarbonate and brine. The aqueous layer was extracted with ethyl acetate and the combined organic layers were dried over sodium sulfate and concentrated in vacuo to afford the title compound (6.88 g, 98%) as colorless oil, used in the next step without further purification. MS (EI): 431.4 (M+H)⁺.

Step 3: (1R,2R)-4-(tert-Butyl-dimethyl-silanyloxy)-cyclopentane-1,2-dicarboxylic acid monoethyl ester (epimeric mixture)

To a solution of (1R,2R)-4-(tert-Butyl-dimethyl-silanyloxy)-cyclopentane-1,2-dicarboxylic acid 1-ethyl ester 2-(tert-Butyl-dimethyl-silanyl) Ester (epimeric mixture, 12.09 g) in ethanol (340 mL) and tetrahydrofuran (114 mL) was slowly added a solution of potassium carbonate (16.68 g) in water (114 mL). After 45 min at room temperature, the solvents were removed in vacuo. Brine was added to the residue and the mixture was cooled to 0° C. then the pH was adjusted to 4-5 using a 10% aqueous solution of potassium hydrogenosulfate. The resulting mixture was extracted with diethylether. The combined organic layers were washed with brine then dried over sodium sulfate and concentrated in vacuo to afford the title compound (8.03 g, 90%) as light yellow oil, used in the next step without further purification. MS (EI): 315.2 (M−H)⁻.

Step 4: (1R,2R)-4-(tert-Butyl-dimethyl-silanyloxy)-2-hydroxymethyl-cyclopentanecarboxylic acid ethyl ester (epimeric mixture)

To a cold (ice bath) solution of (1R,2R)-4-(tert-Butyl-dimethyl-silanyloxy)-cyclopentane-1,2-dicarboxylic acid monoethyl ester (epimeric mixture, 0.7 g) in tetrahydrofuran (3.5 mL) was slowly added a borane complex with tetrahydrofuran (1M, 2.7 mL). The resulting solution was stirred for 3 h in the ice bath then slowly poured into water. The mixture was extracted with diethylether. The combined organic layers were washed with brine and dried over sodium sulfate then concentrated in vacuo. The residue was purified by flash chromatography on silica gel with cyclohexane/ethylacetate (6:1 v/v) as eluant to afford the title compound (0.49 g, 73%) as light yellow oil. MS (EI): 303.2 (M+H)+.

Step 5: (1R,2R)-4-(tert-Butyl-dimethyl-silanyloxy)-2-(4-chloro-phenoxymethyl)-cyclopentanecarboxylic acid ethyl ester (epimeric mixture)

To a cold (ice bath) mixture of (1R,2R)-4-(tert-Butyl-dimethyl-silanyloxy)-2-hydroxymethyl-cyclopentanecarboxylic acid ethyl ester (epimeric mixture, 250 mg), 4-chlorophenol (136 mg) and triphenylphoshine (256 mg) in dichloromethane (4 mL) and tetrahydrofuran (1.5 mL) was slowly added a solution of di-tert-butyl-azodicarboxylate (225 mg) in tetrahydrofuran (2.5 mL). The reaction mixture was stirred at room temperature for 2.5 days then concentrated in vacuo and the residue was purified by flash chromatography on silica gel with a gradient of cyclohexane/ethylacetate (1:0 to 9:1 v/v) as eluant to afford the title compound (0.304 g, 89%) as light yellow oil. MS (EI): 413.2 (M+H)+.

Step 6: (1R,2R)-2-(4-Chloro-phenoxymethyl)-4-hydroxy-cyclopentanecarboxylic acid ethyl ester (epimeric mixture)

To a cold (ice bath) solution of (1R,2R)-4-(tert-Butyl-dimethyl-silanyloxy)-2-(4-chloro-phenoxymethyl)-cyclopentanecarboxylic acid ethyl ester (epimeric mixture, 529 mg) in tetrahydrofuran (20 mL) was slowly added pyridine (8.1 g) and a pyridine-hydrofluoric acid complex (70% HF w/w, 9.07 g). The mixture was stirred 3 h at room temperature then solid sodium hydrogenocarbonate an aqueous saturated solution of sodium hydrogenocarbonate were added to adjust the pH to 7. The mixture was extracted with dichloromethane and the combined organic layers were washed with an aqueous saturated solution of sodium hydrogenocarbonate, dried over sodium sulfate and concentrated in vacuo. The residue was purified by flash chromatography on silica gel with a gradient of cyclohexane/ethylacetate (6:1 to 1:1 v/v) as eluant to afford the title compound (0.346 g, 90%) as a light yellow oil. MS (EI): 299.1 (M+H)+.

Step 7: (1R,2R)-2-(4-Chloro-phenoxymethyl)-4-methanesulfonyloxy-cyclopentanecarboxylic acid ethyl ester (epimeric mixture)

To a cold (ice bath) solution of (1R,2R)-2-(4-Chloro-phenoxymethyl)-4-hydroxy-cyclopentanecarboxylic acid ethyl ester (epimeric mixture, 312 mg) and triethylamine (528 mg) in dichloromethane (6 mL) was added methanesulfonyl chloride (580 mg). The reaction mixture was stirred 36 h at room temperature then hydrochloric acid (1N) was added. The reaction mixture was extracted with dichloromethane. The combined organic layers were washed with an aqueous half-saturated solution of sodium carbonate and half saturated brine then dried over sodium sulfate and concentrated in vacuo. The residue was purified by flash chromatography on silica gel with a gradient of cyclohexane/ethylacetate (3:1 to 3:1 v/v) as eluant to afford the title compound (0.380 g, 97%) as a light yellow oil. MS (EI): 377.1 (M+H)+.

Step 8: (1R,2R)-2-(4-Chloro-phenoxymethyl)-4-(2-chloro-phenylsulfanyl)-cyclopentanecarboxylic acid ethyl ester (epimeric mixture)

To a solution of 2-chlorobenzenthiol (306 mg) in tetrahydrofuran (4 mL) was added a suspension of sodium hydride in oil (55% w/w, 107 mg). The white suspension was cooled down to 0° C. then a solution of (1R,2R)-2-(4-Chloro-phenoxymethyl)-4-methanesulfonyloxy-cyclopentanecarboxylic acid ethyl ester (epimeric mixture, 343 mg) in tetrahydrofuran (5 mL) was slowly added. The reaction mixture was stirred at room temperature for 4 days. Hydrochloric acid (1N) was added and the mixture was extracted with ethyl acetate. The combined organic layers were washed with an aqueous saturated solution of sodiumcarbonate and brine then dried over sodium sulfate and concentrated in vacuo. The residue was purified by flash chromatography on silica gel with a gradient of cyclohexane/ethylacetate (19:1 to 3:1 v/v) as eluant to afford the title compound (0.205 g, 53%) as light yellow oil. MS (EI): 424.0 (M+H)+.

Step 9: (1R,2R)-4-(2-Chloro-benzenesulfonyl)-2-(4-chloro-phenoxymethyl)-cyclopentanecarboxylic acid ethyl ester (epimeric mixture)

To a cold (ice bath) solution of (1R,2R)-2-(4-Chloro-phenoxymethyl)-4-(2-chloro-phenylsulfanyl)-cyclopentanecarboxylic acid ethyl ester (epimeric mixture, 176 mg) in dichloromethane (3 mL) was slowly added a solution of meta-chloroperbenzoic acid (0.428 mg) in several portions, over 4 h. The reaction mixture was stirred 2 days at room temperature then diluted with dichloromethane. The mixture was washed with an aqueous solution of sodium hydrogenocarbonate (20% w/w) then an aqueous half-saturated solution of sodium carbonate and water. The aqueous layers were extracted with dichloromethane and the combined organic layers were dried over sodium sulfate and concentrated in vacuo. The residue was purified by flash chromatography on silica gel with a gradient of cyclohexane/ethylacetate (9:1 to 3:1 v/v) as eluant to afford the title compound (161 mg, 85%) as light yellow oil. MS (EI): 458.0 (M+H)+.

Step 10: (1R,2R)-4-(2-Chloro-benzenesulfonyl)-2-(4-chloro-phenoxymethyl)-cyclopentanecarboxylic acid (epimeric mixture)

To a solution of (1R,2R)-4-(2-Chloro-benzenesulfonyl)-2-(4-chloro-phenoxymethyl)-cyclopentanecarboxylic acid ethyl ester (epimeric mixture, 132 mg) in tetrandrofuran (2.4 mL), methanol (0.6 mL) and water (1.2 mL) was added lithium hydroxide monohydrate (14 mg). The mixture was stirred at 80° C. for 2.5 h then concentrated in vacuo. The residue was dissolved in water and the pH was adjusted to 1 with hydrochloric acid (2N). The precipitate was filtered, washed with water and dried in vacuo to afford the title compound (103 mg, 83%) as a white solid. MS (EI): 446.1 (M+NH$_4$)+.

Step 11: (1R,2R)-4-(2-Chloro-benzenesulfonyl)-2-(4-chloro-phenoxymethyl)-cyclopentanecarboxylic acid cyanomethyl-amide (epimeric mixture)

To a mixture of (1R,2R)-4-(2-Chloro-benzenesulfonyl)-2-(4-chloro-phenoxymethyl)-cyclopentanecarboxylic acid (epimeric mixture, 50 mg) in dimethylformamide (2 mL) was added 1-(3-dimethylaminopropyl)-3-ethylcarbodiimide hydrochloride (46 mg), hydroxybenzotriazole (24 mg) and ethyldiisopropylamine (61 mg). After 45 min, aminoacetonitrile (8 mg) was added and the reaction mixture was stirred for 2 days then partitioned between ethyl acetate and an aqueous saturated solution of sodium hydrogenocarbonate. The aqueous layer was extracted with ethyl acetate and the combined organic layers were washed with water then dried over sodium sulfate and concentrated in vacuo. The residue was purified by flash chromatography on silica gel with dichloromethane/methanol (19:1 v/v) as eluant to afford the title compound (53 mg, 97%) as light yellow oil. MS (EI): 467.0 (M+H)$^+$.

Step 12: (1R,2R,4S)-4-(2-Chloro-benzenesulfonyl)-2-(4-chloro-phenoxymethyl)-cyclopentanecarboxylic acid cyanomethyl-amide and (1R,2R,4R)-4-(2-Chloro-benzenesulfonyl)-2-(4-chloro-phenoxymethyl)-cyclopentanecarboxylic acid cyanomethyl-amide (1R,2R)-4-(2-Chloro-benzenesulfonyl)-2-(4-chloro-phenoxymethyl)-cyclopentanecarboxylic acid cyanomethyl-amide (epimeric mixture, 52 mg) was subjected to chiral preparative HPLC on Reprosil Chiral NR® using a Heptane/0.01N NH$_4$Ac in EtOH 60:40 v/v as eluant.

Fraction 1 (Rt: 17 min): (1R,2R,4S)-4-(2-Chloro-benzenesulfonyl)-2-(4-chloro-phenoxymethyl)-cyclopentanecarboxylic acid cyanomethyl-amide (11 mg, 21%). MS (EI): 467.1 (M+H)$^+$.

Fraction 2 (Rt: 21 min): (1R,2R,4R)-4-(2-Chloro-benzenesulfonyl)-2-(4-chloro-phenoxymethyl)-cyclopentanecarboxylic acid cyanomethyl-amide (10 mg, 19%). MS (EI): 467.1 (M+H)$^+$.

Example 70 and Example 71

(1R,2R,4S)-4-(2-Chloro-benzenesulfonyl)-2-(4-chloro-phenoxymethyl)-cyclopentanecarboxylic acid (1-cyano-cyclopropyl)-amide and (1R,2R,4R)-4-(2-Chloro-benzenesulfonyl)-2-(4-chloro-phenoxymethyl)-cyclopentanecarboxylic acid (1-cyano-cyclopropyl)-amide

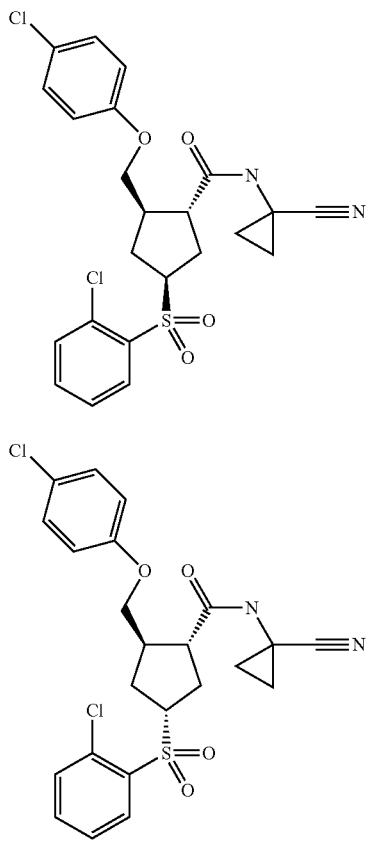

Step 1: (1R,2R)-4-(2-Chloro-benzenesulfonyl)-2-(4-chloro-phenoxymethyl)-cyclopentanecarboxylic acid (1-cyano-cyclopropyl)-amide (epimeric mixture)

The title compound was synthesized in analogy to Example 68/69, Step 11, from (1R,2R)-4-(2-Chloro-benzenesulfonyl)-2-(4-chloro-phenoxymethyl)-cyclopentanecarboxylic acid (epimeric mixture) and 1-amino-cyclopropyl cyanic hydrochloride to afford the desired product as a yellow oil. MS (EI): 493.2 (M)$^+$.

Step 2: (1R,2R,4S)-4-(2-Chloro-benzenesulfonyl)-2-(4-chloro-phenoxymethyl)-cyclopentanecarboxylic acid (1-cyano-cyclopropyl)-amide and (1R,2R,4R)-4-(2-Chloro-benzenesulfonyl)-2-(4-chloro-phenoxymethyl)-cyclopentanecarboxylic acid (1-cyano-cyclopropyl)-amide (1R,2R)-4-(2-Chloro-benzenesulfonyl)-2-(4-chloro-phenoxymethyl)-cyclopentanecarboxylic acid (1-cyano-cyclopropyl)-amide (epimeric mixture, 55 mg) was subjected to chiral preparative HPLC on Reprosil Chiral NR® using a Heptane/0.01N NH$_4$Ac in EtOH 60:40 v/v as eluant. Fraction 1 (Rt: 16 min): (1R,2R,4S)-4-(2-Chloro-benzenesulfonyl)-2-(4-chloro-phenoxymethyl)-cyclopentanecarboxylic acid (1-cyano-cyclopropyl)-amide (13 mg, 24%). MS (EI): 493.3 (M)$^+$.

Fraction 2 (Rt: 22 min): (1R,2R,4R)-4-(2-Chloro-benzenesulfonyl)-2-(4-chloro-phenoxymethyl)-cyclopentanecarboxylic acid (1-cyano-cyclopropyl)-amide (13 mg, 24%). MS (EI): 493.3 (M)$^+$.

Example 72

(1R,2R,4R) and (1S,2S,4S)-2-Methoxy-4-[4-(1-methyl-1H-pyrazol-5-yl)-2-trifluoromethyl-benzenesulfonyl]-cyclopentanecarboxylic acid (1-cyano-cyclopropyl)-amide

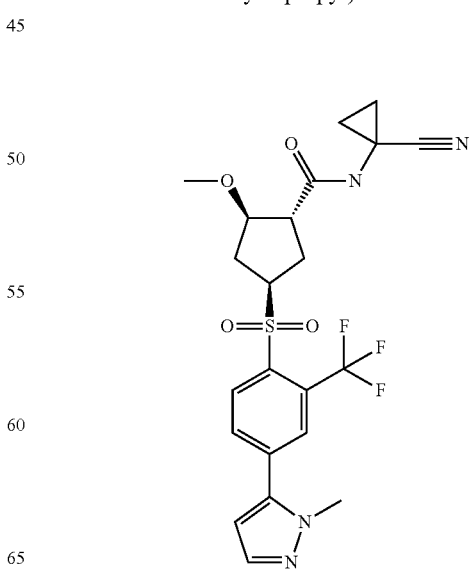

-continued

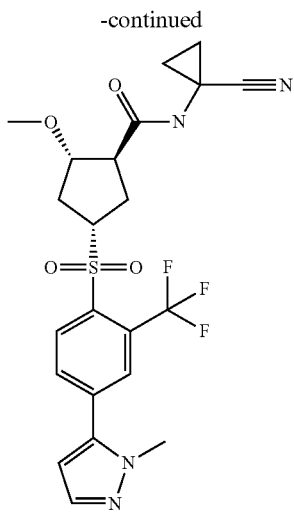

The title compound was prepared in analogy to example 62 using 1-methyl-5-(4.4.5.5-tetramethyl-1.3.2-dioxaborolan-2-yl)-1H-pyrazole instead of 2.4-difluorophenylboronic acid. White solid. MS (EI): 497.3 (M+H)+.

-continued

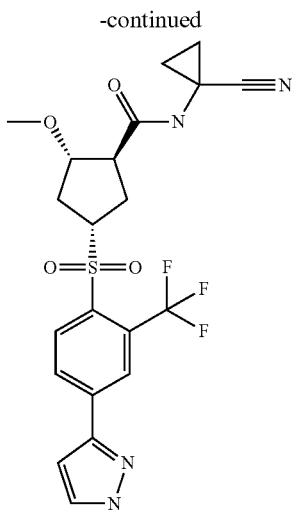

The title compound was prepared in analogy to example 62 using 1H-pyrazole-5-boronic acid pinacol ester instead of 2.4-difluorophenylboronic acid. Off-white solid. MS (EI): 483.2 (M+H)+.

Example 73

(1R,2R,4R) and (1S,2S,4S)-2-Methoxy-4-[4-(1H-pyrazol-3-yl)-2-trifluoromethyl-benzenesulfonyl]-cyclopentanecarboxylic acid (1-cyano-cyclopropyl)-amide

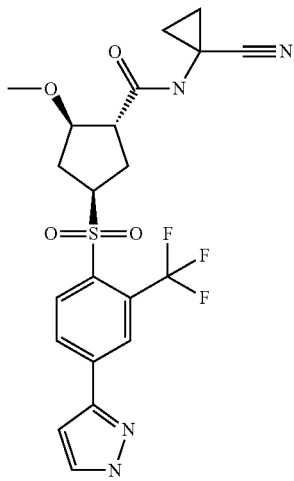

Example 74

(1R,2R,4R) and (1S,2S,4S)-4-(3',4'-Difluoro-3-trifluoromethyl-biphenyl-4-sulfonyl)-2-methoxy-cyclopentanecarboxylic acid (1-cyano-cyclopropyl)-amide

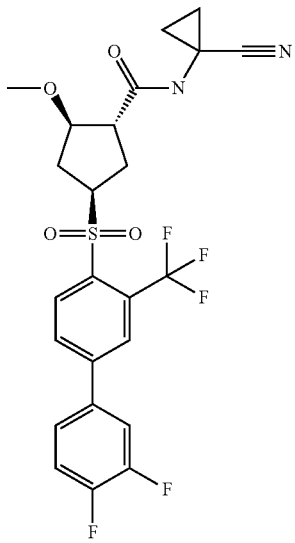

-continued

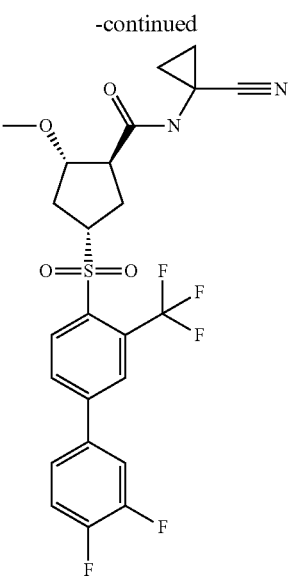

The title compound was prepared in analogy to example 62 using 3.4-difluorophenylboronic acid instead of 2.4-difluorophenylboronic acid. Off-white solid. MS (EI): 529.2 (M+H)⁺.

Example 75

(1R,2R,4R) and (1S,2S,4S)-4-(4'-Methanesulfonyl-3-trifluoromethyl-biphenyl-4-sulfonyl)-2-methoxy-cyclopentanecarboxylic acid (1-cyano-cyclopropyl)-amide

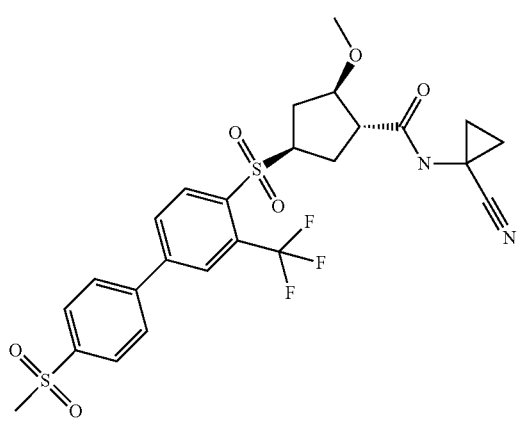

-continued

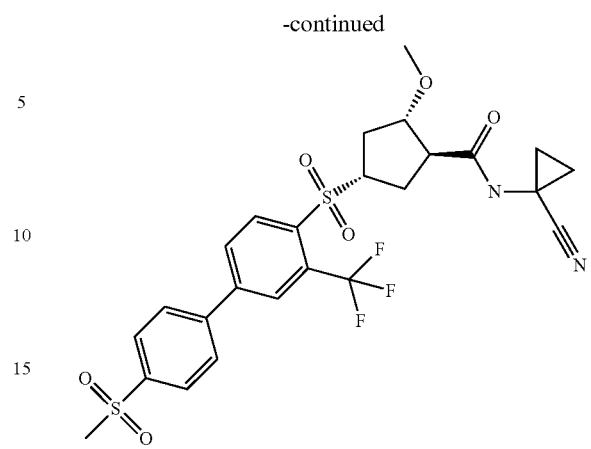

The title compound was prepared in analogy to example 62 using 4-(methylsulfonyl)-phenylboronic acid instead of 2.4-difluorophenylboronic acid. White solid. MS (EI): 571.3 (M+H)⁺.

Example 76

(1R,2R,4R) and (1S,2S,4S)-2-Methoxy-4-(4'-sulfamoyl-3-trifluoromethyl-biphenyl-4-sulfonyl)-cyclopentanecarboxylic acid (1-cyano-cyclopropyl)-amide

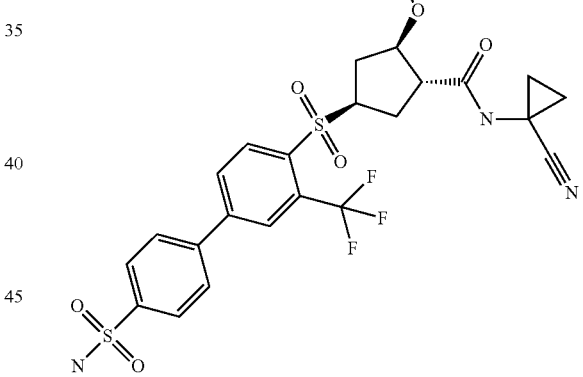

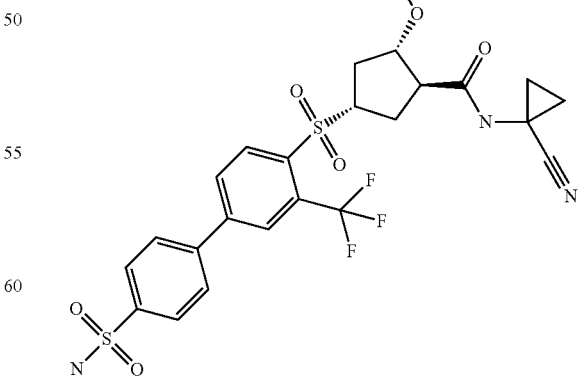

The title compound was prepared in analogy to example 62 using 4-(4.4.5.5-tetramethyl-1.3.2-dioxaborolan-2-yl)-benzenesulfonamide instead of 2.4-difluorophenylboronic acid. Light brown solid. MS (EI): 572.2 (M+H)+.

Example 77

(1R,2R,4R) and (1S,2S,4S)-2-Methoxy-4-[4-(2-methyl-pyridin-4-yl)-2-trifluoromethyl-benzenesulfonyl]-cyclopentanecarboxylic acid (1-cyano-cyclopropyl)-amide

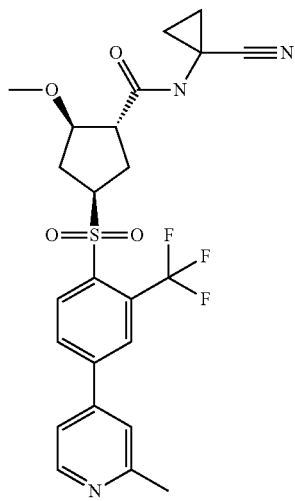

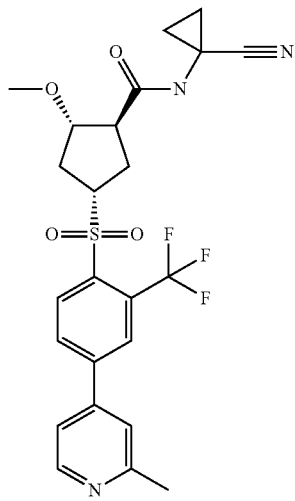

The title compound was prepared in analogy to example 62 using 2-picoline-4-boronic acid instead of 2.4-difluorophenylboronic acid. White solid. MS (EI): 508.2 (M+H)+.

Example 78

(1R,2R,4R) and (1S,2S,4S)-2-Methoxy-4-[4-(6-methoxy-pyridin-3-yl)-2-trifluoromethyl-benzenesulfonyl]-cyclopentanecarboxylic acid (1-cyano-cyclopropyl)-amide

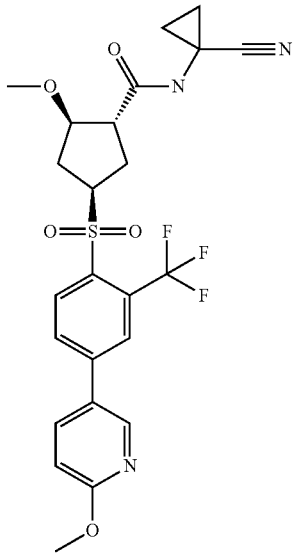

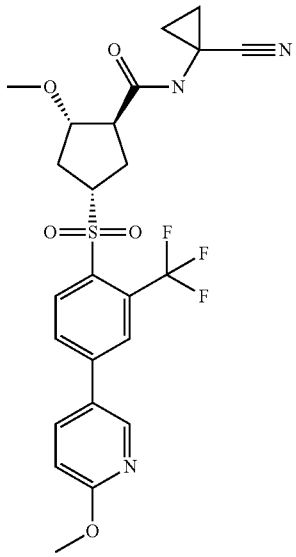

The title compound was prepared in analogy to example 62 using 2-methoxy-5-pyridineboronic acid instead of 2.4-difluorophenylboronic acid. Light brown solid. MS (EI): 524.2 (M+H)+.

Example 79

(1S,3S) and (1R,3R)-3-(2-Chloro-4-fluoro-benzene-sulfonyl)-cyclopentanecarboxylic acid cyanomethyl-amide

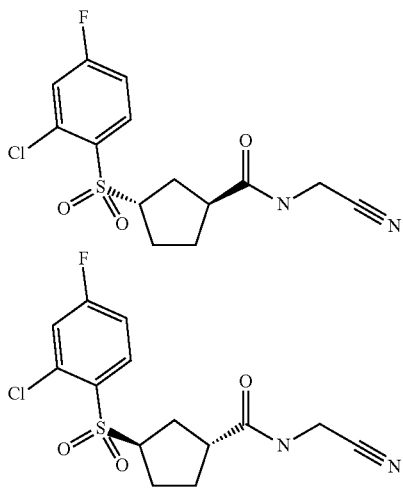

Step 1: Rac-3-Oxo-cyclopentanecarboxylic acid tert-butyl ester

To a cold (ice bath) solution of 3-oxo-1-cyclopentanecarboxylic acid (1.50 g), tert-butylalcohol (1.05 g) and 4-dimethylaminopyridine (140 mg) in dichloromethane (9 mL) was added a solution of dicyclocarbodiimide in dichloromethane (9 mL). The mixture was stirred 3 hours at ca. 2° C. then diethylether (30 mL) was added and the precipitate was filtered off and discarded. The solution was concentrated in vacuo. The residue was purified by flash chromatography on silica gel with cyclohexane/ethyl acetate (9:1 v/v) as eluant to afford the title compound (1.80 g, 96%) as colorless oil. MS (EI): 111 (M-OtBu.)$^+$.

Step 2: Rac-(1S,3R)-3-Hydroxy-cyclopentanecarboxylic acid tert-butyl ester

To a cold (ice bath) solution of Rac-3-Oxo-cyclopentanecarboxylic acid tert-butyl ester (1.43 g) in methanol (9 mL) was added sodium borohydride (0.293 g). The mixture was stirred 25 min at 0-5° C. then concentrated in vacuo. Ethyl acetate was added to the residue and the mixture was washed with water, dried over sodium sulfate and concentrated in vacuo. The residue was purified by flash chromatography on silica gel with dichloromethane/methanol (19:1 v/v) as eluant to afford the title compound (0.963 g, 67%) as colorless oil. MS (EI): 187.1 (M+H)$^+$.

Step 3: Rac-(1S,3R)-3-Methanesulfonyloxy-cyclopentanecarboxylic acid tert-butyl ester To a cold (−20° C.) solution of Rac-(1S,3R)-3-Hydroxy-cyclopentanecarboxylic acid tert-butyl ester (0.905 g) in dichloromethane (12 mL) was added methanesulfonylchloride (0.664 g) and triethylamine (0.636 g). The reaction mixture was stirred 10 min at −20° C. then poured into ice-water. Organic layer was washed with brine and dried over sodium sulfate then concentrated in vacuo to afford the title compound (1.15 g, 89%) as light yellow oil, used without further purification in the next step. MS (EI): 282 (M+NH$_4$)$^+$.

Step 4: Rac-(1S,3S)-3-(2-Chloro-4-fluoro-phenylsulfanyl)-cyclopentanecarboxylic acid tert-butyl ester To a mixture of 2-chloro-4-fluorophenol (1.06 g) in tetrahydrofuran (15 mL) was added sodium hydride (55% dispersion in oil, 322 mg) and the white suspension was stirred 15 min then cooled down to 0-5° C. A solution of Rac-(1S,3R)-3-Methanesulfonyloxy-cyclopentanecarboxylic acid tert-butyl ester in tetrahydrofuran (15 mL) was added slowly and the reaction mixture was stirred at room temperature overnight. Hydrochloric acid (1M) was added and the reaction mixture was extracted with ethyl acetate. Combined organic layers were washed with an aqueous saturated solution of sodium carbonate and brine then dried over sodium sulfate and concentrated in vacuo. The residue was purified by flash chromatography on silica gel with a gradient of cyclohexane/ethyl acetate (99:1 to 98:2 v/v) as eluant to afford the title compound (0.793 g, 88%) as light yellow oil. MS (EI): 348.2 (M+NH$_4$)$^+$.

Step 5: Rac-(1S,3S)-3-(2-Chloro-4-fluoro-benzenesulfonyl)-cyclopentanecarboxylic acid tert-butyl ester The title compound was synthesized in analogy to Example 68/69, Step 9, from Rac-(1S,3S)-3-(2-Chloro-4-fluoro-phenylsulfanyl)-cyclopentanecarboxylic acid tert-butyl ester to afford the desired product as a light yellow oil. MS (EI): 380.1 (M+NH$_4$)$^+$.

Step 6: Rac-(1S,3S)-3-(2-Chloro-4-fluoro-benzenesulfonyl)-cyclopentanecarboxylic acid To a mixture of Rac-(1S,3S)-3-(2-Chloro-4-fluoro-benzenesulfonyl)-cyclopentanecarboxylic acid tert-butyl ester (278 mg) in dichloromethane (4 mL) was added trifluoroacetic acid (1.34 g). The reaction mixture was stirred overnight at room temperature and the volatiles were removed in vacuo to afford the title compound (282 mg, quant.) as light brown oil, used in the next step without further purification. MS (EI): 305.1 (M−H)$^-$.

Step 7: (1S,3S) and (1R,3R)-3-(2-Chloro-4-fluoro-benzenesulfonyl)-cyclopentanecarboxylic acid cyanomethyl-amide The title compound was synthesized in analogy to Example 68/69, Step 11, from Rac-(1S,3S)-3-(2-Chloro-4-fluoro-benzenesulfonyl)-cyclopentanecarboxylic acid to afford the desired product as a light yellow oil. MS (EI): 362.1 (M+NH$_4$)$^+$.

Example 80

(1S,3S)-3-[2-Chloro-4-(2,2,2-trifluoro-1-methyl-ethoxy)-benzenesulfonyl]-cyclopentanecarboxylic acid cyanomethyl-amide (epimeric mixture of racemate)

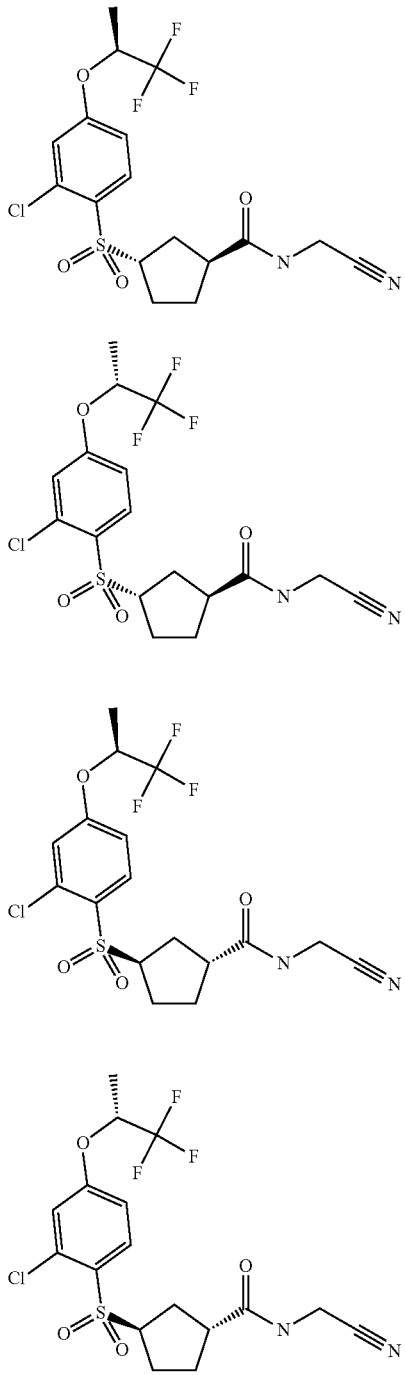

To a mixture of Rac-(1S,3S)-3-(2-Chloro-4-fluoro-benzenesulfonyl)-cyclopentanecarboxylic acid cyanomethyl-amide (40 mg) in dimethylformamide (3 mL) was added Rac-1,1,1-trifluoroisopropanol (40 mg) and cesium carbonate (113 mg). The reaction mixture was stirred at 50° C. overnight then diluted with ethyl acetate and washed with water and brine then dried over sodium sulfate and concentrated in vacuo. The residue was purified by flash chromatography on silica gel with dichloromethane/methanol (98:2 v/v) as eluant to afford the title compound (36 mg, 70%) as colorless oil. MS (EI): 437.0 (M−H)⁻.

Example 81

(1R,2R,4R) and (1S,2S,4S)-2-Methoxy-4-[4-(6-methyl-pyridin-3-yl)-2-trifluoromethyl-benzenesulfonyl]-cyclopentanecarboxylic acid (1-cyano-cyclopropyl)-amide

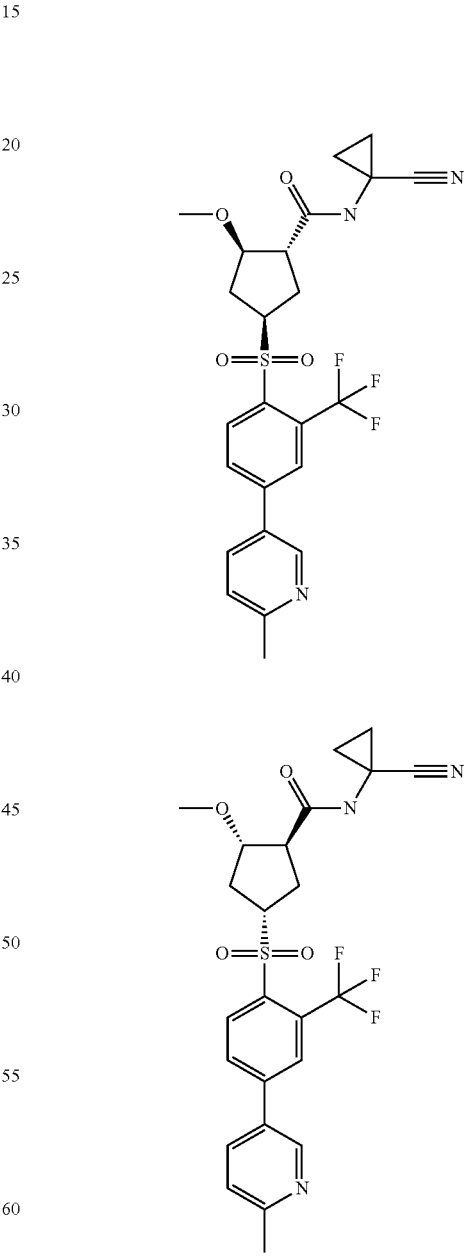

The title compound was prepared in analogy to example 62 using 2-methyl-5-pyridinylboronic acid instead of 2.4-difluorophenylboronic acid. White solid. MS (EI): 508.2 (M+H)⁺.

Example 82

(1R,2R,4R) and (1S,2S,4S)-2-Methoxy-4-(4-pyrimidin-5-yl-2-trifluoromethyl-benzenesulfonyl)-cyclopentanecarboxylic acid (1-cyano-cyclopropyl)-amide

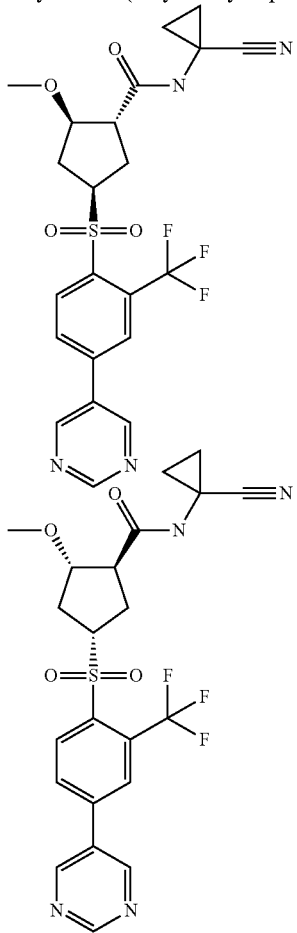

The title compound was prepared in analogy to example 62 using pyrimidine-5-boronic acid instead of 2.4-difluorophenylboronic acid. White solid. MS (EI): 495.2 (M+H)+.

Example 83

(1R,2R,4R) and (1S,2S,4S)-4-[4-(5-Methanesulfonyl-pyridin-3-yl)-2-trifluoromethyl-benzenesulfonyl]-2-methoxy-cyclopentanecarboxylic acid (1-cyano-cyclopropyl)-amide

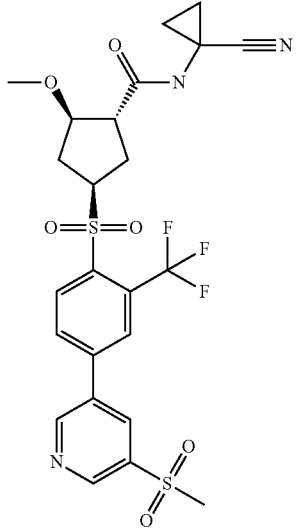

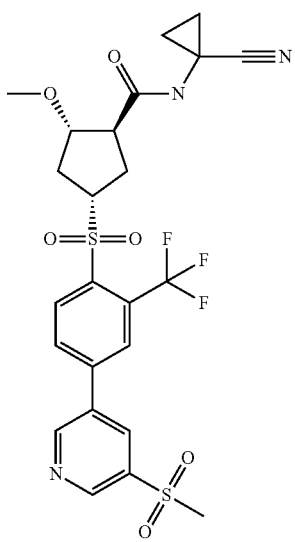

The title compound was prepared in analogy to example 62 using 5-(methylsulfonyl)-3-pyridineboronic acid instead of 2.4-difluorophenylboronic acid. White solid. MS (EI): 572.2 (M+H)+.

Example 84

(1R,2R,4R) and (1S,2S,4S)-4-[4-(5-Fluoro-pyridin-3-yl)-2-trifluoromethyl-benzenesulfonyl]-2-methoxy-cyclopentanecarboxylic acid (1-cyano-cyclopropyl)-amide

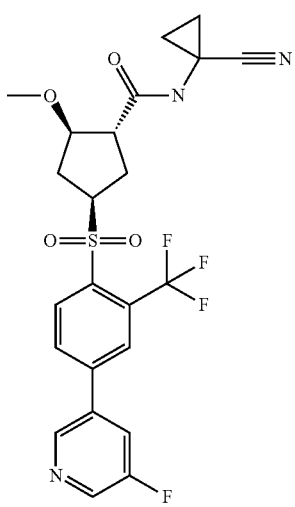

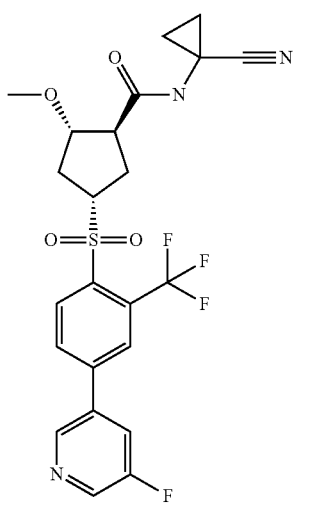

The title compound was prepared in analogy to example 62 using 3-fluoropyridine-5-boronic acid pinacol ester instead of 2.4-difluorophenylboronic acid. Light yellow solid. MS (EI): 512.3 (M+H)$^+$.

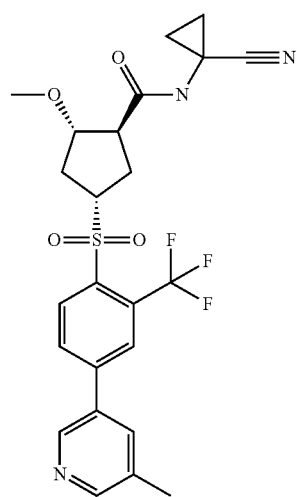

The title compound was prepared in analogy to example 62 using 5-methyl-3-pyridinyl-boronic acid instead of 2.4-difluorophenylboronic acid. White solid. MS (EI): 508.1 (M+H)$^+$.

Example 85

(1R,2R,4R) and (1S,2S,4S)-2-Methoxy-4-[4-(5-methyl-pyridin-3-yl)-2-trifluoromethyl-benzenesulfonyl]-cyclopentanecarboxylic acid (1-cyano-cyclopropyl)-amide Example 86

(1R,2R,4R) and (1S,2S,4S)-2-Methoxy-4-[4-(5-methoxy-pyridin-3-yl)-2-trifluoromethyl-benzenesulfonyl]-cyclopentanecarboxylic acid (1-cyano-cyclopropyl)-amide

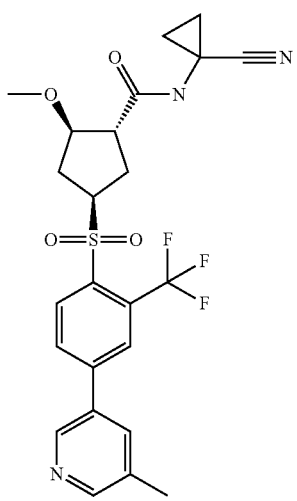

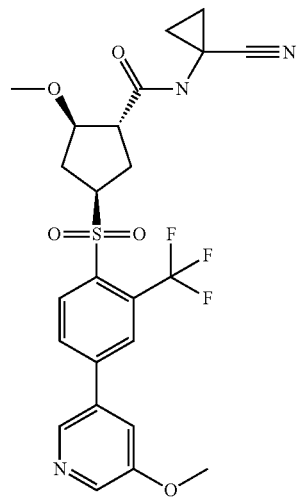

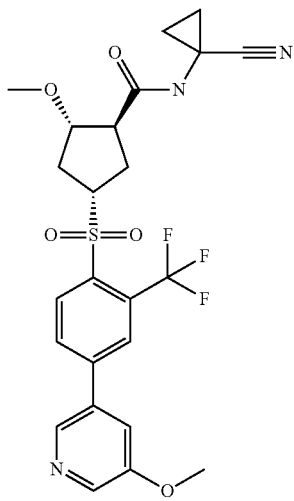

The title compound was prepared in analogy to example 62 using 5-methoxypyridine-3-boronic acid instead of 2.4-difluorophenylboronic acid. Off-white solid. MS (EI): 524.2 (M+H)$^+$.

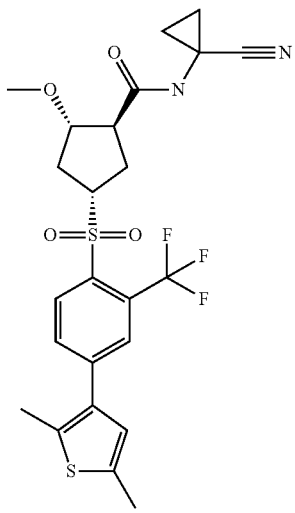

The title compound was prepared in analogy to example 62 using 2.5-dimethylthiophene-3-boronic acid instead of 2.4-difluorophenylboronic acid. Light yellow solid. MS (EI): 527.2 (M+H)$^+$.

Example 87

(1R,2R,4R) and (1S,2S,4S)-4-[4-(2,5-Dimethyl-thiophen-3-yl)-2-trifluoromethyl-benzenesulfonyl]-2-methoxy-cyclopentanecarboxylic acid (1-cyano-cyclopropyl)-amide Example 88

(1R,2R,4R) and (1S,2S,4S)-4-[2-Chloro-4-(3-methyl-6-oxo-6H-pyridazin-1-yl)-benzenesulfonyl]-2-methoxy-cyclopentanecarboxylic acid (1-cyano-cyclopropyl)-amide

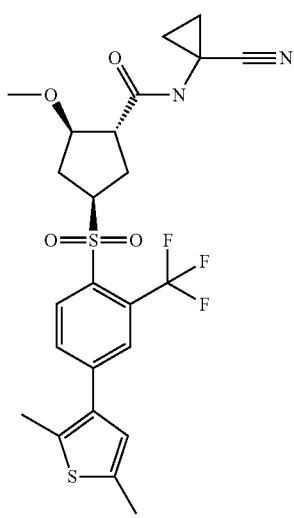

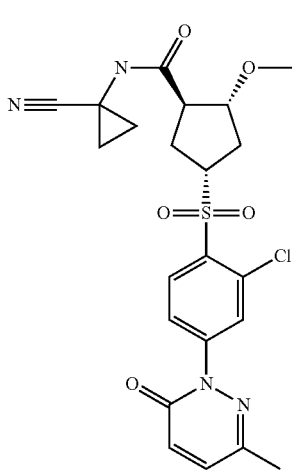

-continued

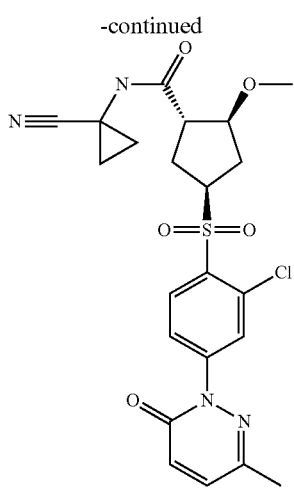

The title compound was prepared in analogy to example 57 using 6-methyl-3(2H)-pyridazinone instead of 4-fluorophenol. White solid. MS (EI): 489.1 (M–H)⁻.

Example 89

(1R,2R,4R) and (1S,2S,4S)-4-(2-Chloro-4-methoxy-benzenesulfonyl)-2-methoxy-cyclopentanecarboxylic acid (1-cyano-cyclopropyl)-amide

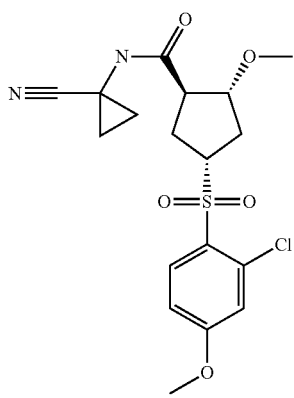

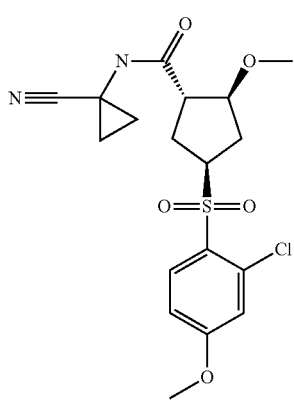

The title compound can be prepared in analogy to example 57 using methanol instead of 4-fluorophenol. White solid. MS (EI): 411.2 (M–H)⁻.

Example 90

(1R,2R,4R) and (1S,2S,4S)-4-[4-(5-Chloro-pyridin-3-yl)-2-trifluoromethyl-benzenesulfonyl]-2-methoxy-cyclopentanecarboxylic acid (1-cyano-cyclopropyl)-amide

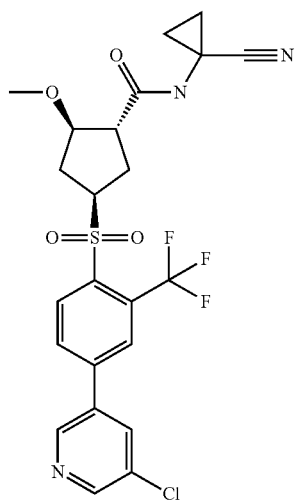

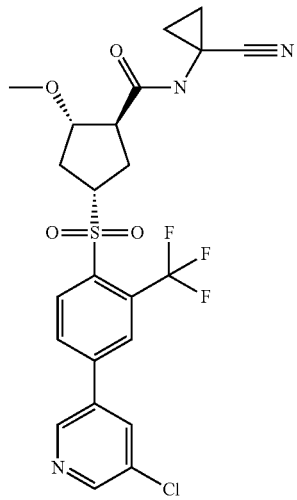

The title compound was prepared in analogy to example 62 using 3-chloropyridine-5-boronic acid instead of 2.4-difluorophenylboronic acid. Off-white solid. MS (EI): 528.2 (M+H)⁺.

Example 91

(1R,2R,4R) and (1S,2S,4S)-4-[4-(3,5-Dimethyl-isoxazol-4-yl)-2-trifluoromethyl-benzenesulfonyl]-2-methoxy-cyclopentanecarboxylic acid (1-cyanocyclopropyl)-amide

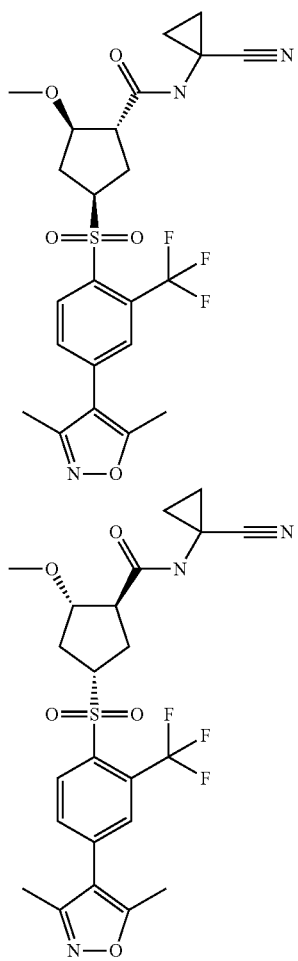

The title compound was prepared in analogy to example 62 using 3,5-dimethyl-isoxazole-4-boronic acid instead of 2.4-difluorophenylboronic acid. Light brown foam. MS (EI): 512.3 (M+H)⁺.

Example 92

(1S,3S) and (1R,3R)-3-(2-Chloro-4-fluoro-benzenesulfonyl)-cyclopentanecarboxylic acid (1-cyanocyclopropyl)-amide

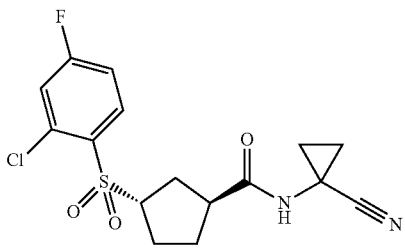

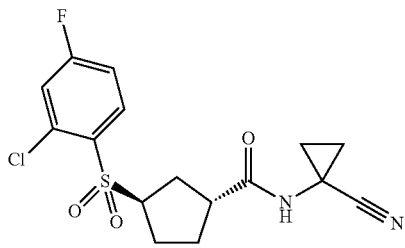

The title compound was synthesized in analogy to Example 68/69, Step 11, from rac-(1S,3S)-3-(2-chloro-4-fluoro-benzenesulfonyl)-cyclopentanecarboxylic acid and 1-amino-cyclopropanecarbonitrile to afford the desired product as a light yellow oil. MS (EI): 371.0 (M+H)⁺.

Example 93

(1S,3S)-3-[2-Chloro-4-((R/S)-2,2,2-trifluoro-1-methyl-ethoxy)-benzenesulfonyl]-cyclopentanecarboxylic acid and (1R,3R)-3-[2-Chloro-4-((R/S)-2,2,2-trifluoro-1-methyl-ethoxy)-benzenesulfonyl]-cyclopentanecarboxylic acid

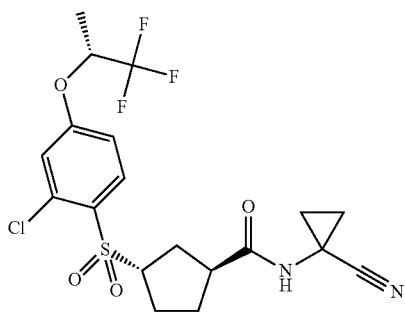

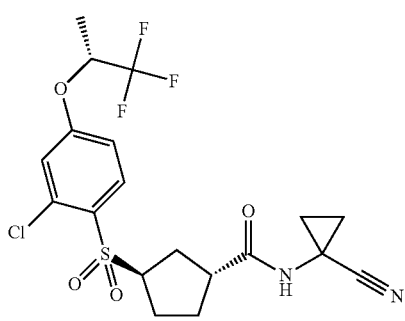

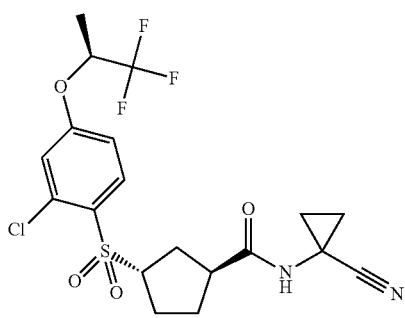

119

-continued

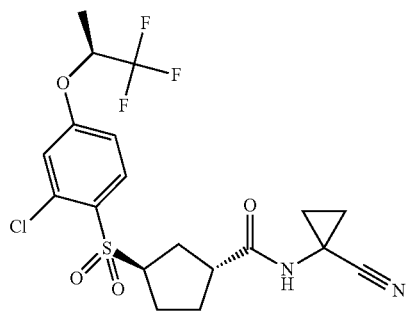

The title compound was synthesized in analogy to Example 80, from Rac-(1S,3S)-3-(2-chloro-4-fluoro-benzenesulfonyl)-cyclopentanecarboxylic acid (1-cyano-cyclopropyl)-amide and 1,1,1-trifluoro-propan-2-ol to afford the desired product as a light yellow oil. MS (EI): 465.1 (M+H)$^+$.

Example 94

(1S,3S) and (1R,3R)-3-(2-Chloro-4-morpholin-4-yl-benzenesulfonyl)-cyclopentanecarboxylic acid (1-cyano-cyclopropyl)-amide

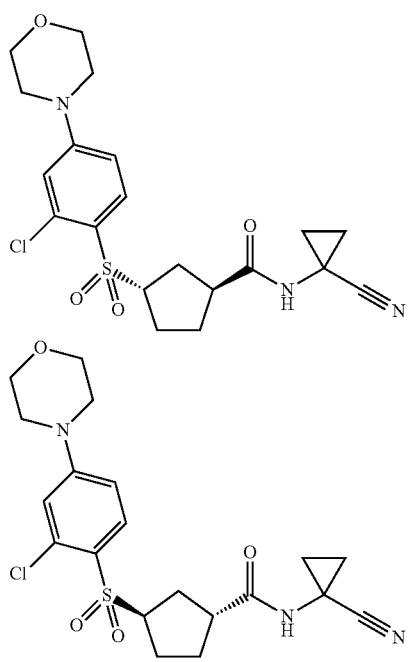

The title compound was synthesized in analogy to Example 80, from Rac-(1S,3S)-3-(2-chloro-4-fluoro-benzenesulfonyl)-cyclopentanecarboxylic acid (1-cyano-cyclopropyl)-amide and morpholine to afford the desired product as a light yellow oil. MS (EI): 438.2 (M+H)$^+$.

120

Example 95

(1S,3S) and (1R,3R)-3-[2-chloro-4-(2-oxa-6-aza-spiro[3.3]hept-6-yl)-benzenesulfonyl]-cyclopentanecarboxylic acid (1-cyano-cyclopropyl)-amide

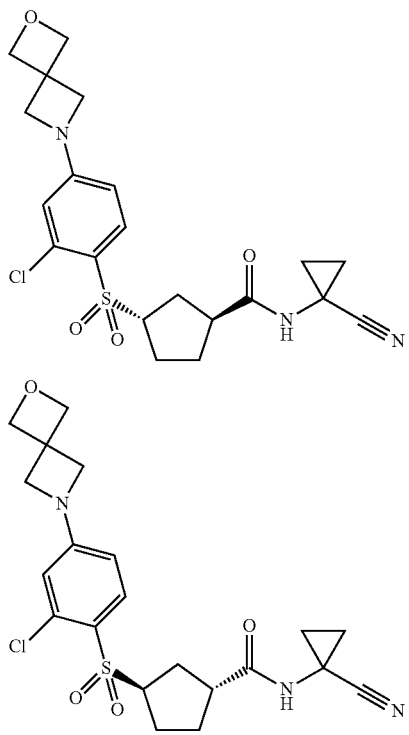

The title compound was synthesized in analogy to Example 80, from Rac-(1S,3S)-3-(2-chloro-4-fluoro-benzenesulfonyl)-cyclopentanecarboxylic acid (1-cyano-cyclopropyl)-amide and 2-oxa-6-aza-spiro[3.3]heptane as oxalic acid salt (CAS [1045709-32-7]; Angew. Chem. Int. Ed. 2008, 47, 4512-4515) to afford the desired product as a light yellow oil. MS (EI): 450.2 (M+H)$^+$.

Example 96

(1S,3S) and (1R,3R)-3-[2-chloro-4-(3,3-difluoro-pyrrolidin-1-yl)-benzenesulfonyl]-cyclopentanecarboxylic acid (1-cyano-cyclopropyl)-amide

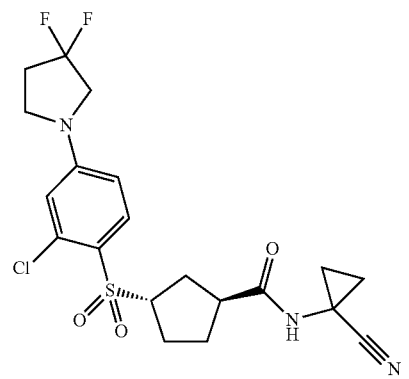

-continued

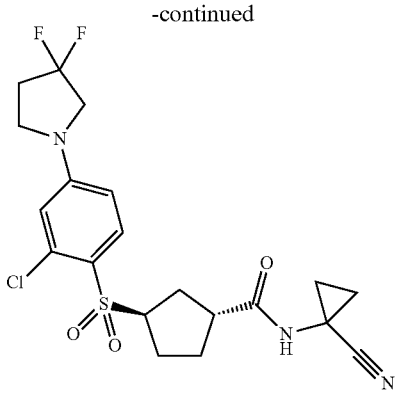

The title compound was synthesized in analogy to Example 80, from rac-(1S,3S)-3-(2-chloro-4-fluoro-benzenesulfonyl)-cyclopentanecarboxylic acid (1-cyano-cyclopropyl)-amide and 3,3-difluoro-pyrrolidine to afford the desired product as a light yellow oil. MS (EI): 458.2 (M+H)⁺.

Example 97

(1S,3S) and (1R,3R)-3-[2-chloro-4-(4-ethyl-piperazin-1-yl)-benzenesulfonyl]-cyclopentanecarboxylic acid (1-cyano-cyclopropyl)-amide

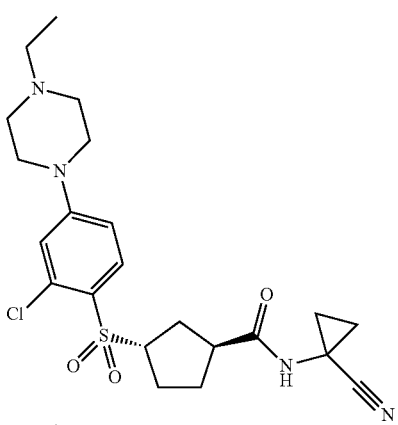

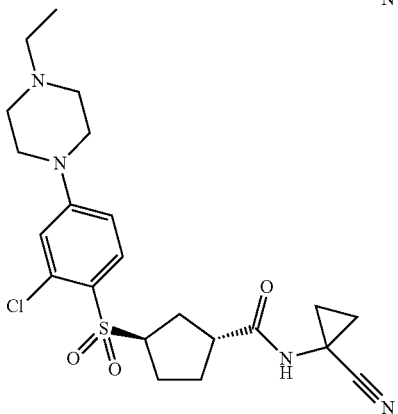

The title compound was synthesized in analogy to Example 80, from rac-(1S,3S)-3-(2-chloro-4-fluoro-benzenesulfonyl)-cyclopentanecarboxylic acid (1-cyano-cyclopropyl)-amide and 1-ethyl-piperazine to afford the desired product as a light yellow oil. MS (EI): 465.2 (M+H)⁺.

Example 98 and Example 99

(1S,3S) and (1R,3R)-3-[2-chloro-4-(2,2,2-trifluoro-ethoxy)-benzenesulfonyl]-cyclopentanecarboxylic acid (1-cyano-cyclopropyl)-amide and (1S,3R) and (1R,3S)-3-[2-chloro-4-(2,2,2-trifluoro-ethoxy)-benzenesulfonyl]-cyclopentanecarboxylic acid (1-cyano-cyclopropyl)-amide

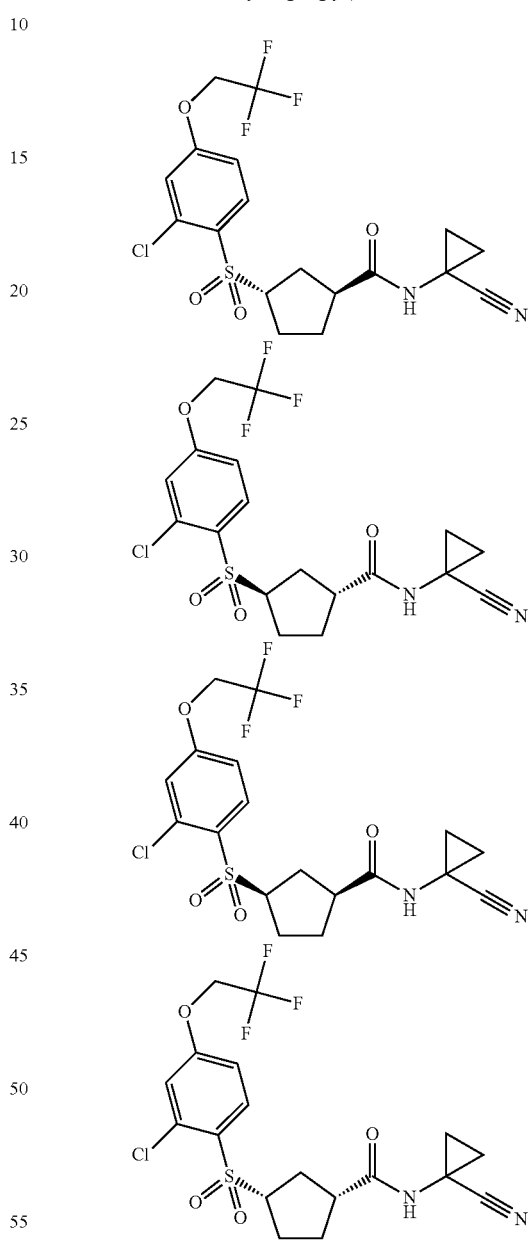

To a mixture of rac-(1S,3S)-3-(2-chloro-4-fluoro-benzenesulfonyl)-cyclopentanecarboxylic acid (1-cyano-cyclopropyl)-amide (70 mg) in dimethylformamide (4 mL) was added 2,2,2-trifluoro-ethanol (57 mg) and cesium carbonate (185 mg). The reaction mixture was stirred at 50° C. overnight then diluted with ethyl acetate and washed with water and brine then dried over sodium sulfate and concentrated in vacuo. The residue was purified by flash chromatography on silica gel with cyclohexane/ethyl acetate (1:1 v/v) as eluant. 2

Fractions were collected and evaporated to dried in vacuo to afford to afford the title compounds.

Fraction 1 (Rf: 0.3 in cyclohexane/ethyl acetate 1:3): 26 mg; white foam; rac-(1S,3S)-3-[2-chloro-4-(2,2,2-trifluoro-ethoxy)-benzenesulfonyl]-cyclopentanecarboxylic acid (1-cyano-cyclopropyl)-amide. MS (EI): 450.9 (M+H)$^+$.

Fraction 2 (Rf: 0.5 in cyclohexane/ethyl acetate 1:3): 54 mg, white, foam; rac-(1S,3R)-3-[2-chloro-4-(2,2,2-trifluoro-ethoxy)-benzenesulfonyl]-cyclopentanecarboxylic acid (1-cyano-cyclopropyl)-amide. MS (EI): 450.9 (M+H)$^+$.

Example 100 and Example 101

(1S,3S) and (1R,3R)-3-(2-chloro-4-pyrazol-1-yl-benzenesulfonyl)-cyclopentanecarboxylic acid (1-cyano-cyclopropyl)-amide and (1S,3R) and (1R,3S)-3-(2-chloro-4-pyrazol-1-yl-benzenesulfonyl)-cyclopentanecarboxylic acid (1-cyano-cyclopropyl)-amide

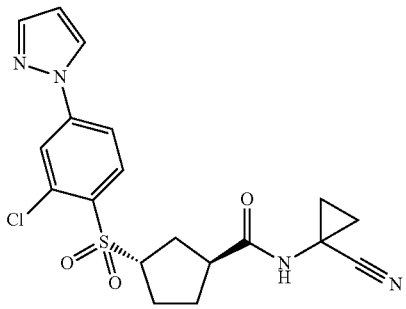

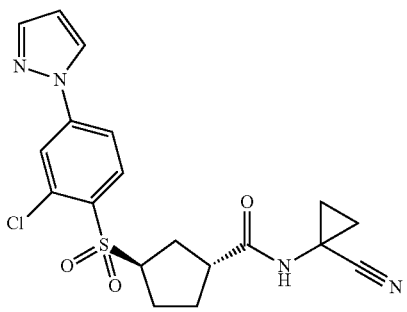

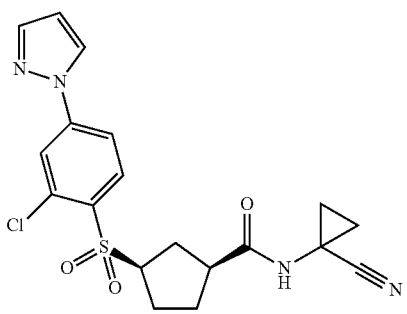

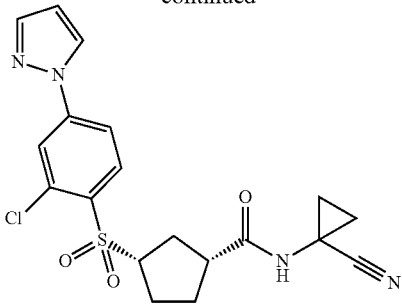

The title compounds were synthesized in analogy to Example 98/99, from rac-(1S,3S)-3-(2-chloro-4-fluoro-benzenesulfonyl)-cyclopentanecarboxylic acid (1-cyano-cyclopropyl)-amide and 1H-pyrazole to afford the desired products.

Fraction 1 (Rf: 0.4 in cyclohexane/ethyl acetate 1:3): 18 mg; white solid; rac-(1S,3S)-3-(2-chloro-4-pyrazol-1-yl-benzenesulfonyl)-cyclopentanecarboxylic acid (1-cyano-cyclopropyl)-amide. MS (EI): 419.2 (M+H)$^+$.

Fraction 2 (Rf: 0.2 in cyclohexane/ethyl acetate 1:3): 10 mg, white solid; rac-(1S,3R)-3-(2-chloro-4-pyrazol-1-yl-benzenesulfonyl)-cyclopentanecarboxylic acid (1-cyano-cyclopropyl)-amide. MS (EI): 419.2 (M+H)$^+$.

Example 102

(1S,3S) and (1R,3R)-3-[2-Chloro-4-(4-cyclopropyl-piperazin-1-yl)-benzenesulfonyl]-cyclopentanecarboxylic acid (1-cyano-cyclopropyl)-amide

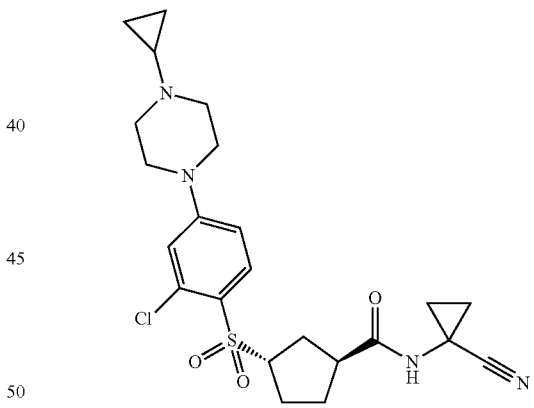

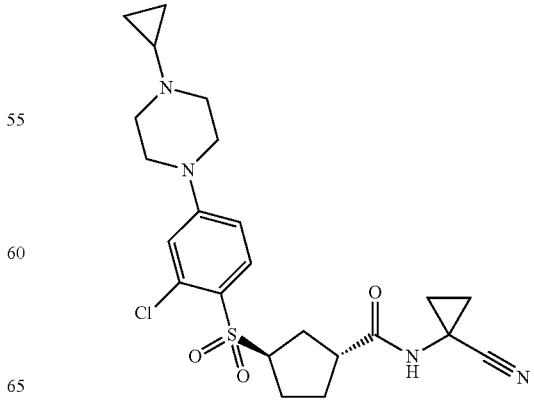

The title compound was synthesized in analogy to Example 80, from rac-(1S,3S)-3-(2-chloro-4-fluoro-benzenesulfonyl)-cyclopentanecarboxylic acid (1-cyano-cyclopropyl)-amide and 1-cyclopropyl-piperazine to afford the desired product as an off-white solid. MS (EI): 477.1 $(M+H)^+$.

Example 103 and Example 104

(1R,2R,4S)-4-(2-Chloro-benzenesulfonyl)-2-methoxymethyl-cyclopentanecarboxylic acid cyanomethyl-amide and (1R,2R,4R)-4-(2-Chloro-benzenesulfonyl)-2-methoxymethyl-cyclopentanecarboxylic acid cyanomethyl-amide

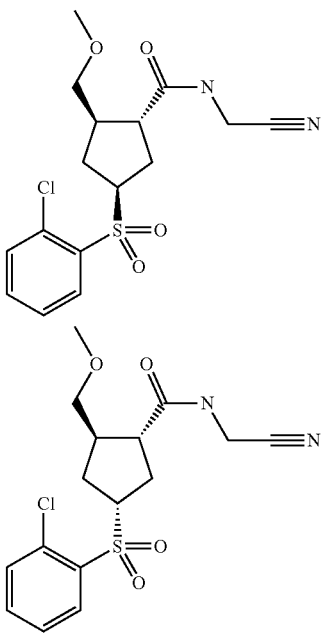

Step 1: (1R,2R)-4-(tert-Butyl-dimethyl-silanyloxy)-2-methoxymethyl-cyclopentanecarboxylic acid ethyl ester (epimeric mixture)

To a solution of (1R,2R)-4-(tert-Butyl-dimethyl-silanyloxy)-2-hydroxymethyl-cyclopentanecarboxylic acid ethyl ester (Example 68/69 step 4, epimeric mixture, 509 mg) in iodomethane (24 g) was added silver oxide (3.9 g) in several portions over 8 days. After 12 days at room temperature, the reaction mixture was concentrated in vacuo, diluted with dichloromethane, filtered and concentrated in vacuo. The residue was purified by flash chromatography on silica gel with a gradient of cyclohexane/EtOAc (1:0 to 9:1 v/v) as eluant to afford the title compound (228 mg, 43%) as light yellow oil. MS (EI): 317.1 $(M+H)^+$.

Step 2: (1R,2R)-4-Hydroxy-2-methoxymethyl-cyclopentanecarboxylic acid ethyl ester (epimeric mixture)

The title compound was synthesized in analogy to Example 68/69, Step 6, from (1R,2R)-4-(tert-Butyl-dimethyl-silanyloxy)-2-methoxymethyl-cyclopentanecarboxylic acid ethyl ester (epimeric mixture) to afford the desired product as a yellow oil. MS (EI): 157.0 $(M-EtO.)^+$.

Step 3: (1R,2R)-4-Methanesulfonyloxy-2-methoxymethyl-cyclopentanecarboxylic acid ethyl ester (epimeric mixture)

The title compound was synthesized in analogy to Example 68/69, Step 7, from (1R,2R)-4-Hydroxy-2-methoxymethyl-cyclopentanecarboxylic acid ethyl ester (epimeric mixture) to afford the desired product as a yellow oil. MS (EI): 281.1 $(M+H)^+$.

Step 4: (1R,2R)-4-(2-Chloro-phenylsulfanyl)-2-methoxymethyl-cyclopentanecarboxylic acid ethyl ester (epimeric mixture)

The title compound was synthesized in analogy to Example 68/69, Step 8, from (1R,2R)-4-Methanesulfonyloxy-2-methoxymethyl-cyclopentanecarboxylic acid ethyl ester (epimeric mixture) to afford the desired product as a yellow oil. MS (EI): 328 $(M)^+$.

Step 5: (1R,2R)-4-(2-Chloro-benzenesulfonyl)-2-methoxymethyl-cyclopentanecarboxylic acid ethyl ester (epimeric mixture)

The title compound was synthesized in analogy to Example 68/69, Step 9, from (1R,2R)-4-(2-Chloro-phenylsulfanyl)-2-methoxymethyl-cyclopentanecarboxylic acid ethyl ester (epimeric mixture) to afford the desired product as a light yellow oil. MS (EI): 360 $(M)^+$.

Step 6: (1R,2R)-4-(2-Chloro-benzenesulfonyl)-2-methoxymethyl-cyclopentanecarboxylic acid (epimeric mixture)

The title compound was synthesized in analogy to Example 68/69, Step 10, from (1R,2R)-4-(2-Chloro-benzenesulfonyl)-2-methoxymethyl-cyclopentanecarboxylic acid ethyl ester (epimeric mixture) to afford the desired product as an off-white gum. MS (EI): 350.2 $(M+NH_4)^+$.

Step 7: (1R,2R)-4-(2-Chloro-benzenesulfonyl)-2-methoxymethyl-cyclopentanecarboxylic acid cyanomethyl-amide (epimeric mixture)

The title compound was synthesized in analogy to Example 68/69, Step 11, from (1R,2R)-4-(2-Chloro-benzenesulfonyl)-2-methoxymethyl-cyclopentanecarboxylic acid (epimeric mixture) and aminoacetonitrile to afford the desired product as a light yellow foam. MS (EI): 371.0 $(M+H)^+$.

Step 8: (1R,2R,4S)-4-(2-Chloro-benzenesulfonyl)-2-methoxymethyl-cyclopentanecarboxylic acid cyanomethyl-amide and (1R,2R,4R)-4-(2-Chloro-benzenesulfonyl)-2-methoxymethyl-cyclopentanecarboxylic acid cyanomethyl-amide (1R,2R)-4-(2-Chloro-benzenesulfonyl)-2-methoxymethyl-cyclopentanecarboxylic acid cyanomethyl-amide (epimeric mixture, 54 mg) was subjected to chiral preparative HPLC on Reprosil Chiral NR® using a Heptane/0.01N $NH_4Ac$ in EtOH 70:30 v/v as eluant. Fraction 1 (Rt: 22 min): (1R,2R,4S)-4-(2-Chloro-benzenesulfonyl)-2-methoxymethyl-cyclopentanecarboxylic acid cyanomethyl-amide (12 mg, 22%). MS (EI): 371.1 $(M+H)^+$. Fraction 2 (Rt: 28 min): (1R,2R,4R)-4-(2-Chloro-benzenesulfonyl)-2-methoxymethyl-cyclopentanecarboxylic acid cyanomethyl-amide (19 mg, 35%). MS (EI): 371.0 (M+H)⁺.

Example 105 and Example 106

(1R,2R,4S)-4-(2-Chloro-benzenesulfonyl)-2-methoxymethyl-cyclopentanecarboxylic acid (1-cyano-cyclopropyl)-amide and (1R,2R,4R)-4-(2-Chloro-benzenesulfonyl)-2-methoxymethyl-cyclopentanecarboxylic acid (1-cyano-cyclopropyl)-amide

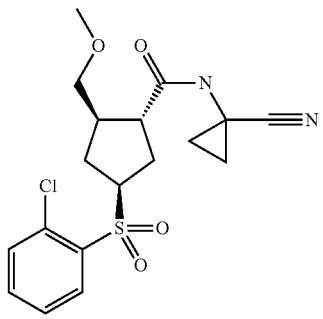

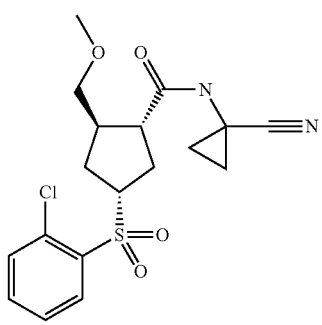

Step 1: (1R,2R)-4-(2-Chloro-benzenesulfonyl)-2-methoxymethyl-cyclopentanecarboxylic acid (1-cyano-cyclopropyl)-amide (epimeric mixture)

The title compound was synthesized in analogy to Example 68/69, Step 11, from (1R,2R)-4-(2-Chloro-benzenesulfonyl)-2-methoxymethyl-cyclopentanecarboxylic acid (epimeric mixture) and 1-amino-cyclopropyl cyanic hydrochloride to afford the desired product as a yellow foam. MS (EI): 397.0 (M+H)⁺.

Step 2: (1R,2R,4S)-4-(2-Chloro-benzenesulfonyl)-2-methoxymethyl-cyclopentanecarboxylic acid (1-cyano-cyclopropyl)-amide and (1R,2R,4R)-4-(2-Chloro-benzenesulfonyl)-2-methoxymethyl-cyclopentanecarboxylic acid (1-cyano-cyclopropyl)-amide (1R,2R)-4-(2-Chloro-benzenesulfonyl)-2-methoxymethyl-cyclopentanecarboxylic acid (1-cyano-cyclopropyl)-amide (epimeric mixture, 57 mg) was subjected to chiral preparative HPLC on Reprosil Chiral NR® using a Heptane/0.01N NH₄Ac in EtOH 60:40 v/v as eluant. Fraction 1 (Rt: 21 min): (1R,2R,4S)-4-(2-Chloro-benzenesulfonyl)-2-methoxymethyl-cyclopentanecarboxylic acid (1-cyano-cyclopropyl)-amide (12 mg, 20%). MS (EI): 397.1 (M)⁺. Fraction 2 (Rt: 27 min): (1R,2R,4R)-4-(2-Chloro-benzenesulfonyl)-2-methoxymethyl-cyclopentanecarboxylic acid (1-cyano-cyclopropyl)-amide (19 mg, 33%). MS (EI): 397.1 (M)⁺.

Example 107

(1R,2R,4R)-4-(2-Chloro-benzenesulfonyl)-2-(6-hydroxy-pyridazin-3-yloxymethyl)-cyclopentanecarboxylic acid cyanomethylamide and (1R,2R,4S)-4-(2-Chloro-benzenesulfonyl)-2-(6-hydroxy-pyridazin-3-yloxymethyl)-cyclopentanecarboxylic acid cyanomethylamide

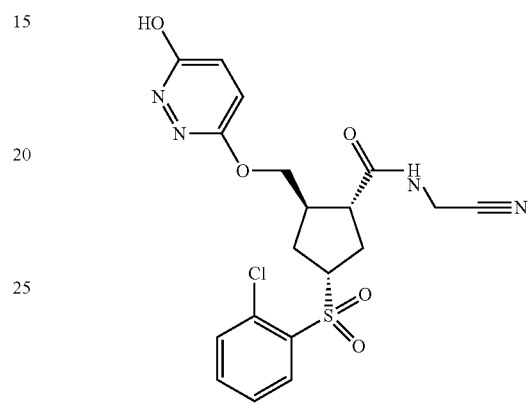

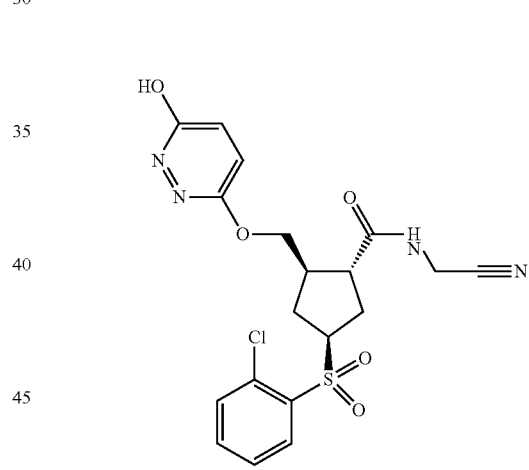

Step 1: (1R,2R)-4-(tert-Butyl-dimethyl-silanyloxy)-2-(6-hydroxy-pyridazin-3-yloxymethyl)-cyclopentanecarboxylic acid ethyl ester (epimeric mixture)

The title compound was synthesized in analogy to Example 68/69, Step 5, from (1R,2R)-4-(tert-butyl-dimethyl-silanyloxy)-2-hydroxymethyl-cyclopentanecarboxylic acid ethyl ester (epimeric mixture, Example 69, Step 4) and pyridazine-3,6-diol to afford the desired product as a white gum. MS (EI): 385.3 (M−H)⁻.

Step 2: (1R,2R)-4-Hydroxy-2-(6-hydroxy-pyridazin-3-yloxymethyl)-cyclopentanecarboxylic acid ethyl ester (epimeric mixture)

The title compound was synthesized in analogy to Example 68/69, Step 6, from (1R,2R)-4-(tert-butyl-dimethylsilanyloxy)-2-(6-hydroxy-pyridazin-3-yloxymethyl)-cyclopentanecarboxylic acid ethyl ester (epimeric mixture) to afford the desired product as an off-white foam. MS (EI): 283.2 (M+H)+.

Step 3: (1R,2R)-2-(6-Hydroxy-pyridazin-3-yloxymethyl)-4-methanesulfonyloxy-cyclopentanecarboxylic acid ethyl ester (epimeric mixture)

The title compound was synthesized in analogy to Example 68/69, Step 7, from (1R,2R)-4-hydroxy-2-(6-hydroxy-pyridazin-3-yloxymethyl)-cyclopentanecarboxylic acid ethyl ester (epimeric mixture) to afford the desired product as a colorless liquid. MS (EI): 359.2 (M–H)−.

Step 4: (1R,2R)-4-(2-Chloro-phenylsulfanyl)-2-(6-hydroxy-pyridazin-3-yloxymethyl)-cyclopentanecarboxylic acid ethyl ester (epimeric mixture)

The title compound was synthesized in analogy to Example 68/69, Step 8, from (1R,2R)-2-(6-hydroxy-pyridazin-3-yloxymethyl)-4-methanesulfonyloxy-cyclopentanecarboxylic acid ethyl ester (epimeric mixture) and 2-chlorobenzenetiol to afford the desired product as a light yellow oil. MS (EI): 409.2 (M+H)+.

Step 5: (1R,2R)-4-(2-Chloro-benzenesulfonyl)-2-(6-hydroxy-pyridazin-3-yloxymethyl)-cyclopentanecarboxylic acid ethyl ester (epimeric mixture)

The title compound was synthesized in analogy to Example 68/69, Step 9, from (1R,2R)-4-(2-chloro-phenylsulfanyl)-2-(6-hydroxy-pyridazin-3-yloxymethyl)-cyclopentanecarboxylic acid ethyl ester (epimeric mixture) to afford the desired product as a yellow oil. MS (EI): 441.1 (M+H)+.

Step 6: (1R,2R)-4-(2-Chloro-benzenesulfonyl)-2-(6-hydroxy-pyridazin-3-yloxymethyl)-cyclopentanecarboxylic acid (epimeric mixture)

The title compound was synthesized in analogy to Example 68/69, Step 10, from (1R,2R)-4-(2-chloro-benzenesulfonyl)-2-(6-hydroxy-pyridazin-3-yloxymethyl)-cyclopentanecarboxylic acid ethyl ester (epimeric mixture) to afford the desired product as an off-white gum. MS (EI): 411.2 (M–H)−.

Step 7: (1R,2R)-4-(2-Chloro-benzenesulfonyl)-2-(6-hydroxy-pyridazin-3-yloxymethyl)-cyclopentanecarboxylic acid cyanomethyl-amide (epimeric mixture)

The title compound was synthesized in analogy to Example 68/69, Step 11, from (1R,2R)-4-(2-chloro-benzenesulfonyl)-2-(6-hydroxy-pyridazin-3-yloxymethyl)-cyclopentanecarboxylic acid (epimeric mixture) and 1-amino-acetonitrile to afford the desired product as a light yellow gum. MS (EI): 469.2 (M+H)+.

Example 108

(1R,2R,4S)-4-(2-Chloro-benzenesulfonyl)-2-(6-hydroxy-pyridazin-3-yloxymethyl)-cyclopentanecarboxylic acid(1-cyano-cyclopropyl)-amide and (1R,2R,4R)-4-(2-Chloro-benzenesulfonyl)-2-(6-hydroxy-pyridazin-3-yloxymethyl)-cyclopentanecarboxylic acid(1-cyano-cyclopropyl)-amide

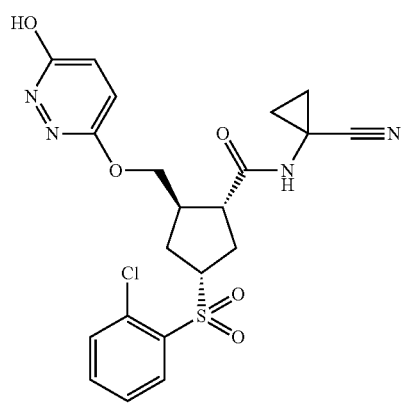

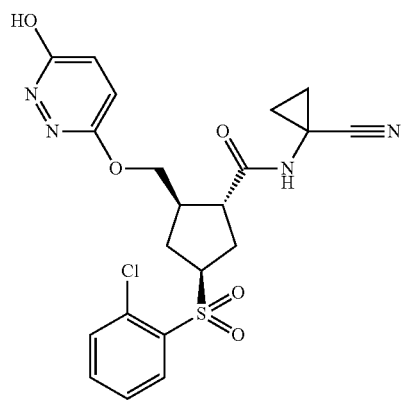

The title compound was synthesized in analogy to Example 68/69, Step 11, from (1R,2R)-4-(2-chloro-benzenesulfonyl)-2-(6-hydroxy-pyridazin-3-yloxymethyl)-cyclopentanecarboxylic acid (epimeric mixture) and 1-amino-cyclopropyl cyanic hydrochloride to afford the desired product as an orange oil. MS (EI): 495.2 (M+H)+.

Example 109

(1R,2R,4R) and (1S,2S,4S)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide

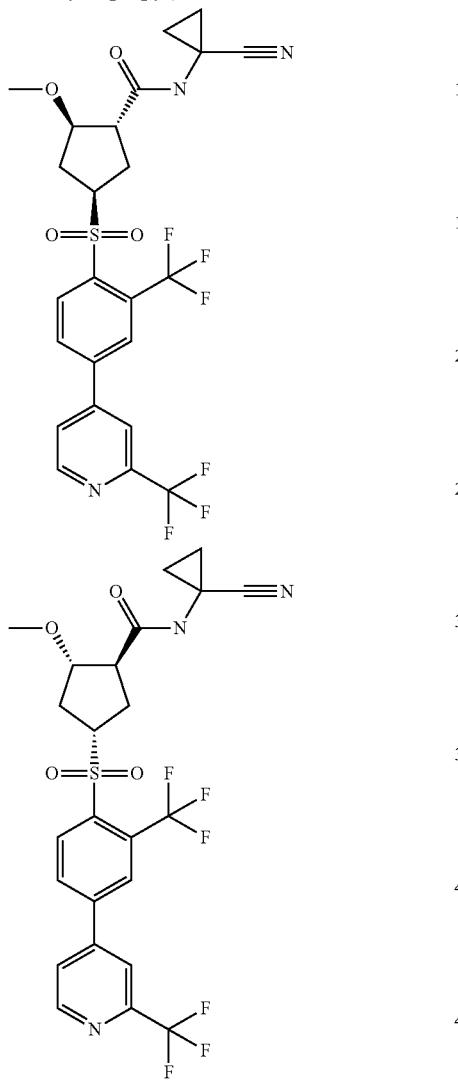

Argon was bubbled through a mixture of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide (150 mg, 0.303 mmol, example 58), bis(pinacolato)diboron (157 mg, 0.363 mmol), [1,1'-bis(diphenylphosphino)ferrocene]palladium(II) chloride 1:1 complex with DCM (49 mg, 0.0606 mmol) and potassium acetate (149 mg, 1.514 mmol, dried at 125° C. under high vakuum overnight) in DMSO (2.5 ml) for 3 minutes. The mixture was then heated to 80° C. and after 2 h was allowed to cool to room temperature and diluted with water. The pH was adjusted to 2 with 0.1N HCl. and the brown mixture was extracted 3 times with EtOAc. The combined organic layers were washed with water (acidified with 0.1N HCl) and brine, dried over Na₂SO₄ and evaporated to obtain 270 mg of a brown gum.

86 mg of this brown gum were dissolved in DMF (3 ml) and 2-bromo-2-trifluoromethylpyridine (51 mg, 0.224 mmol), Na₂CO₃ (53 mg, 0.505 mmol) and water (250 ul) were added and argon was bubbled through the mixture for 15 minutes. Then [1,1'-bis(diphenyl-phosphino)ferrocene]palladium(II) chloride 1:1 complex with DCM (15 mg, 0.01869 mmol) was added and the dark brown mixture was heated to 80° C. for 1 h, then cooled to room temperature and poured onto a mixture of saturated NaHCO₃ solution and ice. The mixture was extracted 3 times with EtOAc and the combined extracts were washed with water and brine, dried over Na₂SO₄ and evaporated. The remaining residue was purified by silica column chromatography (DCM/EtOAc 95:5) to obtain the title compound. (44 mg, 42%) as light grey foam. MS (EI): 562.2 (M+H)⁺.

Example 110

(1R,2R,4R) and (1S,2S,4S)-2-Methoxy-4-(4-pyridazin-4-yl-2-trifluoromethyl-benzenesulfonyl)-cyclopentanecarboxylic acid (1-cyano-cyclopropyl)-amide

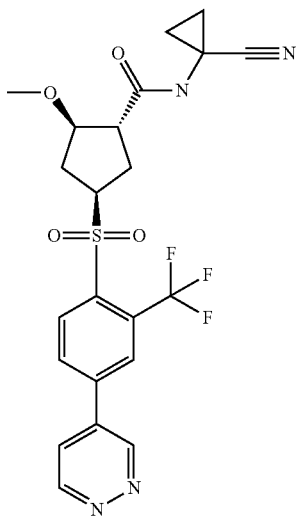

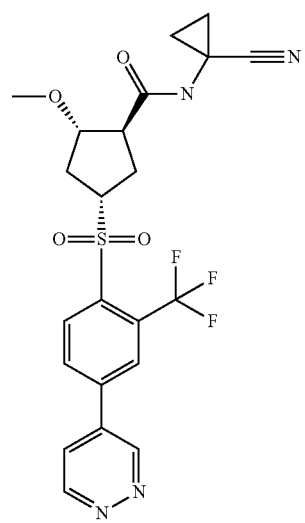

133

The title compound was prepared in analogy to example 109 using 4-bromopyridazine hydrochloride instead of 2-bromo-2-trifluoromethylpyridine. Light brown solid. MS (EI): 495.3 (M+H)+.

Example 111

(1R,2R,4R) and (1S,2S,4S)-2-Methoxy-4-(4-pyrazin-2-yl-2-trifluoromethyl-benzenesulfonyl)-cyclopentanecarboxylic acid (1-cyano-cyclopropyl)-amide

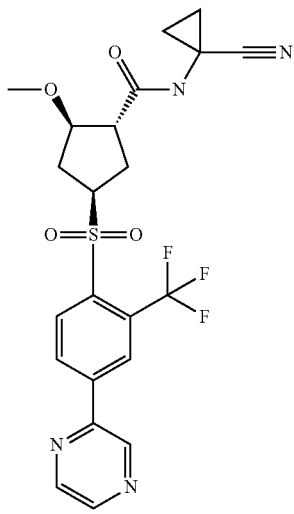

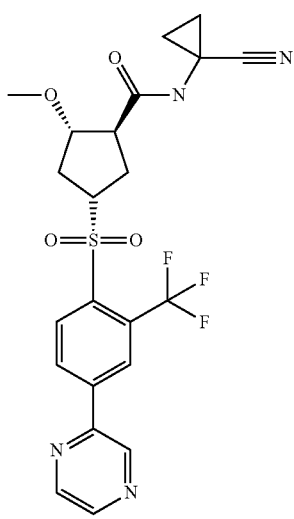

The title compound was prepared in analogy to example 109 using 2-bromopyrazine instead of 2-bromo-2-trifluoromethylpyridine. Grey solid. MS (EI): 495.2 (M+H)+.

134

Example 112

(1R,2R,4R) and (1S,2S,4S)-4-(4-Bromo-2-trifluoromethyl-benzenesulfonyl)-2-isopropoxy-cyclopentanecarboxylic acid (1-cyano-cyclopropyl)-amide

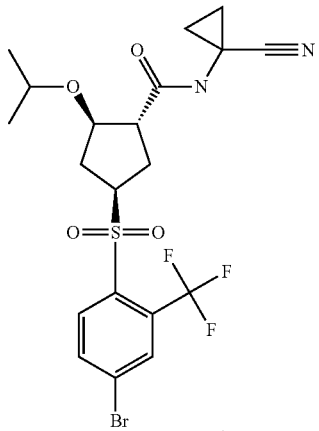

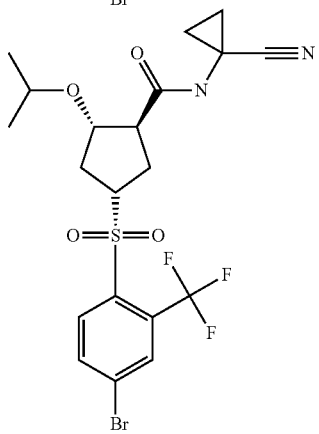

Step 1: (1R,2S,4s)-4-{[tert-Butyl(diphenyl)silyl]oxy}cyclopentane-1,2-diol Trimethylamine N-oxide (937 mg, 8.4 mmol) and pyridine (499 ul, 6.2 mmol) were added to a solution of tert-butyl-(cyclopent-3-enyloxy)-diphenyl-silane (2000 mg, 6.2 mmol, example 46, step 1) in t-butanol (20 ml) and water (6 ml). Then osmium tetroxide (189 mg of a 2.5 wt % solution in t-butanol, 0.019 mmol) was added and the reaction mixture was refluxed over night. Then sodium bisulfate solution was added at room temperature and the t-butanol was removed under reduced pressure. The remaining aqueous phase was extracted 3 times with ether and the combined organic phases were washed with water and brine, dried (Na₂SO₄) and concentrated. The remaining residue was purified by silica column chromatography (heptane/EtOAc 70:30 to 30:70) to obtain the title compound (2210 mg, 100%) as colorless oil. MS (EI): 357.2 (M+H)+.

Step 2:: Trans tert-Butyl-(2,2-dimethyl-tetrahydro-cyclopenta[1,3]dioxol-5-yloxy)-diphenyl-silane (1R,2S,4s)-4-{[tert-Butyl(diphenyl)silyl])oxy}cyclopentane-1,2-diol (900 mg, 2.52 mmol) was dissolved in DCM (10 ml) and DMP (3.13 ml, 25.24 mmol) and a catalytic amount of PPTS was added. The reaction mixture was stirred at room temperature over night. Then a saturated NaHCO$_3$ solution was added, the mixture was extracted twice with ether and the combined organic phases were washed with brine, dried (Na$_2$SO$_4$) and concentrated. The remaining residue was purified by silica column chromatography (heptane/EtOAc 95:5) to obtain the title compound (958 mg, 96%) as colorless oil. MS (EI): 397.2 (M+H)$^+$.

Step 3: (1S,2R,4S) and (1R,2S,4R)-4-(tert-Butyl-diphenyl-silanyloxy)-2-isopropoxy-cyclopentanol To a solution of trans tert-butyl-(2,2-dimethyl-tetrahydro-cyclopenta[1,3]dioxol-5-yloxy)-diphenyl-silane (1020 mg, 2.57 mmol) in DCM (30 ml) were added borane dimethyl sulfide complex (542 µl, 5.14 mmol) and boron trifluoride diethyl etherate (649 µl, 5.14 mmol) at 0° C. and the reaction mixture was stirred at room temperature over night. Then water was added and the mixture was extracted 3 times with ether. The combined extracts were washed with saturated NaHCO$_3$ solution and brine, dried (Na$_2$SO$_4$) and evaporated. The remaining residue was purified by silica column chromatography (heptane/EtOAc 9:1) to obtain the title compound (846 mg, 83%) as colorless oil. MS (EI): 399.2 (M+H)$^+$.

Step 4: (1S,2R,4S) and (1R,2S,4R)-4-(tert-Butyl-diphenyl-silanyloxy)-2-isopropoxy-cyclopentanecarbonitrile (1S,2R,4S) and (1R,2S,4R)-4-(tert-Butyl-diphenyl-silanyloxy)-2-isopropoxy-cyclopentanol (510 mg, 1.28 mmol) was dissolved in DCM (12 ml) and pyridine was added (206 µl, 2.56 mmol). The mixture was cooled to −35° C. and a solution of trifluoromethanesulfonic anhydride (253 µl, 1.54 mmol) in DCM (3 ml) was added. After the reaction mixture had been stirred for 5 h at −20° C. it was concentrated and passed trough a short plug of silica gel and then evaporated to dryness. The remaining oil was dissolved in THF (12 ml) and a solution of tertrabutylammonium cyanide in THF (3 ml) was added dropwise at −45° C. The reaction mixture was stirred at room temperature over night and then evaporated. The remaining yellow oil was purified by silica column chromatography (heptane/EtOAc 9:1) to obtain the title compound (311 mg, 60%) as colorless oil. MS (EI): 408.4 (M+H)$^+$.

Step 5: (1S,2R,4S) and (1R,2S,4R)-4-Hydroxy-2-isopropoxy-cyclopentanecarbonitrile The title compound was prepared in analogy to example 46, step 5 and was obtained as light yellow oil. MS (EI): 228.3 (M+OAc)$^-$.

Step 6: Methanesulfonic acid (1S,3S,4R) and (1R,3R,4S)-3-cyano-4-isopropoxy-cyclopentyl ester The title compound was prepared in analogy to example 46, step 6 and was obtained as yellow oil. MS (EI): 306.3 (M+OAc)$^-$.

Step 7: (1S,2R,4R) and (1R,2S4S)-4-(4-Bromo-2-trifluoromethyl-phenylsulfanyl)-2-isopropoxy-cyclopentanecarbonitrile The title compound was prepared in analogy to example 46, step 7 and was obtained as colorless oil. MS (EI): 468.0 (M+OAc)-.

Step 8: (1S,2R,4R) and (1R,2S,4S)-4-(4-Bromo-2-trifluoromethyl-benzenesulfonyl)-2-isopropoxy-cyclopentanecarbonitrile The title compound was prepared in analogy to example 46, step 8 and was obtained as colorless oil. MS (EI): 440.1 (M+H)$^+$.

Step 9: (1R,2R,4R) and (1S,2S,4S)-4-(4-Bromo-2-trifluoromethyl-benzenesulfonyl)-2-isopropoxy-cyclopentanecarboxylic acid methyl ester The title compound was prepared in analogy to example 46, step 9 and was obtained as colorless oil. MS (EI): 473.0 (M+H)$^+$.

Step 10: Lithium (1R,2R,4R) and (1S,2S,4S)-4-(4-bromo-2-trifluoromethyl-benzenesulfonyl)-2-isopropoxy-cyclopentanecarboxylate The title compound was prepared in analogy to example 46, step 10 and was obtained as white solid. MS (EI): 557.1 (M−H)$^-$.

Step 11: (1R,2R,4R) and (1S,2S,4S)-4-(4-Bromo-2-trifluoromethyl-benzenesulfonyl)-2-isopropoxy-cyclopentanecarboxylic acid (1-cyano-cyclopropyl)-amide The title compound was prepared in analogy to example 46, step 11 using HATU/N-ethyl-N,N-diisopropyl amine in DMF instead of EDCI/HOBt/N-ethyl-N,N-diisopropyl amine in acetonitrile and was obtained as white solid. MS (EI): 523.4 (M−H)$^-$.

Example 113

(1R,2R,4R) and (1S,2S,4S)-4-(4-Bromo-2-trifluoromethyl-benzenesulfonyl)-2-ethoxy-cyclopentanecarboxylic acid (1-cyano-cyclopropyl)-amide

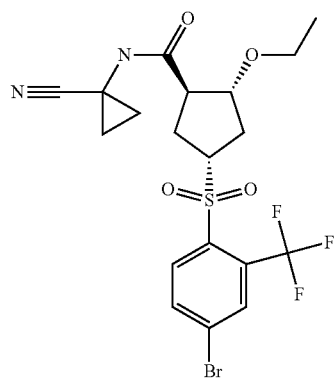

-continued

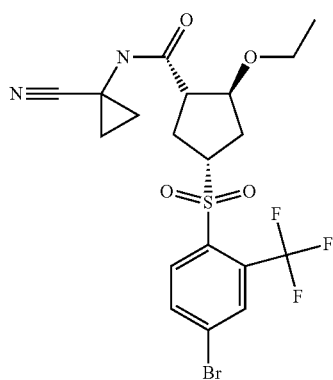

The title compound was prepared in analogy to example 46 using ethyliodide instead of methyliodide in step 4 and 4-bromo-2-trifluoromethyl-benzenethiol instead of 2-(trifluoromethyl)-thiophenol in step 7. White solid. MS (EI): 507.0 (M−H)⁻.

Example 114

(1R,2R,4R) and (1S,2S,4S)-2-Ethoxy-4-[4-(2-methyl-pyridin-4-yl)-2-trifluoromethyl-benzenesulfonyl]-cyclopentanecarboxylic acid (1-cyano-cyclopropyl)-amide

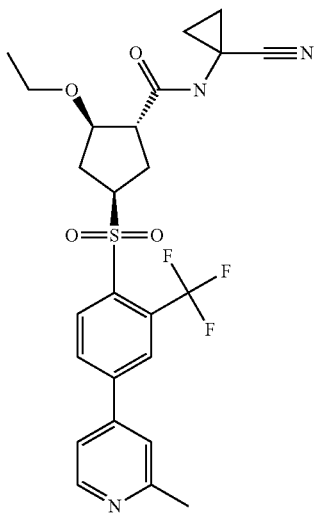

-continued

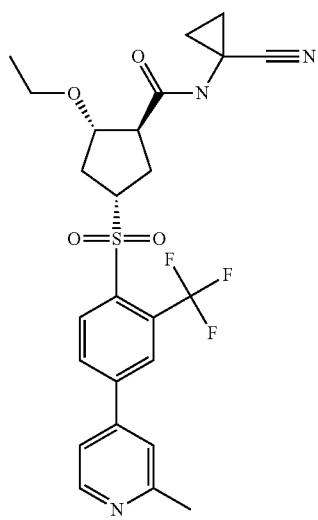

The title compound was prepared in analogy to example 62 using 2-picoline-4-boronic acid instead of 2.4-difluorophenylboronic acid and (1R,2R,4R) and (1S,2S,4S)-4-(4-bromo-2-trifluoromethyl-benzenesulfonyl)-2-ethoxy-cyclopentanecarboxylic acid (1-cyano-cyclopropyl)-amide instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 522.3 (M+H)⁺.

Example 115

(1R,2R,4R) and (1S,2S,4S)-4-[4-(3,5-Dimethyl-isoxazol-4-yl)-2-trifluoromethyl-benzenesulfonyl]-2-ethoxy-cyclopentanecarboxylic acid (1-cyano-cyclopropyl)-amide

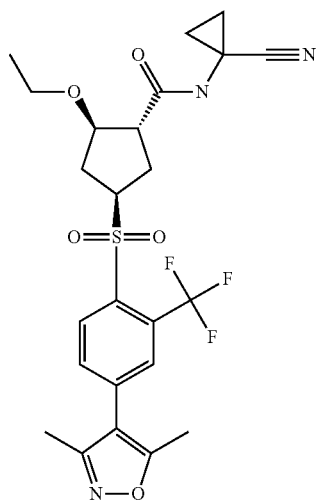

-continued

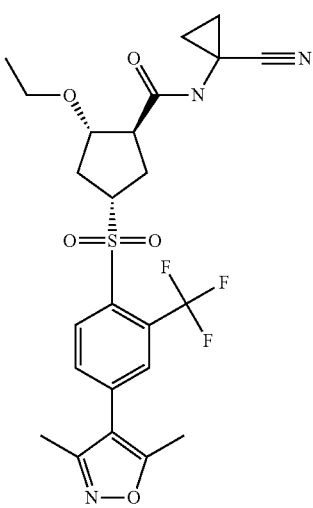

The title compound was prepared in analogy to example 62 using 3,5-dimethyl-isoxazole-4-boronic acid instead of 2.4-difluorophenylboronic acid and (1R,2R,4R) and (1S,2S,4S)-4-(4-bromo-2-trifluoromethyl-benzenesulfonyl)-2-ethoxy-cyclopentanecarboxylic acid (1-cyano-cyclopropyl)-amide instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 526.0 (M+H)⁺.

Example 116

(1R,2R,4R) and (1S,2S,4S)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide

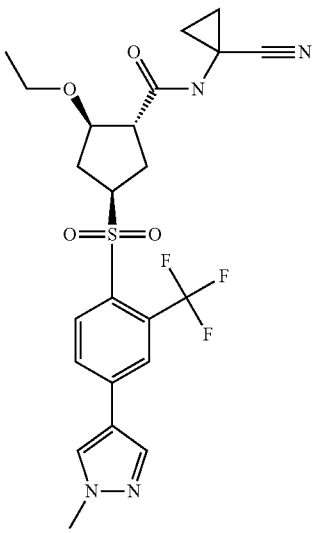

-continued

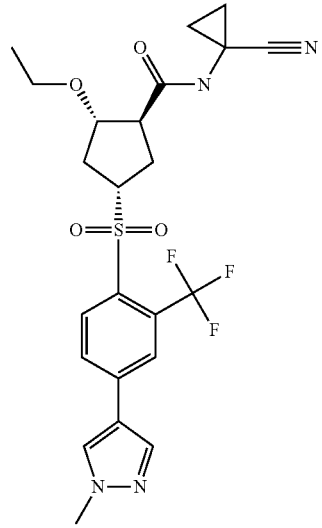

The title compound was prepared in analogy to example 62 using 1-methyl-4-(4.4.5.5-tetramethyl-1.3.2-dioxaborolan)-1H-pyrazole instead of 2.4-difluorophenylboronic acid and (1R,2R,4R) and (1S,2S,4S)-4-(4-bromo-2-trifluoromethyl-benzenesulfonyl)-2-ethoxy-cyclopentanecarboxylic acid (1-cyano-cyclopropyl)-amide instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. Light yellow solid. MS (EI): 509.2 (M−H)⁻.

Example 117

(1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide

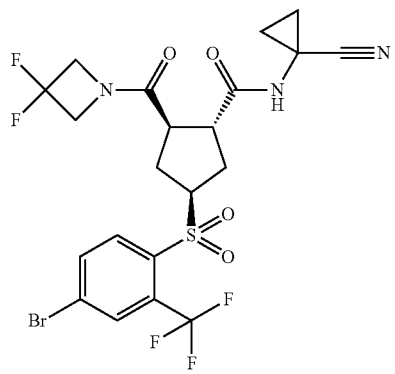

Step 1: (1R,2R)-2-(3,3-Difluoro-azetidine-1-carbonyl)-4-oxo-cyclopentanecarboxylic acid ethyl ester To a mixture of (1R,2R,4R)-4-Benzenesulfonyl-2-(morpholine-4-carbonyl)-cyclopentanecarboxylic acid cyanomethyl-amide (3 g, 15 mmol, example 1, step 1) in dimethylformamide (40 mL) was added 1-(3-dimethylaminopropyl)-3-ethylcarbodiimide hydrochloride (5.86 g, 30 mmol), hydroxybenzotriazole (3.1 g mg, 22 mmol) and ethyldiisopropylamine (15.4 mL, 90 mmol). After 45 mM, 3,3-difluoroazetidine hydrochloride (1.94 g, 15 mmol) was added and the reaction mixture was stirred for 24 h then partitioned between ethyl acetate and an aqueous saturated solution of sodium hydrogenocarbonate. The aqueous layer was extracted with ethyl acetate and the combined organic layers were washed with water then dried over sodium sulfate and concentrated in vacuo. The residue was purified by flash chromatography on silica gel with a gradient of cyclohexane/ ethyl acetate (2:1 then 1:1 v/v) as eluant to afford the title compound (2.35 g, 57%) as yellow solid. MS (EI): 276.2 (M+H)$^+$.

Step 2: (1R,2R,4R)-2-(3,3-Difluoro-azetidine-1-carbonyl)-4-hydroxy-cyclopentanecarboxylic acid ethyl ester A suspension of 2.3 g (1R,2R)-2-(3,3-Difluoro-azetidine-1-carbonyl)-4-oxo-cyclopentanecarboxylic acid ethyl ester in 50.6 mL aqueous buffer (30 mM 2-(N-morpholino)ethanesulfonic acid; 0.5 M D-glucose [2.7 equ.]; 2 mM Magnesium chloride) was adjusted to pH 6.5 at 35° C. Under stirring the reduction was started by the addition of the cofactor NADP (23 mg [0.03 equ.]), the cofactor regeneration enzyme-glucose dehydrogenase (23 mg GDH 102 [Codexis]) and the reductase (23 mg KRED-NADP-131 [Codexis]). During the 17 h reaction time at 35° C. the pH was kept at pH 6.5 by the addition of 8.25 mL 1M NaOH. Under stirring the mixture was mixed with 1.5 g filter aid—Dicalite—and 30 mL ethyl acetate for at least 10 min. at room temperature. Subsequently the filter aid was washed with 30 ml water and 70 mL ethyl acetate. Afterwards the filter aid was discarded. The filtrate was extracted trice with 100 mL ethyl acetate. Treatment of the combined organic phases with sodium sulfate, evaporation and drying over night on a high vacuum yielded in 2.21 g of the title compound. MS: 278.2 (M+H)$^+$; chiral GC: ee 99.5% [BGB-172, 60 m; H2; 10° C./min, 100° C. to 180° C.; 1° C./min, 180° C. to 230° C.].

Step 3: (1R,2R,4R)-2-(3,3-Difluoro-azetidine-1-carbonyl)-4-methanesulfonyloxy-cyclopentanecarboxylic acid ethyl ester The title compound was prepared in analogy to Example 68/69, step 7, using (1R,2R,4R)-2-(3,3-Difluoro-azetidine-1-carbonyl)-4-hydroxy-cyclopentanecarboxylic acid ethyl ester. Yellow solid. MS (EI): 356.2 (M+H)$^+$.

Step 4: (1R,2R,4S)-4-(4-Bromo-2-trifluoromethyl-phenylsulfanyl)-2-(3,3-difluoro-azetidine-1-carbonyl)-cyclopentanecarboxylic acid ethyl ester The title compound was prepared in analogy to Example 68/69, step 8, using (1R,2R,4R)-2-(3,3-Difluoro-azetidine-1-carbonyl)-4-methanesulfonyloxy-cyclopentanecarboxylic acid ethyl ester and 4-Bromo-2-trifluoromethyl-benzenethiol (Example 58, intermediate 1). Light yellow oil. MS (EI): 518.0 (M+H)$^+$.

Step 5: (1R,2R,4S)-4-(4-Bromo-2-trifluoromethyl-benzenesulfonyl)-2-(3,3-difluoro-azetidine-1-carbonyl)-cyclopentanecarboxylic acid ethyl ester The title compound was prepared in analogy to Example 68/69, step 9, using (1R,2R,4S)-4-(4-Bromo-2-trifluorom- ethyl-phenylsulfanyl)-2-(3,3-difluoro-azetidine-1-carbonyl)-cyclopentanecarboxylic acid ethyl ester. White foam. MS (EI): 550.1 (M+H)$^+$.

Step 6: (1R,2R,4S)-4-(4-Bromo-2-trifluoromethyl-benzenesulfonyl)-2-(3,3-difluoro-azetidine-1-carbonyl)-cyclopentanecarboxylic acid The title compound was prepared in analogy to Example 68/69, step 10, using (1R,2R,4S)-4-(4-Bromo-2-trifluoromethyl-benzenesulfonyl)-2-(3,3-difluoro-azetidine-1-carbonyl)-cyclopentanecarboxylic acid ethyl ester. White solid. MS (EI): 521.98 (M+H)$^+$.

Step 7: (1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide To a mixture of (1R,2R,4S)-4-(4-Bromo-2-trifluoromethyl-benzenesulfonyl)-2-(3,3-difluoro-azetidine-1-carbonyl)-cyclopentanecarboxylic acid (150 mg, 0.29 mmol), N,N-diisopropylethylamine (0.15 mL, 0.87 mmol), 2-(1H-7-Azabenzotriazol-1-yl)-1,1,3,3-tetramethyl uronium hexafluorophosphate methanaminium (221 mg, 0.58 mmol) in acetonitrile was added 1-amino-cyclopropyl cyanic hydrochloride (41 mg, 0.34 mmol). The reaction mixture was stirred at room temperature for 16 h then concentrated in vacuo and partitioned between ethyl acetate and an aqueous solution of sodium carbonate (5% w/w). The aqueous layer was extracted with ethyl acetate then the combined organic layers were washed with aqueous hydrochloric acid (1N) and brine then dried over sodium sulfate and concentrated in vacuo. The residue was purified by flash chromatography on silica gel with a gradient of dichloromethane/methanol (98:2 v/v) as eluant to afford the title compound (144 mg, 85%) as a brown solid. MS (EI): 584.0 (M−H)$^-$.

Example 118

(1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide

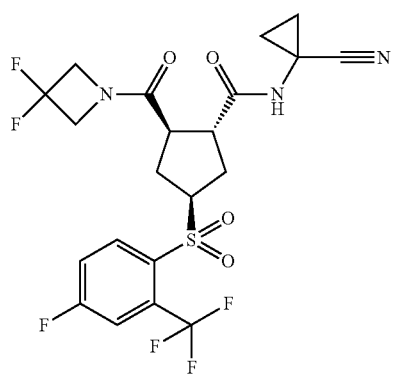

Intermediate 1:
4-Fluoro-2-trifluoromethyl-benzenethiol

The title compound was prepared in analogy to Example 58, Intermediate 1, using 4-fluoro-2-trifluoromethyl-benzene sulfonyl chloride. Colorless liquid. MS (EI): 195.1 (M−H)$^-$.

Step 1: (1R,2R,4S)-2-(3,3-Difluoro-azetidine-1-carbonyl)-4-(4-fluoro-2-trifluoromethyl-phenylsulfanyl)-cyclopentanecarboxylic acid ethyl ester The title compound was prepared in analogy to Example 68/69, step 8, using (1R,2R,4R)-2-(3,3-Difluoro-azetidine-1-carbonyl)-4-methanesulfonyloxy-cyclopentanecarboxylic acid ethyl ester (Example 117, step 3) and 4-fluoro-2-trifluoromethyl-benzenethiol (Intermediate 2). Light yellow oil. MS (EI): 456.1 (M+H)+.

Step 2: (1R,2R,4S)-2-(3,3-Difluoro-azetidine-1-carbonyl)-4-(4-fluoro-2-trifluoromethyl-benzenesulfonyl)-cyclopentanecarboxylic acid ethyl ester The title compound was prepared in analogy to Example 68/69, step 9, using (1R,2R,4S)-2-(3,3-Difluoro-azetidine-1-carbonyl)-4-(4-fluoro-2-trifluoromethyl-phenylsulfanyl)-cyclopentanecarboxylic acid ethyl ester. White foam. MS (EI): 488.3 (M+H)+.

Step 3: (1R,2R,4S)-2-(3,3-Difluoro-azetidine-1-carbonyl)-4-(4-fluoro-2-trifluoromethyl-benzenesulfonyl)-cyclopentanecarboxylic acid The title compound was prepared in analogy to Example 68/69, step 10, using (1R,2R,4S)-2-(3,3-Difluoro-azetidine-1-carbonyl)-4-(4-fluoro-2-trifluoromethyl-benzenesulfonyl)-cyclopentanecarboxylic acid ethyl ester. White solid. MS (EI): 460.0 (M+H)+.

Step 4: (1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide The title compound was prepared in analogy to Example 117, step 7, using (1R,2R,4S)-2-(3,3-Difluoro-azetidine-1-carbonyl)-4-(4-fluoro-2-trifluoromethyl-benzenesulfonyl)-cyclopentanecarboxylic acid and 1-amino-cyclopropyl cyanic hydrochloride. White solid. MS (EI): 524.1 (M+H)+.

Example 119

(1R,2R,4R)-4-(2-Chloro-4-fluoro-benzenesulfonyl)-2-(3,3-difluoro-azetidine-1-carbonyl)-cyclopentanecarboxylic acid (1-cyano-cyclopropyl)-amide

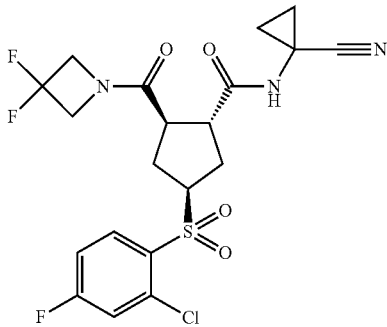

Step 1: (1R,2R,4S)-4-(2-Chloro-4-fluoro-phenylsulfanyl)-2-(3,3-difluoro-azetidine-1-carbonyl)-cyclopentanecarboxylic acid ethyl ester The title compound was prepared in analogy to Example 68/69, step 8, using (1R,2R,4R)-2-(3,3-Difluoro-azetidine-1-carbonyl)-4-methanesulfonyloxy-cyclopentanecarboxylic acid ethyl ester (Example 117, step 3) and 4-fluoro-2-chloro-benzenethiol. Light yellow solid. MS (EI): 422.7 (M+H)+.

Step 2: (1R,2R,4S)-4-(2-Chloro-4-fluoro-benzenesulfonyl)-2-(3,3-difluoro-azetidine-1-carbonyl)-cyclopentanecarboxylic acid ethyl ester The title compound was prepared in analogy to Example 68/69, step 9, using (1R,2R,4S)-4-(2-Chloro-4-fluoro-phenylsulfanyl)-2-(3,3-difluoro-azetidine-1-arbonyl)-cyclopentanecarboxylic acid ethyl ester. White gum. MS (EI): 454.1 (M+H)+.

Step 3: (1R,2R,4S)-4-(2-Chloro-4-fluoro-benzenesulfonyl)-2-(3,3-difluoro-azetidine-1-carbonyl)-cyclopentanecarboxylic acid The title compound was prepared in analogy to Example 68/69, step 10, using (1R,2R,4S)-4-(2-Chloro-4-fluoro-benzenesulfonyl)-2-(3,3-difluoro-azetidine-1-carbonyl)-cyclopentanecarboxylic acid ethyl ester. White solid. MS (EI): 426.0 (M+H)+.

Step 4: (1R,2R,4R)-4-(2-Chloro-4-fluoro-benzenesulfonyl)-2-(3,3-difluoro-azetidine-1-carbonyl)-cyclopentanecarboxylic acid (1-cyano-cyclopropyl)-amide The title compound was prepared in analogy to Example 117, step 7, using (1R,2R,4S)-4-(2-Chloro-4-fluoro-benzenesulfonyl)-2-(3,3-difluoro-azetidine-1-carbonyl)-cyclopentanecarboxylic acid and 1-amino-cyclopropyl cyanic hydrochloride. Off-white solid. MS (EI): 490.1 (M+H)+.

Example 120

(1R,2R,4R)-2-(3,3-Difluoro-azetidine-1-carbonyl)-4-[4-(1-methyl-1H-pyrazol-4-yl)-2-trifluoromethyl-benzenesulfonyl]-cyclopentanecarboxylic acid (1-cyano-cyclopropyl)-amide

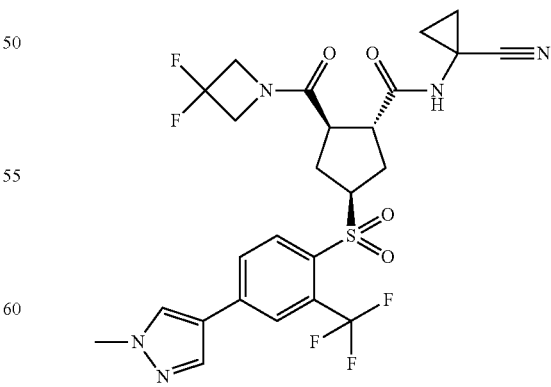

A mixture of (1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide (Example 117, 143 mg, 0.24 mmol), 1-methyl-4-(4,4,5,5-tetramethyl-1,3,2-dioxaborolan)-1H-Pyrazole (75 mg, 0.36 mmol), sodium carbonate (70 mg, 0.66 mmol) and 1,1'-bis(diphenylphosphino)ferrocene)Palladium (II) chloride (20 mg, 0.024 mmol) in N,N-dimethylformamide (4 mL) an water (0.35 mL) was degazed (vacuum/nitrogen cycles) and stirred at 80° C. for 2 h. The reaction mixture was cooled down and partitioned between ethyl acetate and a saturated aqueous solution of sodium hydrogenocarbonate. The aqueous layer was extracted with ethyl acetate then the combined organic layers were washed with water and brine then dried over sodium sulfate and concentrated in vacuo. The residue was purified by flash chromatography on silica gel with a gradient of dichloromethane/methanol (98:2 v/v) as eluant to afford the title compound (48 mg, 34%) as a light yellow solid. MS (EI): 586.1 (M−H)⁻.

Example 121

(1R,2R,4R)-2-(3,3-Difluoro-azetidine-1-carbonyl)-4-[4-(2-methyl-pyridin-4-yl)-2-trifluoromethyl-benzenesulfonyl]-cyclopentanecarboxylic acid (1-cyano-cyclopropyl)-amide

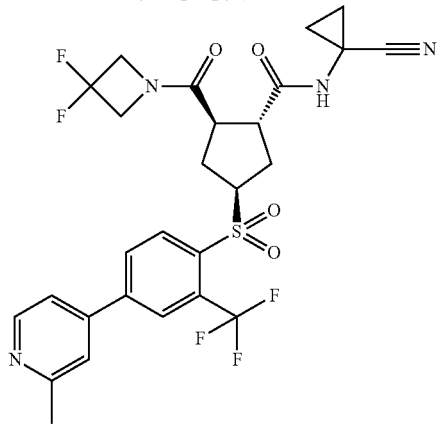

The title compound was prepared in analogy to Example 120 using (1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide (Example 117) and 2-picoline-4-boronic acid. Yellow solid. MS (EI): 597.1 (M+H)⁺.

Example 122

(1R,2R,4R)-4-[4-(2-Chloro-pyridin-4-yl)-2-trifluoromethyl-benzenesulfonyl]-2-(3,3-difluoro-azetidine-1-carbonyl)-cyclopentanecarboxylic acid (1-cyano-cyclopropyl)-amide

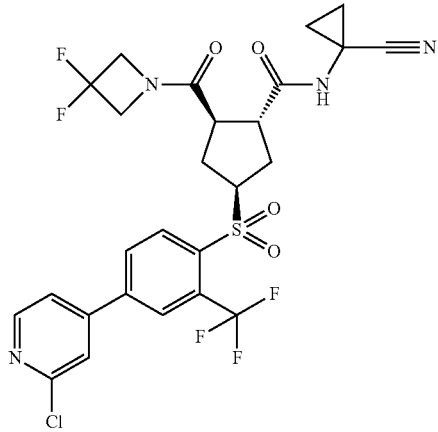

The title compound was prepared in analogy to Example 120 using (1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide (Example 117) and 2-chloropyridine-4-boronic acid. Light brown solid. MS (EI): 617.1 (M+H)⁺.

Example 123

(1R,2R,4R)-4-[4-(6-Chloro-pyrazin-2-yl)-2-trifluoromethyl-benzenesulfonyl]-2-(3,3-difluoro-azetidine-1-carbonyl)-cyclopentanecarboxylic acid (1-cyano-cyclopropyl)-amide

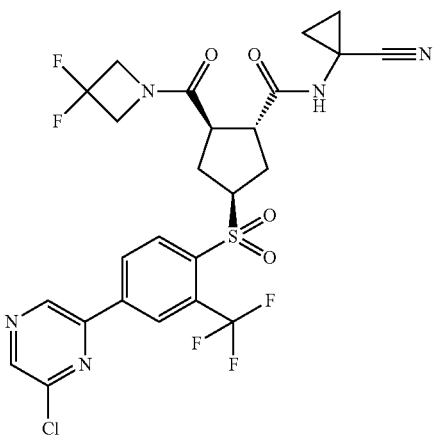

The title compound was prepared in analogy to Example 120 using (1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide (Example 117) and 6-chloropyrazine. Light brown solid. MS (EI): 618.3 (M+H)⁺.

Example 124

(1R,2R,4R)-2-(3,3-Difluoro-azetidine-1-carbonyl)-4-[4-(2-methyl-2H-pyrazol-3-yl)-2-trifluoromethyl-benzenesulfonyl]-cyclopentanecarboxylic acid (1-cyano-cyclopropyl)-amide

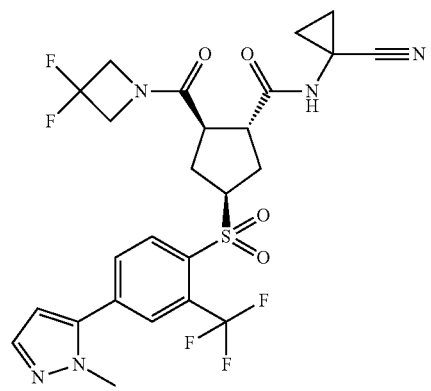

The title compound was prepared in analogy to Example 120 using (1R,2R,4R)-4-(4-Bromo-2-trifluoromethyl-benzenesulfonyl)-2-(3,3-difluoro-azetidine-1-carbonyl)-cyclopentanecarboxylic acid ((1-cyano-cyclopropyl)-amide (Example 117) and 1-methyl-5-(4,4,4,5,5-tetramethyl-1,3,2-dioxaborolan-2-yl)1H-pyrazole. Light yellow foam. MS (EI): 586.2 (M+H)+.

Example 125

(1R,2R,4R)-4-(4-Cyclopropyl-2-trifluoromethyl-benzenesulfonyl)-2-(3,3-difluoro-azetidine-1-carbonyl)-cyclopentanecarboxylic acid (1-cyano-cyclopropyl)-amide

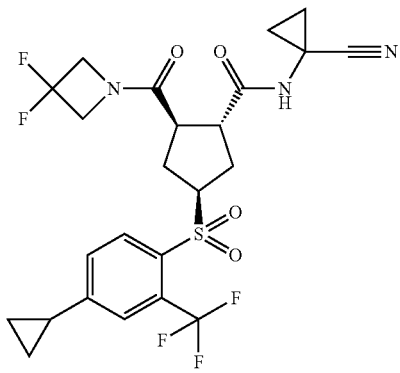

The title compound was prepared in analogy to Example 120 using (1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide (Example 117) and cyclopropylboronic acid. Light yellow foam. MS (EI): 546.2 (M+H)+.

Example 126

(1R,2R,4R)-4-[4-(5'-Chloro-[2,2]bipyrazinyl-6-yl)-2-trifluoromethyl-benzenesulfonyl]-2-(3,3-difluoro-azetidine-1-carbonyl)-cyclopentanecarboxylic acid (1-cyano-cyclopropyl)-amide

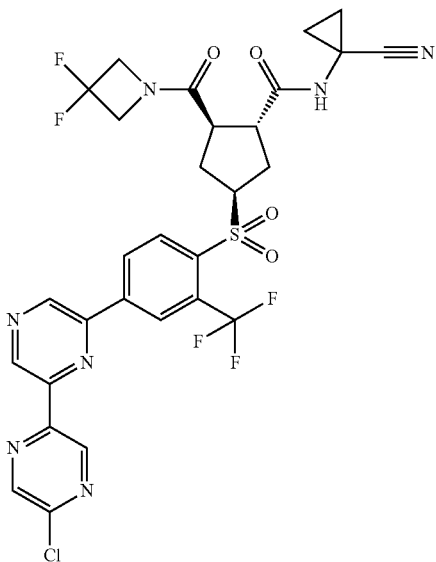

The title compound was isolated beside Example 123 as a side product during the reaction between (1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide (Example 117) and 6-chloropyrazine. Off-white solid. MS (EI): 686.12 (M+H)+.

Example 127

2-(3,3-Difluoro-azetidine-1-carbonyl)-4-[4-(oxetan-3-yloxy)-2-trifluoromethyl-benzenesulfonyl]-cyclopentanecarboxylic acid (1-cyano-cyclopropyl)-amide

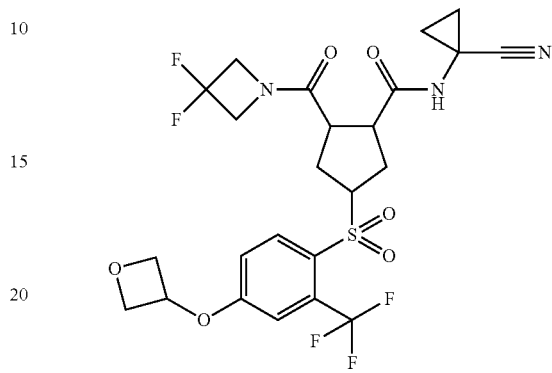

A mixture of (1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide (Example 118, 87 mg, 0.16 mmol), cesium carbonate (162 mg, 0.49 mmol) and 3-hydroxyoxetane (35 mg, 0.5 mmol) in N,N-dimethylformamide (3 mL) was stirred at 50° C. for 16 h. The reaction mixture was partitioned between ethyl acetate and a saturated aqueous solution of sodium hydrogenocarbonate. The aqueous layer was extracted with ethyl acetate then the combined organic layers were washed with water and brine then dried over sodium sulfate and concentrated in vacuo. The residue was purified by flash chromatography on silica gel with a gradient of dichloromethane/methanol (98:2 v/v) as eluant to afford the title compound (34 mg, 35%) as a white solid. MS (EI): 578.13 (M+H)+.

Example 128

2-(3,3-Difluoro-azetidine-1-carbonyl)-4-(4-pyrazol-1-yl-2-trifluoromethyl-benzenesulfonyl)-cyclopentanecarboxylic acid (1-cyano-cyclopropyl)-amide

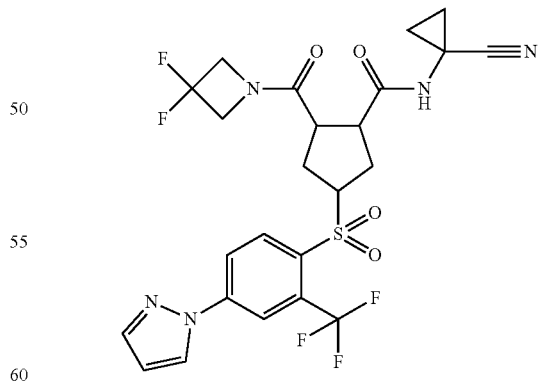

The title compound was prepared in analogy to Example 127 using (1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide (Example 118) and pyrazole. White foam. MS (EI): 572.14 (M+H)+.

Example 129

(1R,2R,4R)-4-[4-(4-Cyclopropyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide

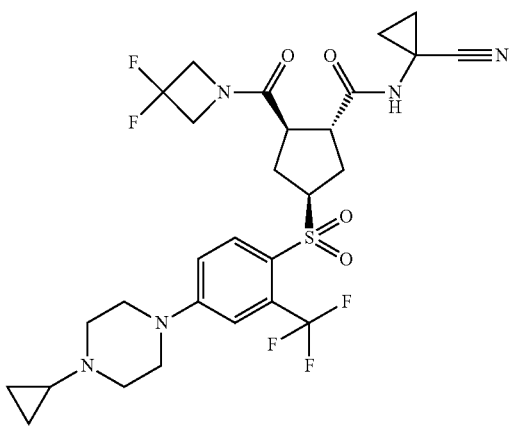

The title compound was prepared in analogy to Example 127 using (1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide (Example 118) and 1-cyclopropylpiperazine-bis-hydrochloric acid. White solid. MS (EI): 630.2 $(M+H)^+$.

Example 131

4-[4-(4-Acetyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide

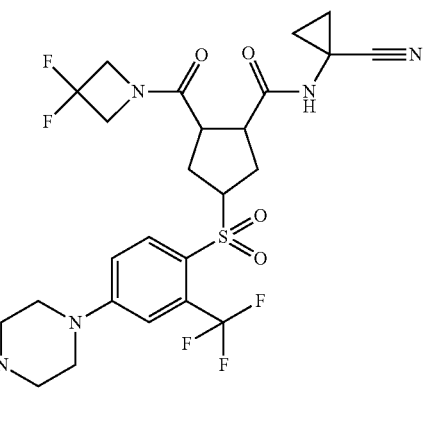

The title compound was prepared in analogy to Example 127 using (1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide (Example 118) and 1-acetyl-piperazine. White solid. MS (EI): 632.2 $(M+H)^+$.

Example 130

(1R,2R,4R)-4-[4-(4-tert-Butyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide

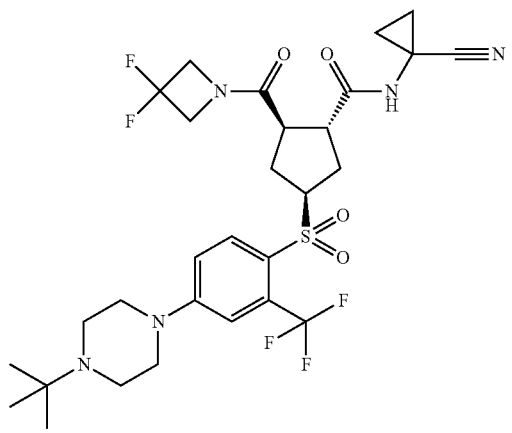

The title compound was prepared in analogy to Example 127 using (1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide (Example 118) and 1-tert-butyl-piperazine. Light yellow foam. MS (EI): 646.2 $(M+H)^+$.

Example 132

2-(3,3-Difluoro-azetidine-1-carbonyl)-4-[4-(3,3-difluoro-pyrrolidin-1-yl)-2-trifluoromethyl-benzenesulfonyl]-cyclopentanecarboxylic acid (1-cyano-cyclopropyl)-amide

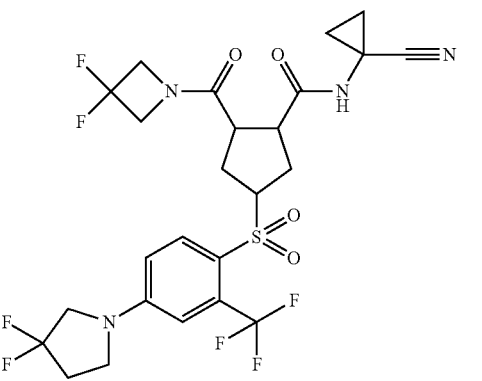

The title compound was prepared in analogy to Example 127 using (1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide (Example 118) and 3,3-difluoropyrrolidine hydrochloride. Off-white solid. MS (EI): 611.2 $(M+H)^+$.

Example 133

(1R,2R,4R)-2-(3,3-Difluoro-azetidine-1-carbonyl)-4-[4-(2-oxa-6-aza-spiro[3.3]hept-6-yl)-2-trifluoromethyl-benzenesulfonyl]-cyclopentanecarboxylic acid (1-cyano-cyclopropyl)-amide

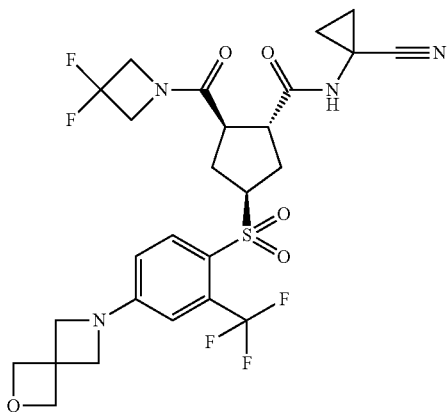

The title compound was prepared in analogy to Example 127 using (1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide (Example 118) and 2-oxa-6-aza-spiro[3.3]heptane, oxalic acid salt (Ang. Chem. Int. Ed. Engl. 2008, 47, 4512; CAS: [1045709-32-7]). White solid. MS (EI): 603.2 (M+H)$^+$.

Example 134

(1R,2R,4R)-4-[2-Chloro-4-(2,2,2-trifluoro-ethoxy)-benzenesulfonyl]-2-(3,3-difluoro-azetidine-1-carbonyl)-cyclopentanecarboxylic acid (1-cyano-cyclopropyl)-amide

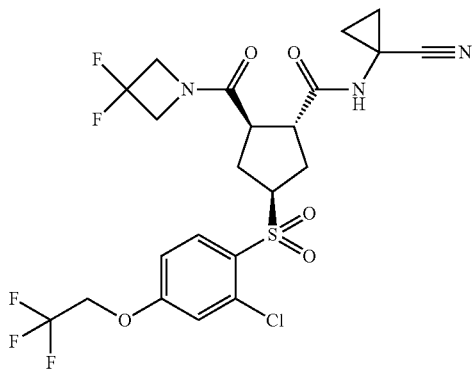

To a mixture of 2,2,2-trifluoroethanol (0.014 mL, 0.20 mmol) and sodium hydride (dispersion in oil, 55% w/w (9 mg, 20 mmol) in N,N-dimethylformamide (2 mL) was added (1R,2R,4R)-4-(2-Chloro-4-fluoro-benzenesulfonyl)-2-(3,3-difluoro-azetidine-1-carbonyl)-cyclopentanecarboxylic acid (1-cyano-cyclopropyl)-amid (Example 119, 80 mg, 0.16 mmol) at room temperature. The reaction mixture was stirred at 50° C. for 16 h, then was partitioned between ethyl acetate and a saturated aqueous solution of sodium hydrogenocarbonate. The aqueous layer was extracted with ethyl acetate then the combined organic layers were washed with water and brine then dried over sodium sulfate and concentrated in vacuo. The residue was purified by flash chromatography on silica gel with a gradient of dichloromethane/methanol (98:2 v/v) as eluant to afford the title compound (32 mg, 31%) as an off-white gum. MS (EI): 570.0 (M+H)$^+$.

Example 135

(1R,2R,4R)-4-[2-Chloro-4-((S)-2,2,2-trifluoro-1-methyl-ethoxy)-benzenesulfonyl]-2-(3,3-difluoro-azetidine-1-carbonyl)-cyclopentanecarboxylic acid (1-cyano-cyclopropyl)-amide

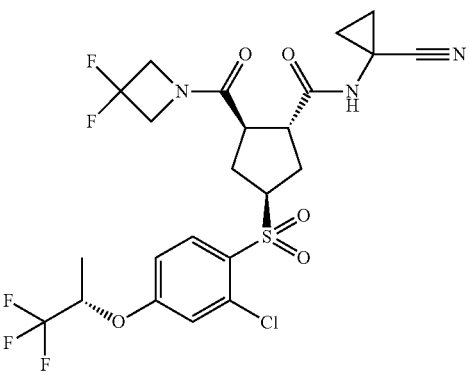

The title compound was prepared in analogy to Example 134 using (1R,2R,4R)-4-(2-Chloro-4-fluoro-benzenesulfonyl)-2-(3,3-difluoro-azetidine-1-carbonyl)-cyclopentanecarboxylic acid (1-cyano-cyclopropyl)-amid (Example 119) and (S)-1,1,1-trifluoro-propan-2-ol. Off-white solid. MS (EI): 584.1 (M+H)$^+$.

Example 136

(1R,2R,4R)-4-[2-Chloro-4-(3,3-difluoro-azetidin-1-yl)-benzenesulfonyl]-2-(3,3-difluoro-azetidine-1-carbonyl)-cyclopentanecarboxylic acid (1-cyano-cyclopropyl)-amide

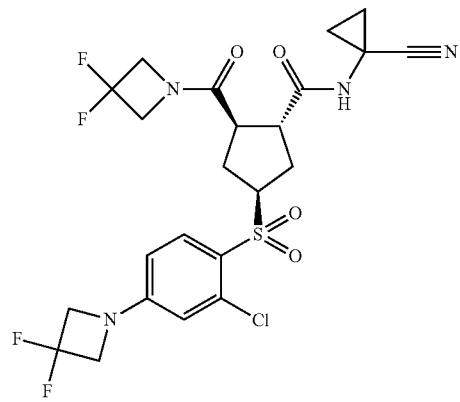

The title compound was prepared in analogy to Example 134 using (1R,2R,4R)-4-(2-Chloro-4-fluoro-benzenesulfonyl)-2-(3,3-difluoro-azetidine-1-carbonyl)-cyclopentanecarboxylic acid (1-cyano-cyclopropyl)-amide (Example 119) and 3,3-difluoroazetidine. Off-white solid. MS (EI): 563.1 (M+H)$^+$.

Example 137

(1R,2R,4R)-4-(4-Bromo-2-trifluoromethyl-benzene-sulfonyl)-2-methoxy-cyclopentanecarboxylic acid (1-cyano-cyclopropyl)-amide

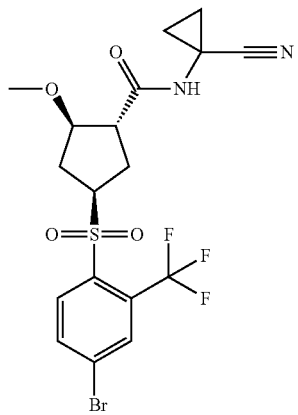

Racemic (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide (example 58) was subjected to chiral preparative HPLC on Chiralpak AD using heptane/isopropanol 75:25 as eluant. The title compound was eluated as the second peak. MS (EI): 495.1 (M+H)$^+$.

Example 138

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide

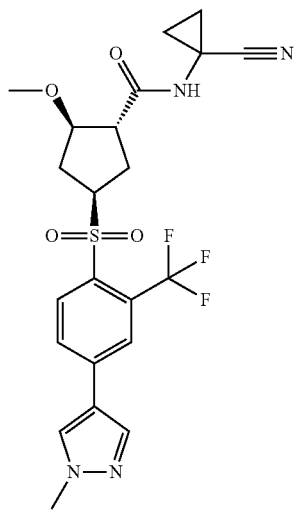

The title compound was prepared in analogy to example 62 using 1-methyl-4-(4.4.5.5-tetramethyl-1.3.2-dioxaborolan)-1H-pyrazole instead of 2.4-difluorophenylboronic acid and (1R,2R,4R)-4-(4-bromo-2-trifluoromethyl-benzenesulfonyl)-2-methoxy-cyclopentanecarboxylic acid (1-cyano-cyclopropyl)-amide (example 137) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. Light brown solid. MS (EI): 497.2 (M+H)$^+$.

Example 139

(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide

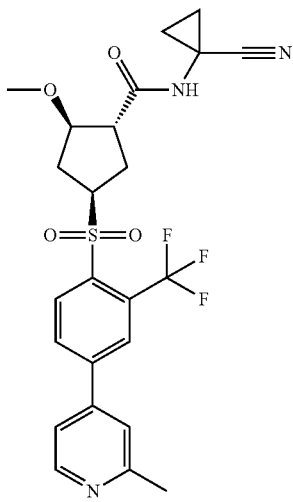

The title compound was prepared in analogy to example 62 using 2-picoline-4-boronic acid instead of 2.4-difluorophenylboronic acid and (1R,2R,4R)-4-(4-bromo-2-trifluoromethyl-benzenesulfonyl)-2-methoxy-cyclopentanecarboxylic acid (1-cyano-cyclopropyl)-amide (example 137) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. Pink solid. MS (EI): 508.1 (M+H)$^+$.

Example 140

(1R,2R,4R) and (1S,2S,4S)-2-Isopropoxy-4-[4-(2-methyl-pyridin-4-yl)-2-trifluoromethyl-benzenesulfonyl]-cyclopentanecarboxylic acid (1-cyano-cyclopropyl)-amide

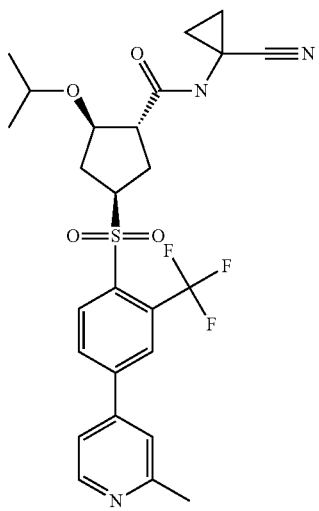

155

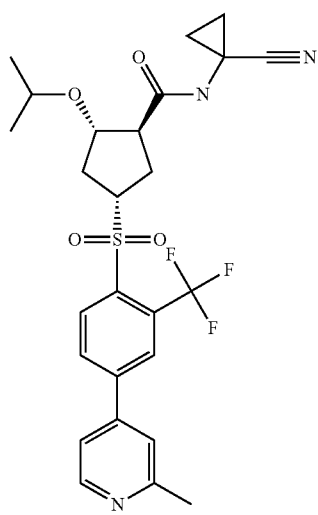

The title compound was prepared in analogy to example 62 using 2-picoline-4-boronic acid instead of 2.4-difluorophenylboronic acid and (1R,2R,4R) and (1S,2S,4S)-4-(4-bromo-2-trifluoromethyl-benzenesulfonyl)-2-isopropoxy-cyclopentanecarboxylic acid (1-cyano-cyclopropyl)-amide instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 536.2 (M+H)⁺.

156

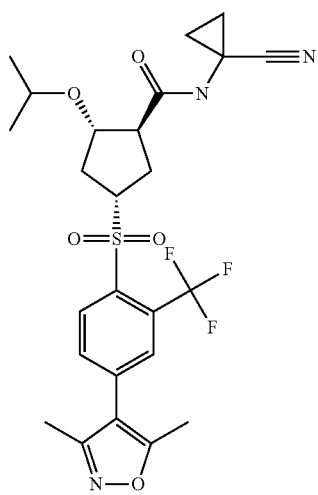

The title compound was prepared in analogy to example 62 using 3,5-dimethyl-isoxazole-4-boronic acid instead of 2.4-difluorophenylboronic acid and (1R,2R,4R) and (1S,2S,4S)-4-(4-bromo-2-trifluoromethyl-benzenesulfonyl)-2-isopropoxy-cyclopentanecarboxylic acid (1-cyano-cyclopropyl)-amide instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 538.2 (M–H)⁻.

Example 141

(1R,2R,4R) and (1S,2S,4S)-4-[4-(3,5-Dimethyl-isoxazol-4-yl)-2-trifluoromethyl-benzenesulfonyl]-2-isopropoxy-cyclopentanecarboxylic acid (1-cyano-cyclopropyl)-amide

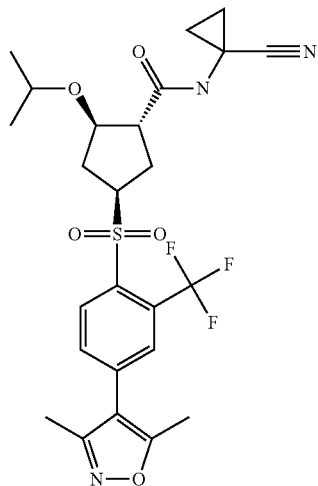

Example 142

(1R,2R,4R) and (1S,2S,4S)-2-Isopropoxy-4-[4-(1-methyl-1H-pyrazol-4-yl)-2-trifluoromethyl-benzenesulfonyl]-cyclopentanecarboxylic acid (1-cyano-cyclopropyl)-amide

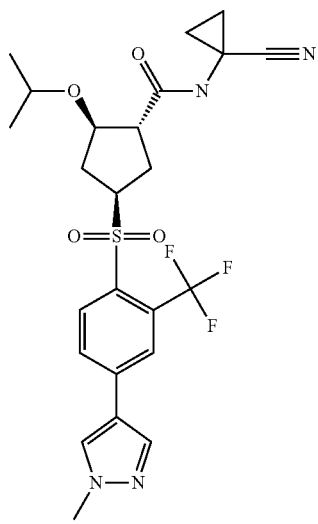

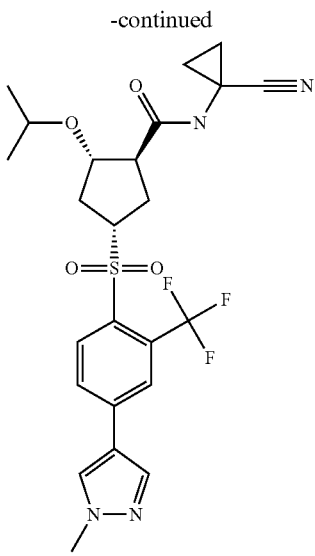

The title compound was prepared in analogy to example 62 using 1-methyl-4-(4.4.5.5-tetramethyl-1.3.2-dioxaborolan)-1H-pyrazole instead of 2.4-difluorophenylboronic acid and (1R,2R,4R) and (1S,2S,4S)-4-(4-bromo-2-trifluoromethyl-benzenesulfonyl)-2-isopropoxy-cyclopentanecarboxylic acid (1-cyano-cyclopropyl)-amide instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. Colorless solid. MS (EI): 523.2 (M−H)⁻.

Example 143 and Example 144

(1R,2R,4S)-4-(2-Chloro-benzenesulfonyl)-2-(4-fluoro-phenoxymethyl)-cyclopentanecarboxylic acid cyanomethyl-amide and (1R,2R,4R)-4-(2-Chloro-benzenesulfonyl)-2-(4-fluoro-phenoxymethyl)-cyclopentanecarboxylic acid cyanomethyl-amide

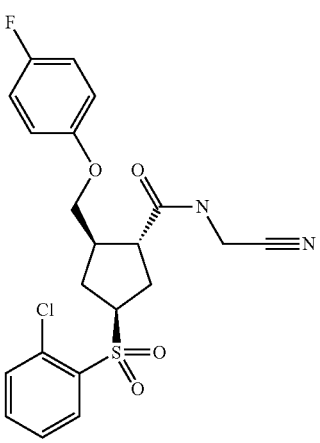

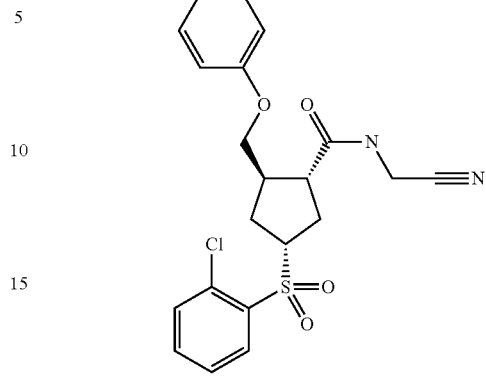

Step 1: (1R,2R)-4-(tert-Butyl-dimethyl-silanyloxy)-2-(4-fluoro-phenoxymethyl)-cyclopentanecarboxylic acid ethyl ester (epimeric mixture)

The title compound was prepared in analogy to example 68 step 5 using (1R,2R)-4-(tert-Butyl-dimethyl-silanyloxy)-2-hydroxymethyl-cyclopentanecarboxylic acid ethyl ester (example 68 step 4) and 4-fluorophenol. Colorless oil (74%). MS (EI): 397.2 (M+H)⁺.

Step 2: (1R,2R)-2-(4-Fluoro-phenoxymethyl)-4-hydroxy-cyclopentanecarboxylic acid ethyl ester (epimeric mixture)

The title compound was prepared in analogy to example 68 step 6 using (1R,2R)-4-(tert-Butyl-dimethyl-silanyloxy)-2-(4-fluoro-phenoxymethyl)-cyclopentanecarboxylic acid ethyl ester (epimeric mixture, example 143 and 144 step 1). Yellow oil (92%). MS (EI): 283.2 (M+H)⁺.

Step 3: (1R,2R)-2-(4-Fluoro-phenoxymethyl)-4-methanesulfonyloxy-cyclopentanecarboxylic acid ethyl ester (epimeric mixture)

The title compound was prepared in analogy to example 68 step 7 using (1R,2R)-2-(4-Fluoro-phenoxymethyl)-4-hydroxy-cyclopentanecarboxylic acid ethyl ester (epimeric mixture, example 143 and 144 step 2). Yellow oil (93%). MS (EI): 378.3 (M+NH₄)⁺.

Step 4: (1R,2R)-4-(2-Chloro-4-fluoro-phenylsulfanyl)-2-(4-fluoro-phenoxymethyl)-cyclopentanecarboxylic acid ethyl ester (epimeric mixture)

The title compound was prepared in analogy to example 68 step 8 using (1R,2R)-2-(4-Fluoro-phenoxymethyl)-4-methanesulfonyloxy-cyclopentanecarboxylic acid ethyl ester (epimeric mixture, example 143 and 144 step 3) and 2-chloro-4-fluorothiophenol. Yellow oil (56%). MS (EI): 378.3 (M+NH₄)⁺.

Step 5: (1R,2R)-4-(2-Chloro-4-fluoro-benzenesulfonyl)-2-(4-fluoro-phenoxymethyl)-cyclopentanecarboxylic acid ethyl ester (epimeric mixture)

The title compound was prepared in analogy to example 68 step 9 using (1R,2R)-4-(2-Chloro-4-fluoro-phenylsulfanyl)-2-(4-fluoro-phenoxymethyl)-cyclopentanecarboxylic acid ethyl ester (epimeric mixture, example 143 and 144 step 4). Yellow oil (94%). MS (EI): 459.2 (M+H)⁺.

Step 6: (1R,2R)-4-(2-Chloro-4-fluoro-benzenesulfonyl)-2-(4-fluoro-phenoxymethyl)-cyclopentanecarboxylic acid (epimeric mixture)

The title compound was prepared in analogy to example 68 step 10 using (1R,2R)-4-(2-Chloro-4-fluoro-benzenesulfonyl)-2-(4-fluoro-phenoxymethyl)-cyclopentanecarboxylic acid ethyl ester (epimeric mixture, example 143 and 144 step 5). Off white gum (quant.). MS (EI): 429.3 (M−H)⁻.

Step 7: (1R,2R)-4-(2-Chloro-4-fluoro-benzenesulfonyl)-2-(4-fluoro-phenoxymethyl)-cyclopentanecarboxylic acid cyanomethyl-amide (epimeric mixture)

The title compound was prepared in analogy to example 68 step 11 using (1R,2R)-4-(2-Chloro-4-fluoro-benzenesulfonyl)-2-(4-fluoro-phenoxymethyl)-cyclopentanecarboxylic acid (epimeric mixture, example 143 and 144 step 6) and aminoacetonitrile. Light yellow foam gum (44%). MS (EI): 469.3 (M+H)⁺.

Step 8: (1R,2R,4S)-4-(2-Chloro-benzenesulfonyl)-2-(4-fluoro-phenoxymethyl)-cyclopentanecarboxylic acid cyanomethyl-amide and (1R,2R,4R)-4-(2-Chloro-benzenesulfonyl)-2-(4-fluoro-phenoxymethyl)-cyclopentanecarboxylic acid cyanomethyl-amide The title compound was prepared in analogy to example 68 step 12 using (1R,2R)-4-(2-Chloro-4-fluoro-benzenesulfonyl)-2-(4-fluoro-phenoxymethyl)-cyclopentanecarboxylic acid cyanomethyl-amide (epimeric mixture, example 143 and 144 step 7).

Fraction 1 (Rt: 15 min): (1R,2R,4S)-4-(2-Chloro-benzenesulfonyl)-2-(4-fluoro-phenoxymethyl)-cyclopentanecarboxylic acid cyanomethyl-amide (53%). MS (EI): 469.2 (M+H)⁺.

Fraction 2 (Rt: 17 min): (1R,2R,4R)-4-(2-Chloro-benzenesulfonyl)-2-(4-fluoro-phenoxymethyl)-cyclopentanecarboxylic acid cyanomethyl-amide (10%). MS (EI): 469.2 (M+H)⁺.

Example 145 and Example 146

(1R,2R,4S)-4-(2-Chloro-4-fluoro-benzenesulfonyl)-2-(4-fluoro-phenoxymethyl)-cyclopentanecarboxylic acid (1-cyano-cyclopropyl)-amide and (1R,2R,4R)-4-(2-Chloro-4-fluoro-benzenesulfonyl)-2-(4-fluoro-phenoxymethyl)-cyclopentanecarboxylic acid (1-cyano-cyclopropyl)-amide

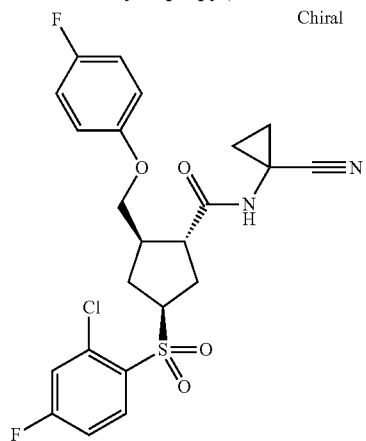

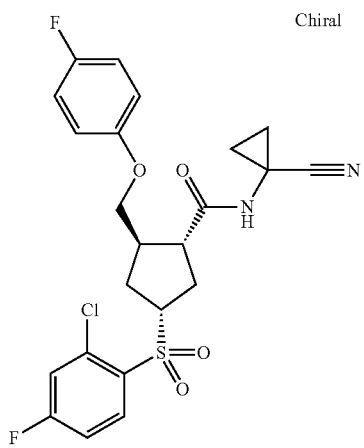

Step 1: (1R,2R)-4-(2-Chloro-4-fluoro-benzenesulfonyl)-2-(4-fluoro-phenoxymethyl)-cyclopentanecarboxylic acid (1-cyano-cyclopropyl)-amide (epimeric mixture)

The title compound was prepared in analogy to example 68 step 11 using (1R,2R)-4-(2-Chloro-4-fluoro-benzenesulfonyl)-2-(4-fluoro-phenoxymethyl)-cyclopentanecarboxylic acid (epimeric mixture, example 143 and 144 step 6) and 1-aminocyclopropanecarbonitrile. Light orange oil (51%). MS (EI): 493.4 (M−H)⁻.

Step 2: (1R,2R,4S)-4-(2-Chloro-4-fluoro-benzenesulfonyl)-2-(4-fluoro-phenoxymethyl)-cyclopentanecarboxylic acid (1-cyano-cyclopropyl)-amide and (1R,2R,4R)-4-(2-Chloro-4-fluoro-benzenesulfonyl)-2-(4-fluoro-phenoxymethyl)-cyclopentanecarboxylic acid (1-cyano-cyclopropyl)-amide The title compound was prepared in analogy to example 68 step 12 using (1R,2R)-4-(2-Chloro-4-fluoro-benzenesulfonyl)-2-(4-fluoro-phenoxymethyl)-cyclopentanecarboxylic acid cyanomethyl-amide (epimeric mixture, example 145 and 146 step 1).

Fraction 1 (Rt: 14 min): (1R,2R,4S)-4-(2-Chloro-4-fluoro-benzenesulfonyl)-2-(4-fluoro-phenoxymethyl)-cyclopentanecarboxylic acid (1-cyano-cyclopropyl)-amide (39%). MS (EI): 495.3 (M+H)⁺.

Fraction 2 (Rt: 17 min): (1R,2R,4R)-4-(2-Chloro-4-fluoro-benzenesulfonyl)-2-(4-fluoro-phenoxymethyl)-cyclopentanecarboxylic acid (1-cyano-cyclopropyl)-amide (16%). MS (EI): 495.3 (M+H)⁺.

Example 147

(1R,2R,4S)-4-[2-Chloro-4-(4-ethyl-piperazin-1-yl)-benzenesulfonyl]-2-(4-fluoro-phenoxymethyl)-cyclopentanecarboxylic acid cyanomethyl-amide Chiral

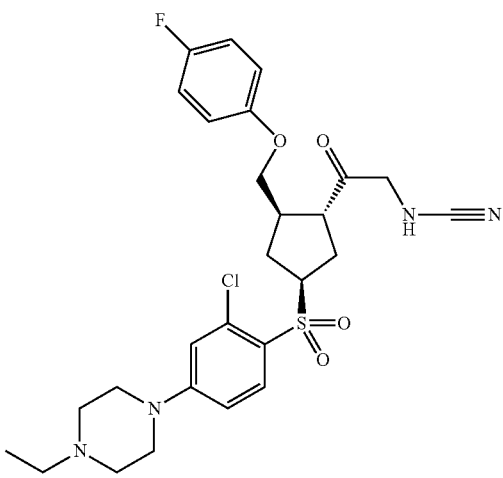

The title compound was prepared in analogy to example 127 using (1R,2R,4S)-4-(2-chloro-4-fluoro-benzenesulfonyl)-2-(4-fluoro-phenoxymethyl)-cyclopentanecarboxylic acid (1-cyano-cyclopropyl)-amide (example 145) and 1-ethyl-piperazine. Yellow oil. MS (EI): 563.2 (M+H)$^+$.

Example 148

(1R,2R,4R)-4-(2-Chloro-benzenesulfonyl)-2-[4-(4-fluoro-phenyl)-piperidin-1-ylmethyl]-cyclopentanecarboxylic acid (1-cyano-cyclopropyl)-amide Chiral

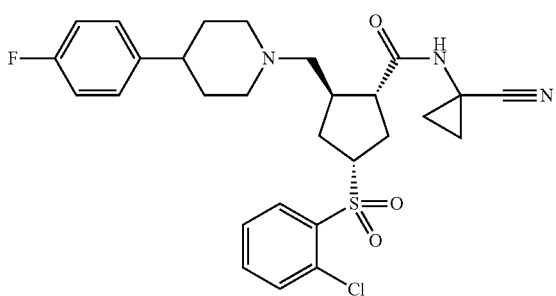

Step 1: (1R,2R)-4-(tert-Butyl-dimethyl-silanyloxy)-2-(toluene-4-sulfonyloxymethyl)-cyclopentanecarboxylic acid ethyl ester (epimeric mixture)

To a cold (0° C.) solution of (1R,2R)-4-(tert-Butyl-dimethyl-silanyloxy)-2-hydroxymethyl-cyclopentanecarboxylic acid ethyl ester (example 68 step 4, 500 mg) and triethyl amine (836 mg) in dichloromethane (5 mL) was added toluene-4-sulfonyl chloride (1.53 g). The reaction mixture was stirred overnight at room temperature then partitioned between hydrochloric acid (1N) and dichloromethane. The aqueous layers was extracted with dichloromethane and the combined organic layers were washed with half saturated aqueous solution of sodium hydrogenocarbonate and brine, then dried over sodium sulfate, filtered and concentrated in vacuo. The residue was purified by flash chromatography on silica gel with a gradient of cyclohexane/ethyl acetate (1:0 to 19:1 v/v) as eluant to afford the title compound (602 mg, 80%) as a yellow liquid.

Step 2: (1R,2R,4S)-4-(tert-Butyl-dimethyl-silanyloxy)-2-[4-(4-fluoro-phenyl)-piperidin-1-ylmethyl]-cyclopentanecarboxylic acid ethyl ester A solution of (1R,2R)-4-(tert-Butyl-dimethyl-silanyloxy)-2-(toluene-4-sulfonyloxymethyl)-cyclopentanecarboxylic acid ethyl ester (example 148, step 1, epimeric mixture, 410 mg), 4-(4-Fluoro-phenyl)-piperidine (cas # 6716-98-9, 291 mg), sodium iodide (1.36 g) and triethylamine (545 mg) in N,N-dimethylformamide (2.8 mL) was stirred at 90° C. over 6 h. The reaction mixture was partitioned between ethyl acetate and an aqueous saturated solution of sodium hydrogenocarbonate. The aqueous layer was extracted with ethyl acetate and the combined organic layers were dried over sodium sulfate, filtered and concentrated in vacuo. The residue was purified by flash chromatography on silica gel with a gradient of cyclohexane/ethyl acetate (9:1 to 1:1 v/v) as eluant to afford the title compound (170 mg, 41%) as a yellow liquid. MS (EI): 464.4 (M+H)$^+$.

Step 3: (1R,2R,4S)-2-[4-(4-Fluoro-phenyl)-piperidin-1-ylmethyl]-4-hydroxy-cyclopentanecarboxylic acid ethyl ester The title compound was prepared in analogy to example 68 step 6 using (1R,2R,4S)-4-(tert-Butyl-dimethyl-silanyloxy)-2-[4-(4-fluoro-phenye-piperidin-1-ylmethyl]-cyclopentanecarboxylic acid ethyl ester (example 148 step 2). Orange liquid (quant.). MS (EI): 350.4 (M+H)$^+$.

Step 4: (1R,2R,4S)-2-[4-(4-Fluoro-phenyl)-piperidin-1-ylmethyl]-4-methanesulfonyloxy-cyclopentanecarboxylic acid ethyl ester The title compound was prepared in analogy to example 68 step 7 using (1R,2R,4S)-2-[4-(4-Fluoro-phenyl)-piperidin-1-ylmethyl]-4-hydroxy-cyclopentanecarboxylic acid ethyl ester (example 148 step 3). Orange semi-solid (91%). MS (EI): 428.3 (M+H)$^+$.

Step 5: (1R,2R,4R)-4-(2-Chloro-phenylsulfanyl)-2-[4-(4-fluoro-phenyl)-piperidin-1-ylmethyl]-cyclopentanecarboxylic acid To a solution of 2-chlorobenzenethiol (141 mg) in tetrahydrofuran (2 mL) was added sodium hydride (dispersion in oil, 55% w/w, 50 mg). The mixture was stirred 20 min at room temperature. Then the mixture was cooled down to 0° C. and a solution of (1R,2R,4S)-2-[4-(4-Fluoro-phenyl)-piperidin-1-ylmethyl]-4-methanesulfonyloxy-cyclopentanecarboxylic acid ethyl ester (example 148 step 4, 180 mg) in tetrahydrofuran (2 mL) was added dropwise. The reaction mixture was stirred at room temperature over 24 h then partitioned between hydrochloric acid (1N) and ethyl acetate. The aqueous layer was extracted with ethyl acetate and the combined organic layers were washed with a saturated aqueous solution of sodium carbonate and brine then dried over sodium sulfate, filtered and concentrated in vacuo. The residue was purified by flash chromatography on silica gel with a gradient of dichloromethane:methanol (98:2 to 9:1 v/v) as eluant to afford the title compound (31 mg, 16%) as a light brown solid. MS (EI): 448.1 (M+H)$^+$.

Step 6: (1R,2R,4R)-4-(2-Chloro-phenylsulfanyl)-2-[4-(4-fluoro-phenyl)-piperidin-1-ylmethyl]-cyclopentanecarboxylic acid (1-cyano-cyclopropyl)-amide The title compound was prepared in analogy to example 68 step 11 using (1R,2R,4R)-4-(2-Chloro-phenylsulfanyl)-2-[4-(4-fluoro-phenyl)-piperidin-1-ylmethyl]-cyclopentanecarboxylic acid (example 148 step 5) and 1-amino-cyclopropanecarbonitrile. Light yellow foam (52%). MS (EI): 512.3 (M+H)+.

Step 7: (1R,2R,4R)-4-(2-Chloro-benzenesulfonyl)-2-[4-(4-fluoro-phenyl)-piperidin-1-ylmethyl]-cyclopentanecarboxylic acid (1-cyano-cyclopropyl)-amide The title compound was prepared in analogy to example 68 step 9 using (1R,2R,4R)-4-(2-chloro-phenylsulfanyl)-2-[4-(4-fluoro-phenyl)-piperidin-1-ylmethyl]-cyclopentanecarboxylic acid (1-cyano-cyclopropyl)-amide (example 148 step 6). Yellow oil (58%). MS (EI): 544.3 (M+H)+.

Example 149

(1R,2R,4R) and (1S,2S,4S)-4-[2-Chloro-4-(4-methyl-pyrazol-1-yl)-benzenesulfonyl]-2-methoxy-cyclopentanecarboxylic acid (1-cyano-cyclopropyl)-amide

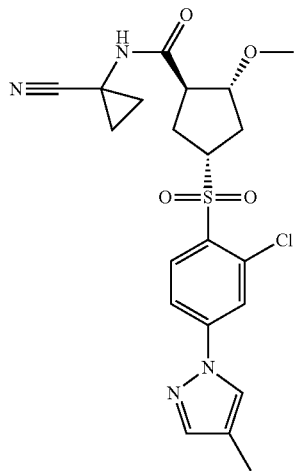

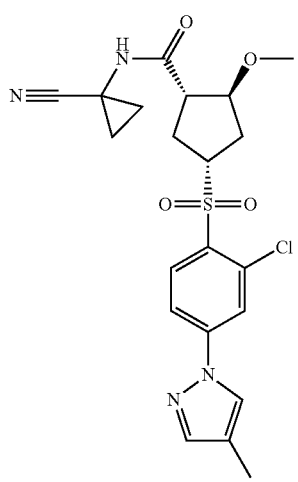

The title compound was prepared in analogy to example 57 using 4-methylpyrazole instead of 4-fluorophenol. Colorless oil. MS (EI): 463.1 (M+H)+.

Example 150

(1R,2R,4R) and (1S,2S,4S)-4-(2-Chlorophenylsulfonyl)-N-(1-cyanocyclopropyl)-2-(4-methylbenzyloxy)cyclopentanecarboxamide

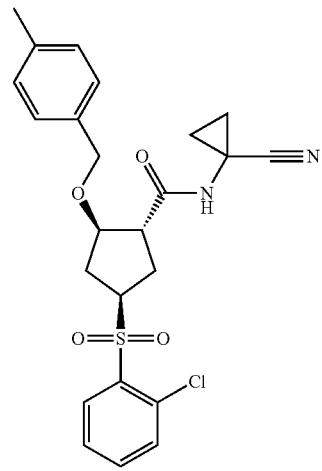

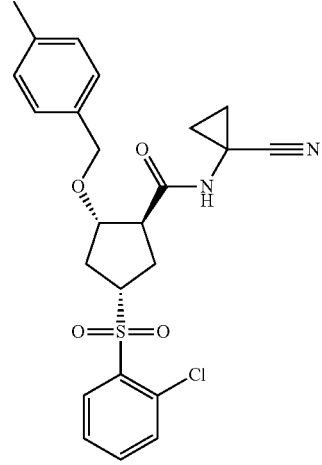

Step 1: (1R,2R,4R) and (1S,2S,4S)-4-(2-Chloro-benzenesulfonyl)-2-(4-methyl-benzyloxy)-cyclopentanecarboxylic acid methyl ester A mixture of (1R,2R,4R) and (1S,2S,4S)-4-(2-chloro-benzenesulfonyl)-2-hydroxy-cyclopentanecarboxylic acid methyl ester (80 mg, 0.251 mmol, example 48, step 5), 1-(bromomethyl)-4-methylbenzene (232 mg, 1.25 mmol) and silver (I) oxide (116 mg, 0.502 mmol) in DCM (2 ml) was stirred at room temperature for 60 h. The reaction mixture was filtered through a pad of Celite, the pad was washed with DCM and the filtrate was evaporated. The remaining grey oil was purified by silica gel chromatography (heptane/EtOAc 80:20-70:30) to obtain the title compound (63 mg, 56%) as colorless oil. MS (EI): 423.1 (M+H)+.

Step 2: Lithium (1R,2R,4R) and (1S,2S,4S)-4-(2-chloro-benzenesulfonyl)-2-(4-methyl-benzyloxy)-cyclopentanecarboxylate The title compound was prepared in analogy to example 46, step 10 and was obtained as light yellow solid.

Step 3: (1R,2R,4R) and (1S,2S,4S)-4-(2-Chlorophenylsulfonyl)-N-(1-cyanocyclopropyl)-2-(4-methyl-benzyloxy)cyclopentanecarboxamide The title compound was prepared in analogy to example 46, step 11 using HATU/N-ethyl-N,N-diisopropyl amine in DMF instead of EDCI/HOBt/N-ethyl-N,N-diisopropyl amine in acetonitrile and was obtained as white solid. MS (EI): 473.1 (M+H)$^+$.

Example 151

(1R,2R,4R) and (1S,2S,4S)-2-(4-Chloro-2-(trifluoromethyl)benzyloxy)-4-(2-chlorophenylsulfonyl)-N-(1-cyanocyclopropyl)cyclopentanecarboxamide

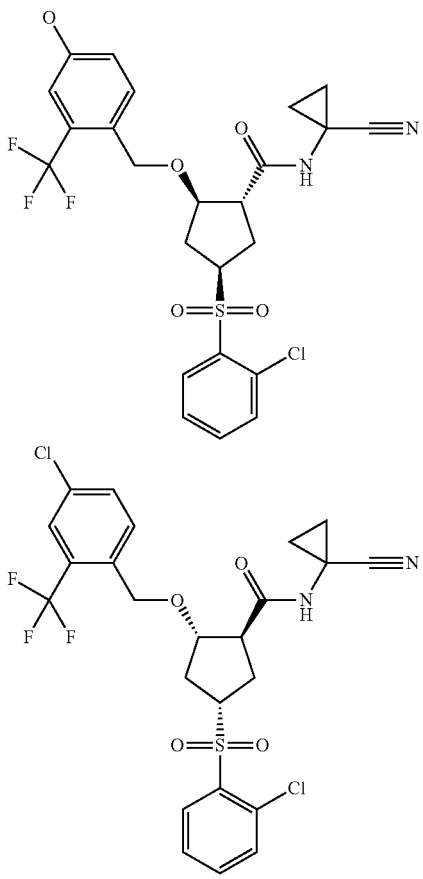

The title compound was prepared in analogy to example 150 using 1-(bromomethyl)-4-chloro-2-(trifluoromethyl) benzene instead of 1-(bromomethyl)-4-methylbenzene. White solid. MS (EI): 561.1 (M+H)$^+$.

Example 152

Formic acid (1R,2R,4S)-4-(4-bromo-2-trifluoromethyl-benzenesulfonyl)-2-(1-cyano-cyclopropylcarbamoyl)-cyclopentylmethyl ester

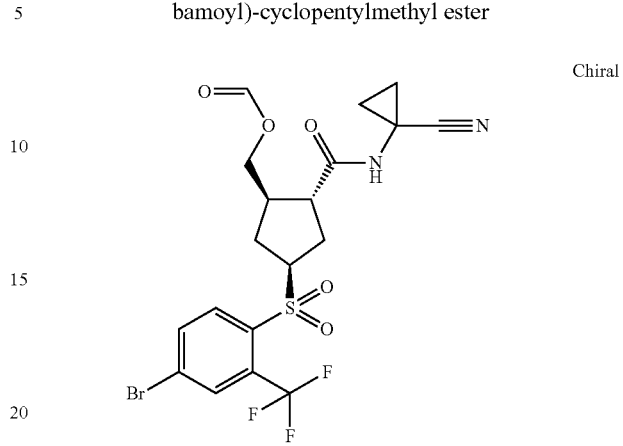

Step 1: (1R,2R)-4-(tert-Butyl-dimethyl-silanyloxy)-2-trityloxymethyl-cyclopentanecarboxylic acid ethyl ester (epimeric mixture)

To a solution of (1R,2R)-4-(tert-Butyl-dimethyl-silanyloxy)-2-hydroxymethyl-cyclopentanecarboxylic acid ethyl ester (epimeric mixture, Example 68 step 4, 1.08 g) in acetonitrile (16 mL) was added 1-tritylpyridimium tetrafluoroborate (1.6 g). The turbid mixture was stirred at room temperature over 2 days and 1-tritylpyridimium tetrafluoroborate (0.5 g) was again added and the mixture was stirred 4 days at room temperature then concentrated in vacuo. The residue was purified by flash chromatography on silica gel with a gradient of cyclohexane:ethyl:acetate (98:2 to 95:2 v/v) as eluant to afford the title compound (1.31 g, 68%) as a light yellow oil. MS (EI): 562.3 (M+NH$_4$)$^+$.

Step 2: (1R,2R)-4-Hydroxy-2-trityloxymethyl-cyclopentanecarboxylic acid ethyl ester (epimeric mixture)

The title compound was prepared in analogy to example 68 step 6 using (1R,2R)-4-(tert-Butyl-dimethyl-silanyloxy)-2-trityloxymethyl-cyclopentanecarboxylic acid ethyl ester (epimeric mixture, example 152 step 1). Orange oil (94%). MS (EI): 453.2 (M+Na)$^+$.

Step 3: (1R,2R)-4-Methanesulfonyloxy-2-trityloxymethyl-cyclopentanecarboxylic acid ethyl ester (epimeric mixture)

The title compound was prepared in analogy to example 68 step 7 using (1R,2R)-4-Hydroxy-2-trityloxymethyl-cyclopentanecarboxylic acid ethyl ester (epimeric mixture, example 152 step 2). Yellow oil (77%).

Step 4: (1R,2R,4S)-4-(4-Bromo-2-trifluoromethyl-phenylsulfanyl)-2-trityloxymethyl-cyclopentanecarboxylic acid ethyl ester The title compound was prepared in analogy to example 68 step 8 using (1R,2R)-4-methanesulfonyloxy-2-trityloxymethyl-cyclopentanecarboxylic acid ethyl ester (epimeric mixture, example 152 step 3) and 4-bromo-2-trifluoromethyl-benzenethiol (example 58, intermediate 1). Colorless oil (43%). MS (EI): 691.0 (M+Na)$^+$.

Step 5: (1R,2R,4S)-4-(4-Bromo-2-trifluoromethyl-benzenesulfonyl)-2-trityloxymethyl-cyclopentanecarboxylic acid ethyl ester The title compound was prepared in analogy to example 68 step 9 using (1R,2R,4S)-4-(4-bromo-2-trifluoromethyl-phenylsulfanyl)-2-trityloxymethyl-cyclopentanecarboxylic acid ethyl ester (example 152 step 4). White foam (27%). MS (EI): 725.0 (M+Na)+.

Step 6: (1R,2R,4S)-4-(4-Bromo-2-trifluoromethyl-benzenesulfonyl)-2-trityloxymethyl-cyclopentanecarboxylic acid The title compound was prepared in analogy to example 68 step 10 using (1R,2R,4S)-4-(4-Bromo-2-trifluoromethyl-benzenesulfonyl)-2-trityloxymethyl-cyclopentanecarboxylic acid ethyl ester (example 152 step 5). Offwhite foam (quant.). MS (EI): 673.2 (M−H)−.

Step 7: (1R,2R,4S)-4-(4-Bromo-2-trifluoromethyl-benzenesulfonyl)-2-trityloxymethyl-cyclopentanecarboxylic acid (1-cyano-cyclopropyl)-amide The title compound was prepared in analogy to example 68 step 11 using (1R,2R,4S)-4-(4-bromo-2-trifluoromethyl-benzenesulfonyl)-2-trityloxymethyl-cyclopentanecarboxylic acid (example 152 step 6). White foam (73%). MS (EI): 761.1 (M+Na)+.

Step 8: Formic acid (1R,2R,4S)-4-(4-bromo-2-trifluoromethyl-benzenesulfonyl)-2-(1-cyano-cyclopropylcarbamoyl)-cyclopentylmethyl ester A mixture of (1R,2R,4S)-4-(4-bromo-2-trifluoromethyl-benzenesulfonyl)-2-trityloxymethyl-cyclopentanecarboxylic acid (1-cyano-cyclopropyl)-amide (example 152 step 7, 10 mg) in concentrated formic acid (0.2 mL) was stirred at room temperature during 1.5 h. The reaction mixture was partitioned between ethyl acetate and a saturated aqueous solution of sodium hydrogenocarbonate. The organic layer was washed with water, dried over sodium sulfate, filtered and concentrated in vacuo. The residue was purified by flash chromatography on silica gel with a gradient of cyclohexane:ethyl acetate (3:1 to 1:1 v/v) as eluant to afford the title compound (2 mg, 25%) as a colorless oil. MS (EI): 524 (M)+.

Example 153

(1R,2R,4S)-4-(2-Chloro-4-fluoro-benzenesulfonyl)-2-(4-methoxy-benzyloxymethyl)-cyclopentanecarboxylic acid (1-cyano-cyclopropyl)-amide

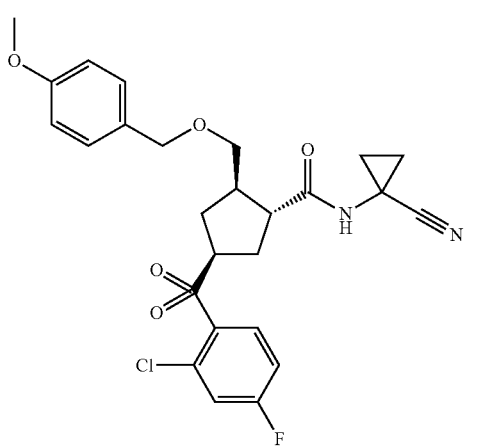

Chiral

Step 1:
(1R,2R,4R)-4-Hydroxy-cyclopentane-1,2-dicarboxylic acid monoethyl ester

A solution of (1R,2R)-4-oxo-cyclopentane-1,2-dicarboxylic acid monoethyl ester (example 1, step 1, 6.0 g) in an aqueous buffer (600 mL, 30 mM; 2-(N-morpholino)ethanesulfonic acid; 0.5 M D-glucose [10 equ.]; 2 mM Magnesium chloride) was adjusted to pH 6.4 at 35° C. Under stirring the reduction was started by the addition of the cofactor NADP (120 mg), the cofactor regeneration enzyme-glucose dehydrogenase (120 mg GDH 102 [Codexis]) and the reductase (1.2 g KRED-NADP-174 [Codexis]). During the 69 h reaction time at 35° C. the pH was kept at pH 6.5 by the addition of 1M NaOH. Afterwards the enzymes were denatured by adjusting to pH 2, adding a total of 300 mL ethyl acetate and a total of 60 g filter aid—Dicalite under stirring of at least 1.5 h. After filtration, two further extractions with 200 mL ethyl acetate, treatment of the combined organic phases with magnesium sulfate, evaporation and drying for 4 h on a high vacuum, 4.1 g of the title compound was isolated. MS: 201.07 (M−H)−; chiral GC: d.r.: 1.4:97.3:1.4: 0.0 [BGB-172 (BGB Analytik AG), 30 m*0.25 mm; 0.25 μm; H2; 2° C./min, 100° C. to 200° C.]. An additional extraction of the aqueous phase with further 200 mL ethyl acetate yielded after treatment with magnesium sulfate, evaporation and drying for 4 h on a high vacuum in 1.62 g of the title compound. MS: 201.07 (M−H)−; chiral GC: d.r.: 1.3:96.3:1.6:0.4. The summing up gave a total yield of 5.72 g (93.9%).

Step 2: (1R,2R,4R)-4-(tert-Butyl-dimethyl-silanyloxy)-cyclopentane-1,2-dicarboxylic acid monoethyl ester The title compound was prepared in analogy to example 68 step 2 and 3 using (1R,2R,4R)-4-hydroxy-cyclopentane-1,2-dicarboxylic acid monoethyl ester acid (example 153 step 1). Colorless liquid (94%). MS (EI): 317.2 (M+H)+.

Step 3: (1R,2R,4R)-4-(tert-Butyl-dimethyl-silanyloxy)-2-hydroxymethyl-cyclopentanecarboxylic acid ethyl ester The title compound was prepared in analogy to example 68 step 4 using (1R,2R,4R)-4-(tert-Butyl-dimethyl-silanyloxy)-cyclopentane-1,2-dicarboxylic acid monoethyl ester (example 153 step 2). Colorless liquid (93%). MS (EI): 303.2 (M+H)+.

Step 4: (1R,2R,4R)-4-(tert-Butyl-dimethyl-silanyloxy)-2-(4-methoxy-benzyloxymethyl)-cyclopentanecarboxylic acid ethyl ester The title compound was prepared in analogy to example 68 step 5 using (1R,2R,4R)-4-(tert-Butyl-dimethyl-silanyloxy)-2-(4-methoxy-benzyloxymethyl)-cyclopentanecarboxylic acid ethyl ester (example 153 step 3). Colorless liquid (28%). MS (EI): 422 (M)+.

Step 5: (1R,2R,4R)-4-Hydroxy-2-(4-methoxy-benzyloxymethyl)-cyclopentanecarboxylic acid ethyl ester The title compound was prepared in analogy to example 68 step 6 using (1R,2R,4R)-4-(tert-Butyl-dimethyl-silanyloxy)-2-(4-methoxy-phenoxymethyl)-cyclopentanecarboxylic acid ethyl ester (example 153 step 4). Light yellow oil (93%). MS (EI): 308 (M)+.

Step 6: (1R,2R,4R)-4-Methanesulfonyloxy-2-(4-methoxy-benzyloxymethyl)-cyclopentanecarboxylic acid ethyl ester The title compound was prepared in analogy to example 68 step 7 using (1R,2R,4R)-4-Hydroxy-2-(4-methoxy-benzyloxymethyl)-cyclopentanecarboxylic acid ethyl ester (example 153 step 5). Colorless oil (56%). MS (EI): 386 (M)⁻.

Step 7: (1R,2R,4S)-4-(2-Chloro-4-fluoro-phenylsulfanyl)-2-(4-methoxy-benzyloxymethyl)-cyclopentanecarboxylic acid ethyl ester The title compound was prepared in analogy to example 68 step 8 using (1R,2R,4R)-4-methanesulfonyloxy-2-(4-methoxy-benzyloxymethyl)-cyclopentanecarboxylic acid ethyl ester (example 153 step 6) and 2-chloro-4-fluorothiophenol. Yellow oil (95%). MS (EI): 452 (M)⁻.

Step 8: (1R,2R,4S)-4-(2-Chloro-4-fluoro-benzenesulfonyl)-2-(4-methoxy-benzyloxymethyl)-cyclopentanecarboxylic acid ethyl ester The title compound was prepared in analogy to example 68 step 9 using (1R,2R,4S)-4-(2-Chloro-4-fluoro-phenylsulfanyl)-2-(4-methoxy-benzyloxymethyl)-cyclopentanecarboxylic acid ethyl ester (example 153 step 7). Colorless oil (81%). MS (EI): 543.1 (M+AcO)⁻.

Step 9: (1R,2R,4S)-4-(2-Chloro-4-fluoro-benzenesulfonyl)-2-(4-methoxy-benzyloxymethyl)-cyclopentanecarboxylic acid (1-cyano-cyclopropyl)-amide The title compound was prepared in analogy to example 68 step 10 and 11 using (1R,2R,4S)-4-(2-chloro-4-fluoro-benzenesulfonyl)-2-(4-methoxy-benzyloxymethyl)-cyclopentanecarboxylic acid ethyl ester (example 153 step 8) and 1-amino-cyclopropanecarbonitrile. Light yellow oil (80%). MS (EI): 521.2 (M+H)⁺.

Example 154

(1R,2R,4R) and (1S,2S,4S)-2-(4-Bromo-benzyloxy)-4-(2-chloro-benzenesulfonyl)-cyclopentanecarboxylic acid (1-cyano-cyclopropyl)-amide

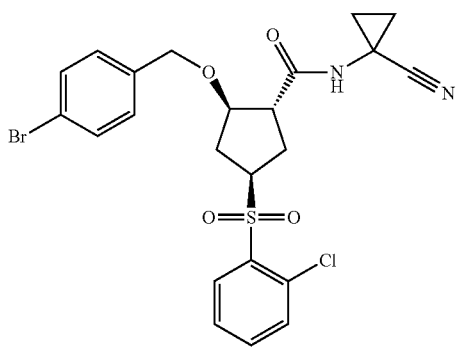

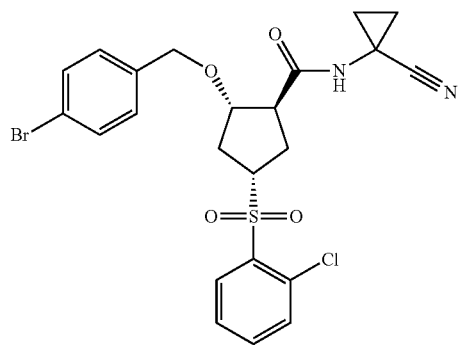

The title compound was prepared in analogy to example 150 using 1-(bromomethyl)-4-bromobenzene instead of 1-(bromomethyl)-4-methylbenzene. Off-white solid. MS (EI): 537.1 (M+H)⁺.

Example 155

(1R,2R,4S)-4-(2-Chloro-4-fluoro-benzenesulfonyl)-2-hydroxymethyl-cyclopentanecarboxylic acid (1-cyano-cyclopropyl)-amide

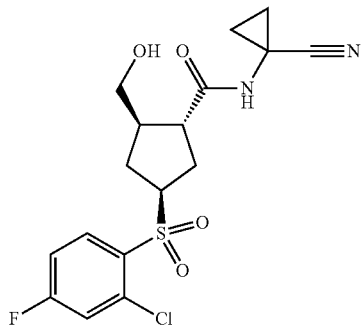

To a cold mixture of (1R,2R,4S)-4-(2-Chloro-4-fluoro-benzenesulfonyl)-2-(4-methoxy-benzyloxymethyl)-cyclopentanecarboxylic acid (1-cyano-cyclopropyl)-amide (example 153, step 9, 171 mg) in dichloromethane (4 mL) was added water (0.2 mL) and dichlorodicyanoquinone (97 mg). The reaction mixture was stirred 90 min at room temperature. The suspension was filtered and the solid was washed with dichloromethane. The resulting liquor was partionned between dichloromethane and saturated aqueous solution of sodium hydrogenocarbonate. The aqueous layer was washed with dichloromethane. The combined organic layers were washed brine, dried over sodium sulfate, filtered and evaporated in vacuo. The residue was purified by flash chromatography on silica gel with a gradient of dichlormethane:methanol (98:2 to 19:1 v/v) as eluant to afford the title compound (101 mg, 77%) as a white solid. MS (EI): 401.1 (M+H)⁺.

Example 156

(1R,2R,4S)-4-(2-Chloro-4-fluoro-benzenesulfonyl)-2-isopropoxymethyl-cyclopentanecarboxylic acid (1-cyano-cyclopropyl)-amide

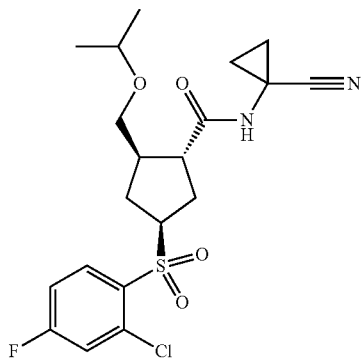

A solution of (1R,2R,4S)-4-(2-Chloro-4-fluoro-benzenesulfonyl)-2-hydroxymethyl-cyclopentanecarboxylic acid (1-cyano-cyclopropyl)-amide (67 mg) in nitromethane (2 mL) was added to anhydrous iron(III)chloride, flushed with nitrogen. Then acetone (60 mg) and triethylsilane (95 mg) was injected. The reaction mixture was stirred over days then partitioned between ethyl acetate and a saturated aqueous solution of sodium hydrogenocarbonate. The aqueous layer was extracted with ethyl acetate. Combined organic layers were washed with brine then concentrated in vacuo. The residue was purified by flash chromatography on silica gel with a gradient of cyclohexane:ethyl acetate (3:1 to 1:1 v/v) then dichloromethane: ethyl acetate (19:1 v/v) as eluant to afford the title compound (15 mg, 20%) as a colorless solid. MS (EI): 441.1 (M−H)⁻.

Example 157

(1R,2R,4R)-4-(2-Chloro-4-fluoro-benzenesulfonyl)-2-fluoromethyl-cyclopentanecarboxylic acid (1-cyano-cyclopropyl)-amide

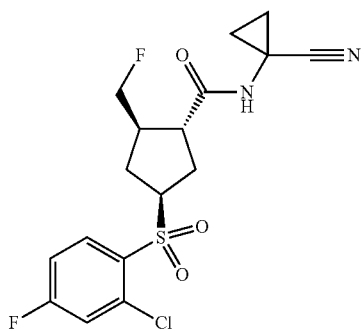

A mixture of (1R,2R,4S)-4-(2-Chloro-4-fluoro-benzenesulfonyl)-2-hydroxymethyl-cyclopentanecarboxylic acid (1-cyano-cyclopropyl)-amide (41 mg), perfluoro-1-butanesulfonyl fluoride (62 mg), triethylamine (62 mg) and triethylamine.trishydrofluoride salt (33 mg) in tetrahydrofuran (1 mL) was stirred 24 h at room temperature. The mixture was then adsorbed unto silica and was purified by flash chromatography on silica gel with a gradient of cyclohexane:ethyl acetate (3:1 to 1:1 v/v) as eluant to afford the title compound (10 mg, 24%) as a colorless solid. MS (EI): 403.3 (M+H)⁺.

Example 158

(1R,2R,4R)-4-[2-Chloro-4-(4-methyl-piperazin-1-yl)-benzenesulfonyl]-2-(3,3-difluoro-azetidine-1-carbonyl)-cyclopentanecarboxylic acid (1-cyano-cyclopropyl)-amide

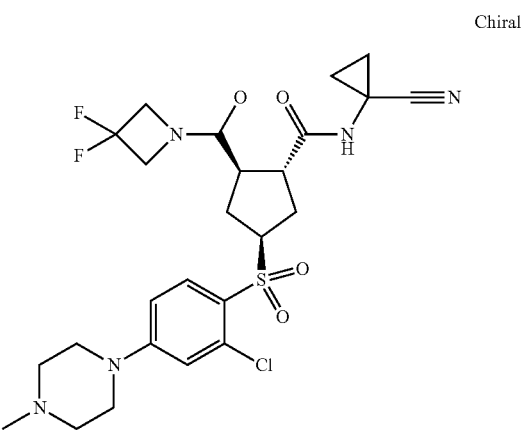

The title compound was prepared in analogy to example 127 using (1R,2R,4R)-4-(2-chloro-4-fluoro-benzenesulfonyl)-2-(3,3-difluoro-azetidine-1-carbonyl)-cyclopentanecarboxylic acid-(1-cyano-cyclopropyl)-amide (example 119 step 4) and N-methylpiperazine. White solid (81%). MS (EI): 570.2 (M+H)⁺.

Example 159

(1R,2R,4R)-4-[2-Chloro-4-(4-cyclopropyl-piperazin-1-yl)-benzenesulfonyl]-2-(3,3-difluoro-azetidine-1-carbonyl)-cyclopentanecarboxylic acid (1-cyano-cyclopropyl)-amide

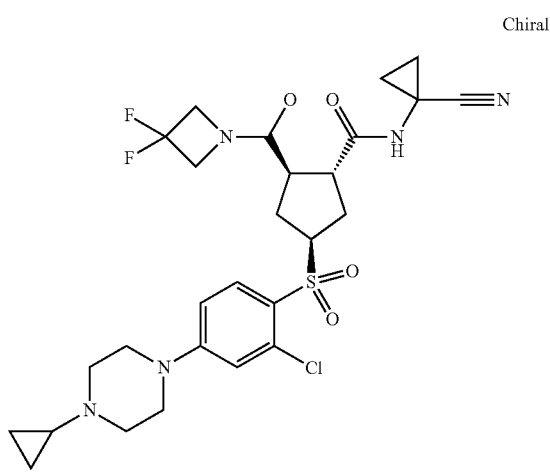

The title compound was prepared in analogy to example 127 using (1R,2R,4R)-4-(2-chloro-4-fluoro-benzenesulfonyl)-2-(3,3-difluoro-azetidine-1-carbonyl)-cyclopentanecarboxylic acid-(1-cyano-cyclopropyl)-amide (example 119 step 4) and N-cyclopropylpiperazine bis hydrobromic salt (CAS # 159974-58-0). White solid (64%). MS (EI): 596.2 (M+H)⁺.

Example 160

(1R,2R,4R)-4-[4-(4-tert-Butyl-piperazin-1-yl)-2-chloro-benzenesulfonyl]-2-(3,3-difluoro-azetidine-1-carbonyl)-cyclopentanecarboxylic acid (1-cyano-cyclopropyl)-amide

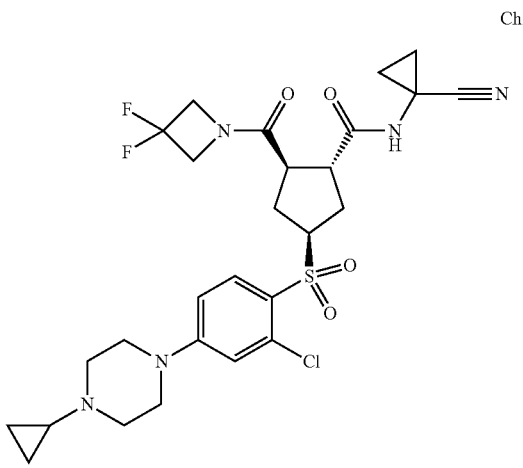

The title compound was prepared in analogy to example 127 using (1R,2R,4R)-4-(2-chloro-4-fluoro-benzenesulfonyl)-2-(3,3-difluoro-azetidine-1-carbonyl)-cyclopentanecarboxylic acid-(1-cyano-cyclopropyl)-amide (example 119 step 4) and N-tertiobutylpiperazine. White solid (74%). MS (EI): 612.2 (M+H)+.

Example 161

(1R,2R,4R) and (1S,2S,4S)-2-Methoxy-4-[4-(4-methyl-piperazin-1-yl)-2-trifluoromethyl-benzenesulfonyl]-cyclopentanecarboxylic acid (1-cyano-cyclopropyl)-amide

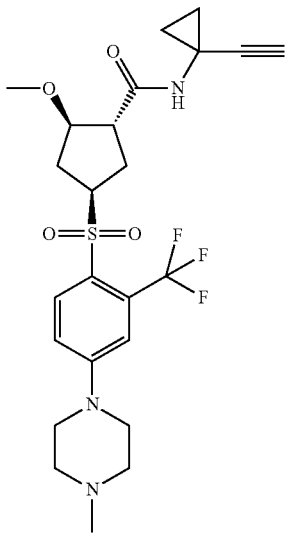

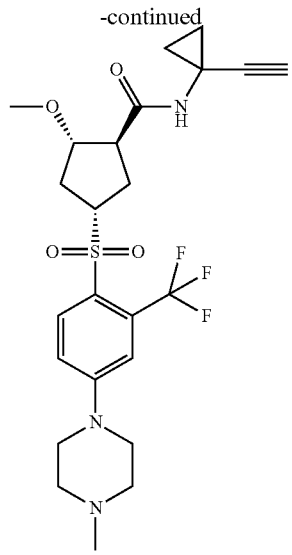

A mixture of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide (50 mg, 0.1009 mmol, example 58), 1-methylpiperazine (25 μl, 0.252 mmol) and N-ethyl-N,N-diisopropyl amine (36 μl, 0.202 mmol) in DMA (1 ml) was heated in a sealed tube to 100° C. for 5 h. Then additional 1-methylpiperazine (25 μl, 0.252 mmol) was added and heating to 100° C. was continued overnight. The mixture was then cooled to room temperature and diluted with water. The pH was adjusted to 10 by addition of saturated Na$_2$CO$_3$ solution and the mixture was extracted 3 times with EtOAc. The combined organic layers were washed two times with Na$_2$CO$_3$ solution (pH 10) and with brine, dried over Na$_2$SO$_4$ and evaporated. The remaining brown gum was purified by silica gel chromatography (DCM/MeOH 98:2-19:1) to obtain the title compound (35 mg, 67%) as white foam. MS (EI): 515.4 (M+H)+.

Example 162

(1R,2R,4S)-4-(2-Chloro-4-fluoro-benzenesulfonyl)-2-(6-chloro-pyridin-3-yloxymethyl)-cyclopentanecarboxylic acid (1-cyano-cyclopropyl)-amide

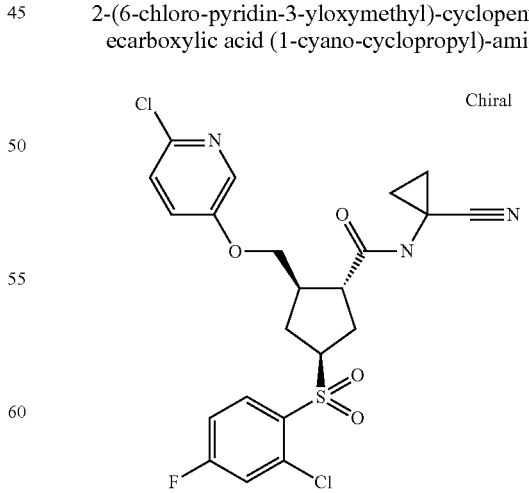

To a cold mixture (ice bath) of (1R,2R,4S)-4-(2-chloro-4-fluoro-benzenesulfonyl)-2-hydroxymethyl-cyclopentanecarboxylic acid (1-cyano-cyclopropyl)-amide (example 155, 28.5 mg), 2-chloro-5-hydroxypyridine (19 mg) and triphenyl phosphine (28 mg) in dichloromethane (1 mL) was added a solution of di-tert-butyl-azodicarboxylate (25 mg) in tetrahydrofuran (1 mL). The reaction mixture was stirred overnight then adsorbed unto silica and was purified by flash chromatography on silica gel with a gradient of cyclohexane:ethyl acetate (4:1 to 1:1 v/v) as eluant to afford the title compound (14 mg, 36%) as a colorless solid. MS (EI): 512.0 (M+H)+.

Example 163

(1R,2R,4S)-4-(2-Chloro-4-fluoro-benzenesulfonyl)-2-(pyridin-4-yloxymethyl)-cyclopentanecarboxylic acid (1-cyano-cyclopropyl)-amide

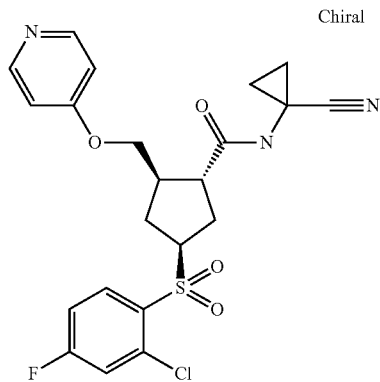

The title compound was prepared in analogy to example 162 using (1R,2R,4S)-4-(2-chloro-4-fluoro-benzenesulfonyl)-2-hydroxymethyl-cyclopentanecarboxylic acid (1-cyano-cyclopropyl)-amide (example 155) and 4-hydroxypyridine. Colorless oil (22%). MS (EI): 478.1 (M+H)+.

Example 164

(1R,2R,4S)-4-(2-Chloro-4-fluoro-benzenesulfonyl)-2-phenoxymethyl-cyclopentanecarboxylic acid (1-cyano-cyclopropyl)-amide

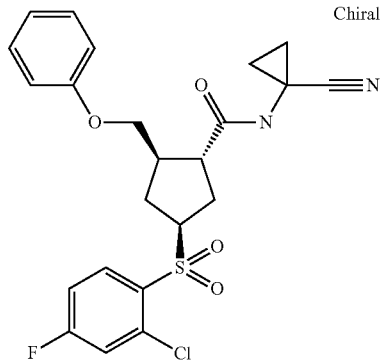

The title compound was prepared in analogy to example 162 using (1R,2R,4S)-4-(2-chloro-4-fluoro-benzenesulfonyl)-2-hydroxymethyl-cyclopentanecarboxylic acid (1-cyano-cyclopropyl)-amide (example 155) and phenol. White solid (71%). MS (EI): 477.1 (M+H)+.

Example 165

(1R,2R,4S)-4-(2-Chloro-4-fluoro-benzenesulfonyl)-2-(pyridin-3-yloxymethyl)-cyclopentanecarboxylic acid (1-cyano-cyclopropyl)-amide

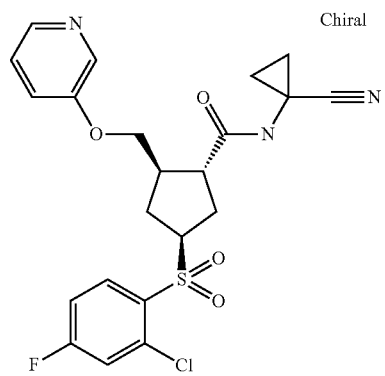

The title compound was prepared in analogy to example 162 using (1R,2R,4S)-4-(2-chloro-4-fluoro-benzenesulfonyl)-2-hydroxymethyl-cyclopentanecarboxylic acid (1-cyano-cyclopropyl)-amide (example 155) and 3-hydroxypyridine. White solid (34%). MS (EI): 478.1 (M+H)+.

Example 166

(1R,2R,4R)-4-[4-(4-Acetyl-piperazin-1-yl)-2-chloro-benzenesulfonyl]-2-(3,3-difluoro-azetidine-1-carbonyl)-cyclopentanecarboxylic acid (1-cyano-cyclopropyl)-amide

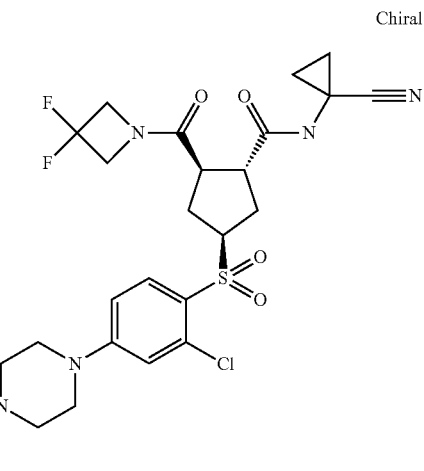

The title compound was prepared in analogy to example 134 using (1R,2R,4R)-4-(2-chloro-4-fluoro-benzenesulfonyl)-2-(3,3-difluoro-azetidine-1-carbonyl)-cyclopentanecarboxylic acid-(1-cyano-cyclopropyl)-amide (example 119 step 4) and 1-acetylpiperazine. White solid (12%). MS (EI): 598.2 (M+H)+.

Example 167

(1R,2R,4R)-4-(2-Chloro-4-pyrazol-1-yl-benzenesulfonyl)-2-(3,3-difluoro-azetidine-1-carbonyl)-cyclopentanecarboxylic acid (1-cyano-cyclopropyl)-amide

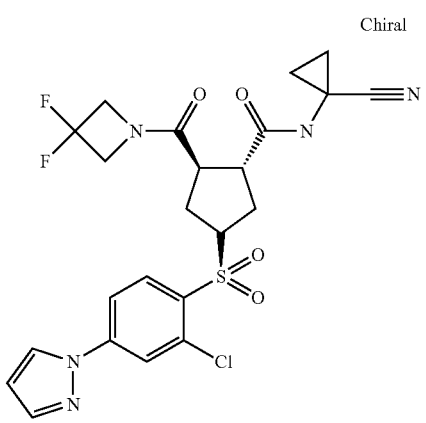

The title compound was prepared in analogy to example 134 using (1R,2R,4R)-4-(2-chloro-4-fluoro-benzenesulfonyl)-2-(3,3-difluoro-azetidine-1-carbonyl)-cyclopentanecarboxylic acid-(1-cyano-cyclopropyl)-amide (example 119 step 4) and pyrazole. White solid (36%). MS (EI): 538.1 (M+H)⁺.

Example 168

(1R,2R,4R)-4-[2-Chloro-4-(2-methoxy-ethoxy)-benzenesulfonyl]-2-(3,3-difluoro-azetidine-1-carbonyl)-cyclopentanecarboxylic acid (1-cyano-cyclopropyl)-amide

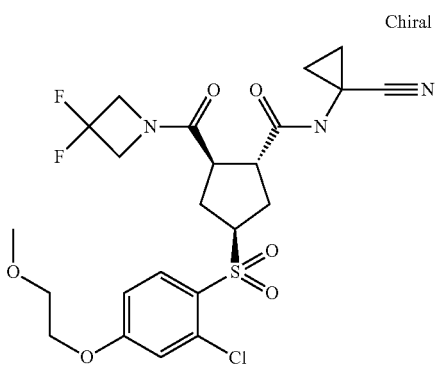

The title compound was prepared in analogy to example 134 using (1R,2R,4R)-4-(2-chloro-4-fluoro-benzenesulfonyl)-2-(3,3-difluoro-azetidine-1-carbonyl)-cyclopentanecarboxylic acid-(1-cyano-cyclopropyl)-amide (example 119 step 4) and 2-methoxyethanol. White solid (37%). MS (EI): 546.1 (M+H)⁺.

Example 169

(1R,2R,4R) and (1S,2S,4S)-4-(4-Bromo-2-trifluoromethyl-benzenesulfonyl)-2-(tetrahydro-pyran-4-yloxy)-cyclopentanecarboxylic acid (1-cyano-cyclopropyl)-amide

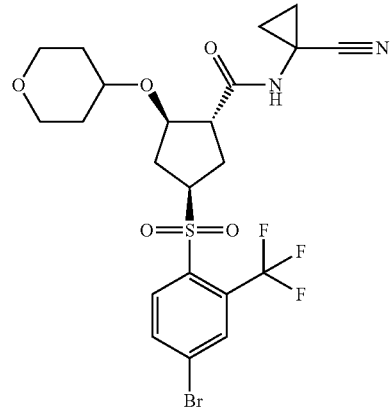

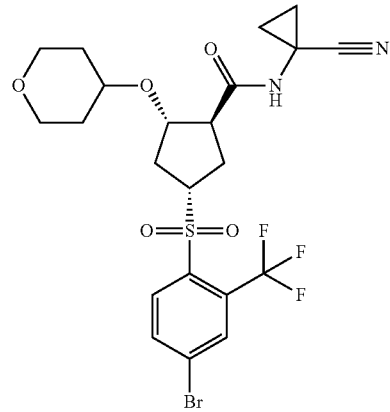

Step 1: tert-Butyl[(3aR,5s,6aS)-octahydro-3aH-spiro[cyclopenta[d][1,3]dioxole-2,4'-pyran]-5-yloxy]diphenylsilane (1R,2S,4s)-4-{[tert-Butyl(diphenyl)silyl]oxy}cyclopentane-1,2-diol (1000 mg, 2.80 mmol, example 112, step 2) was dissolved in DCM (15 ml) and 4,4-dimethoxy-tetrahydro-pyran (1230 mg, 8.41 mmol, CAS 28218-71-5) and a catalytic amount of PPTS were added. The reaction mixture was stirred at reflux temperature over night. Then a saturated NaHCO₃ solution was added, the mixture was extracted 3 times with ether and the combined organic phases were washed with brine, dried (Na₂SO₄) and concentrated. The remaining residue was purified by silica column chromatography (heptane/EtOAc 90:10-80:20) to obtain the title compound (850 mg, 69%) as white solid. MS (EI): 439.4 (M+H)⁺.

Step 2: (1S,2R,4S) and (1R,2S,4R)-4-(tert-Butyl-diphenyl-silanyloxy)-2-(tetrahydro-pyran-4-yloxy)-cyclopentanol To a solution of tert-butyl[(3aR,5s,6aS)-octahydro-3aH-spiro[cyclopenta[d][1,3]dioxole-2,4'-pyran]-5-yloxy]diphenylsilane (830 mg, 1.892 mmol) in DCM (10 ml) were added triethylsilane (1.24 ml, 7.57 mmol) and a 1M solution of TiCl₄ in DCM (2.27 ml, 2.27 mmol) at −78° C. and the reaction mixture was allowed to warm to 0° C. within 3.5 h. Then water was added and the mixture was extracted 3 times with DCM. The combined extracts were washed with brine, dried (Na$_2$SO$_4$) and evaporated. The remaining residue was purified by silica column chromatography (heptane/EtOAc 70:30-60:40) to obtain the title compound (776 mg, 93%) as colorless gum. MS (EI): 441.3 (M+H)$^+$.

Step 3: (1S,2R,4S) and (1R,2S,4R)-4-(tert-Butyl-diphenyl-silanyloxy)-2-(tetrahydro-pyran-4-yloxy)-cyclopentanecarbonitrile The title compound was prepared in analogy to example 112, step 4 and was obtained as colorless gum. MS (EI): 467.3 (M+NH$_4$)$^+$.

Step 4: (1S,2R,4S) and (1R,2S,4R)-4-Hydroxy-2-(tetrahydro-pyran-4-yloxy)-cyclopentanecarbonitrile The title compound was prepared in analogy to example 46, step 5 and was obtained as colorless gum. MS (EI): 270.1 (M+OAc)$^-$.

Step 5: Methanesulfonic acid (1S,3S,4R) and (1R,3R,4S)-3-cyano-4-(tetrahydro-pyran-4-yloxy)-cyclopentyl ester The title compound was prepared in analogy to example 46, step 6 and was obtained as light yellow gum. MS (EI): 348.0 (M+OAc)$^-$.

Step 6: (1S,2R,4R) and (1R,2S,4S)-4-(4-Bromo-2-trifluoromethyl-phenylsulfanyl)-2-(tetrahydro-pyran-4-yloxy)-cyclopentanecarbonitrile The title compound was prepared in analogy to example 46, step 7 using 4-bromo-2-trifluoromethyl-benzenethiol instead of 2-(trifluoromethyl)-thiophenol and was obtained as light yellow oil. MS (EI): 508.0 (M+OAc)$^-$.

Step 7: (1S,2R,4R) and (1R,2S,4S)-4-(4-Bromo-2-trifluoromethyl-benzenesulfonyl)-2-(tetrahydro-pyran-4-yloxy)-cyclopentanecarbonitrile A mixture of (1S,2R,4R) and (1R,2S,4S)-4-(4-bromo-2-trifluoromethyl-phenylsulfanyl)-2-(tetrahydro-pyran-4-yloxy)-cyclopentanecarbonitrile (345 mg, 0.766 mmol) and mCPBA (472 mg, 70%, 1.915 mmol) in DCM (10 ml) was stirred at room temperature overnight. The mixture was diluted with water and extracted 2 times with DCM. The combined extracts were washed with 15% Na$_2$SO$_3$ solution, saturated NaHCO$_3$ solution, dried (Na$_2$SO$_4$) and evaporated. The remaining colorless solid (370 mg) was used in the next reaction step without further purification. MS (EI): 482.0 (M+H)$^+$.

Step 8: (1R,2R,4R) and (1S,2S,4S)-4-(4-Bromo-2-trifluoromethyl-benzenesulfonyl)-2-(tetrahydro-pyran-4-yloxy)-cyclopentanecarboxylic acid methyl ester The title compound was prepared in analogy to example 46, step 9 and was obtained as white solid. MS (EI): 515.2 (M+H)$^+$.

Step 9: Lithium (1R,2R,4R) and (1S,2S,4S)-4-(4-bromo-2-trifluoromethyl-benzenesulfonyl)-2-(tetrahydro-pyran-4-yloxy)-cyclopentanecarboxylate The title compound was prepared in analogy to example 46, step 10 and was obtained as grey solid. MS (EI): 500.9 (M–H)$^-$.

Step 10: (1R,2R,4R) and (1S,2S,4S)-4-(4-Bromo-2-trifluoromethyl-benzenesulfonyl)-2-(tetrahydro-pyran-4-yloxy)-cyclopentanecarboxylic acid (1-cyano-cyclopropyl)-amide The title compound was prepared in analogy to example 46, step 11 using HATU/N-ethyl-N,N-diisopropyl amine in DMF instead of EDCI/HOBt/N-ethyl-N,N-diisopropyl amine in acetonitrile and was obtained as white solid. MS (EI): 563.2 (M–H)$^-$.

Example 170

(1R,2R,4R) and (1S,2S,4S)-4-{4-[1-(2-Hydroxy-ethyl)-1H-pyrazol-4-yl]-2-trifluoromethyl-benzenesulfonyl}-2-methoxy-cyclopentanecarboxylic acid (1-cyano-cyclopropyl)-amide

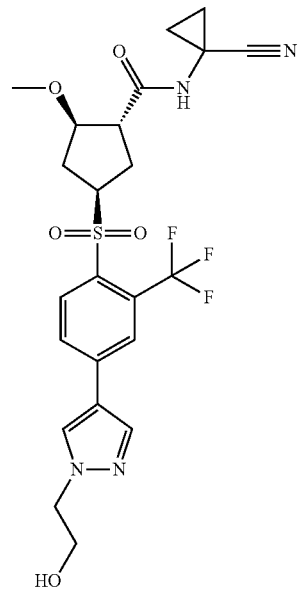

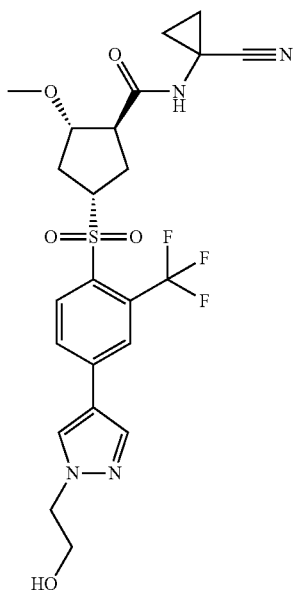

The title compound was prepared in analogy to example 109 using 2-(4-bromo-pyrazol-1-yl)-ethanol (CAS 214614-81-0) instead of 2-bromo-2-trifluoromethylpyridine. Light grey solid. MS (EI): 527.3 (M+H)+.

Example 171

(1R,2R,4R) and (1S,2S,4S)-2-Methoxy-4-(3-trifluoromethyl-biphenyl-4-sulfonyl)-cyclopentanecarboxylic acid (1-cyano-cyclopropyl)-amide

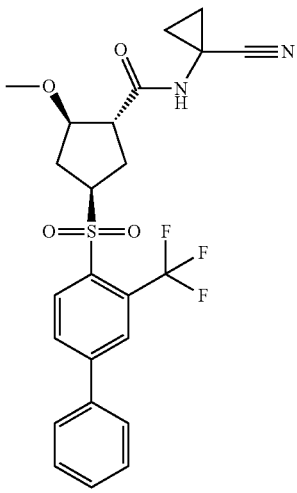

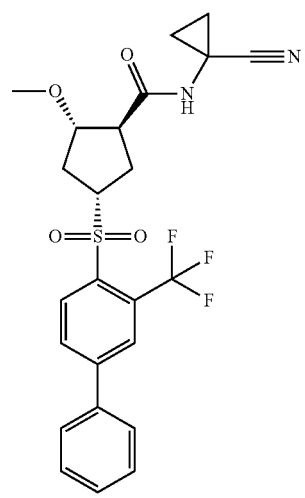

The title compound can be prepared in analogy to example 62 using phenyl-boronic acid instead of 2,4-difluorophenyl-boronic acid. Off-white solid. MS (EI): 493.3 (M+H)+.

Example 172

(1R,2R,4R) and (1S,2S,4S)-2-Methoxy-4-{4-[1-(2-methoxy-ethyl)-1H-pyrazol-4-yl]-2-trifluoromethyl-benzenesulfonyl}-cyclopentanecarboxylic acid (1-cyano-cyclopropyl)-amide

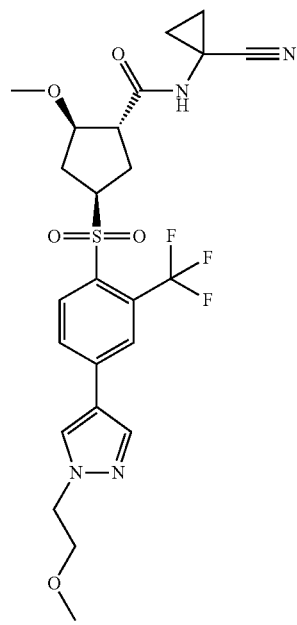

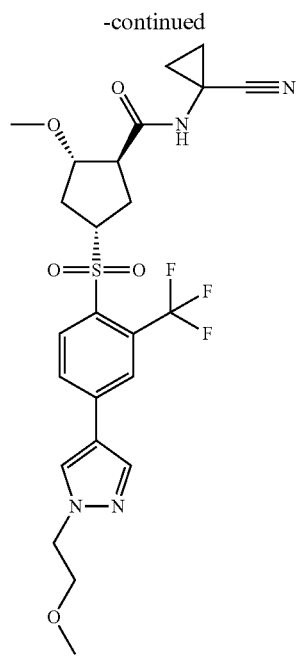

The title compound was prepared in analogy to example 109 using 4-bromo-1-(2-methoxy-ethyl)-1H-pyrazole (CAS 847818-49-9) instead of 2-bromo-2-trifluoromethylpyridine. Off-white solid. MS (EI): 541.4 (M+H)$^+$.

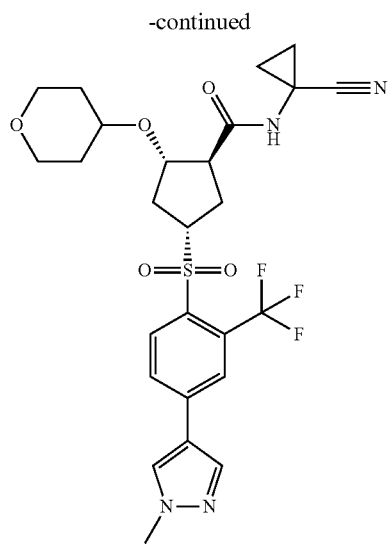

The title compound was prepared in analogy to example 62 using 1-methyl-4-(4.4.5.5-tetramethyl-1.3.2-dioxaborolan)-1H-pyrazole instead of 2,4-difluorophenylboronic acid and (1R,2R,4R) and (1S,2S,4S)-4-(4-bromo-2-trifluoromethyl-benzenesulfonyl)-2-(tetrahydro-pyran-4-yloxy)-cyclopentanecarboxylic acid (1-cyano-cyclopropyl)-amide (example 169) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. Light yellow solid. MS (EI): 565.2 (M−H)$^−$.

Example 173

(1R,2R,4R) and (1S,2S,4S)-4-[4-(1-Methyl-1H-pyrazol-4-yl)-2-trifluoromethyl-benzenesulfonyl]-2-(tetrahydro-pyran-4-yloxy)-cyclopentanecarboxylic acid (1-cyano-cyclopropyl)-amide

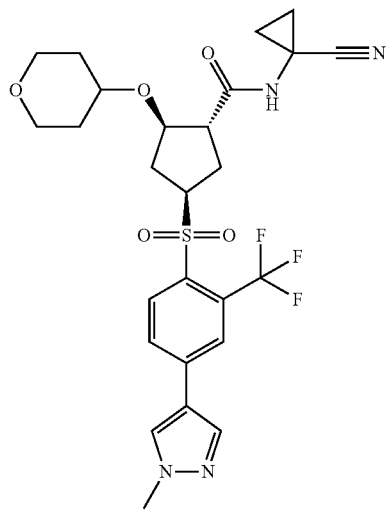

Example 174

(1R,2R,4R) and (1S,2S,4S)-4-[4-(2-Methyl-pyridin-4-yl)-2-trifluoromethyl-benzenesulfonyl]-2-(tetrahydro-pyran-4-yloxy)-cyclopentanecarboxylic acid (1-cyano-cyclopropyl)-amide

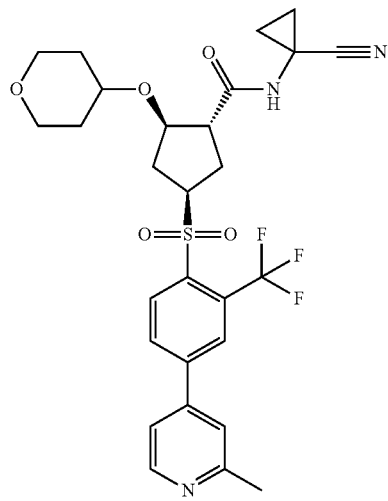

-continued

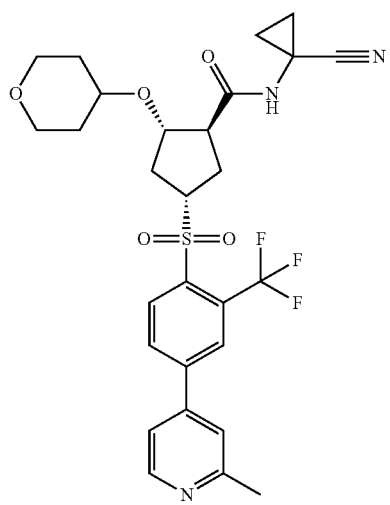

The title compound was prepared in analogy to example 62 using 2-picoline-4-boronic acid instead of 2,4-difluorophenylboronic acid and (1R,2R,4R) and (1S,2S,4S)-4-(4-bromo-2-trifluoromethyl-benzenesulfonyl)-2-(tetrahydro-pyran-4-yloxy)-cyclopentanecarboxylic acid (1-cyano-cyclopropyl)-amide (example 169) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 576.2 (M−H)−.

Example 175

(1R,2R,4R) and (1S,2S,4S)-2-(Tetrahydro-pyran-4-yloxy)-4-(2-trifluoromethyl-benzenesulfonyl)-cyclopentanecarboxylic acid (1-cyano-cyclopropyl)-amide

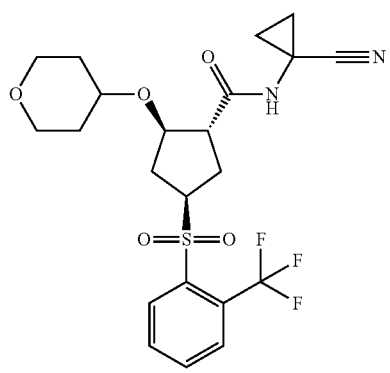

-continued

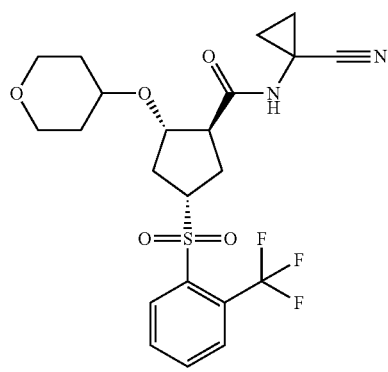

Argon was bubbled through a mixture of (1R,2R,4R) and (1S,2S,4S)-4-(4-bromo-2-trifluoromethyl-benzenesulfonyl)-2-(tetrahydro-pyran-4-yloxy)-cyclopentanecarboxylic acid (1-cyano-cyclopropyl)-amide (40 mg, 0.0707 mmol, example 169) and $K_2CO_3$ (20 mg, 0.1415 mmol) in n-butanol (2 ml) for 10 minutes. Then triphenyl-phosphine (1.48 mg, 0.00566 mmol) and palladium acetate (0.318 mg, 0.001415 mmol) were added and the reaction mixture was stirred at 100° C. for 2 h. The mixture was allowed to cool to room temperature, the solvent was removed and the remaining residue was diluted with water and extracted 3 times with EtOAc. The combined extracts were washed with brine, dried ($Na_2SO_4$) and evaporated. The remaining residue was purified by silica column chromatography (DCM/MeOH 98:2) to obtain the title compound contaminated with a small amount of triphenyl-phosphine oxide. This material was triturated with a small amount of ether to give the title compound (25 mg, 73%) as white solid. MS (EI): 487.3 (M+H)+.

Example 176

(1R,2R,4R) and (1S,2S,4S)-2-Methoxy-4-(4-morpholin-4-yl-2-trifluoromethyl-benzenesulfonyl)-cyclopentanecarboxylic acid (1-cyano-cyclopropyl)-amide

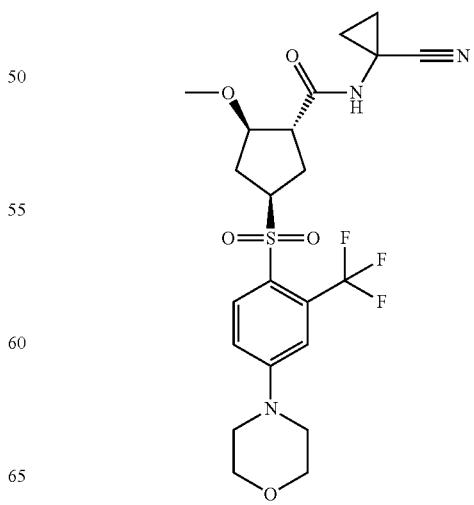

-continued

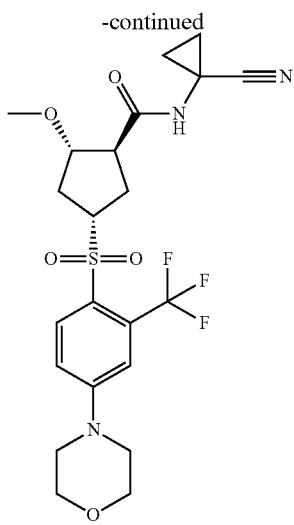

A solution of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide (50 mg, 0.1009 mmol, example 58), morpholine (22 μl, 0.252 mmol) and 2,6-di-tert-butylpyridine (45.4 μl, 0.202 mmol) in DMA (1 ml) was heated in a sealed tube at 100° C. overnight. Then additional morpholine (8.8 μl, 0.1009 mmol) was added and the solution was stirred another 2 h at 100° C. The mixture was then cooled to room temperature and diluted with water. The pH was adjusted to 10 by addition of saturated $Na_2CO_3$ solution and the mixture was extracted 3 times with EtOAc. The combined organic layers were washed two times with $Na_2CO_3$ solution (pH 10) and with brine, dried over $Na_2SO_4$ and evaporated. The remaining light brown solid was purified by silica gel chromatography (DCM/EtOAc 4:1-1:1) to obtain the title compound (33 mg, 65%) as white foam. MS (EI): 502.2 $(M+H)^+$.

Example 177

(1R,2R,4R) and (1S,2S,4S)-4-[4-(4-Isopropyl-piperazin-1-yl)-2-trifluoromethyl-benzenesulfonyl]-2-methoxy-cyclopentanecarboxylic acid (1-cyano-cyclopropyl)-amide

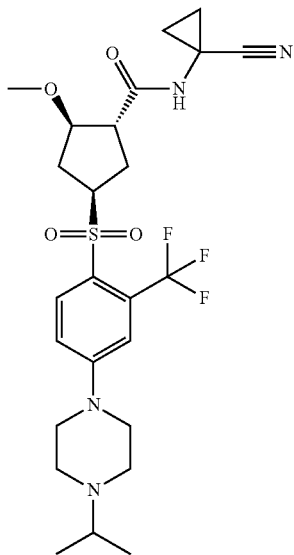

-continued

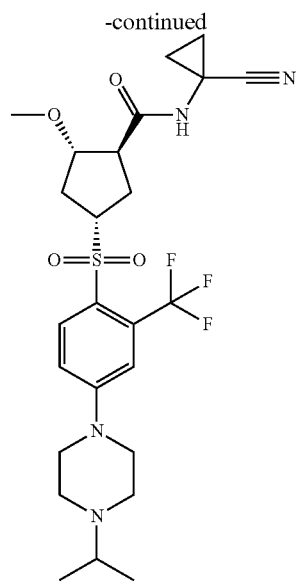

The title compound was prepared in analogy to example 176 using 1-isopropyl-piperazine instead of morpholine. White foam. MS (EI): 543.4 $(M+H)^+$.

Example 178

(1R,2R,4R) and (1S,2S,4S)-4-[4-(4,4-Difluoro-piperidin-1-yl)-2-trifluoromethyl-benzenesulfonyl]-2-methoxy-cyclopentanecarboxylic acid (1-cyano-cyclopropyl)-amide

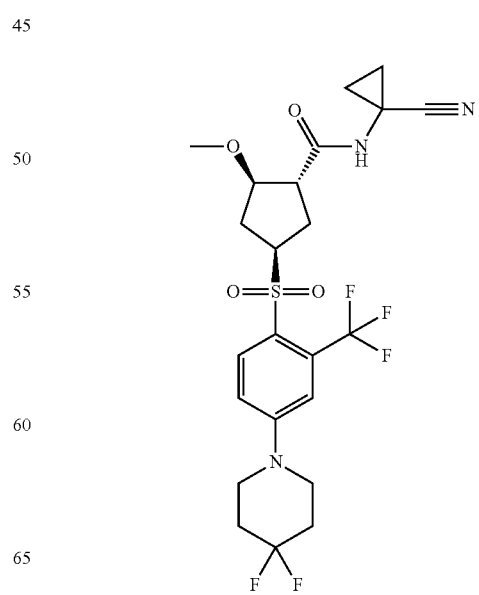

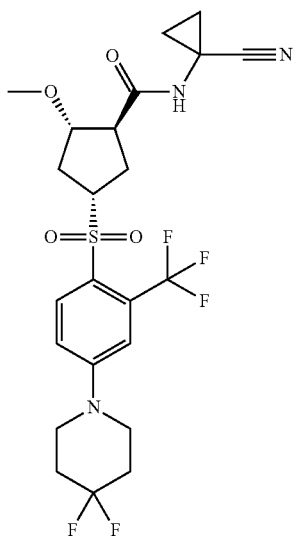

The title compound was prepared in analogy to example 176 using 4,4-difluoro-piperidine instead of morpholine. White solid. MS (EI): 536.2 (M+H)⁺.

Example 179

(4-{4-[(1R,3R,4R) and (1S,3S,4S)-3-(1-Cyano-cyclopropylcarbamoyl)-4-methoxy-cyclopentanesulfonyl]-3-trifluoromethyl-phenyl}-pyrazol-1-yl)-acetic acid methyl ester

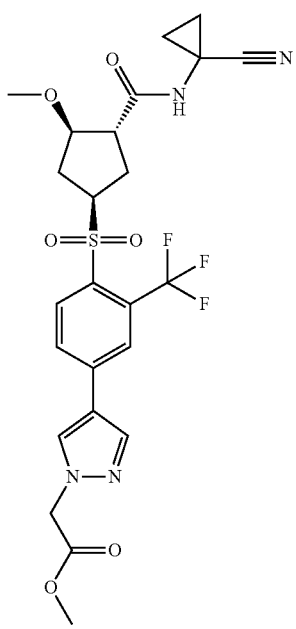

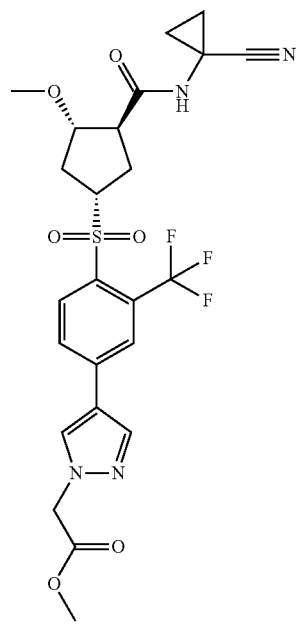

The title compound was prepared in analogy to example 109 using (4-bromo-pyrazol-1-yl)-acetic acid methyl ester (CAS 1072944-71-8) instead of 2-bromo-2-trifluoromethylpyridine. Off-white solid. MS (EI): 555.3 (M+H)⁺.

Example 180

(1R,2R,4R) and (1S,2S,4S)-4-(2-Chlorophenylsulfonyl)-N-(1-cyanocyclopropyl)-2-(2,4-dichloro-5-fluorobenzyloxy)cyclopentanecarboxamide

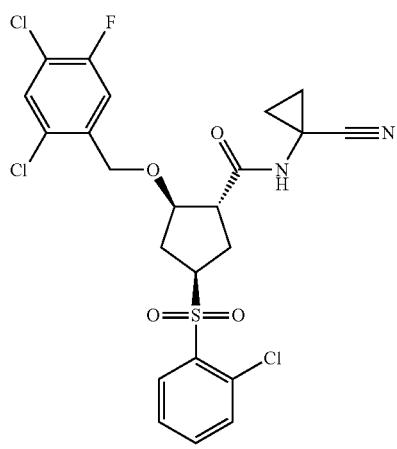

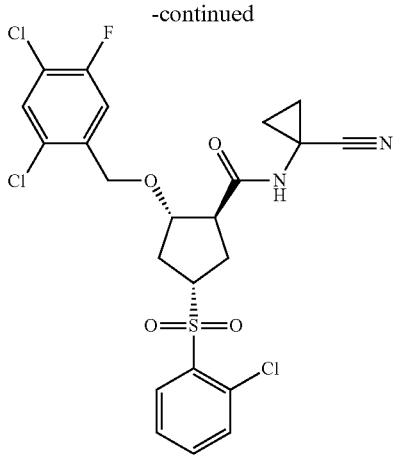

The title compound was prepared in analogy to example 150 using 1-(bromomethyl)-2,4-dichloro-5-fluorobenzene instead of 1-(bromomethyl)-4-methylbenzene. White solid. MS (EI): 547.1 (M+H)⁺.

Example 181

(1R,2R,4R) and (1S,2S,4S)-4-(4-Bromo-2-trifluoromethyl-benzenesulfonyl)-2-[(tetrahydro-1,1-dioxo-2H-thiopyran-4-yl)oxy]-cyclopentanecarboxylic acid (1-cyano-cyclopropyl)-amide

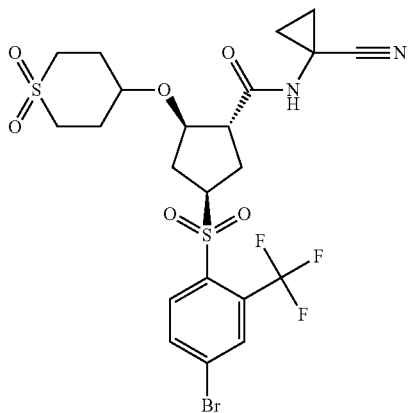

The title compound was prepared in analogy to example 169 using 4,4-dimethoxy-tetrahydro-thiopyran (CAS 61477-16-5) instead of 4,4-dimethoxy-tetrahydro-pyran in step 1 and 5 equivalents of mCPBA instead of 2.5 in step 7. White solid. MS (EI): 611.1 (M–H)⁻.

Example 182

(1R,2R,4R) and (1S,2S,4S)-4-(4-Bromo-2-trifluoromethyl-benzenesulfonyl)-2-cyclobutoxy-cyclopentanecarboxylic acid (1-cyano-cyclopropyl)-amide

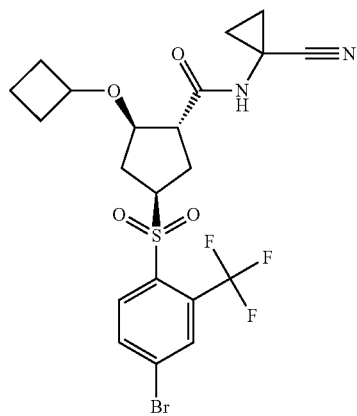

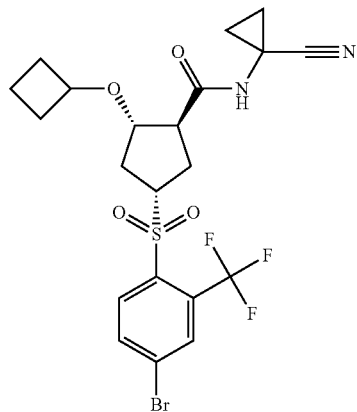

The title compound was prepared in analogy to example 169 using 1,1-dimethoxy-cyclobutane (CAS 4415-90-1) instead of 4,4-dimethoxy-tetrahydro-pyran in step 1. White solid. MS (EI): 537.2 (M+H)⁺.

Example 183

(1R,2R,4R) and (1S,2S,4S)-2-[(tetrahydro-1,1-dioxo-2H-thiopyran-4-yl)oxy]-4-[4-(2-methyl-pyridin-4-yl)-2-trifluoromethyl-benzenesulfonyl]-cyclopentanecarboxylic acid (1-cyano-cyclopropyl)-amide

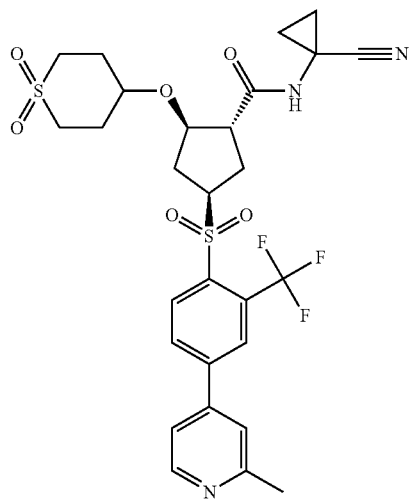

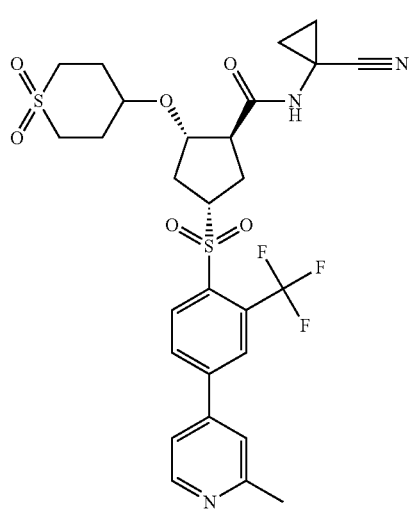

The title compound was prepared in analogy to example 62 using 2-picoline-4-boronic acid instead of 2,4-difluorophenylboronic acid and (1R,2R,4R) and (1S,2S,4S)-4-(4-bromo-2-trifluoromethyl-benzenesulfonyl)-2-[(tetrahydro-1,1-dioxo-2H-thiopyran-4-yl)oxy]-cyclopentanecarboxylic acid (1-cyano-cyclopropyl)-amide (example 181) instead of (1R, 2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 624.3 (M–H)⁻.

Example 184

(1R,2R,4R) and (1S,2S,4S)-2-[(tetrahydro-1,1-dioxo-2H-thiopyran-4-yl)oxy]-4-[4-(1-methyl-1H-pyrazol-4-yl)-2-trifluoromethyl-benzenesulfonyl]-cyclopentanecarboxylic acid (1-cyano-cyclopropyl)-amide

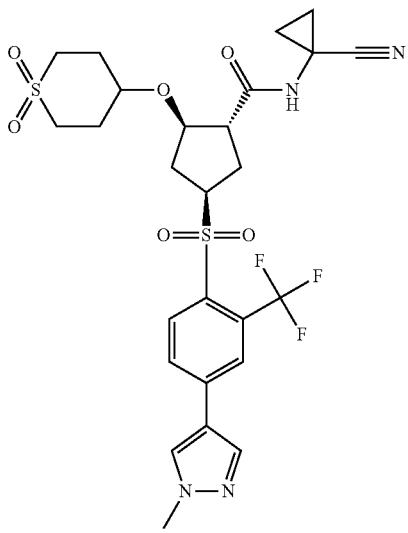

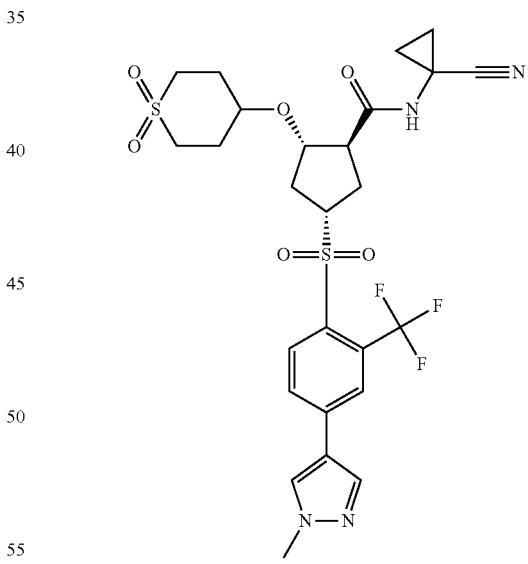

The title compound was prepared in analogy to example 62 using 1-methyl-4-(4.4.5.5-tetramethyl-1.3.2-dioxaborolan)-1H-pyrazole and (1R,2R,4R) and (1S,2S,4S)-4-(4-bromo-2-trifluoromethyl-benzenesulfonyl)-2-[(tetrahydro-1,1-dioxo-2H-thiopyran-4-yl)oxy]-cyclopentanecarboxylic acid (1-cyano-cyclopropyl)-amide (example 181) instead of (1R, 2R,4R) and (1S,2S,4S)-4-(4-bromo-2-trifluoromethyl-benzenesulfonyl)-2-methoxy-cyclopentanecarboxylic acid (1-cyano-cyclopropyl)-amide. Off-white solid. MS (EI): 613.2 (M–H)⁻.

Example 185

(4-{4-[(1R,3R,4R) and (1S,3S,4S)-3-(1-Cyano-cyclopropylcarbamoyl)-4-methoxy-cyclopentanesulfonyl]-3-trifluoromethyl-phenyl}-pyrazol-1-yl)-acetic acid

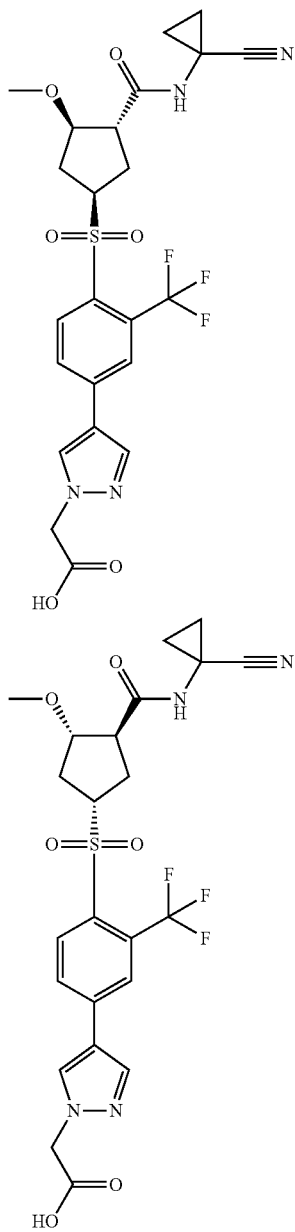

(4-{4-[(1R,3R,4R) and (1S,3S,4S)-3-(1-Cyano-cyclopropylcarbamoyl)-4-methoxy-cyclopentanesulfonyl]-3-trifluoromethyl-phenyl}-pyrazol-1-yl)-acetic acid methyl ester (35 mg, 0.0631 mmol, example 179) was dissolved in a mixture of THF (1 ml) and water (63.1 µl). Then lithium hydroxide monohydrate (5.4 mg, 0.1262 mmol) was added, followed by a few drops of MeOH until everything was dissolved. The light yellow solution was stirred at room temperature for 75 min. Then 6N HCl (8.42 µl) was added, the organic solvents were removed and diluted NaOH was added. The aqueous solution was washed 2 times with ether, acidified with 0.1N and 1N HCl (pH 2) and then extracted with EtOAc and 3 times with DCM. The combined organic layers were washed with diluted HCl and brine, dried ($Na_2SO_4$) and evaporated. The remaining residue was triturated with ether (containing a few drops of EtOAc, DCM and MeOH) to obtain the title compound (28 mg, 81%) as a white solid. MS (EI): 539.2 (M−H)⁻.

Example 186

(1R,2R,4R)-4-(2-Chloro-4-fluoro-benzenesulfonyl)-2-(3,3-difluoro-pyrrolidine-1-carbonyl)-cyclopentanecarboxylic acid (1-cyano-cyclopropyl)-amide

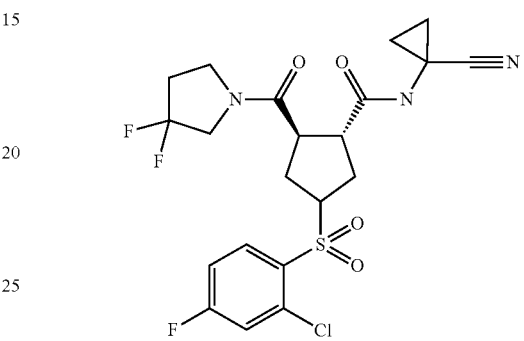

Step 1: (1R,2R)-2-(3,3-Difluoro-pyrrolidine-1-carbonyl)-4-oxo-cyclopentanecarboxylic acid ethyl ester To a mixture of (1R,2R,4R)-4-benzenesulfonyl-2-(morpholine-4-carbonyl)-cyclopentanecarboxylic acid cyanomethyl-amide (example 1 step 1, 3 g) in acetonitrile (60 mL) was successively added 2-(1H-7-azabenzotriazol-1-yl)-1,1,3,3-tetramethyl uronium hexafluorophosphate methanaminium (11.5 g), 3,3-difluoropyrrolidine hydrochloride (2.58 g) and diisopropylethylamine (7.7 mL). The reaction mixture was stirred overnight at room temperature then evaporated in vacuo. The residue was partitioned between ethyl acetate and an aqueous saturated solution of sodium carbonate. The aqueous layer was extracted with ethyl acetate and the combined organic layers were washed with water and brine then dried over sodium sulfate, filtered and concentrated in vacuo. The residue was purified by flash chromatography on silica gel with cyclohexane:ethyl acetate (1:1 v/v) as eluant to afford the title compound (4.04 g, 93%) as a dark green liquid. MS (EI): 290.1 (M+H)⁺.

Step 2: (1R,2R,4R)-2-(3,3-Difluoro-pyrrolidine-1-carbonyl)-4-hydroxy-cyclopentanecarboxylic acid ethyl ester The title compound was prepared in analogy to example 117 step 2 using (1R,2R)-2-(3,3-Difluoro-pyrrolidine-1-carbonyl)-4-oxo-cyclopentanecarboxylic acid ethyl ester (example 186 step 1). Yellow solid (57%). MS (EI): 292.1 (M+H)⁺.

Step 3: (1R,2R,4R)-2-(3,3-Difluoro-pyrrolidine-1-carbonyl)-4-methanesulfonyloxy-cyclopentanecarboxylic acid ethyl ester The title compound was prepared in analogy to example 68/69 step 7 using (1R,2R,4R)-2-(3,3-Difluoro-pyrrolidine- 1-carbonyl)-4-hydroxy-cyclopentanecarboxylic acid ethyl ester (example 186 step 2). Light yellow oil (83%). MS (EI): 370.1 (M+H)⁺.

Step 4: (1R,2R,4S)-4-(2-Chloro-4-fluoro-phenylsulfanyl)-2-(3,3-difluoro-pyrrolidine-1-carbonyl)-cyclopentanecarboxylic acid ethyl ester The title compound was prepared in analogy to example 68/69 step 8 using (1R,2R,4R)-2-(3,3-Difluoro-pyrrolidine-1-carbonyl)-4-methanesulfonyloxy-cyclopentanecarboxylic acid ethyl ester (example 186 step 3) and 2-chloro-4-fluorothiophenol. Light yellow oil (88%). MS (EI): 436.1 (M+H)⁺.

Step 5: (1R,2R,4S)-4-(2-Chloro-4-fluoro-benzenesulfonyl)-2-(3,3-difluoro-pyrrolidine-1-carbonyl)-cyclopentanecarboxylic acid ethyl ester The title compound was prepared in analogy to example 68/69 step 9 using (1R,2R,4S)-4-(2-chloro-4-fluoro-phenylsulfanyl)-2-(3,3-difluoro-pyrrolidine-1-carbonyl)-cyclopentanecarboxylic acid ethyl ester (example 186 step 4). White foam (94%). MS (EI): 468.1 (M+H)⁺.

Step 6: (1R,2R,4S)-4-(2-Chloro-4-fluoro-benzenesulfonyl)-2-(3,3-difluoro-pyrrolidine-1-carbonyl)-cyclopentanecarboxylic acid The title compound was prepared in analogy to example 68/69 step 10 using (1R,2R,4S)-4-(2-chloro-4-fluoro-benzenesulfonyl)-2-(3,3-difluoro-pyrrolidine-1-carbonyl)-cyclopentanecarboxylic acid ethyl ester (example 186 step 5). White solid (99%). MS (EI): 440.1 (M+H)⁺.

Step 7: (1R,2R,4R)-4-(2-Chloro-4-fluoro-benzenesulfonyl)-2-(3,3-difluoro-pyrrolidine-1-carbonyl)-cyclopentanecarboxylic acid (1-cyano-cyclopropyl)-amide The title compound was prepared in analogy to example 117 step 7 using (1R,2R,4S)-4-(2-chloro-4-fluoro-benzenesulfonyl)-2-(3,3-difluoro-pyrrolidine-1-carbonyl)-cyclopentanecarboxylic acid (example 186 step 6) and 1-amino-cyclopropyl cyanic hydrochloride. Yellow foam (85%). MS (EI): 504.1 (M+H)⁺.

Example 187

(1R,2R,4R)-4-(4-Bromo-2-chloro-benzenesulfonyl)-2-(3,3-difluoro-pyrrolidine-1-carbonyl)-cyclopentanecarboxylic acid (1-cyano-cyclopropyl)-amide Chiral

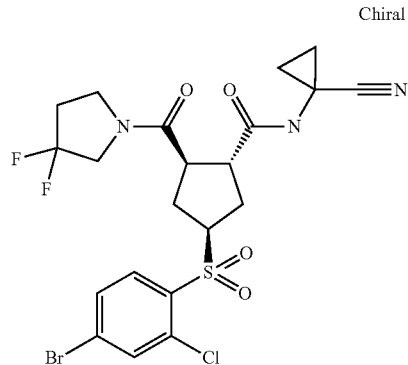

Step 1: (1R,2R,4S)-4-(2-Chloro-4-bromo-phenylsulfanyl)-2-(3,3-difluoro-pyrrolidine-1-carbonyl)-cyclopentanecarboxylic acid ethyl ester The title compound was prepared in analogy to example 68/69 step 8 using (1R,2R,4R)-2-(3,3-Difluoro-pyrrolidine-1-carbonyl)-4-methanesulfonyloxy-cyclopentanecarboxylic acid ethyl ester (example 186 step 3) and 2-chloro-4-bromothiophenol. Light yellow oil (89%). MS (EI): 498.0 (M+H)⁺.

Step 2: (1R,2R,4S)-4-(2-Chloro-4-bromo-benzenesulfonyl)-2-(3,3-difluoro-pyrrolidine-1-carbonyl)-cyclopentanecarboxylic acid ethyl ester The title compound was prepared in analogy to example 68/69 step 9 using (1R,2R,4S)-4-(2-chloro-4-bromo-phenylsulfanyl)-2-(3,3-difluoro-pyrrolidine-1-carbonyl)-cyclopentanecarboxylic acid ethyl ester (example 187 step 1). White foam (93%). MS (EI): 530.0 (M+H)⁺.

Step 3: (1R,2R,4S)-4-(2-Chloro-4-bromo-benzenesulfonyl)-2-(3,3-difluoro-pyrrolidine-1-carbonyl)-cyclopentanecarboxylic acid The title compound was prepared in analogy to example 68/69 step 10 using (1R,2R,4S)-4-(2-chloro-4-bromo-benzenesulfonyl)-2-(3,3-difluoro-pyrrolidine-1-carbonyl)-cyclopentanecarboxylic acid ethyl ester (example 187 step 2). White foam (quant.). MS (EI): 523.9 (M+Na)⁺.

Step 4: (1R,2R,4R)-4-(2-Chloro-4-bromo-benzenesulfonyl)-2-(3,3-difluoro-pyrrolidine-1-carbonyl)-cyclopentanecarboxylic acid (1-cyano-cyclopropyl)-amide The title compound was prepared in analogy to example 117 step 7 using (1R,2R,4S)-4-(2-chloro-4-bromo-benzenesulfonyl)-2-(3,3-difluoro-pyrrolidine-1-carbonyl)-cyclopentanecarboxylic acid (example 187 step 3) and 1-amino-cyclopropyl cyanic hydrochloride. Light yellow foam (93%). MS (EI): 566.0 (M+H)⁺.

Example 188

(1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide Chiral

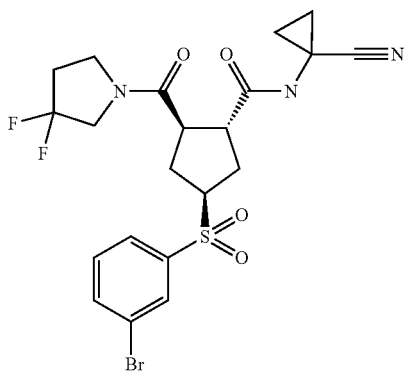

Step 1: (1R,2R,4S)-4-(3-Bromo-phenylsulfanyl)-2-(3,3-difluoro-pyrrolidine-1-carbonyl)-cyclopentanecarboxylic acid ethyl ester The title compound was prepared in analogy to example 68/69 step 8 using (1R,2R,4R)-2-(3,3-difluoro-pyrrolidine-1-carbonyl)-4-methanesulfonyloxy-cyclopentanecarboxylic acid ethyl ester (example 186 step 3) and 3-bromothiophenol. Colorless oil (85%). MS (EI): 464.1 (M+H)⁺.

Step 2: (1R,2R,4S)-4-(3-Bromo-benzenesulfonyl)-2-(3,3-difluoro-pyrrolidine-1-carbonyl)-cyclopentanecarboxylic acid ethyl ester The title compound was prepared in analogy to example 68/69 step 9 using (1R,2R,4S)-4-(3-bromo-phenylsulfanyl)-2-(3,3-difluoro-pyrrolidine-1-carbonyl)-cyclopentanecarboxylic acid ethyl ester (example 188 step 1). Colorless gum (96%). MS (EI): 496.0 (M+H)⁺.

Step 3: (1R,2R,4S)-4-(3-Bromo-benzenesulfonyl)-2-(3,3-difluoro-pyrrolidine-1-carbonyl)-cyclopentanecarboxylic acid The title compound was prepared in analogy to example 68/69 step 10 using (1R,2R,4S)-4-(3-Bromo-benzenesulfonyl)-2-(3,3-difluoro-pyrrolidine-1-carbonyl)-cyclopentanecarboxylic acid ethyl ester (example 188 step 2). White foam (quant.). MS (EI): 468.1 (M+H)⁺.

Step 4: (1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide The title compound was prepared in analogy to example 117 step 7 using (1R,2R,4S)-4-(3-Bromo-benzenesulfonyl)-2-(3,3-difluoro-pyrrolidine-1-carbonyl)-cyclopentanecarboxylic acid (example 188 step 3) and 1-amino-cyclopropyl cyanic hydrochloride. Light yellow foam (89%). MS (EI): 532.1 (M+H)⁺.

Example 189

(1R,2R,4R)-4-[2-Chloro-4-(2,2,2-trifluoro-ethoxy)-benzenesulfonyl]-2-(3,3-difluoro-pyrrolidine-1-carbonyl)-cyclopentanecarboxylic acid (1-cyano-cyclopropyl)-amide

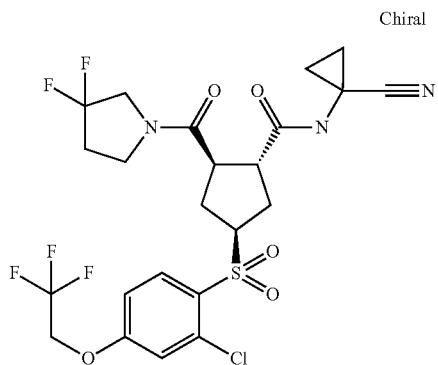

The title compound was prepared in analogy to example 134 using (1R,2R,4R)-4-(2-chloro-4-fluoro-benzenesulfonyl)-2-(3,3-difluoro-pyrrolidine-1-carbonyl)-cyclopentanecarboxylic acid (1-cyano-cyclopropyl)-amide (example 186 step 7) and 2,2,2-trifluoroethanol. White solid (98%). MS (EI): 582.1 (M–H)⁻.

Example 190

(1R,2R,4R)-4-[2-Chloro-4-((S)-2,2,2-trifluoro-1-methyl-ethoxy)-benzenesulfonyl]-2-(3,3-difluoro-pyrrolidine-1-carbonyl)-cyclopentanecarboxylic acid (1-cyano-cyclopropyl)-amide

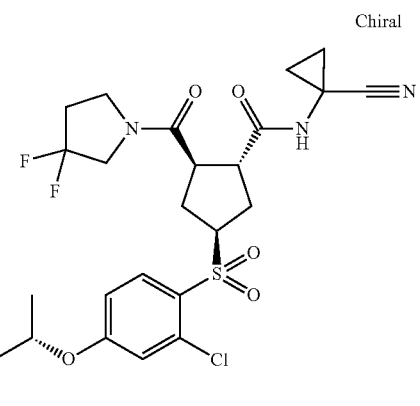

The title compound was prepared in analogy to example 134 using (1R,2R,4R)-4-(2-chloro-4-fluoro-benzenesulfonyl)-2-(3,3-difluoro-pyrrolidine-1-carbonyl)-cyclopentanecarboxylic acid (1-cyano-cyclopropyl)-amide (example 186 step 7) and (S)-1,1,1-trifluoro-propan-2-ol (CAS #: 3539-97-7). White solid (92%). MS (EI): 600.1 (M+H)⁺.

Example 191

(1R,2R,4R)-4-[2-Chloro-4-(4-cyclopropyl-piperazin-1-yl)-benzenesulfonyl]-2-(3,3-difluoro-pyrrolidine-1-carbonyl)-cyclopentanecarboxylic acid (1-cyano-cyclopropyl)-amide

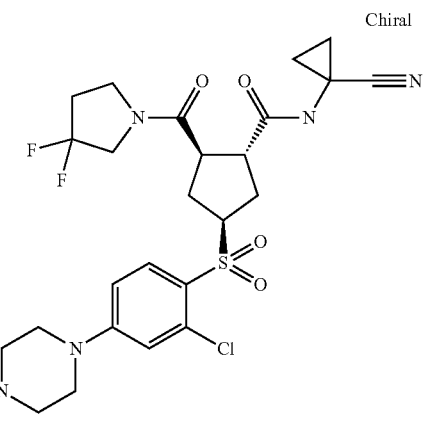

The title compound was prepared in analogy to example 127 using (1R,2R,4R)-4-(2-chloro-4-fluoro-benzenesulfonyl)-2-(3,3-difluoro-pyrrolidine-1-carbonyl)-cyclopentanecarboxylic acid (1-cyano-cyclopropyl)-amide (example 186 step 7) and N-cyclopropylpiperazine bis hydrobromic salt (CAS # 159974-58-0). White solid (73%). MS (EI): 610.3 (M+H)⁺.

Example 192

(1R,2R,4R)-4-[4-(4-tert-Butyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide

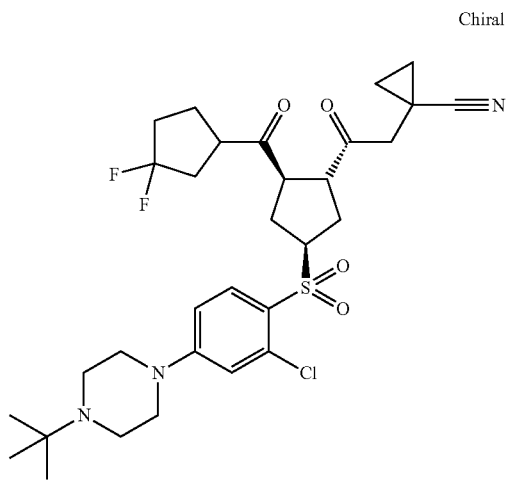

Chiral

The title compound was prepared in analogy to example 127 using (1R,2R,4R)-4-(2-chloro-4-fluoro-benzenesulfonyl)-2-(3,3-difluoro-pyrrolidine-1-carbonyl)-cyclopentanecarboxylic acid (1-cyano-cyclopropyl)-amide (example 186 step 7) and N-tert-butylpiperazine. Light yellow solid (63%). MS (EI): 624.2 (M−H)⁻.

Example 193

(1R,2R,4R) and (1S,2S,4S)-2-Methoxy-4-{4-[4-(2,2,2-trifluoro-ethyl)-piperazin-1-yl]-2-trifluoromethyl-benzenesulfonyl}-cyclopentanecarboxylic acid (1-cyano-cyclopropyl)-amide

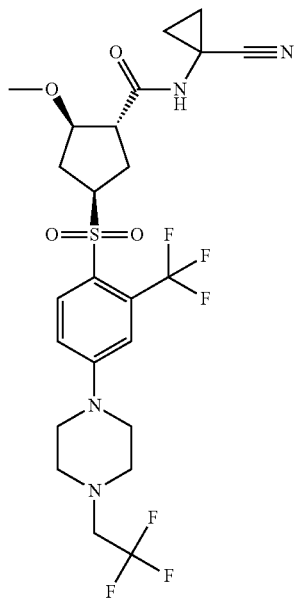

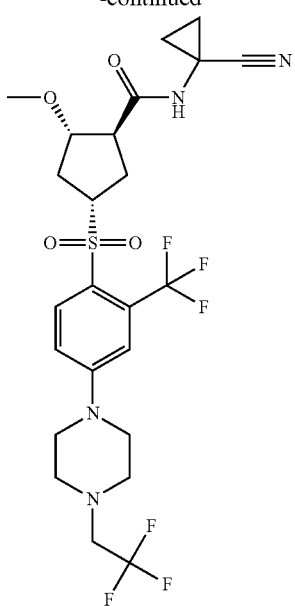

The title compound was prepared in analogy to example 176 using 1-(2,2,2-trifluoro-ethyl)-piperazine instead of morpholine. White foam. MS (EI): 583.2 (M+H)⁺.

Example 194

(1R,2R,4R) and (1S,2S,4S)-4-[4-(1-Carbamoylmethyl-1H-pyrazol-4-yl)-2-trifluoromethyl-benzenesulfonyl]-2-methoxy-cyclopentanecarboxylic acid (1-cyano-cyclopropyl)-amide

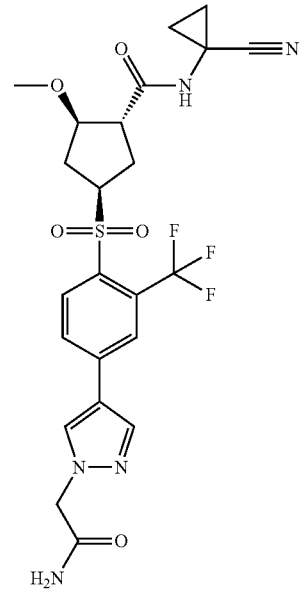

-continued

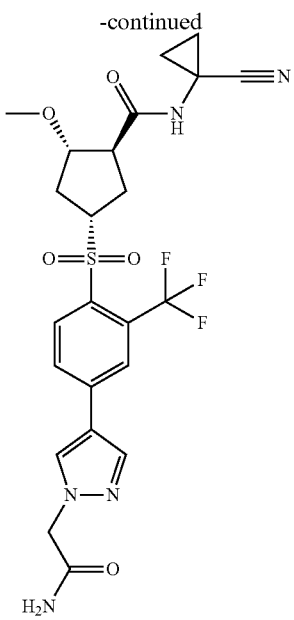

The title compound was prepared in analogy to example 109 using 2-(4-bromo-pyrazol-1-yl)-acetamide (CAS 1177354-50-5) instead of 2-bromo-2-trifluoromethylpyridine. Light brown solid. MS (EI): 540.3 (M+H)$^+$.

Example 195

(1R,2R,4R) and (1S,2S,4S)-4-(4-Bromo-2-trifluoromethyl-benzenesulfonyl)-2-cyclopentyloxy-cyclopentanecarboxylic acid (1-cyano-cyclopropyl)-amide

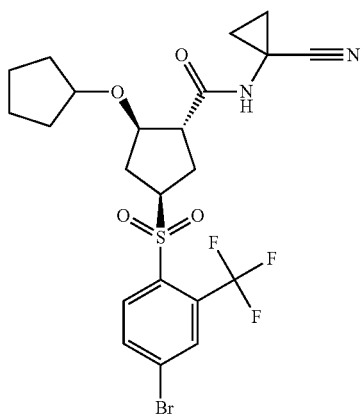

-continued

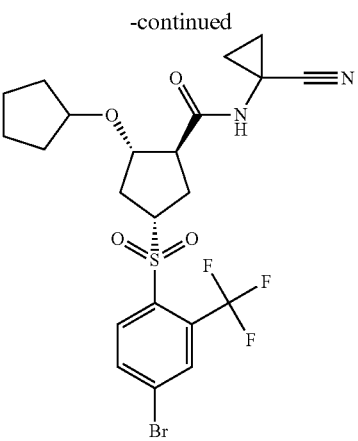

The title compound was prepared in analogy to example 169 using 1,1-dimethoxy-cyclopentane (CAS 931-94-2) instead of 4,4-dimethoxy-tetrahydro-pyran in step 1. White solid. MS (EI): 549.1 (M−H)$^−$.

Example 196

(1R,2R,4R)-4-[2-Chloro-4-(2-methyl-2H-pyrazol-3-yl)-benzenesulfonyl]-2-(3,3-difluoro-pyrrolidine-1-carbonyl)-cyclopentanecarboxylic acid (1-cyano-cyclopropyl)-amide Chiral

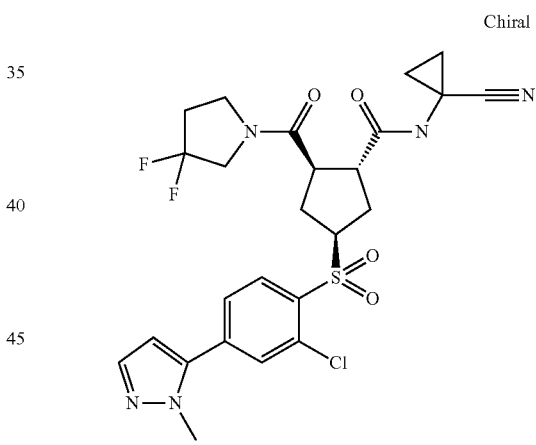

Mixture of (1R,2R,4R)-4-(2-chloro-4-bromo-benzenesulfonyl)-2-(3,3-difluoro-pyrrolidine-1-carbonyl)-cyclopentanecarboxylic acid (1-cyano-cyclopropyl)-amide (Example 187 step 4, 130 mg), 1-methyl-5-(4,4,5,5-tetramethyl-1,3,2-dioxoborolan-2-yl)1H-pyrazole (67 mg), sodium carbonate (66 mg), 1,1'-bis-(diphenylphosphino)ferrocene palladium (II) chloride, 1:1 complex with chloroforme (19 mg) was flushed with argon. Degazed dimethylformamide (4 mL) and water (0.345 mL) were added and the mixture was stirred at 80° C. overnight. The reaction mixture was partitioned between ethyl acetate and a saturated aqueous solution of sodium hydrogenocarbonate. The aqueous layer was extracted with ethyl acetate and the combined organic layers were washed with water and brine then dried over sodium sulfate, filtered and concentrated in vacuo. The residue was purified by flash chromatography on silica gel with dichlo-

Example 197

(1R,2R,4R)-4-[2-Chloro-4-(1-methyl-1H-pyrazol-4-yl)-benzenesulfonyl]-2-(3,3-difluoro-pyrrolidine-1-carbonyl)-cyclopentanecarboxylic acid (1-cyano-cyclopropyl)-amide

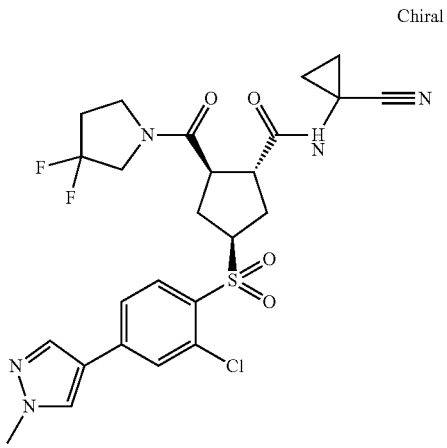

The title compound was prepared in analogy to example 196 using (1R,2R,4R)-4-(2-chloro-4-bromo-benzenesulfonyl)-2-(3,3-difluoro-pyrrolidine-1-carbonyl)-cyclopentanecarboxylic acid (1-cyano-cyclopropyl)-amide (Example 187 step 4) and 1-methyl-4-(4,4,5,5-tetramethyl-1,3,2-dioxoborolan-2-yl)1H-pyrazole. Light yellow solid (76%). MS (EI): 566.1 (M+H)⁺.

Example 198

(1R,2R,4R)-4-[2-Chloro-4-(2-methyl-pyridin-4-yl)-benzenesulfonyl]-2-(3,3-difluoro-pyrrolidine-1-carbonyl)-cyclopentanecarboxylic acid (1-cyano-cyclopropyl)-amide

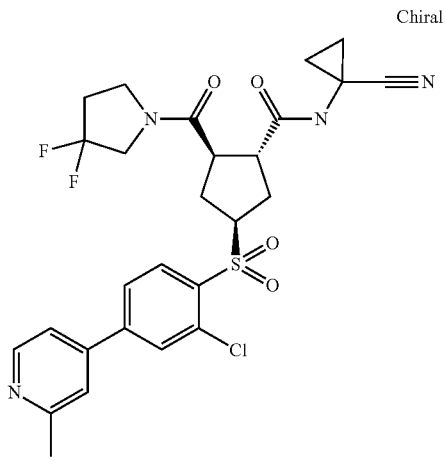

The title compound was prepared in analogy to example 196 using (1R,2R,4R)-4-(2-chloro-4-bromo-benzenesulfonyl)-2-(3,3-difluoro-pyrrolidine-1-carbonyl)-cyclopentanecarboxylic acid (1-cyano-cyclopropyl)-amide (Example 187 step 4) and 2-picoline-4-boronic acid. Light yellow solid (59%). MS (EI): 577.1 (M+H)⁺.

Example 199

(1R,2R,4R)-4-[2-Chloro-4-(2-chloro-pyridin-4-yl)-benzenesulfonyl]-2-(3,3-difluoro-pyrrolidine-1-carbonyl)-cyclopentanecarboxylic acid (1-cyano-cyclopropyl)-amide

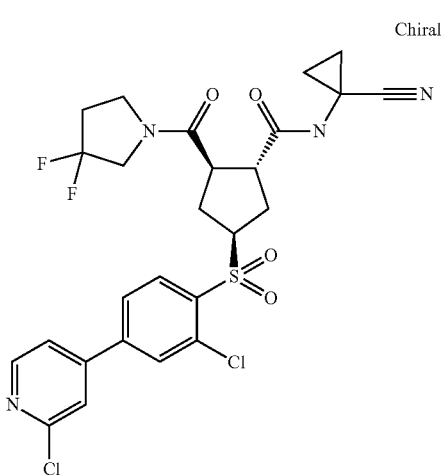

The title compound was prepared in analogy to example 196 using (1R,2R,4R)-4-(2-chloro-4-bromo-benzenesulfonyl)-2-(3,3-difluoro-pyrrolidine-1-carbonyl)-cyclopentanecarboxylic acid (1-cyano-cyclopropyl)-amide (Example 187 step 4) and 2-chloropyridine-4-boronic acid. Light brown solid (58%). MS (EI): 597.1 (M+H)⁺.

Example 200

(1R,2R,4R)-4-(2-Chloro-4-methyl-benzenesulfonyl)-2-(3,3-difluoro-pyrrolidine-1-carbonyl)-cyclopentanecarboxylic acid (1-cyano-cyclopropyl)-amide

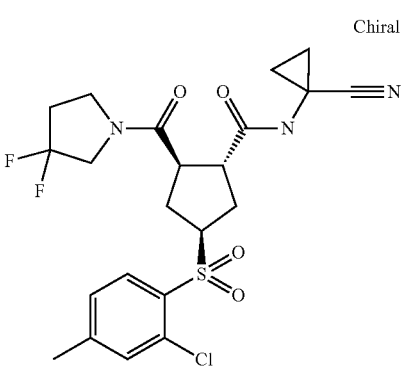

The title compound was prepared in analogy to example 196 using (1R,2R,4R)-4-(2-chloro-4-bromo-benzenesulfonyl)-2-(3,3-difluoro-pyrrolidine-1-carbonyl)-cyclopentanecarboxylic acid (1-cyano-cyclopropyl)-amide (Example 187 step 4) and methylboronic acid. White solid (19%). MS (EI): 500.1 (M+H)⁺.

romethane:methanol (92:2 v/v) as eluant to afford the title compound (114 g, 88%) as a yellow gum. MS (EI): 566.1 (M+H)⁺.

Example 201

(1R,2R,4R)-2-(3,3-Difluoro-pyrrolidine-1-carbonyl)-4-[3-(2-methyl-2H-pyrazol-3-yl)-benzenesulfonyl]-cyclopentanecarboxylic acid (1-cyano-cyclopropyl)-amide

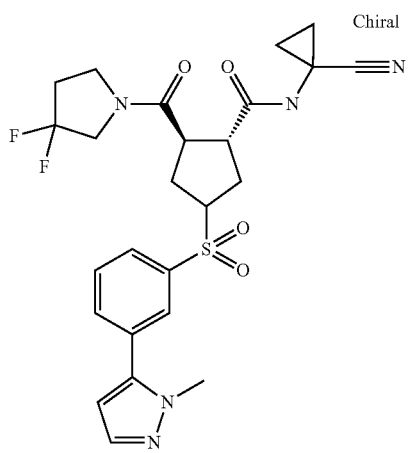

The title compound was prepared in analogy to example 196 using (1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide (Example 188 step 4) and 1-methyl-5-(4,4,5,5-tetramethyl-1,3,2-dioxoborolan-2-yl) 1H-pyrazole. Off-white solid (78%). MS (EI): 532.2 (M+H)$^+$.

Example 202

(1R,2R,4R)-2-(3,3-Difluoro-pyrrolidine-1-carbonyl)-4-[3-(1-methyl-1H-pyrazol-4-yl)-benzenesulfonyl]-cyclopentanecarboxylic acid (1-cyano-cyclopropyl)-amide

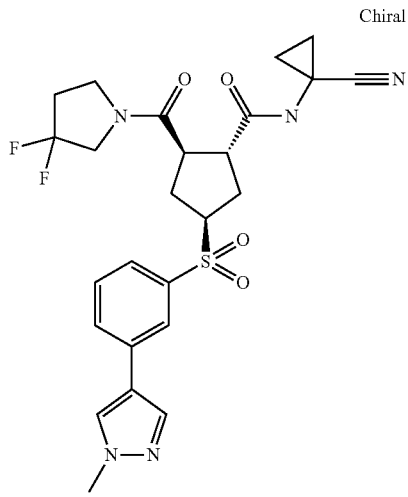

The title compound was prepared in analogy to example 196 using (1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide (Example 188 step 4) and 1-methyl-4-(4,4,5,5-tetramethyl-1,3,2-dioxoborolan-2-yl) 1H-pyrazole. Yellow gum (92%). MS (EI): 532.2 (M+H)$^+$.

Example 203

(1R,2R,4R)-2-(3,3-Difluoro-pyrrolidine-1-carbonyl)-4-[3-(2-methyl-pyridin-4-yl)-benzenesulfonyl]-cyclopentanecarboxylic acid (1-cyano-cyclopropyl)-amide

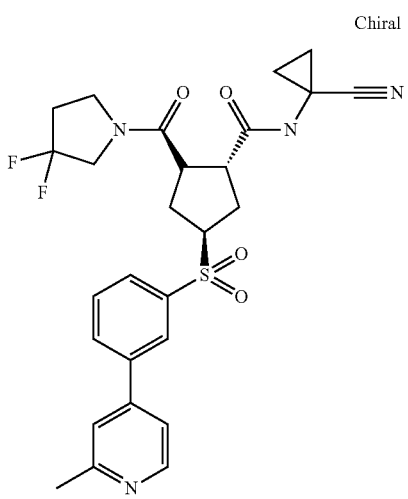

The title compound was prepared in analogy to example 196 using (1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide (Example 188 step 4) and 2-picoline-4-boronic acid. Off-white solid (60%). MS (EI): 543.2 (M+H)$^+$.

Example 204

(1R,2R,4R)-4-[3-(2-Chloro-pyridin-4-yl)-benzenesulfonyl]-2-(3,3-difluoro-pyrrolidine-1-carbonyl)-cyclopentanecarboxylic acid (1-cyano-cyclopropyl)-amide

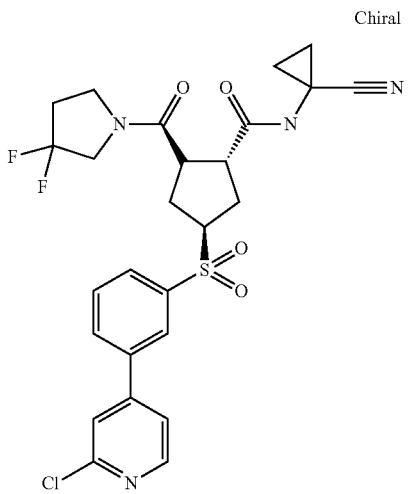

The title compound was prepared in analogy to example 196 using (1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide (Example 188 step 4) and 2-chloropyridine-4-boronic acid. Light brown foam (58%). MS (EI): 563.1 (M+H)⁺.

Example 205

(1R,2R,4R)-2-(3,3-Difluoro-pyrrolidine-1-carbonyl)-4-(toluene-3-sulfonyl)-cyclopentanecarboxylic acid (1-cyano-cyclopropyl)-amide

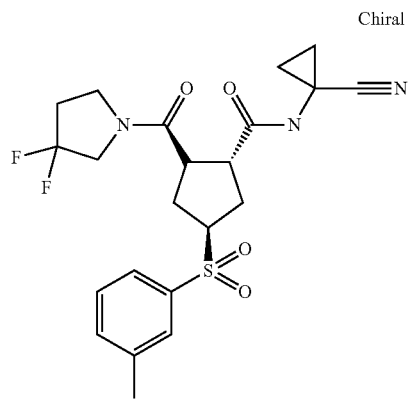

The title compound was prepared in analogy to example 196 using (1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide (Example 188 step 4) and methylboronic acid. White solid (10%). MS (EI): 466.2 (M+H)⁺.

Example 206

(1R,2R,4R) and (1S,2S,4S)-4-[4-(3,3-Difluoro-azetidin-1-yl)-2-trifluoromethyl-benzenesulfonyl]-2-methoxy-cyclopentanecarboxylic acid (1-cyano-cyclopropyl)-amide

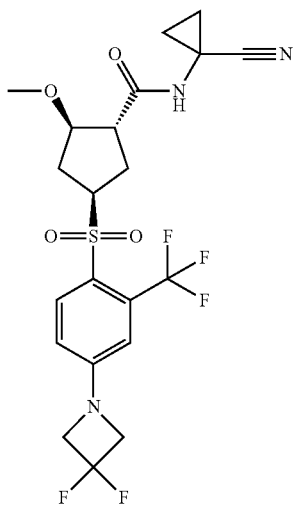

-continued

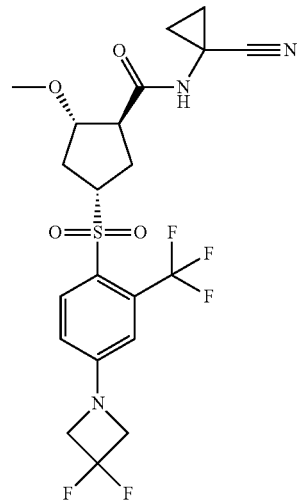

The title compound was prepared in analogy to example 176 using 3,3-difluoro-azetidine instead of morpholine. White solid. MS (EI): 508.1 (M+H)⁺.

Example 207

(1R,2R,4R) and (1S,2S,4S)-4-[4-(4-Hydroxy-piperidin-1-yl)-2-trifluoromethyl-benzenesulfonyl]-2-methoxy-cyclopentanecarboxylic acid (1-cyano-cyclopropyl)-amide

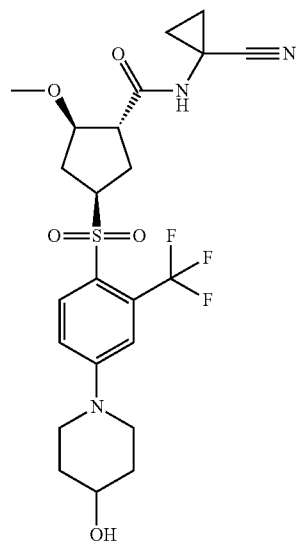

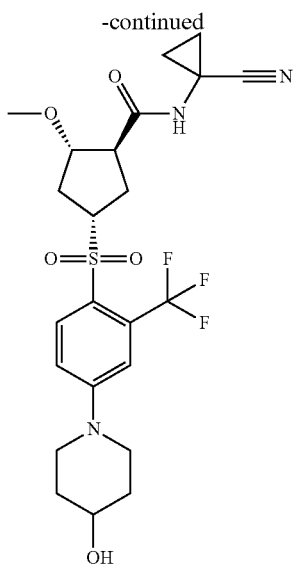

The title compound was prepared in analogy to example 176 using piperidin-4-ol of morpholine. White foam. MS (EI): 516.4 (M+H)+.

Example 208 and 209

(1R,2R,4R)-4-[4-(4-Acetyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide and (1R,2R,4S)-4-[4-(4-Acetyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide

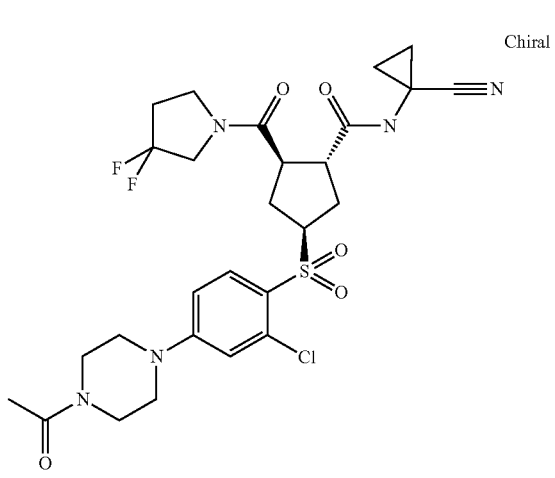

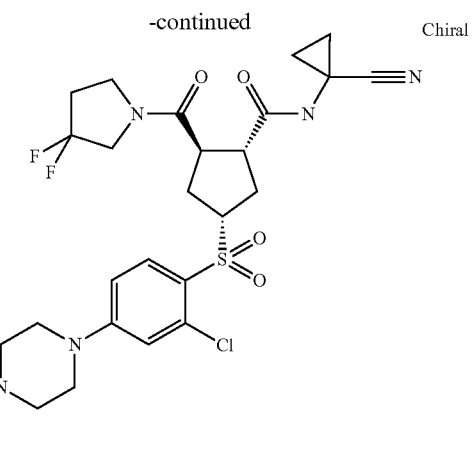

A mixture of (1R,2R,4R)-4-(2-chloro-4-fluoro-benzenesulfonyl)-2-(3,3-difluoro-pyrrolidine-1-carbonyl)-cyclopentanecarboxylic acid (1-cyano-cyclopropyl)-amide (example 186 step 7,100 mg), cesium carbonate (89 mg) and 1-acetylpiperazine (50 mg) in N,N-dimethylformamide (2 mL) was stirred at 50° C. for 4 h. The reaction mixture was partitioned between ethyl acetate and a saturated aqueous solution of sodium hydrogenocarbonate. The aqueous layer was extracted with ethyl acetate then the combined organic layers were washed with water and brine then dried over sodium sulfate and concentrated in vacuo. The residue was purified by preparative HPLC chromatography on Reprosil Chiral NH column with ammonium acetate in ethanol (0.01M)/heptane (40:30 v/v) as eluant to afford the title compounds.

1st fraction eluted: (1R,2R,4S)-4-[4-(4-Acetyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide (30 mg, 22%). Off-white solid. MS (EI): 612.2 (M+H)+.

2nd fraction eluted: (1R,2R,4R)-4-[4-(4-Acetyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide (14 mg, 10%). Off-white solid. MS (EI): 612.2 (M+H)+.

Example 210

(1R,2R,4R) and (1S,2S,4S)-2-Cyclobutoxy-4-[4-(2-methyl-pyridin-4-yl)-2-trifluoromethyl-benzenesulfonyl]-cyclopentanecarboxylic acid (1-cyano-cyclopropyl)-amide

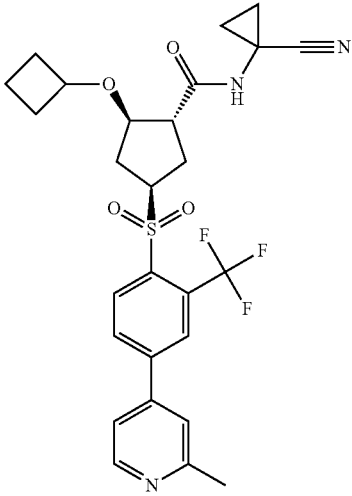

213

-continued

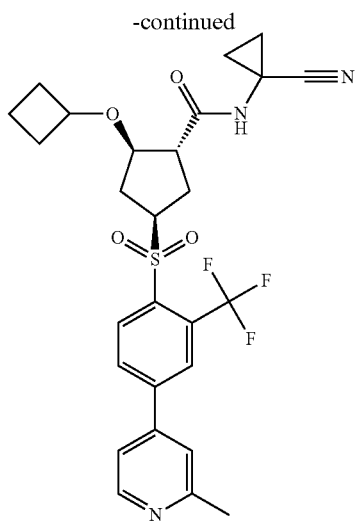

The title compound was prepared in analogy to example 62 using 2-picoline-4-boronic acid instead of 2,4-difluorophenylboronic acid and (1R,2R,4R) and (1S,2S,4S)-4-(4-bromo-2-trifluoromethyl-benzenesulfonyl)-2-cyclobutoxy-cyclopentanecarboxylic acid (1-cyano-cyclopropyl)-amide (example 182) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 548.1 (M+H)$^+$.

214

-continued

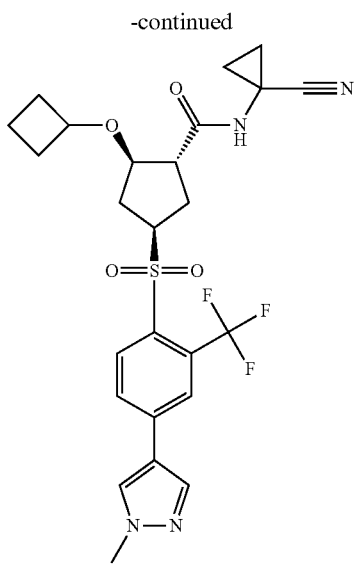

The title compound was prepared in analogy to example 62 using 1-methyl-4-(4.4.5.5-tetramethyl-1.3.2-dioxaborolan)-1H-pyrazole and (1R,2R,4R) and (1S,2S,4S)-4-(4-bromo-2-trifluoromethyl-benzenesulfonyl)-2-cyclobutoxy-cyclopentanecarboxylic acid (1-cyano-cyclopropyl)-amide (example 182) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. Colorless solid. MS (EI): 537.3 (M+H)$^+$.

Example 211

(1R,2R,4R) and (1S,2S,4S)-2-Cyclobutoxy-4-[4-(1-methyl-1H-pyrazol-4-yl)-2-trifluoromethyl-benzenesulfonyl]-cyclopentanecarboxylic acid (1-cyano-cyclopropyl)-amide

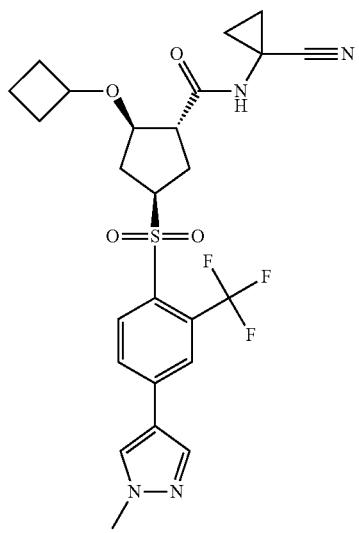

Example 212

(1R,2R,4R) and (1S,2S,4S)-2-Cyclopentyloxy-4-[4-(2-methyl-pyridin-4-yl)-2-trifluoromethyl-benzenesulfonyl]-cyclopentanecarboxylic acid (1-cyano-cyclopropyl)-amide

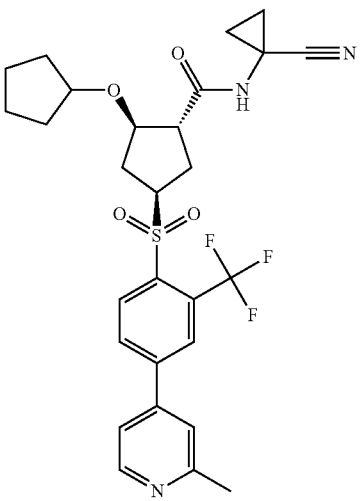

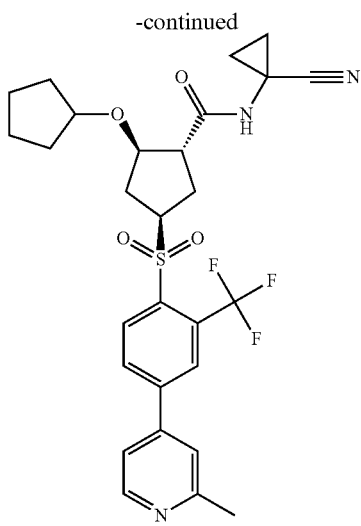

The title compound was prepared in analogy to example 62 using 2-picoline-4-boronic acid instead of 2,4-difluorophenylboronic acid and (1R,2R,4R) and (1S,2S,4S)-4-(4-bromo-2-trifluoromethyl-benzenesulfonyl)-2-cyclopentyloxy-cyclopentanecarboxylic acid (1-cyano-cyclopropyl)-amide (example 195) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 562.3 (M+H)+.

Example 213

(1R,2R,4R) and (1S,2S,4S)-2-Cyclopentyloxy-4-[4-(1-methyl-1H-pyrazol-4-yl)-2-trifluoromethyl-benzenesulfonyl]-cyclopentanecarboxylic acid (1-cyano-cyclopropyl)-amide

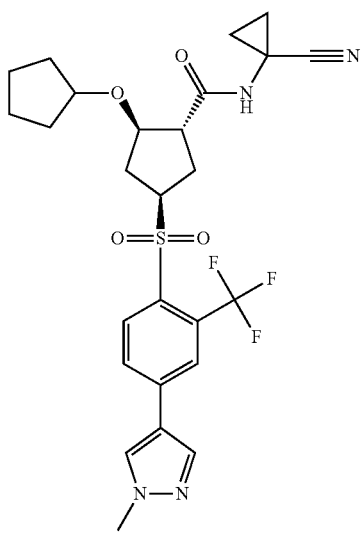

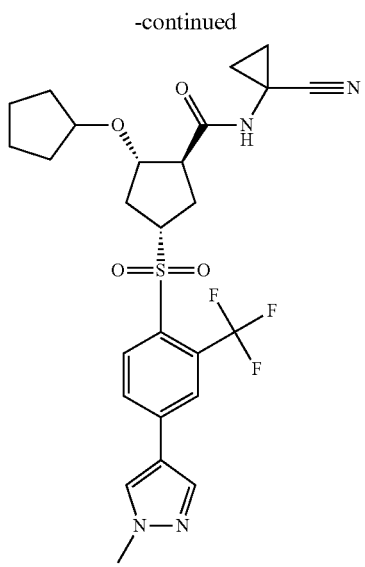

The title compound was prepared in analogy to example 62 using 1-methyl-4-(4.4.5.5-tetramethyl-1.3.2-dioxaborolan)-1H-pyrazole and (1R,2R,4R) and (1S,2S,4S)-4-(4-bromo-2-trifluoromethyl-benzenesulfonyl)-2-cyclopentyloxy-cyclopentanecarboxylic acid (1-cyano-cyclopropyl)-amide (example 195) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 549.3 (M–H)−.

Example 214

(1R,2R,4R) and (1S,2S,4S)-2-Methoxy-4-{4-[1-(3-methyl-oxetan-3-ylmethyl)-1H-pyrazol-4-yl]-2-trifluoromethyl-benzenesulfonyl}-cyclopentanecarboxylic acid (1-cyano-cyclopropyl)-amide

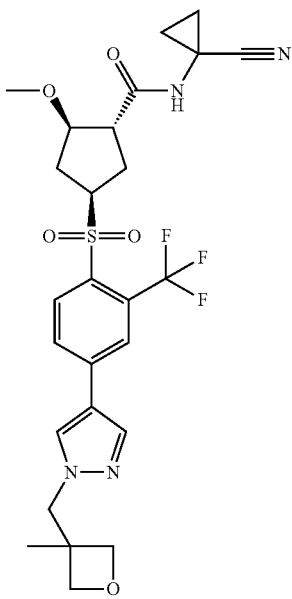

-continued

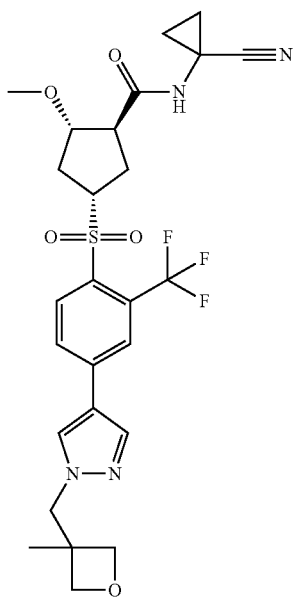

Step 1: 4-Bromo-1-(3-methyl-oxetan-3-ylmethyl)-1H-pyrazole

To a suspension of NaH (98 mg, 55% in mineral oil, 2.25 mmol) in DMF (1.2 ml) was added a solution of 4-bromopyrazole (300 mg, 2.04 mmol) in DMF (2 ml). The reaction mixture was stirred at room temperature for 15 minutes before a solution of 3-bromomethyl-3-methyloxetane (404 mg, 2.45 mmol) in DMF (2 ml) was added slowly. The mixture was stirred at room temperature for 1.5 h, then diluted with saturated NaHCO$_3$ solution and extracted with 3 times with EtOAc. The combined organic layers were washed 2 times with water and with brine, dried (Na$_2$SO$_4$) and evaporated. The remaining colorless oil was purified by silica gel chromatography (heptane/EtOAc 80:20-50:50) to obtain the title compound (444 mg, 94%) as colorless oil. MS (EI): 231.2 (M+H)$^+$.

Step 2: (1R,2R,4R) and (1S,2S,4S)-2-Methoxy-4-{4-[1-(3-methyl-oxetan-3-ylmethyl)-1H-pyrazol-4-yl]-2-trifluoromethyl-benzenesulfonyl}-cyclopentanecarboxylic acid (1-cyano-cyclopropyl)-amide The title compound was prepared in analogy to example 109 using 4-bromo-1-(3-methyl-oxetan-3-ylmethyl)-1H-pyrazole (Intermediate 1, Example 214) instead of 2-bromo-2-trifluoromethylpyridine. Off-white solid. MS (EI): 567.4 (M+H)$^+$.

Example 215

(1R,2R,4R) and (1S,2S,4S)-4-[4-(4-Cyclopropyl-piperazin-1-yl)-2-trifluoromethyl-benzenesulfonyl]-2-methoxy-cyclopentanecarboxylic acid (1-cyano-cyclopropyl)-amide

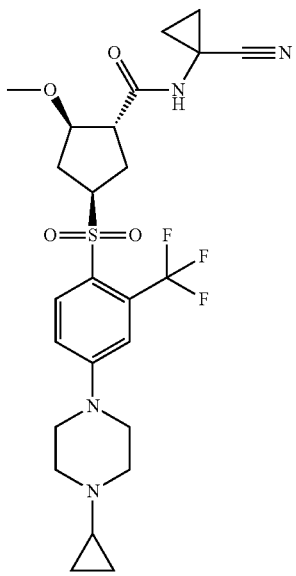

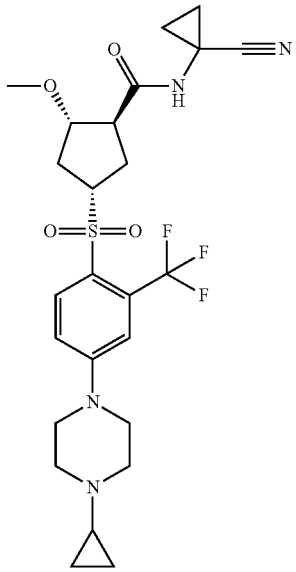

The title compound was prepared in analogy to example 176 using 1-cyclopropyl-piperazine instead of morpholine. White foam. MS (EI): 541.4 (M+H)$^+$.

Example 216

(1R,2R,4R) and (1S,2S,4S)-2-Methoxy-4-[4-(1-methylcarbamoylmethyl-1H-pyrazol-4-yl)-2-trifluoromethyl-benzenesulfonyl]-cyclopentanecarboxylic acid (1-cyano-cyclopropyl)-amide

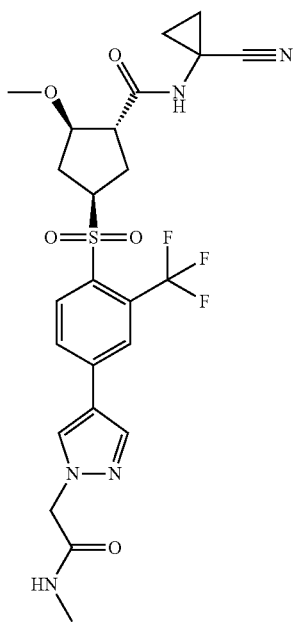

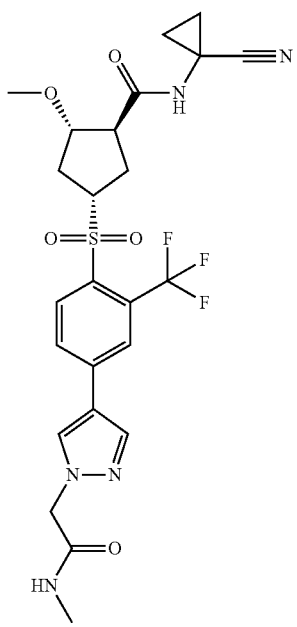

To a solution of (4-{4-[(1R,3R,4R) and (1S,3S,4S)-3-(1-cyano-cyclopropylcarbamoyl)-4-methoxy-cyclopentanesulfonyl]-3-trifluoromethyl-phenyl}-pyrazol-1-yl)-acetic acid (43 mg, 0.0796 mmol, example 185) in DMF (1.5 ml) were added HATU (60 mg, 0.1591 mmol), N-ethyl-N,N-diisopropyl amine (57 µl, 0.318 mmol) and methylamine hydrochloride (8 mg, 0.1193 mmol) and the reaction mixture was stirred at room temperature overnight. Then water was added and the mixture was extracted 3 times with EtOAc. The combined organic layers were washed with water, 0.1N HCl, saturated NaHCO₃ solution and brine, dried (Na₂SO₄) and concentrated. The remaining residue was purified by column chromatography first with silica gel (DCM/MeOH 19:1) and then with SiliaSep™ OT (DCM/MeOH 98:2) to obtain the title compound (5 mg, 11%) as white solid. MS (EI): 454.3 (M+H)⁺.

Example 217

(1R,2R,4R) and (1S,2S,4S)-4-[4-(4-Acetyl-piperazin-1-yl)-2-trifluoromethyl-benzenesulfonyl]-2-methoxy-cyclopentanecarboxylic acid (1-cyano-cyclopropyl)-amide

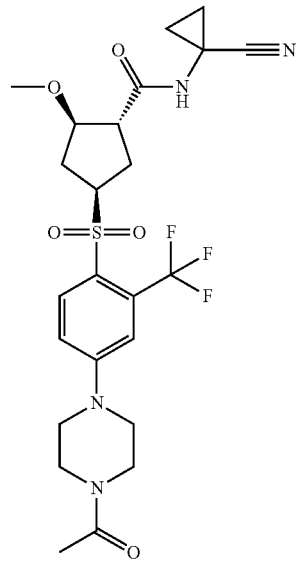

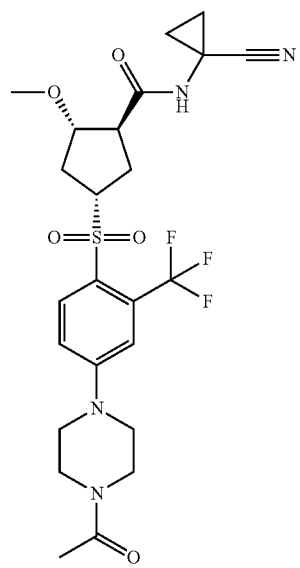

The title compound was prepared in analogy to example 176 using 1-acetyl-piperazine instead of morpholine. White foam. MS (EI): 543.4 (M+H)⁺.

Example 218

(1R,2R,4R) and (1S,2S,4S)-4-[4-(1-Dimethylcarbamoylmethyl-1H-pyrazol-4-yl)-2-trifluoromethyl-benzenesulfonyl]-2-methoxy-cyclopentanecarboxylic acid (1-cyano-cyclopropyl)-amide

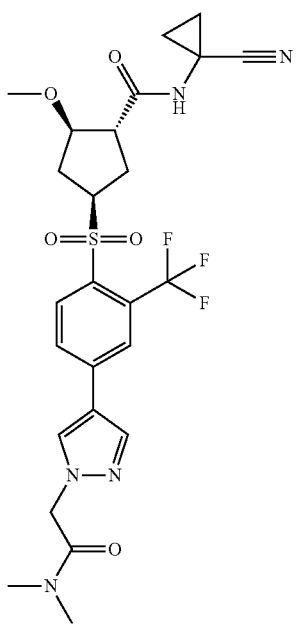

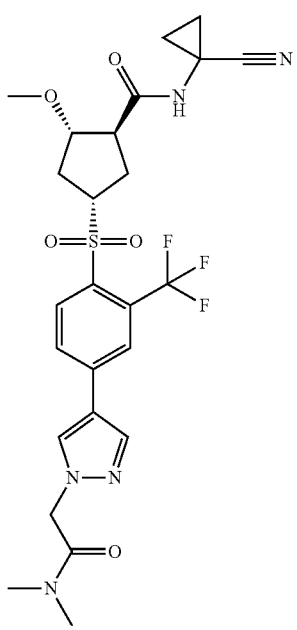

The title compound was prepared in analogy to example 216 using dimethylamine hydrochloride instead of methylamine hydrochloride. White solid. MS (EI): 568.4 (M+H)+.

Example 219

(1R,2R,4R) and (1S,2S,4S)-2-[(tetrahydro-1,1-dioxo-2H-thiopyran-4-yl)oxy]-4-(2-trifluoromethyl-benzenesulfonyl)-cyclopentanecarboxylic acid (1-cyano-cyclopropyl)-amide

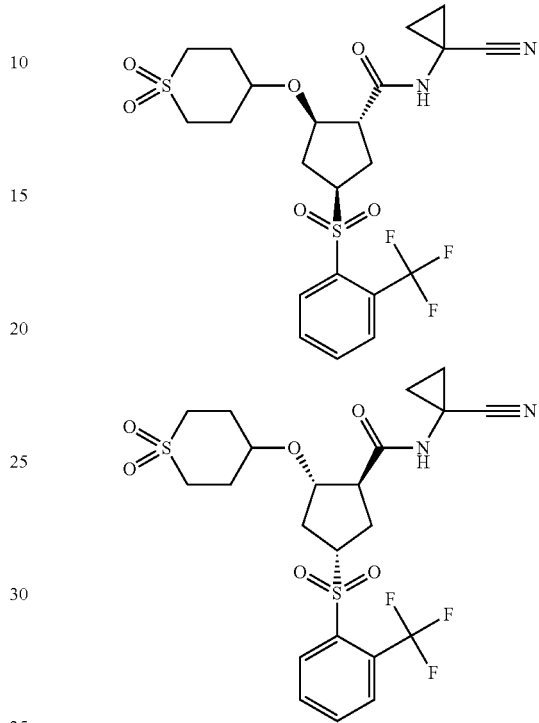

The title compound was prepared in analogy to example 175 using (1R,2R,4R) and (1S,2S,4S)-4-(4-bromo-2-trifluoromethyl-benzenesulfonyl)-2-[(tetrahydro-1,1-dioxo-2H-thiopyran-4-yl)oxy]-cyclopentanecarboxylic acid (1-cyano-cyclopropyl)-amide (example 181) instead of (1R,2R,4R) and (1S,2S,4S)-4-(4-bromo-2-trifluoromethyl-benzenesulfonyl)-2-(tetrahydro-pyran-4-yloxy)-cyclopentanecarboxylic acid (1-cyano-cyclopropyl)-amide. White solid. MS (EI): 533.1 (M−H)−.

Example 220

(1R,2R,4R) and (1S,2S,4S)-2-Cyclobutoxy-4-(2-trifluoromethyl-benzenesulfonyl)-cyclopentanecarboxylic acid (1-cyano-cyclopropyl)-amide

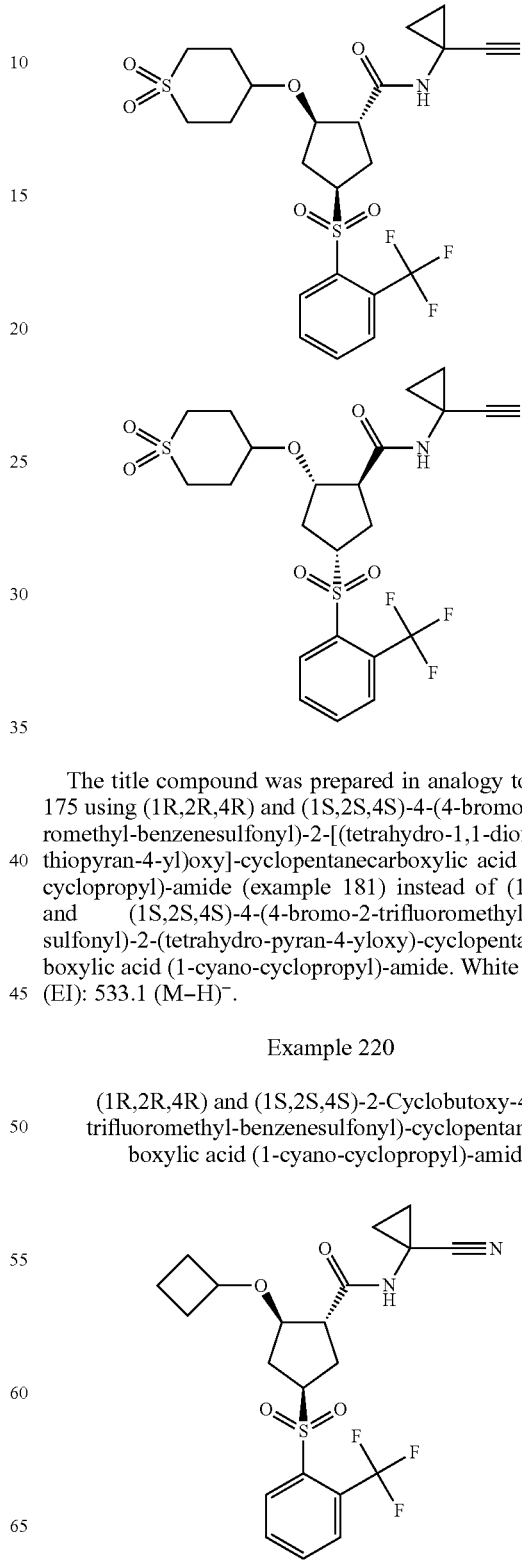

-continued

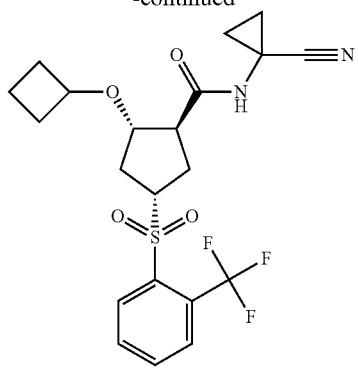

The title compound was prepared in analogy to example 175 using (1R,2R,4R) and (1S,2S,4S)-4-(4-bromo-2-trifluoromethyl-benzenesulfonyl)-2-cyclobutoxy-cyclopentanecarboxylic acid (1-cyano-cyclopropyl)-amide (example 182) instead of (1R,2R,4R) and (1S,2S,4S)-4-(4-bromo-2-trifluoromethyl-benzenesulfonyl)-2-(tetrahydro-pyran-4-yloxy)-cyclopentanecarboxylic acid (1-cyano-cyclopropyl)-amide. White solid. MS (EI): 455.2 (M−H)⁻.

Example 221

(1R,2R,4R) and (1S,2S,4S)-2-Cyclopentyloxy-4-(2-trifluoromethyl-benzenesulfonyl)-cyclopentanecarboxylic acid (1-cyano-cyclopropyl)-amide

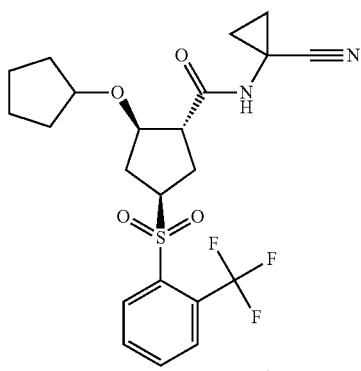

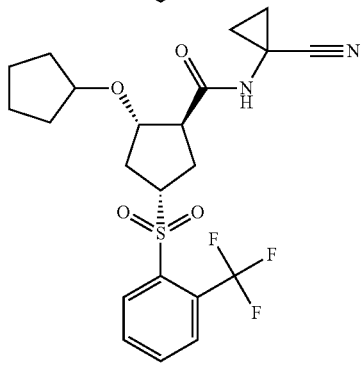

The title compound was prepared in analogy to example 175 using (1R,2R,4R) and (1S,2S,4S)-4-(4-bromo-2-trifluoromethyl-benzenesulfonyl)-2-cyclopentyloxy-cyclopentanecarboxylic acid (1-cyano-cyclopropyl)-amide (example 195) instead of (1R,2R,4R) and (1S,2S,4S)-4-(4-bromo-2-trifluoromethyl-benzenesulfonyl)-2-(tetrahydro-pyran-4-yloxy)-cyclopentanecarboxylic acid (1-cyano-cyclopropyl)-amide. White solid. MS (EI): 469.2 (M−H)⁻.

Example 222

(1R,2R,4R) and (1S,2S,4S)-4-(2-Chloro-benzenesulfonyl)-2-(4-chloro-benzyloxy)-cyclopentanecarboxylic acid (1-cyano-cyclopropyl)-amide

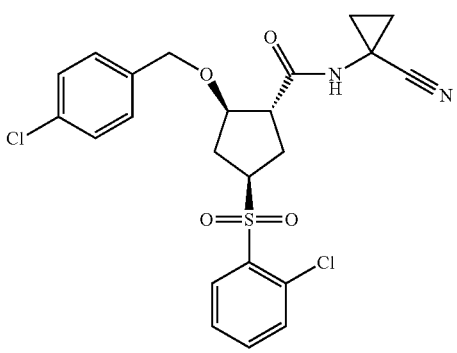

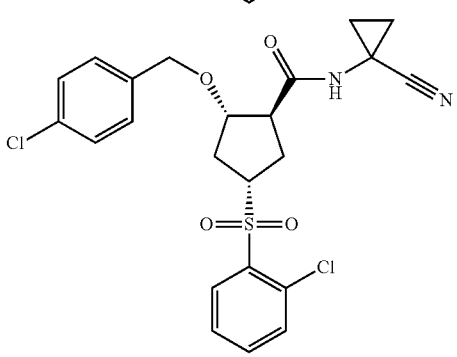

The title compound was prepared in analogy to example 150 using 1-(bromomethyl)-4-chlorobenzene instead of 1-(bromomethyl)-4-methylbenzene. Off-white solid. MS (EI): 593.0 (M+H)⁺.

Example 223

(1R,2R,4R) and (1S,2S,4S)-4-[4-(1-Ethylcarbamoyl-methyl-1H-pyrazol-4-yl)-2-trifluoromethyl-benzenesulfonyl]-2-methoxy-cyclopentanecarboxylic acid (1-cyano-cyclopropyl)-amide

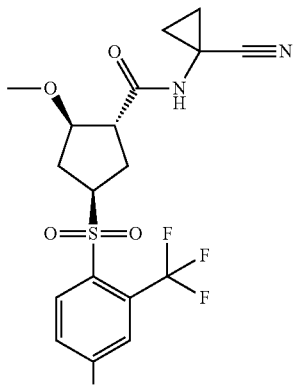

-continued

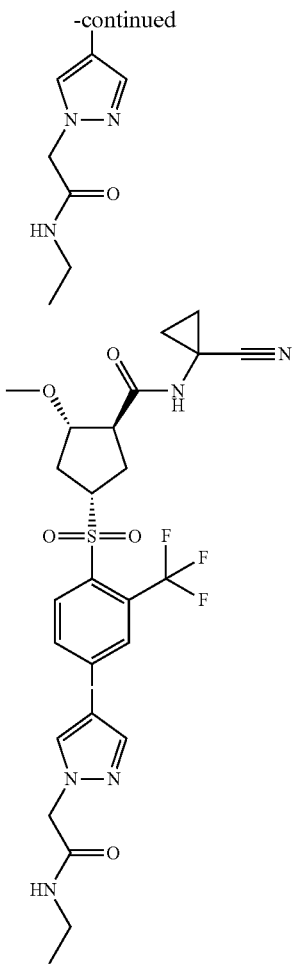

The title compound was prepared in analogy to example 216 using ethylamine hydrochloride instead of methylamine hydrochloride. White solid. MS (EI): 568.4 (M+H)+.

Example 224

(1R,2R,4S)-2-(3,3-Difluoro-pyrrolidine-1-carbonyl)-4-(6-methyl-pyridazine-3-sulfonyl)-cyclopentanecarboxylic acid (1-cyano-cyclopropyl)-amide and (1R,2R,4R)-2-(3,3-Difluoro-pyrrolidine-1-carbonyl)-4-(6-methyl-pyridazine-3-sulfonyl)-cyclopentanecarboxylic acid (1-cyano-cyclopropyl)-amide

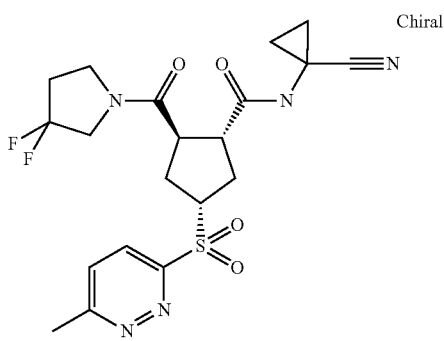

-continued

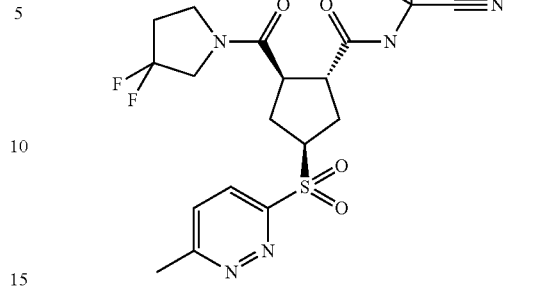

Step 1: (1R,2R,4S)-2-(3,3-Difluoro-pyrrolidine-1-carbonyl)-4-(6-methyl-pyridazin-3-ylsulfanyl)-cyclopentanecarboxylic acid ethyl ester The title compound was prepared in analogy to example 68/69 step 8 using (1R,2R,4R)-2-(3,3-Difluoro-pyrrolidine-1-carbonyl)-4-methanesulfonyloxy-cyclopentanecarboxylic acid ethyl ester (example 186 step 3) and 3-mercapto-6-methylpyridazine. Light yellow liquid (43%). MS (EI): 400.2 (M+H)+.

Step 2: (1R,2R,4S)-2-(3,3-Difluoro-pyrrolidine-1-carbonyl)-4-(6-methyl-pyridazine-3-sulfonyl)-cyclopentanecarboxylic acid ethyl ester The title compound was prepared in analogy to example 68/69 step 9 using (1R,2R,4S)-2-(3,3-Difluoro-pyrrolidine-1-carbonyl)-4-(6-methyl-pyridazin-3-ylsulfanyl)-cyclopentanecarboxylic acid ethyl ester (example 224 step 1). White foam (79%). MS (EI): 448.2 (M+NH$_4$)+.

Step 3: (1R,2R,4S)-2-(3,3-Difluoro-pyrrolidine-1-carbonyl)-4-(6-methyl-pyridazine-3-sulfonyl)-cyclopentanecarboxylic acid The title compound was prepared in analogy to example 68/69 step 10 using (1R,2R,4S)-2-(3,3-Difluoro-pyrrolidine-1-carbonyl)-4-(6-methyl-pyridazine-3-sulfonyl)-cyclopentanecarboxylic acid ethyl ester (example 224 step 2). Yellow gum (69%). MS (EI): 405.3 (M+H)+.

Step 4: (1R,2R,4S)-2-(3,3-Difluoro-pyrrolidine-1-carbonyl)-4-(6-methyl-pyridazine-3-sulfonyl)-cyclopentanecarboxylic acid (1-cyano-cyclopropyl)-amide and (1R,2R,4R)-2-(3,3-Difluoro-pyrrolidine-1-carbonyl)-4-(6-methyl-pyridazine-3-sulfonyl)-cyclopentanecarboxylic acid (1-cyano-cyclopropyl)-amide The title compound was prepared in analogy to example 117 step 7 using (1R,2R,4S)-2-(3,3-Difluoro-pyrrolidine-1-carbonyl)-4-(6-methyl-pyridazine-3-sulfonyl)-cyclopentanecarboxylic acid (example 224 step 3) and 1-amino-cyclopropyl cyanic hydrochloride. Light yellow foam (20%). MS (EI): 468.2 (M+H)+.

Example 225 and 226

(1R,2R,4R)-4-(5-Chloro-pyridine-2-sulfonyl)-2-(3,3-difluoro-pyrrolidine-1-carbonyl)-cyclopentanecarboxylic acid (1-cyano-cyclopropyl)-amide and (1R,2R,4S)-4-(5-Chloro-pyridine-2-sulfonyl)-2-(3,3-difluoro-pyrrolidine-1-carbonyl)-cyclopentanecarboxylic acid (1-cyano-cyclopropyl)-amide

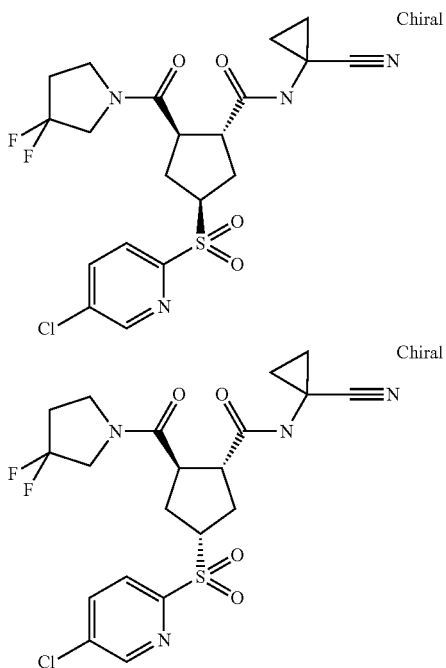

Step 1: (1R,2R,4S)-4-(5-Chloro-pyridin-2-ylsulfanyl)-2-(3,3-difluoro-pyrrolidine-1-carbonyl)-cyclopentanecarboxylic acid ethyl ester The title compound was prepared in analogy to example 68/69 step 8 using (1R,2R,4R)-2-(3,3-Difluoro-pyrrolidine-1-carbonyl)-4-methanesulfonyloxy-cyclopentanecarboxylic acid ethyl ester (example 186 step 3) and 5-chloropyridine-2-thiol. Yellow solid (83%). MS (EI): 419.1 (M+H)$^+$.

Step 2: (1R,2R,4S)-4-(5-Chloro-pyridine-2-sulfonyl)-2-(3,3-difluoro-pyrrolidine-1-carbonyl)-cyclopentanecarboxylic acid ethyl ester The title compound was prepared in analogy to example 68/69 step 9 using (1R,2R,4S)-4-(5-Chloro-pyridin-2-ylsulfanyl)-2-(3,3-difluoro-pyrrolidine-1-carbonyl)-cyclopentanecarboxylic acid ethyl ester (example 225 step 1). Colorless oil (93%). MS (EI): 451.1 (M+H)$^+$.

Step 3: (1R,2R,4S)-4-(5-Chloro-pyridine-2-sulfonyl)-2-(3,3-difluoro-pyrrolidine-1-carbonyl)-cyclopentanecarboxylic acid The title compound was prepared in analogy to example 68/69 step 10 using (1R,2R,4S)-4-(5-Chloro-pyridine-2-sulfonyl)-2-(3,3-difluoro-pyrrolidine-1-carbonyl)-cyclopentanecarboxylic acid ethyl ester (example 225 step 2). Light brown solid (99%). MS (EI): 423.2 (M+H)$^+$.

Step 4: (1R,2R,4R)-4-(5-Chloro-pyridine-2-sulfonyl)-2-(3,3-difluoro-pyrrolidine-1-carbonyl)-cyclopentanecarboxylic acid (1-cyano-cyclopropyl)-amide and (1R,2R,4S)-4-(5-Chloro-pyridine-2-sulfonyl)-2-(3,3-difluoro-pyrrolidine-1-carbonyl)-cyclopentanecarboxylic acid (1-cyano-cyclopropyl)-amide To a mixture of (1R,2R,4S)-4-(5-Chloro-pyridine-2-sulfonyl)-2-(3,3-difluoro-pyrrolidine-1-carbonyl)-cyclopentanecarboxylic acid (98 mg), N,N-diisopropylethylamine (0.12 mL), 2-(1H-7-Azabenzotriazol-1-yl)-1,1,3,3-tetramethyl uronium hexafluorophosphate methanaminium (178 mg) in acetonitrile was added 1-amino-cyclopropyl cyanic hydrochloride (34 mg). The reaction mixture was stirred at room temperature for 16 h then concentrated in vacuo and partitioned between ethyl acetate and a saturated aqueous solution of sodium hydrogenocarbonate. The aqueous layer was extracted with ethyl acetate then the combined organic layers were washed with water and brine then dried over sodium sulfate and concentrated in vacuo. The residue was purified by flash chromatography on silica gel with dichloromethane/methanol (98:2 v/v) as eluant to afford the title compounds.

1$^{st}$ fraction eluted: (1R,2R,4R)-4-(5-Chloro-pyridine-2-sulfonyl)-2-(3,3-difluoro-pyrrolidine-1-carbonyl)-cyclopentanecarboxylic acid (1-cyano-cyclopropyl)-amide (50 mg, 44%). Light yellow solid. MS (EI): 487.1 (M+H)$^+$.

2$^{nd}$ fraction eluted: (1R,2R,4S)-4-(5-Chloro-pyridine-2-sulfonyl)-2-(3,3-difluoro-pyrrolidine-1-carbonyl)-cyclopentanecarboxylic acid (1-cyano-cyclopropyl)-amide (5 mg, 4%). Yellow gum. MS (EI): 487.1 (M+H)$^+$.

Example 227 and 228

(1R,2R,4R)-2-(3,3-Difluoro-pyrrolidine-1-carbonyl)-4-(pyridine-2-sulfonyl)-cyclopentanecarboxylic acid (1-cyano-cyclopropyl)-amide and (1R,2R,4S)-2-(3,3-Difluoro-pyrrolidine-1-carbonyl)-4-(pyridine-2-sulfonyl)-cyclopentanecarboxylic acid (1-cyano-cyclopropyl)-amide

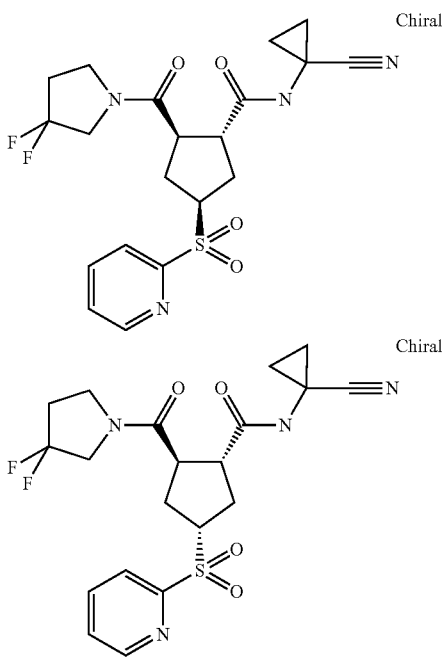

Step 1: (1R,2R)-2-(3,3-Difluoro-pyrrolidine-1-carbonyl)-4-(pyridin-2-ylsulfanyl)-cyclopentanecarboxylic acid ethyl ester (epimeric mixture)

The title compound was prepared in analogy to example 68/69 step 8 using (1R,2R,4R)-2-(3,3-Difluoro-pyrrolidine-1-carbonyl)-4-methanesulfonyloxy-cyclopentanecarboxylic acid ethyl ester (example 186 step 3) and 2-mercaptopyridine. Light brown semi-solid (74%). MS (EI): 385.3 (M+H)$^+$.

Step 2: (1R,2R)-2-(3,3-difluoro-pyrrolidine-1-carbonyl)-4-(pyridine-2-sulfonyl)-cyclopentanecarboxylic acid ethyl ester (epimeric mixture)

The title compound was prepared in analogy to example 68/69 step 9 using (1R,2R)-2-(3,3-Difluoro-pyrrolidine-1-carbonyl)-4-(pyridin-2-ylsulfanyl)-cyclopentanecarboxylic acid ethyl ester (epimeric mixture, example 227 and 228 step 1). White gum (92%). MS (EI): 417.3 (M+H)$^+$.

Step 3: (1R,2R)-4-(5-Chloro-pyridine-2-sulfonyl)-2-(3,3-difluoro-pyrrolidine-1-carbonyl)-cyclopentanecarboxylic acid (epimeric mixture)

The title compound was prepared in analogy to example 68/69 step 10 using (1R,2R)-2-(3,3-difluoro-pyrrolidine-1-carbonyl)-4-(pyridine-2-sulfonyl)-cyclopentanecarboxylic acid ethyl ester (epimeric mixture, example 227 and 228 step 2). Yellow solid (quant.). MS (EI): 389.2 (M+H)$^+$.

Step 4: (1R,2R,4R)-2-(3,3-Difluoro-pyrrolidine-1-carbonyl)-4-(pyridine-2-sulfonyl)-cyclopentanecarboxylic acid (1-cyano-cyclopropyl)-amide and (1R,2R,4S)-2-(3,3-Difluoro-pyrrolidine-1-carbonyl)-4-(pyridine-2-sulfonyl)-cyclopentanecarboxylic acid (1-cyano-cyclopropyl)-amide To a mixture of (1R,2R)-4-(5-Chloro-pyridine-2-sulfonyl)-2-(3,3-difluoro-pyrrolidine-1-carbonyl)-cyclopentanecarboxylic acid (epimeric mixture, 119 mg), N,N-diisopropylethylamine (0.16 mL), 2-(1H-7-Azabenzotriazol-1-yl)-1,1,3,3-tetramethyl uronium hexafluorophosphate methanaminium (235 mg) in acetonitrile (3 mL) was added 1-amino-cyclopropyl cyanic hydrochloride (45 mg). The reaction mixture was stirred at room temperature for 16 h then concentrated in vacuo and partitioned between ethyl acetate and a saturated aqueous solution of sodium hydrogenocarbonate. The aqueous layer was extracted with ethyl acetate then the combined organic layers were washed with water and brine then dried over sodium sulfate and concentrated in vacuo. The residue was purified by flash chromatography on silica gel with dichloromethane/methanol (98:2 v/v) as eluant to afford the title compounds.

1$^{st}$ fraction eluted: (1R,2R,4R)-2-(3,3-Difluoro-pyrrolidine-1-carbonyl)-4-(pyridine-2-sulfonyl)-cyclopentanecarboxylic acid (1-cyano-cyclopropyl)-amide (18 mg, 13%). Light yellow solid. MS (EI): 453.1 (M+H)$^+$.

2$^{nd}$ fraction eluted: (1R,2R,4S)-2-(3,3-Difluoro-pyrrolidine-1-carbonyl)-4-(pyridine-2-sulfonyl)-cyclopentanecarboxylic acid (1-cyano-cyclopropyl)-amide (49 mg, 35%). Yellow gum. MS (EI): 453.1 (M+H)$^+$.

Example 229

(1R,2R,4R) and (1S,2S,4S)-2-Cyclopentyloxy-4-[4-(4-isopropyl-piperazin-1-yl)-2-trifluoromethyl-benzenesulfonyl]-cyclopentanecarboxylic acid (1-cyano-cyclopropyl)-amide

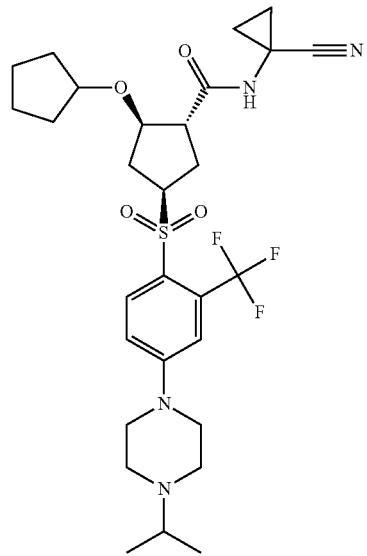

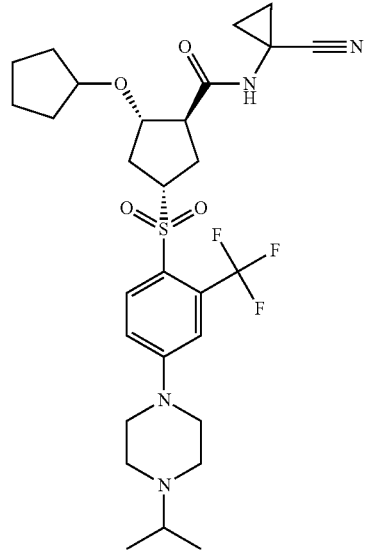

The title compound was prepared in analogy to example 176 using 1-isopropyl-piperazine instead of morpholine and (1R,2R,4R) and (1S,2S,4S)-4-(4-bromo-2-trifluoromethyl-benzenesulfonyl)-2-cyclopentyloxy-cyclopentanecarboxylic acid (1-cyano-cyclopropyl)-amide (example 195) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 595.4 (M−H)$^−$.

Example 230

(1R,2R,4R) and (1S,2S,4S)-2-Cyclopentyloxy-4-{4-[4-(2,2,2-trifluoro-ethyl)-piperazin-1-yl]-2-trifluoromethyl-benzenesulfonyl}-cyclopentanecarboxylic acid (1-cyano-cyclopropyl)-amide

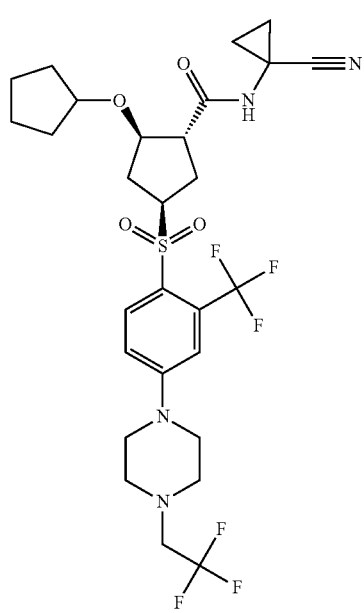

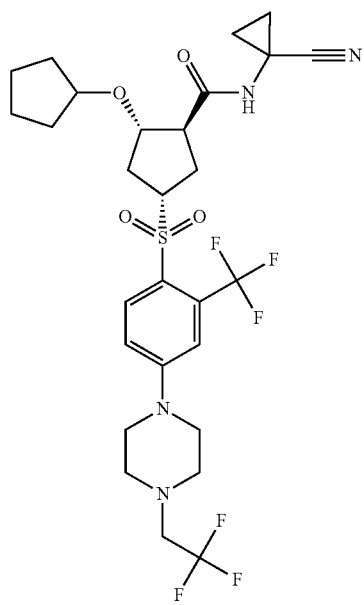

The title compound was prepared in analogy to example 176 using 1-(2,2,2-trifluoro-ethyl)-piperazine instead of morpholine and (1R,2R,4R) and (1S,2S,4S)-4-(4-bromo-2-trifluoromethyl-benzenesulfonyl)-2-cyclopentyloxy-cyclopentanecarboxylic acid (1-cyano-cyclopropyl)-amide (example 195) instead of (1R,2R,4R) and (1S,2S,4S)-4-(4-bromo-2-trifluoromethyl-benzenesulfonyl)-2-methoxy-cyclopentanecarboxylic acid (1-cyano-cyclopropyl)-amide. White solid. MS (EI): 635.2 (M−H)⁻.

Example 231

(1R,2R,4R) and (1S,2S,4S)-2-Phenoxy-4-(2-trifluoromethyl-benzenesulfonyl)-cyclopentanecarboxylic acid (1-cyano-cyclopropyl)-amide

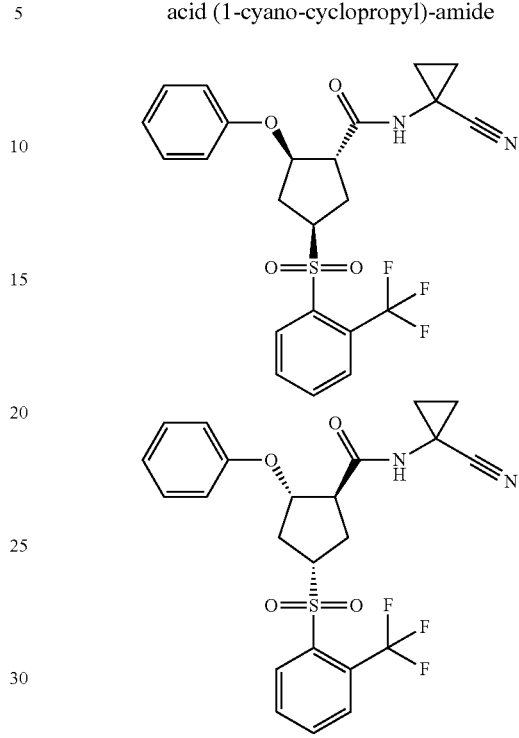

Step 1: (1S,2R,4S) and (1R,2S,4R)-4-(tert-Butyl-diphenyl-silanyloxy)-2-phenoxy-cyclopentanol A mixture of (1R,2S,4s)-4-{[tert-butyl(diphenyl)silyl]oxy}cyclopentane-1,2-diol (1000 mg, 2.80 mmol, example 112, step 2), triphenyl-bismuth diacetate (1.6 g, 2.80 mmol) and Cu(OAc)₂ (16 mg, 0.0841 mmol) in DCM (50 ml) was stirred at room temperature for 2.5 h. The reaction mixture was then filtered through a pad of silica gel which was washed with DCM (~300 ml) and the filtrate was evaporated. The remaining residue was purified by silica column chromatography (heptane/EtOAc 19:1-80:20) to give the title compound (809 mg, 67%) as colorless gum. MS (EI): 450.3 (M+NH₄)⁺.

Step 2: (1S,2R,4S) and (1R,2S,4R)-4-(tert-Butyl-diphenyl-silanyloxy)-2-phenoxy-cyclopentanecarbonitrile The title compound was prepared in analogy to example 112, step 4 and was obtained as colorless gum. MS (EI): 442.3 (M+H)⁺.

Step 3: (1S,2R,4S) and (1R,2S,4R)-4-Hydroxy-2-phenoxy-cyclopentanecarbonitrile

The title compound was prepared in analogy to example 46, step 5 and was obtained as colorless oil. MS (EI): 262.0 (M+OAc)⁻.

Step 4: Methanesulfonic acid (1S,3S,4R) and (1R,3R,4S)-3-cyano-4-phenoxy-cyclopentyl ester The title compound was prepared in analogy to example 46, step 6 and was obtained as light yellow gum. MS (EI): 282.1 (M+H)⁺.

Step 5: (1S,2R,4R) and (1R,2S,4S)-2-Phenoxy-4-(2-trifluoromethyl-phenylsulfanyl)-cyclopentanecarbonitrile The title compound was prepared in analogy to example 46, step 7 and was obtained as yellow gum. MS (EI): 422.1 (M+OAc)⁻.

Step 6: (1S,2R,4R) and (1R,2S,4S)-2-Phenoxy-4-(2-trifluoromethyl-benzenesulfonyl)-cyclopentanecarbonitrile The title compound was prepared in analogy to example 169, step 7 and was obtained as colorless gum. MS (EI): 394.0 (M+H)⁺.

Step 7: (1R,2R,4R) and (1S,2S,4S)-2-Phenoxy-4-(2-trifluoromethyl-benzenesulfonyl)-cyclopentanecarboxylic acid methyl ester The title compound was prepared in analogy to example 46, step 9 and was obtained as yellow gum. MS (EI): 429.1 (M+H)⁺.

Step 8: Lithium (1R,2R,4R) and (1S,2S,4S)-2-phenoxy-4-(2-trifluoromethyl-benzenesulfonyl)-cyclopentanecarboxylate The title compound was prepared in analogy to example 46, step 10 and was obtained as mixture with lithium 4-(2-trifluoromethyl-benzenesulfonyl)-cyclopent-1-enecarboxylate. The mixture was used in the next reaction step without further purification. MS (EI): 413.0 (M−H)⁻.

Step 9: (1R,2R,4R) and (1S,2S,4S)-2-Phenoxy-4-(2-trifluoromethyl-benzenesulfonyl)-cyclopentanecarboxylic acid (1-cyano-cyclopropyl)-amide The title compound was prepared in analogy to example 46, step 11 using HATU/N-ethyl-N,N-diisopropyl amine in DMF instead of EDCI/HOBt/N-ethyl-N,N-diisopropyl amine in acetonitrile and was obtained as light yellow foam. MS (EI): 477.1 (M−H)⁻.

Example 232

(1R,2R,4R) and (1S,2S,4S)-2-(4-Chloro-benzyloxy)-4-(2-trifluoromethyl-benzenesulfonyl)-cyclopentanecarboxylic acid (1-cyano-cyclopropyl)-amide

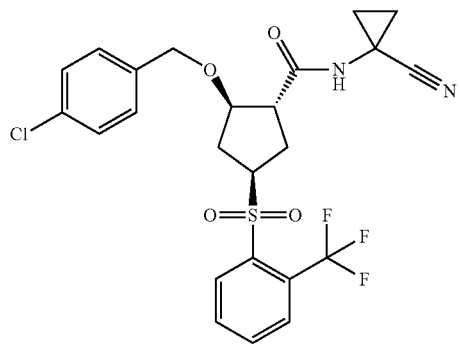

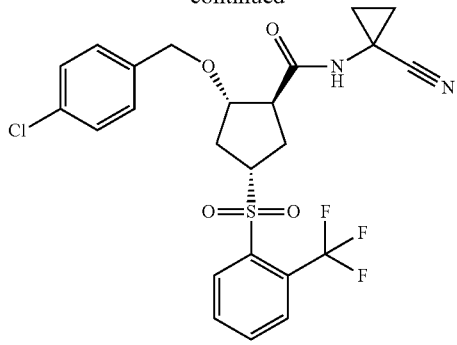

The title compound was prepared in analogy to example 46 using 4-chloro-benzylbromide together with DCM as a solvent instead of methyl iodide in step 4. Off-white solid. MS (EI): 525.1 (M−H)⁻.

Example 233

(1R,2R,4R) and (1S,2S,4S)-2-(4-Chloro-benzyloxy)-4-(2,4-dichloro-benzenesulfonyl)-cyclopentanecarboxylic acid (1-cyano-cyclopropyl)-amide

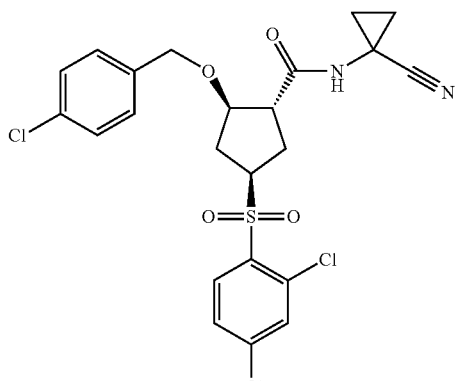

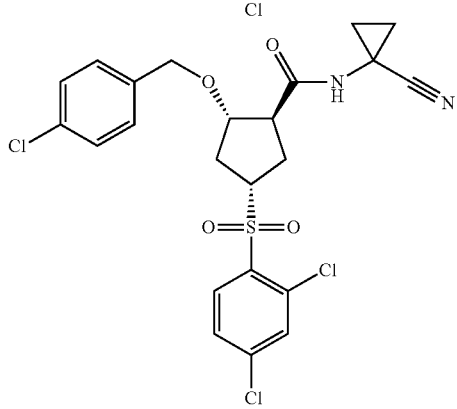

The title compound was prepared in analogy to example 50 using 4-chloro-benzylbromide together with DCM as a solvent instead of methyl iodide in step 4. Off-white solid. MS (EI): 525.0 (M−H)⁻.

Example 234

(1R,2R,4R) and (1S,2S,4S)-2-(4-Chloro-benzyloxy)-4-(2,4-dichloro-benzenesulfonyl)-cyclopentanecarboxylic acid (4-cyano-1-methyl-piperidin-4-yl)-amide

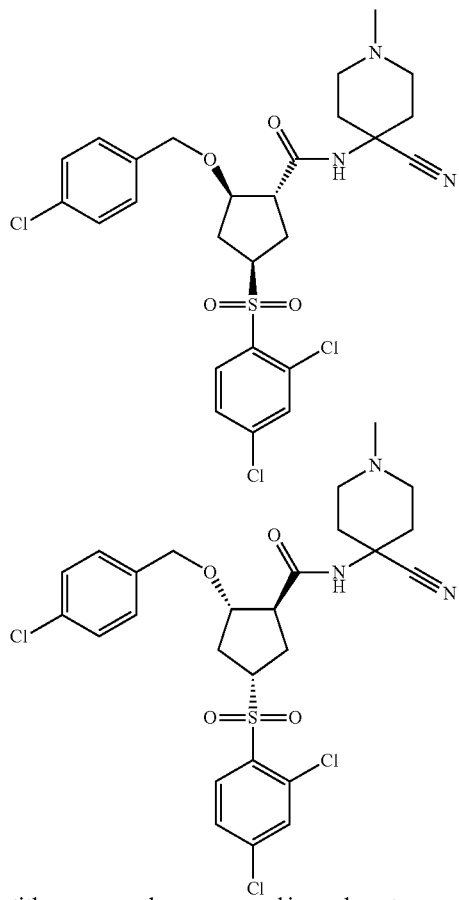

The title compound was prepared in analogy to example 50 using 4-chloro-benzylbromide together with DCM as a solvent instead of methyl iodide in step 4 and 4-amino-4-cyano-1-methylpiperidine (CAS 123194-00-3) instead of 1-amino-1-cyclopropanecarbonitrile hydrochloride in step 11. Light brown foam. MS (EI): 582.2 (M–H)⁻.

Example 235

(1R,2R,4R) and (1S,2S,4S)-2-(4-Chloro-benzyloxy)-4-(2-trifluoromethyl-benzenesulfonyl)-cyclopentanecarboxylic acid (4-cyano-1-methyl-piperidin-4-yl)-amide

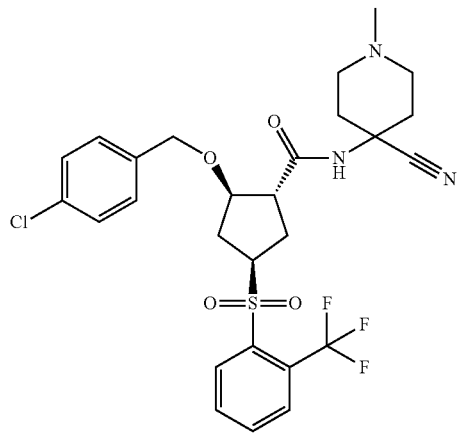

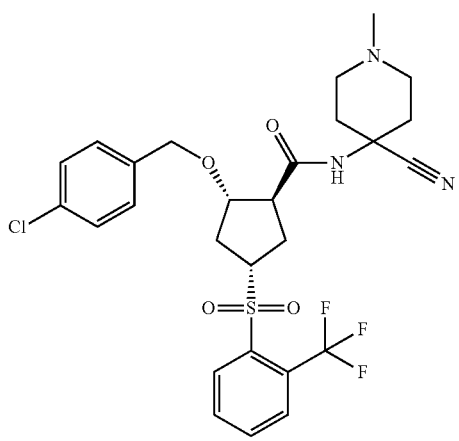

The title compound was prepared in analogy to example 46 using 4-chloro-benzylbromide together with DCM as a solvent instead of methyl iodide in step 4 and 4-amino-4-cyano-1-methylpiperidine (CAS 123194-00-3) instead of 1-amino-1-cyclopropanecarbonitrile hydrochloride in step 11. Light yellow foam. MS (EI): 582.3 (M–H)⁻.

Example 236

(1R,2R,4R) and (1S,2S,4S)-2-Methoxy-4-[4-(1-methyl-1H-pyrazol-4-yl)-2-trifluoromethyl-benzenesulfonyl]-cyclopentanecarboxylic acid (4-cyano-1-methyl-piperidin-4-yl)-amide

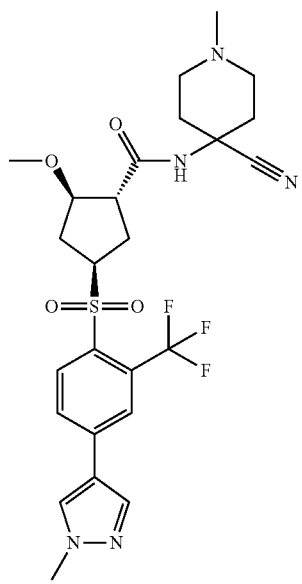

-continued

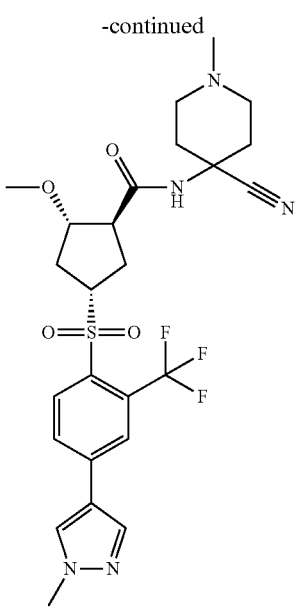

Step 1: (1R,2R,4R) and (1S,2S,4S)-2-Methoxy-4-[4-(1-methyl-1H-pyrazol-4-yl)-2-trifluoromethyl-benzenesulfonyl]-cyclopentanecarboxylic acid methyl ester Argon was bubbled through a mixture of (1R,2R,4R) and (1S,2S,4S)-4-(4-bromo-2-trifluoromethyl-benzenesulfonyl)-2-methoxy-cyclopentanecarboxylic acid methyl ester (250 mg, 0.561 mmol, intermediate in the synthesis of example 58), 1-methyl-4-(4.4.5.5-tetramethyl-1.3.2-dioxaborolan)-1H-pyrazole (145 mg, 0.674 mmol) and Na$_2$CO$_3$ (161 mg, 1.516 mmol) in DMF (4 ml) and water (758 µl) for 15 minutes. Then [1,1'-bis(diphenyl-phosphino)ferrocene]palladium(II) chloride 1:1 complex with DCM (46 mg, 0.0561 mmol) was added and the orange mixture was heated to 80° C. for 3 h. The dark brown reaction mixture was allowed to cool to room temperature and poured onto a mixture of ice and saturated NaHCO$_3$ solution. This mixture was extracted 3 times with EtOAc and the combined extracts were washed 2 times with water and with brine, dried (Na$_2$SO$_4$) and evaporated. The remaining residue was purified by silica column chromatography (DCM/EtOAc 90:10-60:40) to obtain the title compound (232 mg, 93%) as brown foam. MS (EI): 447.3 (M+H)$^+$.

Step 2: Lithium (1R,2R,4R) and (1S,2S,4S)-2-methoxy-4-[4-(1-methyl-1H-pyrazol-4-yl)-2-trifluoromethyl-benzenesulfonyl]-cyclopentanecarboxylate The title compound was prepared in analogy to example 46, step 10 and was obtained as pink solid. MS (EI): 431.1 (M−H)$^−$.

Step 3: (1R,2R,4R) and (1S,2S,4S)-2-Methoxy-4-[4-(1-methyl-1H-pyrazol-4-yl)-2-trifluoromethyl-benzenesulfonyl]-cyclopentanecarboxylic acid (4-cyano-1-methyl-piperidin-4-ye-amide The title compound was prepared in analogy to example 46, step 11 using HATU/N-ethyl-N,N-diisopropyl amine in DMF instead of EDCI/HOBt/N-ethyl-N,N-diisopropyl amine in acetonitrile and 4-amino-4-cyano-1-methylpiperidine (CAS 123194-00-3) instead of 1-amino-1-cyclopropanecarbonitrile hydrochloride and was obtained as light yellow foam. MS (EI): 552.3 (M−H)$^−$.

Example 237

4-Cyano-4-({(1R,2R,4R) and (1S,2S,4S)-2-methoxy-4-[4-(1-methyl-1H-pyrazol-4-yl)-2-trifluoromethyl-benzenesulfonyl]-cyclopentanecarbonyl}-amino)-piperidine-1-carboxylic acid ethyl ester

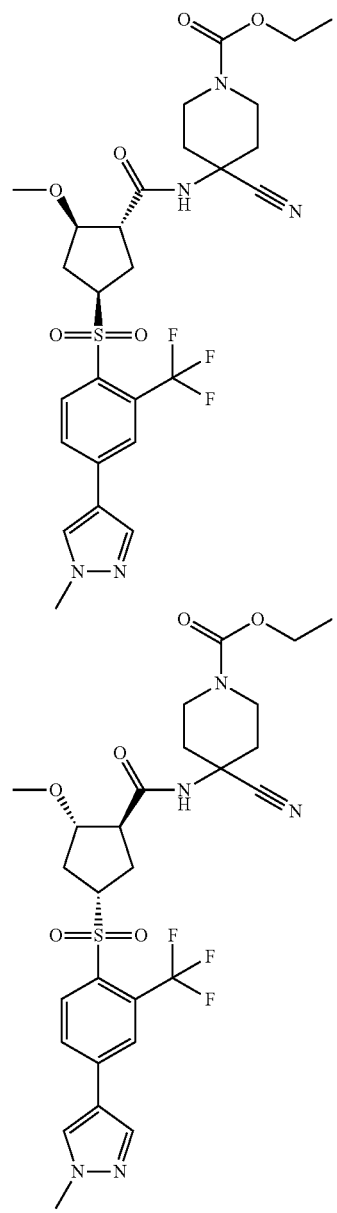

The title compound was prepared in analogy to example 236 using 4-amino-4-cyano-piperidine-1-carboxylic acid ethyl ester (CAS 161315-18-0) instead of 4-amino-4-cyano-1-methylpiperidine in step 3. Light yellow foam. MS (EI): 610.2 (M−H)$^−$.

Example 238

(1R,2R,4R) and (1S,2S,4S)-2-Methoxy-4-[4-(1-methyl-1H-pyrazol-4-yl)-2-trifluoromethyl-benzenesulfonyl]-cyclopentanecarboxylic acid (4-cyano-1-ethyl-piperidin-4-yl)-amide

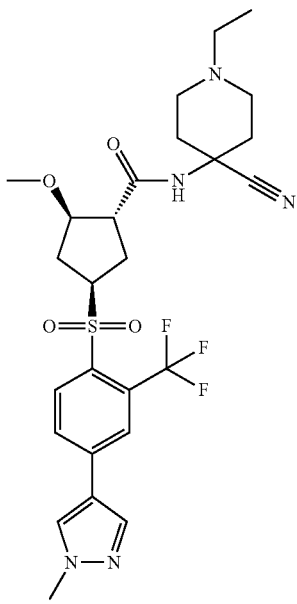

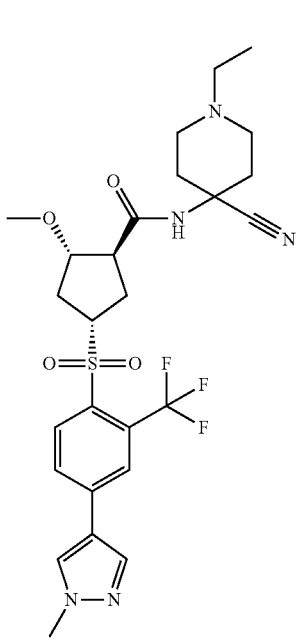

The title compound was prepared in analogy to example 236 using 4-amino-1-ethyl-piperidine-4-carbonitrile (CAS 710350-60-0) instead of 4-amino-4-cyano-1-methylpiperidine in step 3. Light yellow foam. MS (EI): 566.3 (M−H)⁻.

Example 239

(1R,2R,4R) and (1S,2S,4S)-2-(4-Chloro-benzyloxy)-4-(2-trifluoromethyl-benzenesulfonyl)-cyclopentanecarboxylic acid (4-cyano-1-ethyl-piperidin-4-yl)-amide

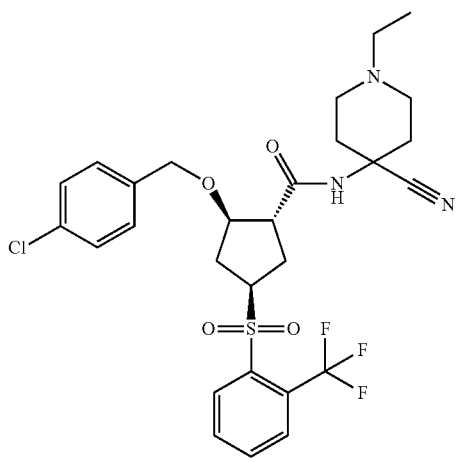

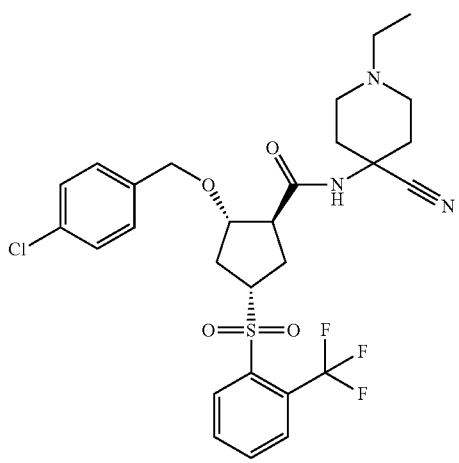

The title compound was prepared in analogy to example 46 using 4-chloro-benzylbromide together with DCM as a solvent instead of methyl iodide in step 4 and 4-amino-1-ethyl-piperidine-4-carbonitrile (CAS 710350-60-0) instead of 1-amino-1-cyclopropanecarbonitrile hydrochloride in step 11. Light brown foam. MS (EI): 596.4 (M−H)⁻.

Example 240
(1R,2R,4R) and (1S,2S,4S)-2-(4-Chloro-benzyloxy)-4-(2,4-dichloro-benzenesulfonyl)-cyclopentanecarboxylic acid (4-cyano-1-ethyl-piperidin-4-yl)-amide

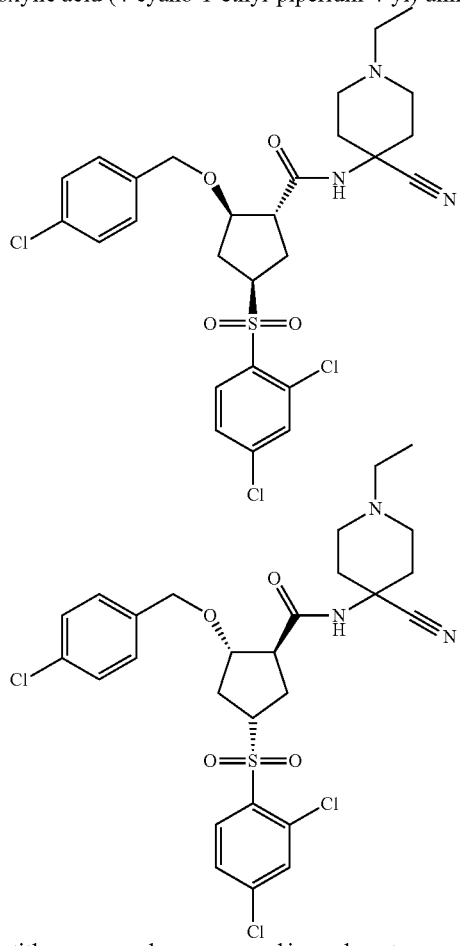

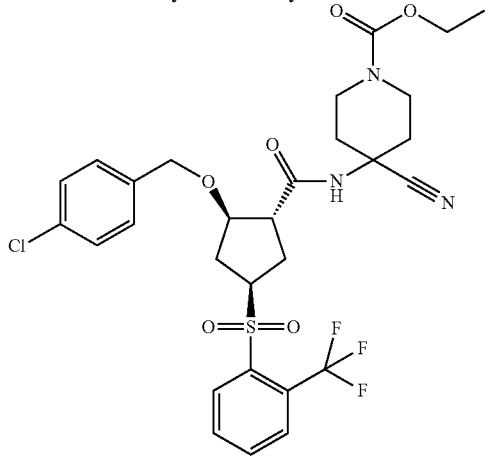

The title compound was prepared in analogy to example 50 using 4-chloro-benzylbromide together with DCM as a solvent instead of methyl iodide in step 4 and 4-amino-1-ethyl-piperidine-4-carbonitrile (CAS 710350-60-0) instead of 1-amino-1-cyclopropanecarbonitrile hydrochloride in step 11. Light brown foam. MS (EI): 596.3 (M–H)⁻.

Example 241
4-{[(1R,2R,4R) and (1S,2S,4S)-2-(4-Chloro-benzyloxy)-4-(2-trifluoromethyl-benzenesulfonyl)-cyclopentanecarbonyl]-amino}-4-cyano-piperidine-1-carboxylic acid ethyl ester

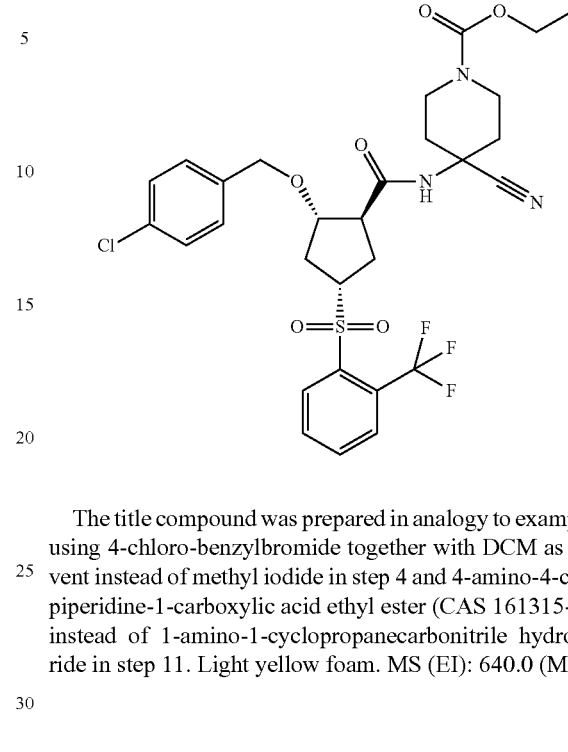

The title compound was prepared in analogy to example 46 using 4-chloro-benzylbromide together with DCM as a solvent instead of methyl iodide in step 4 and 4-amino-4-cyano-piperidine-1-carboxylic acid ethyl ester (CAS 161315-18-0) instead of 1-amino-1-cyclopropanecarbonitrile hydrochloride in step 11. Light yellow foam. MS (EI): 640.0 (M–H)⁻.

Example 242
4-{[(1R,2R,4R) and (1S,2S,4S)-2-(4-Chloro-benzyloxy)-4-(2,4-dichloro-benzenesulfonyl)-cyclopentanecarbonyl]-amino}-4-cyano-piperidine-1-carboxylic acid ethyl ester

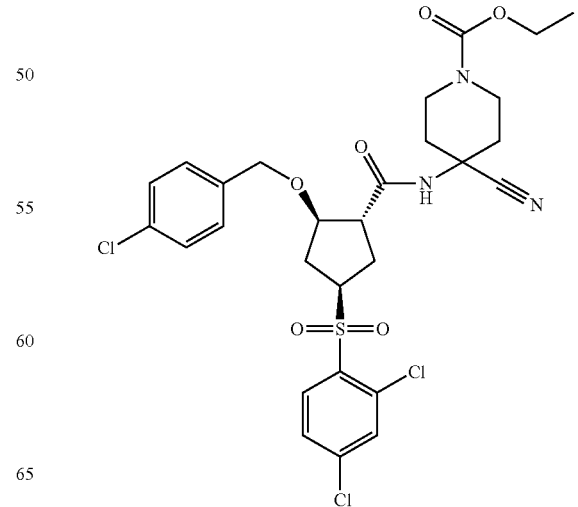

-continued

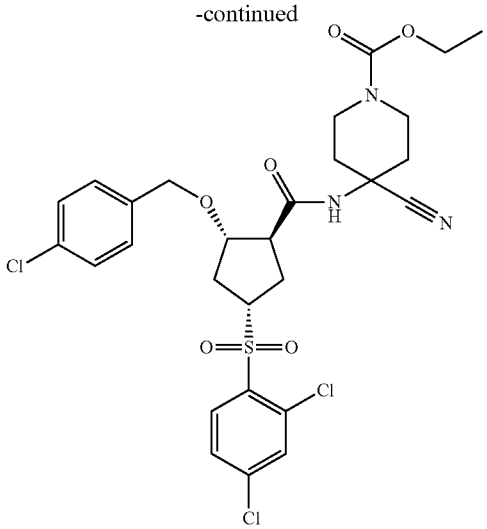

The title compound was prepared in analogy to example 50 using 4-chloro-benzylbromide together with DCM as a solvent instead of methyl iodide in step 4 and 4-amino-4-cyano-piperidine-1-carboxylic acid ethyl ester (CAS 161315-18-0) instead of 1-amino-1-cyclopropanecarbonitrile hydrochloride in step 11. Light brown solid. MS (EI): 640.0 (M–H)⁻.

Example 243

(1R,2R,4R) and (1S,2S,4S)-4-(2-Chloro-benzene-sulfonyl)-2-(4-chloro-phenoxy)-cyclopentanecarboxylic acid (1-cyano-cyclopropyl)-amide

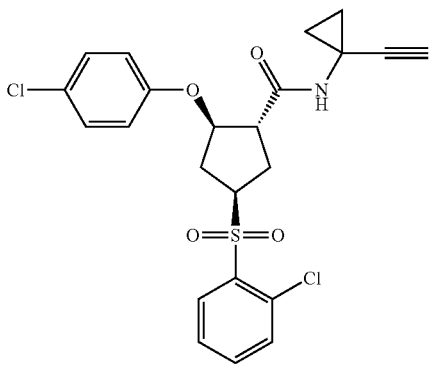

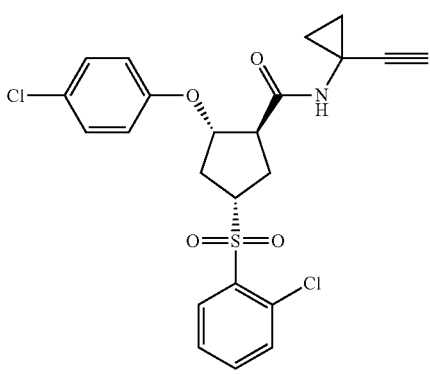

Step 1: (1S,2R,4S) and (1R,2S,4R)-4-(tert-Butyl-diphenyl-silanyloxy)-2-(4-chloro-phenoxy)-cyclopentanol To a solution of tris-(4-chloro-phenyl)-bismuthane (2.1 g, 3.86 mmol) in DCM (25 ml) was added [bis(trifluoroacetoxy)iodo]-benzene (1.71 g, 3.86 mmol) at room temperature under argon and the mixture was stirred for 2.5 h. Then Cu(OAc)₂ (191 mg, 1.053 mmol) and a solution of (1R,2S,4s)-4-{[tert-butyl(diphenyl)silyl]oxy}cyclopentane-1,2-diol (1250 mg, 3.51 mmol, example 112, step 2) in DCM (25 ml) were added and the reaction mixture was stirred at room temperature for 1.5 h. Additional Cu(OAc)₂ (64 mg, 0.351 mmol) was added and stirring was continued for 2 days. Then saturated NaHCO₃ solution was added and the mixture was extracted 2 times with DCM. The combined organic layers were washed with water and brine, dried (Na₂SO₄) and evaporated. The remaining light yellow oil was purified by silica gel chromatography (heptane/EtOAc 95:5-90:10) to obtain the title compound (800 mg, 49%) as light yellow gum. MS (EI): 484.4 (M+NH₄)⁺.

Step 2: (1S,2R,4S) and (1R,2S,4R)-4-(tert-Butyl-diphenyl-silanyloxy)-2-(4-chloro-phenoxy)-cyclopentanecarbonitrile The title compound was prepared in analogy to example 112, step 4 and was obtained as colorless gum. MS (EI): 493.3 (M+NH₄)⁺.

Step 3: (1S,2R,4S) and (1R,2S,4R)-2-(4-Chloro-phenoxy)-4-hydroxy-cyclopentanecarbonitrile The title compound was prepared in analogy to example 46, step 5 and was obtained as light yellow oil. MS (EI): 269.2 (M+OAc)⁻.

Step 4: Methanesulfonic acid (1S,3R,4S) and (1R,3S,4R)-3-(4-chloro-phenoxy)-4-cyano-cyclopentyl ester The title compound was prepared in analogy to example 46, step 6 and was obtained as light yellow gum. MS (EI): 374.0 (M+OAc)⁻.

Step 5: (1S,2R,4R) and (1R,2S,4S)-2-(4-Chloro-phenoxy)-4-(2-chloro-phenylsulfanyl)-cyclopentanecarbonitrile The title compound was prepared in analogy to example 46, step 7 using 2-chloro-thiophenol instead of 2-(trifluoromethyl)-thiophenol and was obtained as light brown gum. MS (EI): 421.8 (M+OAc)⁻.

Step 6: (1S,2R,4R) and (1R,2S,4S)-4-(2-Chloro-benzenesulfonyl)-2-(4-chloro-phenoxy)-cyclopentanecarbonitrile The title compound was prepared in analogy to example 169, step 7 and was obtained as yellow gum. MS (EI): 413.2 (M+NH₄)⁺.

Step 7: (1R,2R,4R) and (1S,2S,4S)-4-(2-Chloro-benzenesulfonyl)-2-(4-chloro-phenoxy)-cyclopentanecarboxylic acid methyl ester The title compound was prepared in analogy to example 46, step 9 and was obtained as colorless gum. MS (EI): 429.0 (M+H)⁺.

Step 8: (1R,2R,4R) and (1S,2S,4S)-4-(2-Chloro-benzenesulfonyl)-2-(4-chloro-phenoxy)-cyclopentanecarboxylic acid (1-cyano-cyclopropyl)-amide To a solution of (1R,2R,4R) and (1S,2S,4S)-4-(2-chloro-benzenesulfonyl)-2-(4-chloro-phenoxy)-cyclopentanecarboxylic acid methyl ester (30 mg, 0.0699 mmol) in DCM (3 ml) was added trimethylaluminium (175 µl, 2M solution in toluene, 0.349 mmol), triethylamine (29.1 µl, 0.210 mmol) and 1-amino-1-cyclopropane-carbonitrile hydrochloride (21 mg, 0.1757 mmol) and the reaction mixture was stirred at 40° C. overnight. The mixture was then cooled to room temperature, diluted with brine and extracted 3 times with DCM. The combined organic layers were washed with water and brine, dried (Na$_2$SO$_4$) and evaporated. The remaining brown semi-solid was purified by silica gel chromatography (DCM/MeOH 100:0-98:2) yielding a yellow solid (5 mg) that was triturated with ether to obtain the title compound (3 mg, 9%) as off-white solid. MS (EI): 477.0 (M+H)$^+$.

Example 244

(1R,2R,4R) and (1S,2S,4S)-2-(2-(4-chlorophenyl)propan-2-yloxy)-4-(2-chlorophenylsulfonyl)-N-(1-cyanocyclopropyl)cyclopentanecarboxamide

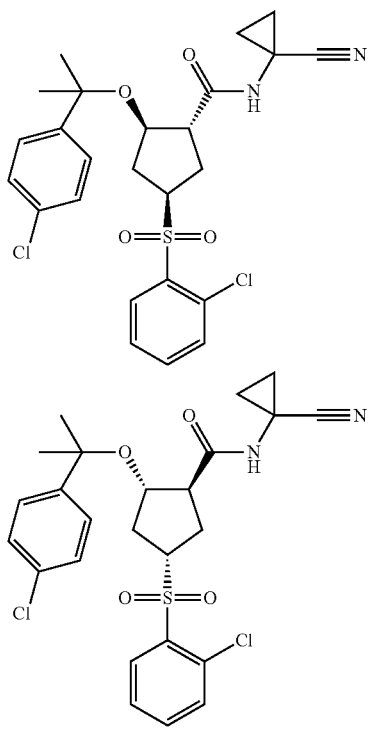

Step 1: 2,2,2-Trichloro-acetimidic acid 1-(4-chloro-phenyl)-1-methyl-ethyl ester To a suspension of sodium hydride (5.63 mg, 0.117 mmol) in ether was added a solution of 2-(4-chloro-phenyl)-propan-2-ol (CAS 1989-25-9) in ether (1.5 ml) at 0° C. The mixture was stirred for 90 minutes, then trichloroacetonitrile (112 µl, 1.11 mmol) was added and stirring was continued for 3 h at 0° C. Then all volatiles were removed and pentane (1 ml) and MeOH (4.74 µl) were added. The suspension was stirred for 1 h. Filtration and concentration of the filtrate yielded the title compound in a mixture with 2-(4-chloro-phenyl)-propan-2-ol which was used in the next reaction step without further purification.

Step 2: (1R,2R,4R) and (1S,2S,4S)-4-(2-Chloro-benzenesulfonyl)-2-[1-(4-chloro-phenyl)-1-methyl-ethoxy]-cyclopentanecarboxylic acid methyl ester (1R,2R,4R) and (1S,2S,4S)-4-(2-Chloro-benzenesulfonyl)-2-hydroxy-cyclopentanecarboxylic acid methyl ester (100 mg, 0.314 mmol, example 48, step 5) and 2,2,2-trichloro-acetimidic acid 1-(4-chloro-phenyl)-1-methyl-ethyl ester (270 mg, 0.514 mmol) were dissolved in a mixture of DCM (1 ml) and cyclohexane (2 ml). Then a solution of trifluoromethanesulfonic acid (0.836 µl, 0.00941 mmol) in DCM (0.1 ml) was added and the reaction mixture was stirred at room temperature for 6 h. Then saturated NaHCO$_3$ solution was added and the mixture was extracted 3 times with ether. The combined organic layers were dried (Na$_2$SO$_4$) and evaporated. The remaining light yellow oil was purified by silica gel chromatography (heptane/EtOAc 4:1-3:1) to obtain the title compound (47 mg, 32%) as white solid. MS (EI): 488.1 (M+NH$_4$)$^+$.

Step 3: Lithium (1R,2R,4R) and (1S,2S,4S)-4-(2-chloro-benzenesulfonyl)-2-[1-(4-chloro-phenyl)-1-methyl-ethoxy]-cyclopentanecarboxylate The title compound was prepared in analogy to example 46, step 10 and was obtained as white solid. MS (EI): 455.2 (M−H)$^-$.

Step 4: (1R,2R,4R) and (1S,2S,4S)-2-(2-(4-chlorophenyl)propan-2-yloxy)-4-(2-chlorophenylsulfonyl)-N-(1-cyanocyclopropyl)cyclopentanecarboxamide The title compound was prepared in analogy to example 46, step 11 using HATU/N-ethyl-N,N-diisopropyl amine in DMF instead of EDCI/HOBt/N-ethyl-N,N-diisopropyl amine in acetonitrile and was obtained as white solid. MS (EI): 519.1 (M−H)$^-$.

Example 245

(1R,2R,4R) and (1S,2S,4S)-4-(2-chlorophenylsulfonyl)-N-(1-cyanocyclopropyl)-2-(2-p-tolylpropan-2-yloxy)cyclopentanecarboxamide

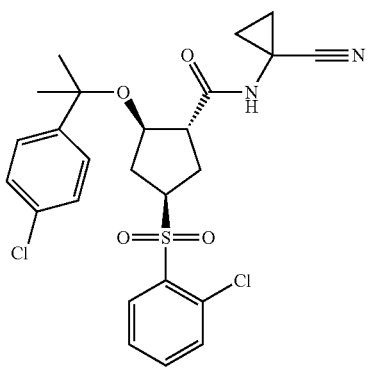

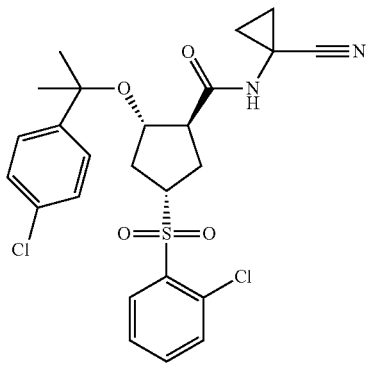

The title compound was prepared in analogy to example 244 using 2-p-tolyl-propan-2-ol instead of 2-(4-chloro-phenyl)-propan-2-ol in step 1. White solid. MS (EI): 499.2 (M−H)⁻.

Example 246

(1S,2S,4S) and (1R,2R,4R)-2-Methoxy-4-[4-(4-methoxymethyl-[1,2,3]triazol-1-yl)-2-trifluoromethyl-benzenesulfonyl]-cyclopentanecarboxylic acid (1-cyano-cyclopropyl)-amide

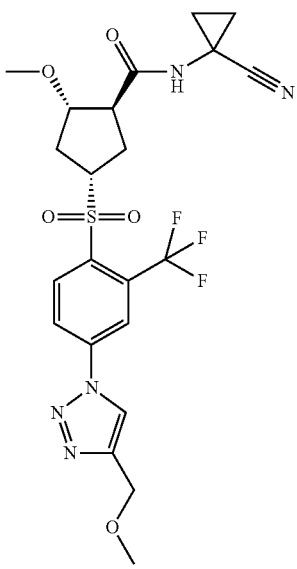

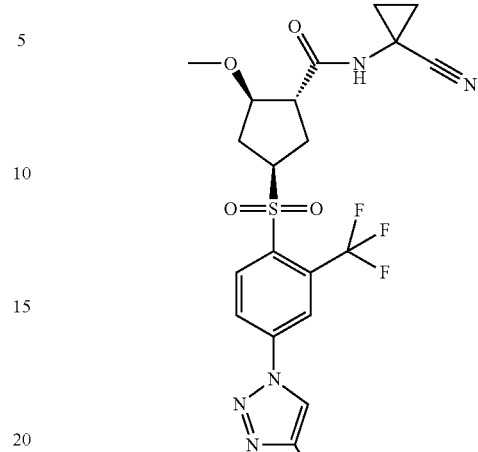

Step 1: (1R,2R,4R) and (1S,2S,4S)-4-(4-Azido-2-trifluoromethyl-benzenesulfonyl)-2-methoxy-cyclopentanecarboxylic acid methyl ester To a solution of (1R,2R,4R) and (1S,2S,4S)-4-(4-bromo-2-trifluoromethyl-benzenesulfonyl)-2-methoxy-cyclopentanecarboxylic acid methyl ester (500 mg, 1.123 mmol, intermediate in the synthesis of example 58) in DMA (5 ml) was added sodium azide (146 mg, 2.246 mmol) and the reaction mixture was heated to 50° C. for 26 h. Then water was added and the mixture was extracted 3 times with EtOAc. The combined organic layers were dried (Na₂SO₄) and evaporated. The remaining brown oil was purified by silica gel chromatography (DCM/EtOAc 95:5) to obtain the title compound (351 mg, 77%) as light brown oil. MS (EI): 466.2 (M+OAc)⁻.

Step 2: (1R,2R,4R) and (1S,2S,4S)-2-Methoxy-4-[4-(4-methoxymethyl-[1,2,3]triazol-1-yl)-2-trifluoromethyl-benzenesulfonyl]-cyclopentanecarboxylic acid methyl ester To a solution of (1R,2R,4R) and (1S,2S,4S)-4-(4-azido-2-trifluoromethyl-benzenesulfonyl)-2-methoxy-cyclopentanecarboxylic acid methyl ester (100 mg, 0.245 mmol) in DCM (5 ml) was added methyl propargyl ether (26 mg, 0.371 mmol) and CuI (20 mg, immobilized on Amberlyst A-21, loading 1.2 mmol CuI/g, prepared according to *Org. Letters* 2006, 8, 1689) and the mixture was placed on a shaker over night. The mixture was then filtered and concentrated and the remaining oil was purified by silica gel chromatography (DCM/MeOH 98:2) to obtain the title compound (62 mg, 53%) as colorless oil. MS (EI): 478.1 (M+H)⁺.

Step 3: Lithium (1R,2R,4R) and (1S,2S,4S)-2-methoxy-4-[4-(4-methoxymethyl-[1,2,3]triazol-1-yl)-2-trifluoromethyl-benzenesulfonyl]-cyclopentanecarboxylate The title compound was prepared in analogy to example 46, step 10 and was obtained as light yellow solid. MS (EI): 462.2 (M−H)⁻.

249

Step 4: (1S,2S,4S) and (1R,2R,4R)-2-Methoxy-4-[4-(4-methoxymethyl-[1,2,3]triazol-1-yl)-2-trifluoromethyl-benzenesulfonyl]-cyclopentanecarboxylic acid (1-cyano-cyclopropyl)-amide The title compound was prepared in analogy to example 46, step 11 using HATU/N-ethyl-N,N-diisopropyl amine in DMF instead of EDCI/HOBt/N-ethyl-N,N-diisopropyl amine in acetonitrile and was obtained as white solid. MS (EI): 526.2 (M−H)⁻.

Example 247

(1R,2R,4R) and (1S,2S,4S)-4-(2-chlorophenylsulfonyl)-N-(1-cyanocyclopropyl)-2-(4-(trifluoromethyl)benzyloxy)cyclopentanecarboxamide

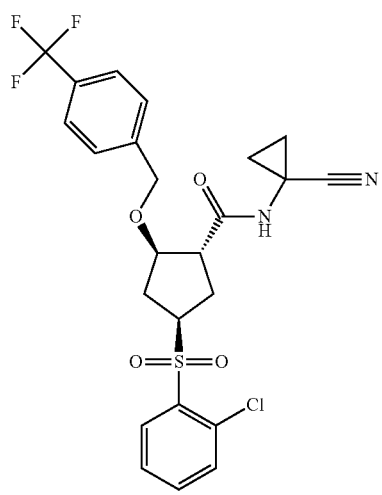

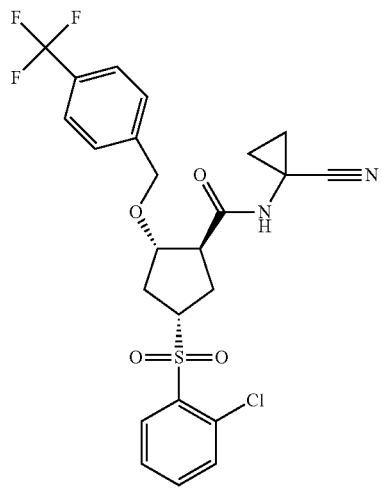

The title compound was prepared in analogy to example 150 using 1-bromomethyl-4-trifluoromethyl-benzene instead of 1-(bromomethyl)-4-methylbenzene. White solid. MS (EI): 527.0 (M+H)⁺.

250

Example 248

(1R,2R,4R) and (1S,2S,4S)-4-(2-Chloro-benzenesulfonyl)-2-(4-chloro-2-methanesulfonyl-benzyloxy)-cyclopentanecarboxylic acid (1-cyano-cyclopropyl)-amide

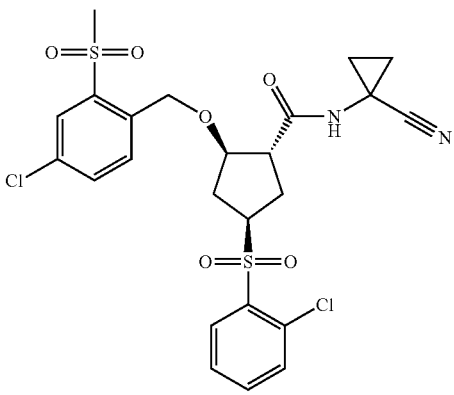

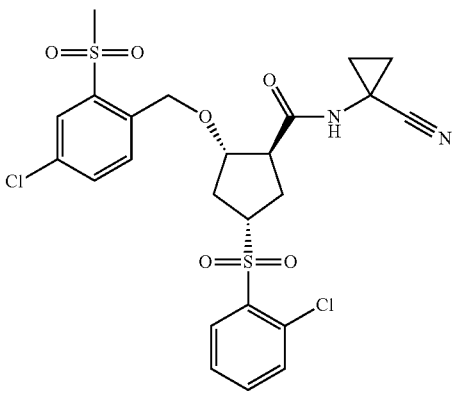

The title compound was prepared in analogy to example 150 using 1-bromomethyl-4-chloro-2-methanesulfonyl-benzene instead of 1-(bromomethyl)-4-methylbenzene. White solid. MS (EI): 571.2 (M+H)⁺.

Example 249

(1R,2R,4R) and (1S,2S,4S)-4-(2-Chloro-benzenesulfonyl)-2-(4-chloro-3-fluoro-benzyloxy)-cyclopentanecarboxylic acid (1-cyano-cyclopropyl)-amide

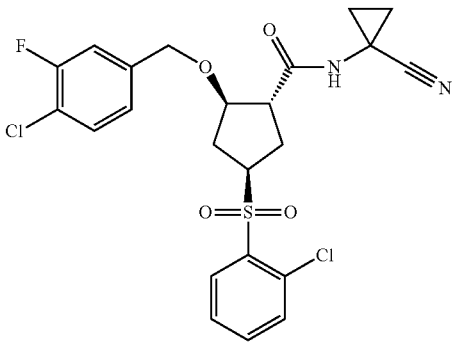

-continued

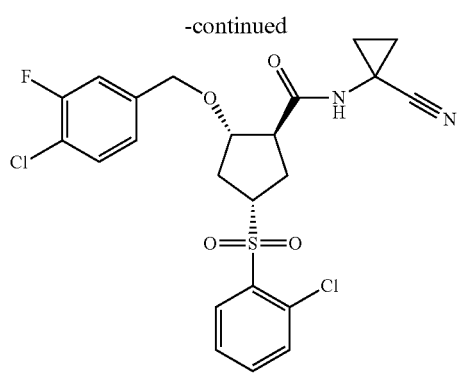

The title compound was prepared in analogy to example 150 using 4-bromomethyl-1-chloro-2-fluoro-benzene instead of 1-(bromomethyl)-4-methylbenzene. Light yellow solid. MS (EI): 511.1 (M+H)+.

Example 250

(1R,2R,4R) and (1S,2S,4S)-4-(2-Chloro-benzene-sulfonyl)-2-(3,4-dichloro-benzyloxy)-cyclopentan-ecarboxylic acid (1-cyano-cyclopropyl)-amide

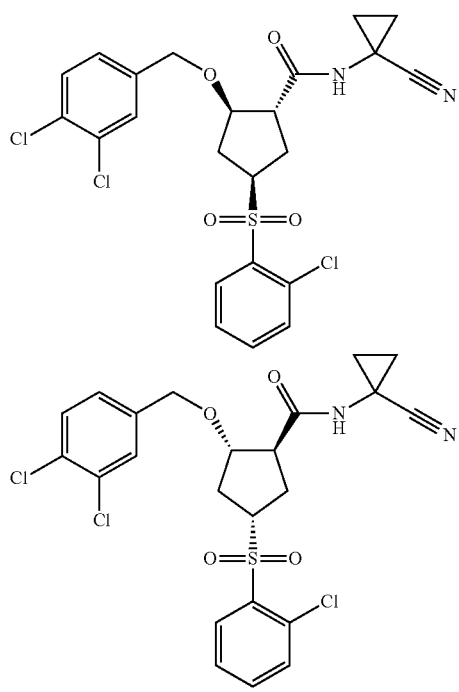

The title compound can be prepared in analogy to example 150 using 4-bromomethyl-1,2-dichloro-benzene instead of 1-(bromomethyl)-4-methylbenzene. Off-white solid. MS (EI): 527.2 (M+H)+.

Example 251

(1R,2R,4R) and (1S,2S,4S)-4-(2-Chloro-benzene-sulfonyl)-2-(4-chloro-2,6-difluoro-benzyloxy)-cyclo-pentanecarboxylic acid (1-cyano-cyclopropyl)-amide

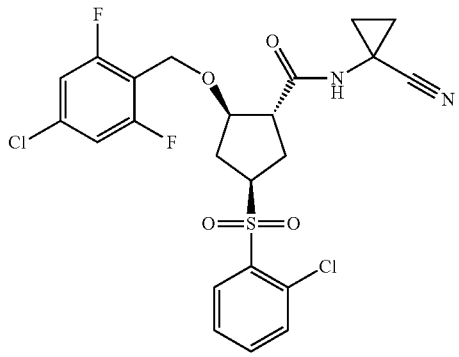

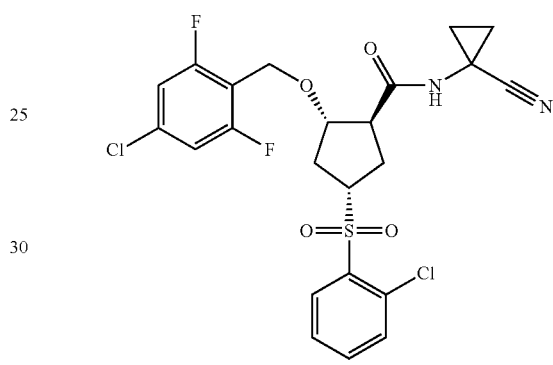

The title compound can be prepared in analogy to example 150 using 2-(bromomethyl)-5-chloro-1,3-difluorobenzene instead of 1-(bromomethyl)-4-methylbenzene. Off-white solid. MS (EI): 529.0 (M+H)+.

Example 252

(1R,2R,4R) and (1S,2S,4S)-4-(2-Chloro-benzene-sulfonyl)-2-(4-chloro-2-fluoro-benzyloxy)-cyclopen-tanecarboxylic acid (1-cyano-cyclopropyl)-amide

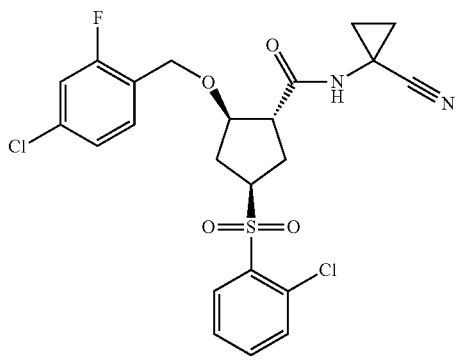

-continued

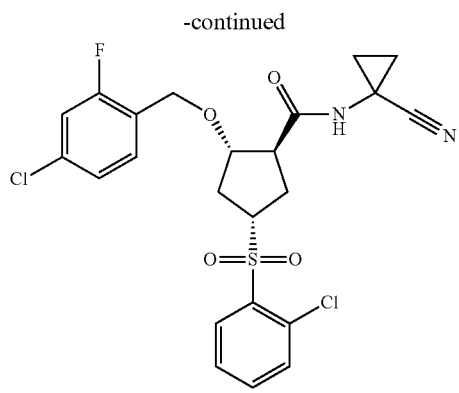

The title compound can be prepared in analogy to example 150 using 1-(bromomethyl)-4-chloro-2-fluorobenzene instead of 1-(bromomethyl)-4-methylbenzene. Off-white solid. MS (EI): 511.1 (M+H)+.

Example 253

(1S,2S,4S) and (1R,2R,4R)-4-{4-[4-(2-Hydroxy-ethyl)-[1,2,3]triazol-1-yl]-2-trifluoromethyl-benzenesulfonyl}-2-methoxy-cyclopentanecarboxylic acid (1-cyano-cyclopropyl)-amide

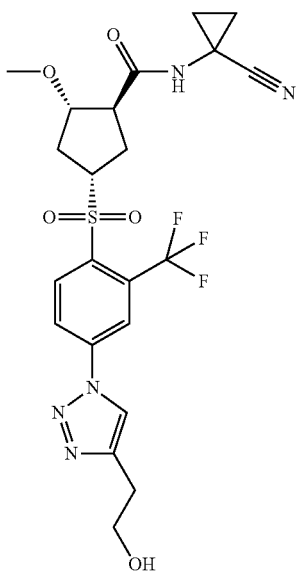

-continued

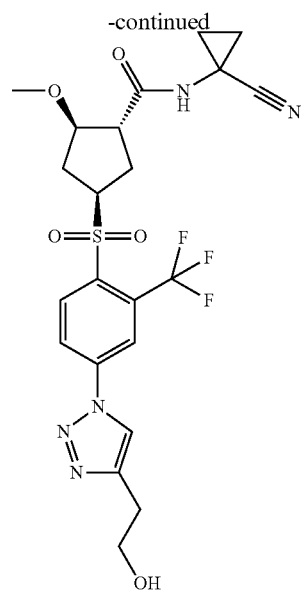

The title compound can be prepared in analogy to example 246 using 3-butyn-1-ol instead of methyl propargyl ether. Light yellow solid. MS (EI): 528.2 (M+H)+.

Example 254

Cathepsin Enzyme Inhibition Assay

Enzyme activity is measured by observing the increase in fluorescence intensity caused by cleavage of a peptide substrate containing a fluorophore whose emission is quenched in the intact peptide.

Assay buffer: 100 mM potassium phosphate pH 6.5, EDTA-Na 5 mM, Triton X-100 0.001%, DTT 5 mM.

Enzymes (all at 1 nM): human and mouse Cathepsin S, Cat K, Cat B, Cat L.

Substrate (20 µM): Z-Val-Val-Arg-AMC, except for Cat K which uses Z-Leu-Arg-AMC (both from Bachem).

Z=Benzyloxycarbonyl.

AMC=7-Amino-4-Methyl-Coumarin.

DTT=dithiothreitol.

Final volume: 100 µL.

Excitation 360 nm, Emission 465 nm.

Enzyme is added to the substance dilutions in 96-well microtitre plates and the reaction is started with substrate. Fluorescence emission is measured over 20 minutes, during which time a linear increase is observed in the absence of inhibitor. $IC_{50}$ are calculated by standard methods. Inhibition of human Cat S, mouse Cat S, human Cat K, mouse Cat K, human Cat B, mouse Cat B, human Cat L and mouse Cat L have been measured separately. The results obtained for human Cat S are expressed in the following table.

| Example | $IC_{50}$ (µM) | Example | $IC_{50}$ (µM) | Example | $IC_{50}$ (µM) |
|---|---|---|---|---|---|
| 1 | 0.0006 | 86 | 0.0005 | 171 | 0.0012 |
| 2 | 0.0007 | 87 | 0.0002 | 172 | 0.000435 |

-continued

| Example | IC$_{50}$ (µM) | Example | IC$_{50}$ (µM) | Example | IC$_{50}$ (µM) |
|---|---|---|---|---|---|
| 3 | 0.0005 | 88 | 0.0091 | 173 | 0.000217 |
| 4 | 0.0006 | 89 | 0.0074 | 174 | 0.00017 |
| 5 | 0.0006 | 90 | 0.0004 | 175 | 0.00048 |
| 6 | 0.0008 | 91 | 0.0005 | 176 | 0.001467 |
| 7 | 0.0007 | 92 | 0.385 | 177 | 0.000923 |
| 8 | 0.0004 | 93 | 0.565 | 178 | 0.000885 |
| 9 | 0.0009 | 94 | 0.29 | 179 | 0.0003 |
| 10 | 0.425 | 95 | 0.14 | 180 | 0.15745 |
| 11 | 0.003 | 96 | 0.213 | 181 | 0.001325 |
| 12 | 0.0008 | 97 | 0.157 | 182 | 0.0038 |
| 13 | 0.001 | 98 | 0.16 | 183 | 0.0002 |
| 14 | 0.0109 | 99 | 0.5 | 184 | 0.00016 |
| 15 | 0.0074 | 100 | 0.17 | 185 | 0.000725 |
| 16 | 0.0004 | 101 | 0.61 | 186 | 0.00215 |
| 17 | 0.0011 | 102 | 0.27 | 187 | 0.00107 |
| 18 | 0.002 | 103 | 0.0207 | 188 | 0.000985 |
| 19 | 0.0005 | 104 | 1.2033 | 189 | 0.000675 |
| 20 | 0.0043 | 105 | 0.0223 | 190 | 0.00084 |
| 21 | 0.0049 | 106 | 1.01 | 191 | 0.000575 |
| 22 | 0.0055 | 107 | 0.0202 | 192 | 0.000155 |
| 23 | 0.0015 | 108 | 0.0212 | 193 | 0.001667 |
| 24 | 0.0096 | 109 | 0.0004 | 194 | 0.000713 |
| 25 | 0.0026 | 110 | 0.0006 | 195 | 0.000917 |
| 26 | 0.0015 | 111 | 0.0004 | 196 | 0.000215 |
| 27 | 0.0062 | 112 | 0.0006 | 197 | 0.00014 |
| 28 | 0.0255 | 113 | 0.0011 | 198 | 0.000135 |
| 29 | 0.0725 | 114 | 0.0003 | 199 | 0.000135 |
| 30 | 0.001 | 115 | 0.0002 | 200 | 0.000445 |
| 31 | 0.0002 | 116 | 0.0003 | 201 | 0.00034 |
| 32 | 0.0004 | 117 | 0.0011 | 202 | 0.00038 |
| 33 | 0.0016 | 118 | 0.003 | 203 | 0.000195 |
| 34 | 0.0025 | 119 | 0.0061 | 204 | 0.000135 |
| 35 | 0.004 | 120 | 0.0002 | 205 | 0.000325 |
| 36 | 0.0004 | 121 | 0.0002 | 206 | 0.0014 |
| 37 | 0.0009 | 122 | 0.0002 | 207 | 0.000895 |
| 38 | 0.5333 | 123 | 0.0001 | 208 | 0.00145 |
| 39 | 0.445 | 124 | 0.0002 | 209 | 0.00054 |
| 40 | 0.23 | 125 | 0.0003 | 210 | 0.00021 |
| 41 | 0.0001 | 126 | 0.0006 | 211 | 0.000255 |
| 42 | 0.0255 | 127 | 0.0011 | 212 | 0.000215 |
| 43 | 0.345 | 128 | 0.0007 | 213 | 0.00016 |
| 44 | 1.295 | 129 | 0.0006 | 214 | 0.00285 |
| 45 | 0.0001 | 130 | 0.0004 | 215 | 0.0066 |
| 46 | 0.0058 | 131 | 0.0012 | 216 | 0.0016 |
| 47 | 0.0078 | 132 | 0.0012 | 217 | 0.00103 |
| 48 | 0.12 | 133 | 0.0005 | 218 | 0.00092 |
| 49 | 0.0823 | 134 | 0.0014 | 219 | 0.006767 |
| 50 | 0.025 | 135 | 0.0024 | 220 | 0.0036 |
| 51 | 0.02 | 136 | 0.0013 | 221 | 0.00835 |
| 52 | 11.6567 | 137 | 0.0048 | 222 | 0.0058 |
| 53 | 6.6867 | 138 | 0.0004 | 223 | 0.00031 |
| 54 | 0.0021 | 139 | 0.0003 | 224 | 0.032 |
| 55 | 0.0021 | 140 | 0.0002 | 225 | 0.00038 |
| 56 | 0.0248 | 141 | 0.0002 | 226 | 0.05 |
| 57 | 0.0218 | 142 | 0.0002 | 227 | 0.000555 |
| 58 | 0.0062 | 143 | 0.000523 | 228 | 0.091 |
| 59 | 0.004 | 144 | 0.145 | 229 | 7.00E−06 |
| 60 | 0.0265 | 145 | 0.00125 | 230 | 2.75E−05 |
| 61 | 0.0003 | 146 | 0.00225 | 231 | 0.00125 |
| 62 | 0.0014 | 147 | 0.000227 | 232 | 0.00185 |
| 63 | 0.0013 | 148 | 0.515 | 233 | 0.0105 |
| 64 | 0.012 | 149 | 0.001933 | 234 | 0.019 |
| 65 | 0.008 | 150 | 0.004155 | 235 | 0.0073 |
| 66 | 0.0007 | 151 | 0.002995 | 236 | 0.0018 |
| 67 | 0.0006 | 152 | 0.0042 | 237 | 0.0022 |
| 68 | 0.0022 | 153 | 0.0255 | 238 | 0.00235 |
| 69 | 0.81 | 154 | 0.00755 | 239 | 0.00625 |
| 70 | 0.0034 | 155 | 0.1072 | 240 | 0.0255 |
| 71 | 3.0833 | 156 | 0.0315 | 241 | 0.012 |
| 72 | 0.0012 | 157 | 0.0615 | 242 | 0.092 |
| 73 | 0.001 | 158 | 0.00063 | 243 | 0.00145 |
| 74 | 0.0007 | 159 | 0.000385 | 244 | 0.01465 |
| 75 | 0.0005 | 160 | 0.000165 | 245 | 0.01145 |
| 76 | 0.0006 | 161 | 0.0015 | 246 | 0.00125 |
| 77 | 0.0006 | 162 | 0.014667 | 247 | 0.005985 |
| 78 | 0.0003 | 163 | 0.011133 | 248 | 0.0035 |

-continued

| Example | IC$_{50}$ (µM) | Example | IC$_{50}$ (µM) | Example | IC$_{50}$ (µM) |
|---|---|---|---|---|---|
| 79 | 0.6833 | 164 | 0.003 | 249 | 0.00695 |
| 80 | 1.03 | 165 | 0.006833 | 250 | 0.0625 |
| 81 | 0.0006 | 166 | 0.0006 | 251 | 0.00611 |
| 82 | 0.0006 | 167 | 0.001467 | 252 | 0.00499 |
| 83 | 0.0002 | 168 | 0.001267 | 253 | 0.000675 |
| 84 | 0.0007 | 169 | 0.001233 | | |
| 85 | 0.0005 | 170 | 0.000587 | | |

In the foregoing assay, the compounds according to the invention have an IC$_{50}$ which is between 0.00001 and 100 µM, preferably between 0.00001 and 50 µM, more preferably between 0.00001 and 20 µM.

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:
1. A compound of formula (I)

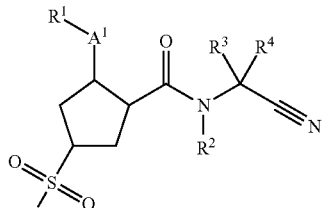

(I)

wherein $A^1$ is selected from the group consisting of oxygen, carbonyl, —CH$_2$O—, —CH$_2$—, and —CONR$^{11}$— or is absent;

$R^1$ is selected from the group consisting of hydrogen, alkyl, haloalkyl, cycloalkyl, phenyl, halophenyl, alkoxybenzyl, carboxy, morpholinyl, alkylmorpholinyl, dioxothiomorpholinyl, 2-oxo-6-aza-spiro[3.3]heptanyl, piperidinyl, alkylpiperidinyl, hydroxypiperidinyl, halophenylpiperidinyl, piperazinyl, alkylpiperazinyl, azetidinyl, haloazetidinyl, hydroxyazetidinyl, alkoxyazetidinyl, 8-oxo-3-aza-bicyclo[3.2.1]octanyl, hydroxypiridazinyl, halopyrrolidinyl, formyl, pyridinyl, halopyridinyl, tetrahydropyranyl and thiopyranyl;

$R^2$ is hydrogen;

$R^3$ and $R^4$ are each independently selected from the group consisting of hydrogen, alkyl and phenyl;

or $R^3$ and $R^4$ together with the carbon atom to which they are attached form cycloalkyl, alkylpiperidinyl or alkoxycarbonylpiperidinyl;

or $R^2$ and $R^3$ together with the nitrogen atom and carbon atom to which they are attached form pyrrolidinyl;

$R^5$ is selected from the group consisting of alkyl, cycloalkyl, cycloalkylalkyl, phenyl, substituted phenyl, benzyl, naphtyl, alkylpyridazinyl, pyridinyl, and halopyridinyl, wherein substituted phenyl is phenyl substituted with one or two substituents independently selected from the group consisting of alkyl, alkoxy, alkoxyalkoxy, halogen, haloalkyl, haloalkoxy, phenyl, halophenyl, halophenyloxy, alkylsulfonylphenyl, aminosulfonylphenyl, pyridinyl, alkylpyridinyl, halopyridinyl, alkoxypyridinyl, haloalkylpyridinyl, alkylsulfonylpyridinyl, alkylthiazolyl, piperidinyl, halopiperidinyl, hydroxypiperidinyl, 1H-pyrazolyl, alkyl-1H-pyrazolyl, alkyl-2H-pyrazolyl, hydroxyalkyl-1H-pyrazolyl, alkoxyalkyl-1H-pyrazolyl, alkoxycarbonylpyrazolyl, carboxyalkylpyrazolyl, aminocarbonylalkyl-1H-pyrazolyl, alkylaminocarbonylalkylpyrazolyl, oxetanylalkyl-1H-pyrazolyl, pyrimidinyl, alkylthiophenyl, pyridazinyl, alkyl-6-oxo-6H-pyridazinyl, alkylisoxazolyl, cycloalkylpiperazinyl, pyrazinyl, halopyrazinyl, haloazetidinyl, 2-oxo-6-aza-spiro[3.3]heptanyl, halopyrrolidinyl, alkylpiperazinyl, cycloalkylpiperazinyl, haloalkylpiperazinyl, carbonylpiperazinyl, alkylcarbonylpiperazinyl, oxetanyloxy and morpholinyl; and $R^{11}$ is hydrogen or alkyl;

or a pharmaceutically acceptable salt thereof.

2. A compound according to claim 1 wherein $A^1$ is selected from the group consisting of oxygen, carbonyl, —CH$_2$O—, and —CONR$^{11}$— or is absent;

$R^1$ is selected from the group consisting of hydrogen, alkyl, phenyl, halophenyl, carboxy, morpholinyl, alkylmorpholinyl, dioxothiomorpholinyl, 2-oxo-6-aza-spiro[3.3] heptanyl, piperidinyl, alkylpiperidinyl, hydroxypiperidinyl, piperazinyl, alkylpiperazinyl, azetidinyl, haloazetidinyl, hydroxyazetidinyl, alkoxyazetidinyl, 8-oxo-3-aza-bicyclo[3.2.1]octanyl, hydroxypiridazinyl and halopyrrolidinyl;

$R^2$ is hydrogen;

$R^3$ and $R^4$ are each independently selected from the group consisting of hydrogen, alkyl and phenyl;

or $R^3$ and $R^4$ together with the carbon atom to which they are attached form cycloalkyl or alkylpiperidinyl;

or $R^2$ and $R^3$ together with the nitrogen atom and carbon atom to which they are attached form pyrrolidinyl; and $R^5$ is selected from the group consisting of alkyl, cycloalkyl, cycloalkylalkyl, phenyl, substituted phenyl, benzyl and naphtyl, wherein substituted phenyl is phenyl substituted with one or two substituents independently selected from the group consisting of alkyl, alkoxy, halogen, haloalkyl, haloalkoxy, halophenyl, halophenyloxy, alkylsulfonylphenyl, aminosulfonylphenyl, pyridinyl, alkylpyridinyl, halopyridinyl, alkoxypyridinyl, haloalkylpyridinyl, alkylsulfonylpyridinyl, alkylthiazolyl, piperidinyl, 1H-pyrazolyl, alkyl-1H-pyrazolyl, alkyl-2H-pyrayzolyl, pyrimidinyl, alkylthiophenyl, pyridazinyl, alkyl-6-oxo-6H-piridazinyl, alkylisoxazolyl, cycloalkylpiperazinyl, pyrazinyl, halopyrazinyl, haloazetidinyl, 2-oxo-6-aza-spiro[3.3] heptanyl, halopyrrolidinyl, alkylpiperazinyl, cycloalkylpiperazinyl, carbonylpiperazinyl and oxetanyloxy.

3. A compound according to claim 1, wherein $A^1$ is selected from the group consisting of oxygen, carbonyl and —CH$_2$O—.

4. A compound according to claim 1, wherein $A^1$ is oxygen.

5. A compound according to claim 1, wherein $R^1$ is alkyl, halophenyl, morpholinyl or haloazetidinyl.

6. A compound according to claim 1, wherein $R^1$ is methyl, ethyl, chlorophenyl or difluoroazetidinyl.

7. A compound according to claim 1, wherein $R^2$ is hydrogen.

8. A compound according to claim 1, wherein $R^3$ and $R^4$ together with the carbon atom to which they are attached form cycloalkyl or alkylpiperidinyl.

9. A compound according to claim 1, wherein $R^3$ and $R^4$ together with the carbon atom to which they are attached form cyclopropyl or methylpiperidinyl.

10. A compound according to claim 1, wherein $R^3$ and $R^4$ together with the carbon atom to which they are attached form cyclopropyl.

11. A compound according to claim 1, wherein $R^5$ is phenyl substituted with one or two substituents independently selected from the group consisting of alkyl, halogen, haloalkyl, haloalkoxy, alkylpyridinyl, haloalkylpyridinyl, alkyl-1H-pyrazolyl and pyridazinyl.

12. A compound according to claim 1, wherein $R^5$ is phenyl substituted with one or two substituents independently selected from the group consisting of methyl, chloro, trifluoromethyl, trifluoroethoxy, methylpyridinyl, trifluoromethylpyridinyl, methyl-1H-pyrazolyl and pyridazinyl.

13. A compound according to claim 1, wherein $R^{11}$ is selected from the group consisting of methyl, ethyl and tert-butyl.

14. A compound according to claim 1 selected from the group consisting of:
- (1R,2R,4R)-4-Benzenesulfonyl-2-(morpholine-4-carbonyl)-cyclopentanecarboxylic acid cyanomethyl-amide;
- (1R,2R,4R)-4-Benzenesulfonyl-2-(morpholine-4-carbonyl)-cyclopentanecarboxylic acid (1-cyano-cyclopropyl)-amide;
- (1R,2R,4R)-4-(2-Chloro-benzenesulfonyl)-2-(morpholine-4-carbonyl)-cyclopentanecarboxylic acid cyanomethyl-amide;
- (1R,2R,4R)-2-(Morpholine-4-carbonyl)-4-(toluene-4-sulfonyl)-cyclopentanecarboxylic acid cyanomethyl-amide;
- (1R,2R,4R)-2-(Morpholine-4-carbonyl)-4-(toluene-3-sulfonyl)-cyclopentanecarboxylic acid cyanomethyl-amide;
- (1R,2R,4R)-4-(2,4-Difluoro-benzenesulfonyl)-2-(morpholine-4-carbonyl)-cyclopentanecarboxylic acid cyanomethyl-amide;
- (1R,2R,4R)-4-(3-Chloro-4-fluoro-benzenesulfonyl)-2-(morpholine-4-carbonyl)-cyclopentanecarboxylic acid cyanomethyl-amide;
- (1R,2R,4R)-4-(4-Chloro-2-methyl-benzenesulfonyl)-2-(morpholine-4-carbonyl)-cyclopentanecarboxylic acid cyanomethyl-amide;

(1R,2R,4R)-4-(2-Chloro-benzenesulfonyl)-2-(morpholine-4-carbonyl)-cyclopentanecarboxylic acid (1-cyano-cyclopropyl)-amide;

(1R,2R,4R)-4-Benzenesulfonyl-2-(1-cyano-cyclopropyl-carbamoyl)-cyclopentanecarboxylic acid;

(1R,2R,4R)-4-Benzenesulfonyl-2-(2-oxa-6-aza-spiro[3.3]heptane-6-carbonyl)-cyclopentanecarboxylic acid (1-cyano-cyclopropyl)-amide;

(1R,2R,4R)-4-Benzenesulfonyl-2-(piperidine-1-carbonyl)-cyclopentanecarboxylic acid (1-cyano-cyclopropyl)-amide;

(1R,2R,4R)-4-Benzenesulfonyl-2-(4-hydroxy-piperidine-1-carbonyl)-cyclopentanecarboxylic acid (1-cyano-cyclopropyl)-amide;

(1R,2R,4R)-4-Benzenesulfonyl-2-(piperazine-1-carbonyl)-cyclopentanecarboxylic acid (1-cyano-cyclopropyl)-amide;

(1R,2R,4R)-4-Benzenesulfonyl-2-(3-hydroxy-azetidine-1-carbonyl)-cyclopentanecarboxylic acid (1-cyano-cyclopropyl)-amide;

(1R,2R,4R)-4-Benzenesulfonyl-2-((2S,6R)-2,6-dimethyl-morpholine-4-carbonyl)-cyclopentanecarboxylic acid (1-cyano-cyclopropyl)-amide;

(1R,2R,4R)-4-Benzenesulfonyl-2-((1R,5S)-8-oxa-3-aza-bicyclo [3.2.1]octane-3-carbonyl)-cyclopentanecarboxylic acid (1-cyano-cyclopropyl)-amide;

(1R,2R,4R)-4-Benzenesulfonyl-2-((1R,5S)-3-oxa-8-aza-bicyclo[3.2.1]octane-8-carbonyl)-cyclopentanecarboxylic acid (1-cyano-cyclopropyl)-amide;

(1R,2R,4R)-4-Benzenesulfonyl-2-(4-methyl-piperidine-1-carbonyl)-cyclopentanecarboxylic acid (1-cyano-cyclopropyl)-amide;

(1R,2R,4R)-4-Benzenesulfonyl-2-(1,1-dioxo-1-thiomorpholine-4-carbonyl)-cyclopentanecarboxylic acid (1-cyano-cyclopropyl)-amide;

(1R,2R,4R)-4-Benzenesulfonyl-2-(3-ethoxy-azetidine-1-carbonyl)-cyclopentanecarboxylic acid (1-cyano-cyclopropyl)-amide;

(1R,2R,4R)-4-Benzenesulfonyl-2-(3-methoxy-azetidine-1-carbonyl)-cyclopentanecarboxylic acid (1-cyano-cyclopropyl)-amide;

(1R,2R,4R)-4-Benzenesulfonyl-2-(pyrrolidine-1-carbonyl)-cyclopentanecarboxylic acid (1-cyano-cyclopropyl)-amide;

(1R,2R,4R)-2-(Azetidine-1-carbonyl)-4-benzenesulfonyl-cyclopentanecarboxylic acid (1-cyano-cyclopropyl)-amide;

(1R,2R,4R)-4-Benzenesulfonyl-cyclopentane-1,2-dicarboxylic acid 1-[(1-cyano-cyclopropyl)-amide]2-diethylamide;

(1R,2R,4R)-4-Benzenesulfonyl-2-(4-methyl-piperazine-1-carbonyl)-cyclopentanecarboxylic acid (1-cyano-cyclopropyl)-amide;

(1R,2R,4R)-4-Benzenesulfonyl-cyclopentane-1,2-dicarboxylic acid 1-[(1-cyano-cyclopropyl)-amide]2-dimethylamide;

(1R,2R,4S)-4-Benzenesulfonyl-cyclopentane-1,2-dicarboxylic acid 1-tert-butylamide 2-[(1-cyano-cyclopropyl)-amide];

(1R,2R,4S)-4-Benzenesulfonyl-cyclopentane-1,2-dicarboxylic acid 1-[(1-cyano-cyclopropyl)-amide]2-methylamide;

(1R,2R,4R)-4-[4-(5-Fluoro-pyridin-2-yl)-2-trifluoromethyl-benzenesulfonyl]-2-methoxy-cyclopentanecarboxylic acid (1-cyano-cyclopropyl)-amide;

(1S,2S,4S)-4-[4-(5-Fluoro-pyridin-2-yl)-2-trifluoromethyl-benzenesulfonyl]-2-methoxy-cyclopentanecarboxylic acid (1-cyano-cyclopropyl)-amide;

(1R,2R,4R)-4-(4-Chloro-2-methyl-benzenesulfonyl)-2-(morpholine-4-carbonyl)-cyclopentanecarboxylic acid (cyano-phenyl-methyl)-amide;

(1R,2R,4R)-4-(4-Chloro-2-methyl-benzenesulfonyl)-2-((2S,6R)-2,6-dimethyl-morpholine-4-carbonyl)-cyclopentanecarboxylic acid cyanomethyl-amide;

(1R,2R,4R)-4-(4-Chloro-2-methyl-benzenesulfonyl)-2-(4-methyl-piperazine-1-carbonyl)-cyclopentanecarboxylic acid cyanomethyl-amide;

(1R,2R,4R)-4-Benzenesulfonyl-2-(morpholine-4-carbonyl)-cyclopentanecarboxylic acid (cyano-dimethyl-methyl)-amide;

(1R,2R,4R)-4-Benzenesulfonyl-2-(morpholine-4-carbonyl)-cyclopentanecarboxylic acid (1-cyano-cyclobutyl)-amide;

(1R,2R,4R)-2-(Morpholine-4-carbonyl)-4-(naphthalene-1-sulfonyl)-cyclopentanecarboxylic acid cyanomethyl-amide;

(1R,2R,4R)-2-(Morpholine-4-carbonyl)-4-(2-trifluoromethyl-benzenesulfonyl)-cyclopentanecarboxylic acid cyanomethyl-amide;

(1R,2R,4R)-2-(Morpholine-4-carbonyl)-4-phenylmethanesulfonyl-cyclopentanecarboxylic acid cyanomethyl-amide;

(1R,2R,4R)-4-(2-Methyl-propane-1-sulfonyl)-2-(morpholine-4-carbonyl)-cyclopentanecarboxylic acid cyanomethyl-amide;

(1R,2R,4R)-4-Cyclopropylmethanesulfonyl-2-(morpholine-4-carbonyl)-cyclopentanecarboxylic acid cyanomethyl-amide;

(1R,2R,4R)-2-Methoxy-4-(4-pyridin-2-yl-2-trifluoromethyl-benzenesulfonyl)-cyclopentanecarboxylic acid (1-cyano-cyclopropyl)-amide;

(1S,2S,4S)-2-Methoxy-4-(4-pyridin-2-yl-2-trifluoromethyl-benzenesulfonyl)-cyclopentanecarboxylic acid (1-cyano-cyclopropyl)-amide;

(1R,2R,4S)-4-Benzenesulfonyl-cyclopentane-1,2-dicarboxylic acid 1-[(1-cyano-cyclopropyl)-amide]2-[(4-fluoro-phenyl)-amide];

3-(2-Chloro-benzenesulfonyl)-cyclopentanecarboxylic acid cyanomethyl-amide;

(S)-1-[(1R,2R,4S)-4-(4-Chloro-2-methyl-benzenesulfonyl)-2-(morpholine-4-carbonyl)-cyclopentanecarbonyl]-pyrrolidine-2-carbonitrile;

(1R,2R,4R)-4-(4-Chloro-2-methyl-benzenesulfonyl)-2-(morpholine-4-carbonyl)-cyclopentanecarboxylic acid (4-cyano-1-methyl-piperidin-4-yl)-amide;

(1R,2R,4R)-2-Methoxy-4-(2-trifluoromethyl-benzenesulfonyl)-cyclopentanecarboxylic acid (1-cyano-cyclopropyl)-amide;

(1S,2S,4S)-2-Methoxy-4-(2-trifluoromethyl-benzenesulfonyl)-cyclopentanecarboxylic acid (1-cyano-cyclopropyl)-amide;

(1R,2R,4R)-2-Methoxy-4-(2-trifluoromethyl-benzenesulfonyl)-cyclopentanecarboxylic acid cyanomethyl-amide;

(1S,2S,4S)-2-Methoxy-4-(2-trifluoromethyl-benzenesulfonyl)-cyclopentanecarboxylic acid cyanomethyl-amide;

(1R,2R,4R)-4-(2-Chloro-benzenesulfonyl)-2-hydroxy-cyclopentanecarboxylic acid (1-cyano-cyclopropyl)-amide;

(1S,2S,4S)-4-(2-Chloro-benzenesulfonyl)-2-hydroxy-cyclopentanecarboxylic acid (1-cyano-cyclopropyl)-amide;
(1R,2R,4R)-4-(2-Chloro-benzenesulfonyl)-2-hydroxy-cyclopentanecarboxylic acid cyanomethyl-amide;
(1S,2S,4S)-4-(2-Chloro-benzenesulfonyl)-2-hydroxy-cyclopentanecarboxylic acid cyanomethyl-amide;
(1R,2R,4R)-4-(2,4-Dichloro-benzenesulfonyl)-2-methoxy-cyclopentanecarboxylic acid (1-cyano-cyclopropyl)-amide;
(1S,2S,4S)-4-(2,4-Dichloro-benzenesulfonyl)-2-methoxy-cyclopentanecarboxylic acid (1-cyano-cyclopropyl)-amide;
(1R,2R,4R)-4-(2,4-Dichloro-benzenesulfonyl)-2-methoxy-cyclopentanecarboxylic acid cyanomethyl-amide;
(1S,2S,4S)-4-(2,4-Dichloro-benzenesulfonyl)-2-methoxy-cyclopentanecarboxylic acid cyanomethyl-amide;
(1S,2S,4R)-4-(2-Chloro-benzenesulfonyl)-2-hydroxy-cyclopentanecarboxylic acid (1-cyano-cyclopropyl)-amide;
(1R,2R,4S)-4-(2-Chloro-benzenesulfonyl)-2-hydroxy-cyclopentanecarboxylic acid (1-cyano-cyclopropyl)-amide;
(1S,2S,4R)-4-(2-Chloro-benzenesulfonyl)-2-hydroxy-cyclopentanecarboxylic acid cyanomethyl-amide;
(1R,2R,4S)-4-(2-Chloro-benzenesulfonyl)-2-hydroxy-cyclopentanecarboxylic acid cyanomethyl-amide;
(1R,2R,4R)-2-Propoxy-4-(2-trifluoromethyl-benzenesulfonyl)-cyclopentanecarboxylic acid (1-cyano-cyclopropyl)-amide;
(1S,2S,4S)-2-Propoxy-4-(2-trifluoromethyl-benzenesulfonyl)-cyclopentanecarboxylic acid (1-cyano-cyclopropyl)-amide;
(1R,2R,4R)-2-Propoxy-4-(2-trifluoromethyl-benzenesulfonyl)-cyclopentanecarboxylic acid cyanomethyl-amide;
(1S,2S,4S)-2-Propoxy-4-(2-trifluoromethyl-benzenesulfonyl)-cyclopentanecarboxylic acid cyanomethyl-amide;
(1R,2R,4R)-4-(2-Chloro-4-fluoro-benzenesulfonyl)-2-methoxy-cyclopentanecarboxylic acid (1-cyano-cyclopropyl)-amide;
(1S,2S,4S)-4-(2-Chloro-4-fluoro-benzenesulfonyl)-2-methoxy-cyclopentanecarboxylic acid (1-cyano-cyclopropyl)-amide;
(1R,2R,4R)-4-[2-Chloro-4-(4-fluoro-phenoxy)-benzenesulfonyl]-2-methoxy-cyclopentanecarboxylic acid (1-cyano-cyclopropyl)-amide;
(1S,2S,4S)-4-[2-Chloro-4-(4-fluoro-phenoxy)-benzenesulfonyl]-2-methoxy-cyclopentanecarboxylic acid (1-cyano-cyclopropyl)-amide;
(1R,2R,4R)-4-(4-Bromo-2-trifluoromethyl-benzenesulfonyl)-2-methoxy-cyclopentanecarboxylic acid (1-cyano-cyclopropyl)-amide;
(1S,2S,4S)-4-(4-Bromo-2-trifluoromethyl-benzenesulfonyl)-2-methoxy-cyclopentanecarboxylic acid (1-cyano-cyclopropyl)-amide;
(1R,2R,4R)-4-(2-Chloro-4-pyrazol-1-yl-benzenesulfonyl)-2-methoxy-cyclopentanecarboxylic acid (1-cyano-cyclopropyl)-amide;
(1S,2S,4S)-4-(2-Chloro-4-pyrazol-1-yl-benzenesulfonyl)-2-methoxy-cyclopentanecarboxylic acid (1-cyano-cyclopropyl)-amide;
(1R,2R,4R)-4-[2-Chloro-4-((R/S)-2,2,2-trifluoro-1-methyl-ethoxy)-benzenesulfonyl]-2-methoxy-cyclopentanecarboxylic acid (1-cyano-cyclopropyl)-amide;
(1S,2S,4S)-4-[2-Chloro-4-((R/S)-2,2,2-trifluoro-1-methyl-ethoxy)-benzenesulfonyl]-2-methoxy-cyclopentanecarboxylic acid (1-cyano-cyclopropyl)-amide;
(1R,2R,4R)-2-Methoxy-4-[4-(4-methyl-thiazol-2-yl)-2-trifluoromethyl-benzenesulfonyl]-cyclopentanecarboxylic acid (1-cyano-cyclopropyl)-amide;
(1S,2S,4S)-2-Methoxy-4-[4-(4-methyl-thiazol-2-yl)-2-trifluoromethyl-benzenesulfonyl]-cyclopentanecarboxylic acid (1-cyano-cyclopropyl)-amide;
(1R,2R,4R)-4-(2',4'-Difluoro-3-trifluoromethyl-biphenyl-4-sulfonyl)-2-methoxy-cyclopentanecarboxylic acid (1-cyano-cyclopropyl)-amide;
(1S,2S,4S)-4-(2',4'-Difluoro-3-trifluoromethyl-biphenyl-4-sulfonyl)-2-methoxy-cyclopentanecarboxylic acid (1-cyano-cyclopropyl)-amide;
(1R,2R,4R)-4-(4'-Fluoro-3-trifluoromethyl-biphenyl-4-sulfonyl)-2-methoxy-cyclopentanecarboxylic acid (1-cyano-cyclopropyl)-amide;
(1S,2S,4S)-4-(4'-Fluoro-3-trifluoromethyl-biphenyl-4-sulfonyl)-2-methoxy-cyclopentanecarboxylic acid (1-cyano-cyclopropyl)-amide;
(1R,2R,4R)-4-(2-Chloro-4-piperidin-1-yl-benzenesulfonyl)-2-methoxy-cyclopentanecarboxylic acid (1-cyano-cyclopropyl)-amide;
(1S,2S,4S)-4-(2-Chloro-4-piperidin-1-yl-benzenesulfonyl)-2-methoxy-cyclopentanecarboxylic acid (1-cyano-cyclopropyl)-amide;
(1R,2R,4R)-4-[2-Chloro-4-(2,2,2-trifluoro-ethoxy)-benzenesulfonyl]-2-methoxy-cyclopentanecarboxylic acid (1-cyano-cyclopropyl)-amide;
(1S,2S,4S)-4-[2-Chloro-4-(2,2,2-trifluoro-ethoxy)-benzenesulfonyl]-2-methoxy-cyclopentanecarboxylic acid (1-cyano-cyclopropyl)-amide;
(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;
(1S,2S,4S)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;
(1R,2R,4R)-4-[4-(2,5-Dimethyl-2H-pyrazol-3-yl)-2-trifluoromethyl-benzenesulfonyl]-2-methoxy-cyclopentanecarboxylic acid (1-cyano-cyclopropyl)-amide;
(1S,2S,4S)-4-[4-(2,5-Dimethyl-2H-pyrazol-3-yl)-2-trifluoromethyl-benzenesulfonyl]-2-methoxy-cyclopentanecarboxylic acid (1-cyano-cyclopropyl)-amide;
(1R,2R,4S)-4-(2-Chloro-benzenesulfonyl)-2-(4-chloro-phenoxymethyl)-cyclopentanecarboxylic acid cyanomethyl-amide;
(1R,2R,4R)-4-(2-Chloro-benzenesulfonyl)-2-(4-chloro-phenoxymethyl)-cyclopentanecarboxylic acid cyanomethyl-amide;
(1R,2R,4S)-4-(2-Chloro-benzenesulfonyl)-2-(4-chloro-phenoxymethyl)-cyclopentanecarboxylic acid (1-cyano-cyclopropyl)-amide;
(1R,2R,4R)-4-(2-Chloro-benzenesulfonyl)-2-(4-chloro-phenoxymethyl)-cyclopentanecarboxylic acid (1-cyano-cyclopropyl)-amide;
(1R,2R,4R)-2-Methoxy-4-[4-(1-methyl-1H-pyrazol-5-yl)-2-trifluoromethyl-benzenesulfonyl]-cyclopentanecarboxylic acid (1-cyano-cyclopropyl)-amide;
(1S,2S,4S)-2-Methoxy-4-[4-(1-methyl-1H-pyrazol-5-yl)-2-trifluoromethyl-benzenesulfonyl]-cyclopentanecarboxylic acid (1-cyano-cyclopropyl)-amide;
(1R,2R,4R)-2-Methoxy-4-[4-(1H-pyrazol-3-yl)-2-trifluoromethyl-benzenesulfonyl]-cyclopentanecarboxylic acid (1-cyano-cyclopropyl)-amide;

(1S,2S,4S)-2-Methoxy-4-[4-(1H-pyrazol-3-yl)-2-trifluoromethyl-benzenesulfonyl]-cyclopentanecarboxylic acid (1-cyano-cyclopropyl)-amide;
(1R,2R,4R)-4-(3',4'-Difluoro-3-trifluoromethyl-biphenyl-4-sulfonyl)-2-methoxy-cyclopentanecarboxylic acid (1-cyano-cyclopropyl)-amide;
(1S,2S,4S)-4-(3',4'-Difluoro-3-trifluoromethyl-biphenyl-4-sulfonyl)-2-methoxy-cyclopentanecarboxylic acid (1-cyano-cyclopropyl)-amide;
(1R,2R,4R)-4-(4'-Methanesulfonyl-3-trifluoromethyl-biphenyl-4-sulfonyl)-2-methoxy-cyclopentanecarboxylic acid (1-cyano-cyclopropyl)-amide;
(1S,2S,4S)-4-(4'-Methanesulfonyl-3-trifluoromethyl-biphenyl-4-sulfonyl)-2-methoxy-cyclopentanecarboxylic acid (1-cyano-cyclopropyl)-amide;
(1R,2R,4R)-2-Methoxy-4-(4'-sulfamoyl-3-trifluoromethyl-biphenyl-4-sulfonyl)-cyclopentanecarboxylic acid (1-cyano-cyclopropyl)-amide;
(1S,2S,4S)-2-Methoxy-4-(4'-sulfamoyl-3-trifluoromethyl-biphenyl-4-sulfonyl)-cyclopentanecarboxylic acid (1-cyano-cyclopropyl)-amide;
(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;
(1S,2S,4S)-2-Methoxy-4-[4-(2-methyl-pyridin-4-yl)-2-trifluoromethyl-benzenesulfonyl]-cyclopentanecarboxylic acid (1-cyano-cyclopropyl)-amide;
(1R,2R,4R)-2-Methoxy-4-[4-(6-methoxy-pyridin-3-yl)-2-trifluoromethyl-benzenesulfonyl]-cyclopentanecarboxylic acid (1-cyano-cyclopropyl)-amide;
(1S,2S,4S)-2-Methoxy-4-[4-(6-methoxy-pyridin-3-yl)-2-trifluoromethyl-benzenesulfonyl]-cyclopentanecarboxylic acid (1-cyano-cyclopropyl)-amide;
(1R,3R)-3-(2-Chloro-4-fluoro-benzenesulfonyl)-cyclopentanecarboxylic acid cyanomethyl-amide;
(1S,3S)-3-(2-Chloro-4-fluoro-benzenesulfonyl)-cyclopentanecarboxylic acid cyanomethyl-amide;
(1R,3R)-3-[2-Chloro-4-((R/S)-2,2,2-trifluoro-1-methyl-ethoxy)-benzenesulfonyl]-cyclopentanecarboxylic acid cyanomethyl-amide;
(1S,3S)-3-[2-Chloro-4-((R/S)-2,2,2-trifluoro-1-methyl-ethoxy)-benzenesulfonyl]-cyclopentanecarboxylic acid cyanomethyl-amide;
(1R,2R,4R)-2-Methoxy-4-[4-(6-methyl-pyridin-3-yl)-2-trifluoromethyl-benzenesulfonyl]-cyclopentanecarboxylic acid (1-cyano-cyclopropyl)-amide;
(1S,2S,4S)-2-Methoxy-4-[4-(6-methyl-pyridin-3-yl)-2-trifluoromethyl-benzenesulfonyl]-cyclopentanecarboxylic acid (1-cyano-cyclopropyl)-amide;
(1R,2R,4R)-2-Methoxy-4-(4-pyrimidin-5-yl-2-trifluoromethyl-benzenesulfonyl)-cyclopentanecarboxylic acid (1-cyano-cyclopropyl)-amide;
(1S,2S,4S)-2-Methoxy-4-(4-pyrimidin-5-yl-2-trifluoromethyl-benzenesulfonyl)-cyclopentanecarboxylic acid (1-cyano-cyclopropyl)-amide;
(1R,2R,4R)-4-[4-(5-Methanesulfonyl-pyridin-3-yl)-2-trifluoromethyl-benzenesulfonyl]-2-methoxy-cyclopentanecarboxylic acid (1-cyano-cyclopropyl)-amide;
(1S,2S,4S)-4-[4-(5-Methanesulfonyl-pyridin-3-yl)-2-trifluoromethyl-benzenesulfonyl]-2-methoxy-cyclopentanecarboxylic acid (1-cyano-cyclopropyl)-amide;
(1R,2R,4R)-4-[4-(5-Fluoro-pyridin-3-yl)-2-trifluoromethyl-benzenesulfonyl]-2-methoxy-cyclopentanecarboxylic acid (1-cyano-cyclopropyl)-amide;
(1S,2S,4S)-4-[4-(5-Fluoro-pyridin-3-yl)-2-trifluoromethyl-benzenesulfonyl]-2-methoxy-cyclopentanecarboxylic acid (1-cyano-cyclopropyl)-amide;
(1R,2R,4R)-2-Methoxy-4-[4-(5-methyl-pyridin-3-yl)-2-trifluoromethyl-benzenesulfonyl]-cyclopentanecarboxylic acid (1-cyano-cyclopropyl)-amide;
(1S,2S,4S)-2-Methoxy-4-[4-(5-methyl-pyridin-3-yl)-2-trifluoromethyl-benzenesulfonyl]-cyclopentanecarboxylic acid (1-cyano-cyclopropyl)-amide;
(1R,2R,4R)-2-Methoxy-4-[4-(5-methoxy-pyridin-3-yl)-2-trifluoromethyl-benzenesulfonyl]-cyclopentanecarboxylic acid (1-cyano-cyclopropyl)-amide;
(1S,2S,4S)-2-Methoxy-4-[4-(5-methoxy-pyridin-3-yl)-2-trifluoromethyl-benzenesulfonyl]-cyclopentanecarboxylic acid (1-cyano-cyclopropyl)-amide;
(1R,2R,4R)-4-[4-(2,5-Dimethyl-thiophen-3-yl)-2-trifluoromethyl-benzenesulfonyl]-2-methoxy-cyclopentanecarboxylic acid (1-cyano-cyclopropyl)-amide;
(1S,2S,4S)-4-[4-(2,5-Dimethyl-thiophen-3-yl)-2-trifluoromethyl-benzenesulfonyl]-2-methoxy-cyclopentanecarboxylic acid (1-cyano-cyclopropyl)-amide;
(1R,2R,4R)-4-[2-Chloro-4-(3-methyl-6-oxo-6H-pyridazin-1-yl)-benzenesulfonyl]-2-methoxy-cyclopentanecarboxylic acid (1-cyano-cyclopropyl)-amide;
(1S,2S,4S)-4-[2-Chloro-4-(3-methyl-6-oxo-6H-pyridazin-1-yl)-benzenesulfonyl]-2-methoxy-cyclopentanecarboxylic acid (1-cyano-cyclopropyl)-amide;
(1R,2R,4R)-4-(2-Chloro-4-methoxy-benzenesulfonyl)-2-methoxy-cyclopentanecarboxylic acid (1-cyano-cyclopropyl)-amide;
(1S,2S,4S)-4-(2-Chloro-4-methoxy-benzenesulfonyl)-2-methoxy-cyclopentanecarboxylic acid (1-cyano-cyclopropyl)-amide;
(1R,2R,4R)-4-[4-(5-Chloro-pyridin-3-yl)-2-trifluoromethyl-benzenesulfonyl]-2-methoxy-cyclopentanecarboxylic acid (1-cyano-cyclopropyl)-amide;
(1S,2S,4S)-4-[4-(5-Chloro-pyridin-3-yl)-2-trifluoromethyl-benzenesulfonyl]-2-methoxy-cyclopentanecarboxylic acid (1-cyano-cyclopropyl)-amide;
(1R,2R,4R)-4-[4-(3,5-Dimethyl-isoxazol-4-yl)-2-trifluoromethyl-benzenesulfonyl]-2-methoxy-cyclopentanecarboxylic acid (1-cyano-cyclopropyl)-amide;
(1S,2S,4S)-4-[4-(3,5-Dimethyl-isoxazol-4-yl)-2-trifluoromethyl-benzenesulfonyl]-2-methoxy-cyclopentanecarboxylic acid (1-cyano-cyclopropyl)-amide;
(1R,3R)-3-(2-Chloro-4-fluoro-benzenesulfonyl)-cyclopentanecarboxylic acid (1-cyano-cyclopropyl)-amide;
(1S,3S)-3-(2-Chloro-4-fluoro-benzenesulfonyl)-cyclopentanecarboxylic acid (1-cyano-cyclopropyl)-amide;
(1R,3R)-3-[2-Chloro-4-((R/S)-2,2,2-trifluoro-1-methyl-ethoxy)-benzenesulfonyl]-cyclopentanecarboxylic acid (1-cyano-cyclopropyl)-amide;
(1S,3S)-3-[2-Chloro-4-((R/S)-2,2,2-trifluoro-1-methyl-ethoxy)-benzenesulfonyl]-cyclopentanecarboxylic acid (1-cyano-cyclopropyl)-amide;
(1R,3R)-3-(2-Chloro-4-morpholin-4-yl-benzenesulfonyl)-cyclopentanecarboxylic acid (1-cyano-cyclopropyl)-amide;
(1S,3S)-3-(2-Chloro-4-morpholin-4-yl-benzenesulfonyl)-cyclopentanecarboxylic acid (1-cyano-cyclopropyl)-amide;
(1R,3R)-3-[2-Chloro-4-(2-oxa-6-aza-spiro[3.3]hept-6-yl)-benzenesulfonyl]-cyclopentanecarboxylic acid (1-cyano-cyclopropyl)-amide;
(1S,3S)-3-[2-Chloro-4-(2-oxa-6-aza-spiro[3.3]hept-6-yl)-benzenesulfonyl]-cyclopentanecarboxylic acid (1-cyano-cyclopropyl)-amide;
(1R,3R)-3-[2-Chloro-4-(3,3-difluoro-pyrrolidin-1-yl)-benzenesulfonyl]-cyclopentanecarboxylic acid (1-cyano-cyclopropyl)-amide;

(1S,3S)-3-[2-Chloro-4-(3,3-difluoro-pyrrolidin-1-yl)-benzenesulfonyl]-cyclopentanecarboxylic acid (1-cyano-cyclopropyl)-amide;

(1R,3R)-3-[2-Chloro-4-(4-ethyl-piperazin-1-yl)-benzenesulfonyl]-cyclopentanecarboxylic acid (1-cyano-cyclopropyl)-amide;

(1S,3S)-3-[2-Chloro-4-(4-ethyl-piperazin-1-yl)-benzenesulfonyl]-cyclopentanecarboxylic acid (1-cyano-cyclopropyl)-amide;

(1R,3R)-3-[2-Chloro-4-(2,2,2-trifluoro-ethoxy)-benzenesulfonyl]-cyclopentanecarboxylic acid (1-cyano-cyclopropyl)-amide;

(1S,3S)-3-[2-Chloro-4-(2,2,2-trifluoro-ethoxy)-benzenesulfonyl]-cyclopentanecarboxylic acid (1-cyano-cyclopropyl)-amide;

(1R,3S)-3-[2-Chloro-4-(2,2,2-trifluoro-ethoxy)-benzenesulfonyl]-cyclopentanecarboxylic acid (1-cyano-cyclopropyl)-amide;

(1S,3R)-3-[2-Chloro-4-(2,2,2-trifluoro-ethoxy)-benzenesulfonyl]-cyclopentanecarboxylic acid (1-cyano-cyclopropyl)-amide;

(1R,3R)-3-(2-Chloro-4-pyrazol-1-yl-benzenesulfonyl)-cyclopentanecarboxylic acid (1-cyano-cyclopropyl)-amide;

(1S,3S)-3-(2-Chloro-4-pyrazol-1-yl-benzenesulfonyl)-cyclopentanecarboxylic acid (1-cyano-cyclopropyl)-amide;

(1R,3S)-3-(2-Chloro-4-pyrazol-1-yl-benzenesulfonyl)-cyclopentanecarboxylic acid (1-cyano-cyclopropyl)-amide;

(1S,3R)-3-(2-Chloro-4-pyrazol-1-yl-benzenesulfonyl)-cyclopentanecarboxylic acid (1-cyano-cyclopropyl)-amide;

(1R,3R)-3-[2-Chloro-4-(4-cyclopropyl-piperazin-1-yl)-benzenesulfonyl]-cyclopentanecarboxylic acid (1-cyano-cyclopropyl)-amide;

(1S,3S)-3-[2-Chloro-4-(4-cyclopropyl-piperazin-1-yl)-benzenesulfonyl]-cyclopentanecarboxylic acid (1-cyano-cyclopropyl)-amide;

(1R,2R,4S)-4-(2-Chloro-benzenesulfonyl)-2-methoxymethyl-cyclopentanecarboxylic acid cyanomethyl-amide;

(1R,2R,4R)-4-(2-Chloro-benzenesulfonyl)-2-methoxymethyl-cyclopentanecarboxylic acid cyanomethyl-amide;

(1R,2R,4S)-4-(2-Chloro-benzenesulfonyl)-2-methoxymethyl-cyclopentanecarboxylic acid (1-cyano-cyclopropyl)-amide;

(1R,2R,4R)-4-(2-Chloro-benzenesulfonyl)-2-methoxymethyl-cyclopentanecarboxylic acid (1-cyano-cyclopropyl)-amide;

(1R,2R,4R)-4-(2-Chloro-benzenesulfonyl)-2-(6-hydroxy-pyridazin-3-yloxymethyl)-cyclopentanecarboxylic acid cyanomethylamide;

(1R,2R,4S)-4-(2-Chloro-benzenesulfonyl)-2-(6-hydroxy-pyridazin-3-yloxymethyl)-cyclopentanecarboxylic acid cyanomethylamide;

(1R,2R,4S)-4-(2-Chloro-benzenesulfonyl)-2-(6-hydroxy-pyridazin-3-yloxymethyl)-cyclopentanecarboxylic acid (1-cyano-cyclopropyl)-amide;

(1R,2R,4R)-4-(2-Chloro-benzenesulfonyl)-2-(6-hydroxy-pyridazin-3-yloxymethyl)-cyclopentanecarboxylic acid (1-cyano-cyclopropyl)-amide;

(1R,2R,4R)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;

(1S,2S,4S)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;

(1R,2R,4R)-2-Methoxy-4-(4-pyridazin-4-yl-2-trifluoromethyl-benzenesulfonyl)-cyclopentanecarboxylic acid (1-cyano-cyclopropyl)-amide;

(1S,2S,4S)-2-Methoxy-4-(4-pyridazin-4-yl-2-trifluoromethyl-benzenesulfonyl)-cyclopentanecarboxylic acid (1-cyano-cyclopropyl)-amide;

(1R,2R,4R)-2-Methoxy-4-(4-pyrazin-2-yl-2-trifluoromethyl-benzenesulfonyl)-cyclopentanecarboxylic acid (1-cyano-cyclopropyl)-amide;

(1S,2S,4S)-2-Methoxy-4-(4-pyrazin-2-yl-2-trifluoromethyl-benzenesulfonyl)-cyclopentanecarboxylic acid (1-cyano-cyclopropyl)-amide;

(1R,2R,4R)-4-(4-Bromo-2-trifluoromethyl-benzenesulfonyl)-2-isopropoxy-cyclopentanecarboxylic acid (1-cyano-cyclopropyl)-amide;

(1S,2S,4S)-4-(4-Bromo-2-trifluoromethyl-benzenesulfonyl)-2-isopropoxy-cyclopentanecarboxylic acid (1-cyano-cyclopropyl)-amide;

(1R,2R,4S)-4-(4-Bromo-2-trifluoromethyl-benzenesulfonyl)-2-ethoxy-cyclopentanecarboxylic acid (1-cyano-cyclopropyl)-amide;

(1S,2S,4R)-4-(4-Bromo-2-trifluoromethyl-benzenesulfonyl)-2-ethoxy-cyclopentanecarboxylic acid (1-cyano-cyclopropyl)-amide;

(1R,2R,4R)-2-Ethoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Ethoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-4-[4-(3,5-Dimethyl-isoxazol-4-yl)-2-trifluoromethyl-benzenesulfonyl]-2-ethoxy-cyclopentanecarboxylic acid (1-cyano-cyclopropyl)-amide;

(1S,2S,4S)-4-[4-(3,5-Dimethyl-isoxazol-4-yl)-2-trifluoromethyl-benzenesulfonyl]-2-ethoxy-cyclopentanecarboxylic acid (1-cyano-cyclopropyl)-amide;

(1R,2R,4R)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-4-(4-Bromo-2-trifluoromethyl-benzenesulfonyl)-2-(3,3-difluoro-azetidine-1-carbonyl)-cyclopentanecarboxylic acid (1-cyano-cyclopropyl)-amide;

(1R,2R,4R)-2-(3,3-Difluoro-azetidine-1-carbonyl)-4-(4-fluoro-2-trifluoromethyl-benzenesulfonyl)-cyclopentanecarboxylic acid (1-cyano-cyclopropyl)-amide;

(1R,2R,4R)-4-(2-Chloro-4-fluoro-benzenesulfonyl)-2-(3,3-difluoro-azetidine-1-carbonyl)-cyclopentanecarboxylic acid (1-cyano-cyclopropyl)-amide;

(1R,2R,4R)-2-(3,3-Difluoro-azetidine-1-carbonyl)-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-(3,3-Difluoro-azetidine-1-carbonyl)-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-4-[4-(2-Chloro-pyridin-4-yl)-2-trifluoromethyl-benzenesulfonyl]-2-(3,3-difluoro-azetidine-1-carbonyl)-cyclopentanecarboxylic acid (1-cyano-cyclopropyl)-amide;

(1R,2R,4R)-4-[4-(6-Chloro-pyrazin-2-yl)-2-trifluoromethyl-benzenesulfonyl]-2-(3,3-difluoro-azetidine-1-carbonyl)-cyclopentanecarboxylic acid (1-cyano-cyclopropyl)-amide;

(1R,2R,4R)-2-(3,3-Difluoro-azetidine-1-carbonyl)-4-[4-(2-methyl-2H-pyrazol-3-yl)-2-trifluoromethyl-benzenesulfonyl]-cyclopentanecarboxylic acid (1-cyano-cyclopropyl)-amide;

(1R,2R,4R)-4-(4-Cyclopropyl-2-trifluoromethyl-benzenesulfonyl)-2-(3,3-difluoro-azetidine-1-carbonyl)-cyclopentanecarboxylic acid (1-cyano-cyclopropyl)-amide;

(1R,2R,4R)-4-[4-(5'-Chloro-[2,2']bipyrazinyl-6-yl)-2-trifluoromethyl-benzenesulfonyl]-2-(3,3-difluoro-azetidine-1-carbonyl)-cyclopentanecarboxylic acid (1-cyano-cyclopropyl)-amide;

2-(3,3-Difluoro-azetidine-1-carbonyl)-4-[4-(oxetan-3-yloxy)-2-trifluoromethyl-benzenesulfonyl]-cyclopentanecarboxylic acid (1-cyano-cyclopropyl)-amide;

2-(3,3-Difluoro-azetidine-1-carbonyl)-4-(4-pyrazol-1-yl-2-trifluoromethyl-benzenesulfonyl)-cyclopentanecarboxylic acid (1-cyano-cyclopropyl)-amide;

(1R,2R,4R)-4-[4-(4-Cyclopropyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide;

(1R,2R,4R)-4-[4-(4-tert-Butyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide;

4-[4-(4-Acetyl-piperazin-1-yl)-2-trifluoromethyl-benzenesulfonyl]-2-(3,3-difluoro-azetidine-1-carbonyl)-cyclopentanecarboxylic acid (1-cyano-cyclopropyl)-amide;

2-(3,3-Difluoro-azetidine-1-carbonyl)-4-[4-(3,3-difluoro-pyrrolidin-1-yl)-2-trifluoromethyl-benzenesulfonyl]-cyclopentanecarboxylic acid (1-cyano-cyclopropyl)-amide;

(1R,2R,4R)-2-(3,3-Difluoro-azetidine-1-carbonyl)-4-[4-(2-oxa-6-aza-spiro[3.3]hept-6-yl)-2-trifluoromethyl-benzenesulfonyl]-cyclopentanecarboxylic acid (1-cyano-cyclopropyl)-amide;

(1R,2R,4R)-4-[2-Chloro-4-(2,2,2-trifluoro-ethoxy)-benzenesulfonyl]-2-(3,3-difluoro-azetidine-1-carbonyl)-cyclopentanecarboxylic acid (1-cyano-cyclopropyl)-amide;

(1R,2R,4R)-4-[2-Chloro-4-((S)-2,2,2-trifluoro-1-methyl-ethoxy)-benzenesulfonyl]-2-(3,3-difluoro-azetidine-1-carbonyl)-cyclopentanecarboxylic acid (1-cyano-cyclopropyl)-amide;

(1R,2R,4R)-4-[2-Chloro-4-(3,3-difluoro-azetidin-1-yl)-benzenesulfonyl]-2-(3,3-difluoro-azetidine-1-carbonyl)-cyclopentanecarboxylic acid (1-cyano-cyclopropyl)-amide;

(1R,2R,4R)-4-(4-Bromo-2-trifluoromethyl-benzenesulfonyl)-2-methoxy-cyclopentanecarboxylic acid (1-cyano-cyclopropyl)-amide;

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Isopropoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Isopropoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-4-[4-(3,5-Dimethyl-isoxazol-4-yl)-2-trifluoromethyl-benzenesulfonyl]-2-isopropoxy-cyclopentanecarboxylic acid (1-cyano-cyclopropyl)-amide;

(1S,2S,4S)-4-[4-(3,5-Dimethyl-isoxazol-4-yl)-2-trifluoromethyl-benzenesulfonyl]-2-isopropoxy-cyclopentanecarboxylic acid (1-cyano-cyclopropyl)-amide;

(1R,2R,4R)-2-Isopropoxy-4-[4-(1-methyl-1H-pyrazol-4-yl)-2-trifluoromethyl-benzenesulfonyl]-cyclopentanecarboxylic acid (1-cyano-cyclopropyl)-amide; and (1S,2S,4S)-2-Isopropoxy-4-[4-(1-methyl-1H-pyrazol-4-yl)-2-trifluoromethyl-benzenesulfonyl]-cyclopentanecarboxylic acid (1-cyano-cyclopropyl)-amide;

or a salt thereof.

15. A compound according to claim 1 selected from the group consisting of:

(1R,2R,4R)-4-(2-Chloro-benzenesulfonyl)-2-(morpholine-4-carbonyl)-cyclopentanecarboxylic acid (1-cyano-cyclopropyl)-amide;

(1R,2R,4R)-4-(4-Chloro-2-methyl-benzenesulfonyl)-2-(morpholine-4-carbonyl)-cyclopentanecarboxylic acid (4-cyano-1-methyl-piperidin-4-yl)-amide;

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4S)-4-(2-Chloro-benzenesulfonyl)-2-(4-chlorophenoxymethyl)-cyclopentanecarboxylic acid (1-cyano-cyclopropyl)-amide;

(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Methoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;

(1S,2S,4S)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;

(1R,2R,4R)-2-Methoxy-4-(4-pyridazin-4-yl-2-trifluoromethyl-benzenesulfonyl)-cyclopentanecarboxylic acid (1-cyano-cyclopropyl)-amide;

(1S,2S,4S)-2-Methoxy-4-(4-pyridazin-4-yl-2-trifluoromethyl-benzenesulfonyl)-cyclopentanecarboxylic acid (1-cyano-cyclopropyl)-amide;

(1R,2R,4R)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-(3,3-Difluoro-azetidine-1-carbonyl)-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-(3,3-Difluoro-azetidine-1-carbonyl)-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-4-[2-Chloro-4-(2,2,2-trifluoro-ethoxy)-benzenesulfonyl]-2-(3,3-difluoro-azetidine-1-carbonyl)-cyclopentanecarboxylic acid (1-cyano-cyclopropyl)-amide;

(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide; and
(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;
or a salt thereof.

16. A compound according to claim 1 selected from the group consisting of:
(1R,2R,4R)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;
(1S,2S,4S)-2-Methoxy-4-[4-(1-methyl-1H-pyrazol-4-yl)-2-trifluoromethyl-benzenesulfonyl]-cyclopentanecarboxylic acid (1-cyano-cyclopropyl)-amide;
(1R,2R,4R)-2-Methoxy-4-[4-(2-methyl-pyridin-4-yl)-2-trifluoromethyl-benzenesulfonyl]-cyclopentanecarboxylic acid (1-cyano-cyclopropyl)-amide;
(1S,2S,4S)-2-Methoxy-4-[4-(2-methyl-pyridin-4-yl)-2-trifluoromethyl-benzenesulfonyl]-cyclopentanecarboxylic acid (1-cyano-cyclopropyl)-amide;
(1R,2R,4R)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;
(1S,2S,4S)-2-Methoxy-4-[2-trifluoromethyl-4-(2-trifluoromethyl-pyridin-4-yl)-benzenesulfonyl]-cyclopentanecarboxylic acid (1-cyano-cyclopropyl)-amide;
(1R,2R,4R)-2-Methoxy-4-(4-pyridazin-4-yl-2-trifluoromethyl-benzenesulfonyl)-cyclopentanecarboxylic acid (1-cyano-cyclopropyl)-amide;
(1S,2S,4S)-2-Methoxy-4-(4-pyridazin-4-yl-2-trifluoromethyl-benzenesulfonyl)-cyclopentanecarboxylic acid (1-cyano-cyclopropyl)-amide;
(1R,2R,4R)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide; and
(1S,2S,4S)-2-Ethoxy-4-[4-(1-methyl-1H-pyrazol-4-yl)-2-trifluoromethyl-benzenesulfonyl]-cyclopentanecarboxylic acid (1-cyano-cyclopropyl)-amide; or a salt thereof.

17. A compound according to claim 1 selected from the group consisting of:
(1R,2R,4S)-4-(2-Chloro-4-fluoro-benzenesulfonyl)-2-(4-fluoro-phenoxymethyl)-cyclopentanecarboxylic acid cyanomethyl-amide;
(1R,2R,4R)-4-(2-Chloro-4-fluoro-benzenesulfonyl)-2-(4-fluoro-phenoxymethyl)-cyclopentanecarboxylic acid cyanomethyl-amide;
(1R,2R,4S)-4-(2-Chloro-4-fluoro-benzenesulfonyl)-2-(4-fluoro-phenoxymethyl)-cyclopentanecarboxylic acid (1-cyano-cyclopropyl)-amide;
(1R,2R,4R)-4-(2-Chloro-4-fluoro-benzenesulfonyl)-2-(4-fluoro-phenoxymethyl)-cyclopentanecarboxylic acid (1-cyano-cyclopropyl)-amide;
(1R,2R,4S)-4-[2-Chloro-4-(4-ethyl-piperazin-1-yl)-benzenesulfonyl]-2-(4-fluoro-phenoxymethyl)-cyclopentanecarboxylic acid cyanomethyl-amide;
(1R,2R,4R)-4-(2-Chloro-benzenesulfonyl)-2-[4-(4-fluoro-phenyl)-piperidin-1-ylmethyl]-cyclopentanecarboxylic acid (1-cyano-cyclopropyl)-amide;
(1R,2R,4R)-4-[2-Chloro-4-(4-methyl-pyrazol-1-yl)-benzenesulfonyl]-2-methoxy-cyclopentanecarboxylic acid (1-cyano-cyclopropyl)-amide;
(1S,2S,4S)-4-[2-Chloro-4-(4-methyl-pyrazol-1-yl)-benzenesulfonyl]-2-methoxy-cyclopentanecarboxylic acid (1-cyano-cyclopropyl)-amide;
(1R,2R,4R)-4-(2-Chlorophenylsulfonyl)-N-(1-cyanocyclopropyl)-2-(4-methylbenzyloxy)cyclopentanecarboxamide;
(1S,2S,4S)-4-(2-Chlorophenylsulfonyl)-N-(1-cyanocyclopropyl)-2-(4-methylbenzyloxy)cyclopentanecarboxamide;
(1R,2R,4R)-2-(4-Chloro-2-(trifluoromethyl)benzyloxy)-4-(2-chlorophenylsulfonyl)-N-(1-cyanocyclopropyl)cyclopentanecarboxamide;
(1S,2S,4S)-2-(4-Chloro-2-(trifluoromethyl)benzyloxy)-4-(2-chlorophenylsulfonyl)-N-(1-cyanocyclopropyl)cyclopentanecarboxamide;
Formic acid (1R,2R,4S)-4-(4-bromo-2-trifluoromethyl-benzenesulfonyl)-2-(1-cyano-cyclopropylcarbamoyl)-cyclopentylmethyl ester;
(1R,2R,4S)-4-(2-Chloro-4-fluoro-benzenesulfonyl)-2-(4-methoxy-benzyloxymethyl)-cyclopentanecarboxylic acid (1-cyano-cyclopropyl)-amide;
(1R,2R,4R)-2-(4-Bromo-benzyloxy)-4-(2-chloro-benzenesulfonyl)-cyclopentanecarboxylic acid (1-cyano-cyclopropyl)-amide;
(1S,2S,4S)-2-(4-Bromo-benzyloxy)-4-(2-chloro-benzenesulfonyl)-cyclopentanecarboxylic acid (1-cyano-cyclopropyl)-amide;
(1R,2R,4S)-4-(2-Chloro-4-fluoro-benzenesulfonyl)-2-hydroxymethyl-cyclopentanecarboxylic acid (1-cyano-cyclopropyl)-amide;
(1R,2R,4S)-4-(2-Chloro-4-fluoro-benzenesulfonyl)-2-isopropoxymethyl-cyclopentanecarboxylic acid (1-cyano-cyclopropyl)-amide;
(1R,2R,4R)-4-(2-Chloro-4-fluoro-benzenesulfonyl)-2-fluoromethyl-cyclopentanecarboxylic acid (1-cyano-cyclopropyl)-amide;
(1R,2R,4R)-4-[2-Chloro-4-(4-methyl-piperazin-1-yl)-benzenesulfonyl]-2-(3,3-difluoro-azetidine-1-carbonyl)-cyclopentanecarboxylic acid (1-cyano-cyclopropyl)-amide;
(1R,2R,4R)-4-[2-Chloro-4-(4-cyclopropyl-piperazin-1-yl)-benzenesulfonyl]-2-(3,3-difluoro-azetidine-1-carbonyl)-cyclopentanecarboxylic acid (1-cyano-cyclopropyl)-amide;
(1R,2R,4R)-4-[4-(4-tert!-Butyl-piperazin-1-yl)-2-chloro-benzenesulfonyl]-2-(3,3-difluoro-azetidine-1-carbonyl)-cyclopentanecarboxylic acid (1-cyano-cyclopropyl)-amide;
(1R,2R,4R)-2-Methoxy-4-[4-(4-methyl-piperazin-1-yl)-2-trifluoromethyl-benzenesulfonyl]-cyclopentanecarboxylic acid (1-cyano-cyclopropyl)-amide;
(1S,2S,4S)-2-Methoxy-4-[4-(4-methyl-piperazin-1-yl)-2-trifluoromethyl-benzenesulfonyl]-cyclopentanecarboxylic acid (1-cyano-cyclopropyl)-amide;
(1R,2R,4S)-4-(2-Chloro-4-fluoro-benzenesulfonyl)-2-(6-chloro-pyridin-3-yloxymethyl)-cyclopentanecarboxylic acid (1-cyano-cyclopropyl)-amide;
(1R,2R,4S)-4-(2-Chloro-4-fluoro-benzenesulfonyl)-2-(pyridin-4-yloxymethyl)-cyclopentanecarboxylic acid (1-cyano-cyclopropyl)-amide;
(1R,2R,4S)-4-(2-Chloro-4-fluoro-benzenesulfonyl)-2-phenoxymethyl-cyclopentanecarboxylic acid (1-cyano-cyclopropyl)-amide;
(1R,2R,4S)-4-(2-Chloro-4-fluoro-benzenesulfonyl)-2-(pyridin-3-yloxymethyl)-cyclopentanecarboxylic acid (1-cyano-cyclopropyl)-amide;
(1R,2R,4R)-4-[4-(4-Acetyl-piperazin-1-yl)-2-chloro-benzenesulfonyl]-2-(3,3-difluoro-azetidine-1-carbonyl)-cyclopentanecarboxylic acid (1-cyano-cyclopropyl)-amide;

(1R,2R,4R)-4-(2-Chloro-4-pyrazol-1-yl-benzenesulfonyl)-2-(3,3-difluoro-azetidine-1-carbonyl)-cyclopentanecarboxylic acid (1-cyano-cyclopropyl)-amide;

(1R,2R,4R)-4-[2-Chloro-4-(2-methoxy-ethoxy)-benzenesulfonyl]-2-(3,3-difluoro-azetidine-1-carbonyl)-cyclopentanecarboxylic acid (1-cyano-cyclopropyl)-amide;

(1R,2R,4R) and (1S,2S,4S)-4-(4-Bromo-2-trifluoromethyl-benzenesulfonyl)-2-(tetrahydro-pyran-4-yloxy)-cyclopentanecarboxylic acid (1-cyano-cyclopropyl)-amide;

(1R,2R,4R)-4-{4-[1-(2-Hydroxy-ethyl)-1H-pyrazol-4-yl]-2-trifluoromethyl-benzenesulfonyl}-2-methoxy-cyclopentanecarboxylic acid (1-cyano-cyclopropyl)-amide;

(1S,2S,4S)-4-{4-[1-(2-Hydroxy-ethyl)-1H-pyrazol-4-yl]-2-trifluoromethyl-benzenesulfonyl}-2-methoxy-cyclopentanecarboxylic acid (1-cyano-cyclopropyl)-amide;

(1R,2R,4R)-2-Methoxy-4-(3-trifluoromethyl-biphenyl-4-sulfonyl)-cyclopentanecarboxylic acid (1-cyano-cyclopropyl)-amide;

(1S,2S,4S)-2-Methoxy-4-(3-trifluoromethyl-biphenyl-4-sulfonyl)-cyclopentanecarboxylic acid (1-cyano-cyclopropyl)-amide;

(1R,2R,4R)-2-Methoxy-4-{4-[1-(2-methoxy-ethyl)-1H-pyrazol-4-yl]-2-trifluoromethyl-benzenesulfonyl}-cyclopentanecarboxylic acid (1-cyano-cyclopropyl)-amide;

(1S,2S,4S)-2-Methoxy-4-{4-[1-(2-methoxy-ethyl)-1H-pyrazol-4-yl]-2-trifluoromethyl-benzenesulfonyl}-cyclopentanecarboxylic acid (1-cyano-cyclopropyl)-amide;

(1R,2R,4R)-4-[4-(1-Methyl-1H-pyrazol-4-yl)-2-trifluoromethyl-benzenesulfonyl]-2-(tetrahydro-pyran-4-yloxy)-cyclopentanecarboxylic acid (1-cyano-cyclopropyl)-amide;

(1S,2S,4S)-4-[4-(1-Methyl-1H-pyrazol-4-yl)-2-trifluoromethyl-benzenesulfonyl]-2-(tetrahydro-pyran-4-yloxy)-cyclopentanecarboxylic acid (1-cyano-cyclopropyl)-amide;

(1R,2R,4R)-4-[4-(2-Methyl-pyridin-4-yl)-2-trifluoromethyl-benzenesulfonyl]-2-(tetrahydro-pyran-4-yloxy)-cyclopentanecarboxylic acid (1-cyano-cyclopropyl)-amide;

(1S,2S,4S)-4-[4-(2-Methyl-pyridin-4-yl)-2-trifluoromethyl-benzenesulfonyl]-2-(tetrahydro-pyran-4-yloxy)-cyclopentanecarboxylic acid (1-cyano-cyclopropyl)-amide;

(1R,2R,4R)-2-(Tetrahydro-pyran-4-yloxy)-4-(2-trifluoromethyl-benzenesulfonyl)-cyclopentanecarboxylic acid (1-cyano-cyclopropyl)-amide;

(1S,2S,4S)-2-(Tetrahydro-pyran-4-yloxy)-4-(2-trifluoromethyl-benzenesulfonyl)-cyclopentanecarboxylic acid (1-cyano-cyclopropyl)-amide;

(1R,2R,4R)-2-Methoxy-4-(4-morpholin-4-yl-2-trifluoromethyl-benzenesulfonyl)-cyclopentanecarboxylic acid (1-cyano-cyclopropyl)-amide;

(1S,2S,4S)-2-Methoxy-4-(4-morpholin-4-yl-2-trifluoromethyl-benzenesulfonyl)-cyclopentanecarboxylic acid (1-cyano-cyclopropyl)-amide;

(1R,2R,4R)-4-[4-(4-Isopropyl-piperazin-1-yl)-2-trifluoromethyl-benzenesulfonyl]-2-methoxy-cyclopentanecarboxylic acid (1-cyano-cyclopropyl)-amide;

(1S,2S,4S)-4-[4-(4-Isopropyl-piperazin-1-yl)-2-trifluoromethyl-benzenesulfonyl]-2-methoxy-cyclopentanecarboxylic acid (1-cyano-cyclopropyl)-amide;

(1R,2R,4R)-4-[4-(4,4-Difluoro-piperidin-1-yl)-2-trifluoromethyl-benzenesulfonyl]-2-methoxy-cyclopentanecarboxylic acid (1-cyano-cyclopropyl)-amide;

(1S,2S,4S)-4-[4-(4,4-Difluoro-piperidin-1-yl)-2-trifluoromethyl-benzenesulfonyl]-2-methoxy-cyclopentanecarboxylic acid (1-cyano-cyclopropyl)-amide;

(4-{4-[(1R,3R,4R)-3-(1-Cyano-cyclopropylcarbamoyl)-4-methoxy-cyclopentanesulfonyl]-3-trifluoromethyl-phenyl}-pyrazol-1-yl)-acetic acid methyl ester;

(4-{4-[(1S,3S,4S)-3-(1-Cyano-cyclopropylcarbamoyl)-4-methoxy-cyclopentanesulfonyl]-3-trifluoromethyl-phenyl}-pyrazol-1-yl)-acetic acid methyl ester;

(1R,2R,4R)-4-(2-Chlorophenylsulfonyl)-N-(1-cyanocyclopropyl)-2-(2,4-dichloro-3-fluorobenzyloxy)cyclopentanecarboxamide;

(1S,2S,4S)-4-(2-Chlorophenylsulfonyl)-N-(1-cyanocyclopropyl)-2-(2,4-dichloro-3-fluorobenzyloxy)cyclopentanecarboxamide;

(1R,2R,4R)-4-(4-Bromo-2-trifluoromethyl-benzenesulfonyl)-2[(tetrahydro-1,1-dioxo-2H-thiopyran-4-yl)oxy]-cyclopentanecarboxylic acid (1-cyano-cyclopropyl)-amide;

(1S,2S,4S)-4-(4-Bromo-2-trifluoromethyl-benzenesulfonyl)-2[(tetrahydro-1,1-dioxo-2H-thiopyran-4-yl)oxy]-cyclopentanecarboxylic acid (1-cyano-cyclopropyl)-amide;

(1R,2R,4R)-4-(4-Bromo-2-trifluoromethyl-benzenesulfonyl)-2-cyclobutoxy-cyclopentanecarboxylic acid (1-cyano-cyclopropyl)-amide;

(1S,2S,4S)-4-(4-Bromo-2-trifluoromethyl-benzenesulfonyl)-2-cyclobutoxy-cyclopentanecarboxylic acid (1-cyano-cyclopropyl)-amide;

(1R,2R,4R)-2-[(tetrahydro-1,1-dioxo-2H-thiopyran-4-yl)oxy]-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-[(tetrahydro-1,1-dioxo-2H-thiopyran-4-yl)oxy]-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-[(tetrahydro-1,1-dioxo-2H-thiopyran-4-yl)oxy]-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-[(tetrahydro-1,1-dioxo-2H-thiopyran-4-yl)oxy]-4-[4-(1-methyl-1H-pyrazol-4-yl)-2-trifluoromethyl-benzenesulfonyl]-cyclopentanecarboxylic acid (1-cyano-cyclopropyl)-amide;

(4-{4-[(1R,3R,4R)-3-(1-Cyano-cyclopropylcarbamoyl)-4-methoxy-cyclopentanesulfonyl]-3-trifluoromethyl-phenyl}-pyrazol-1-yl)-acetic acid;

(4-{4-[(1S,3S,4S)-3-(1-Cyano-cyclopropylcarbamoyl)-4-methoxy-cyclopentanesulfonyl]-3-trifluoromethyl-phenyl}-pyrazol-1-yl)-acetic acid;

(1R,2R,4R)-4-(2-Chloro-4-fluoro-benzenesulfonyl)-2-(3,3-difluoro-pyrrolidine-1-carbonyl)-cyclopentanecarboxylic acid (1-cyano-cyclopropyl)-amide;

(1R,2R,4R)-4-(4-Bromo-2-chloro-benzenesulfonyl)-2-(3,3-difluoro-pyrrolidine-1-carbonyl)-cyclopentanecarboxylic acid (1-cyano-cyclopropyl)-amide;

(1R,2R,4R)-4-(3-Bromo-benzenesulfonyl)-2-(3,3-difluoro-pyrrolidine-1-carbonyl)-cyclopentanecarboxylic acid (1-cyano-cyclopropyl)-amide;

(1R,2R,4R)-4-[2-Chloro-4-(2,2,2-trifluoro-ethoxy)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-((S)-2,2,2-trifluoro-1-methyl-ethoxy)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-(4-cyclopropyl-piperazin-1-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[4-(4-tert-Butyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide;

(1R,2R,4R)-2-Methoxy-4-{4-[4-(2,2,2-trifluoro-ethyl)-piperazin-1-yl]-2-trifluoromethyl-benzenesulfonyl}-cyclopentanecarboxylic acid (1-cyano-cyclopropyl)-amide;

(1S,2S,4S)-2-Methoxy-4-{4-[4-(2,2,2-trifluoro-ethyl)-piperazin-1-yl]-2-trifluoromethyl-benzenesulfonyl}-cyclopentanecarboxylic acid (1-cyano-cyclopropyl)-amide;

(1R,2R,4R)-4-[4-(1-Carbamoylmethyl-1H-pyrazol-4-yl)-2-trifluoromethyl-benzenesulfonyl]-2-methoxy-cyclopentanecarboxylic acid (1-cyano-cyclopropyl)-amide;

(1S,2S,4S)-4-[4-(1-Carbamoylmethyl-1H-pyrazol-4-yl)-2-trifluoromethyl-benzenesulfonyl]-2-methoxy-cyclopentanecarboxylic acid (1-cyano-cyclopropyl)-amide;

(1R,2R,4R)-4-(4-Bromo-2-trifluoromethyl-benzenesulfonyl)-2-cyclopentyloxy-cyclopentanecarboxylic acid (1-cyano-cyclopropyl)-amide;

(1S,2S,4S)-4-(4-Bromo-2-trifluoromethyl-benzenesulfonyl)-2-cyclopentyloxy-cyclopentanecarboxylic acid (1-cyano-cyclopropyl)-amide;

(1R,2R,4R)-4-[2-Chloro-4-(2-methyl-2H-pyrazol-3-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-(1-methyl-1H-pyrazol-4-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-(2-methyl-pyridin-4-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-[2-Chloro-4-(2-chloro-pyridin-4-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-4-(2-Chloro-4-methyl-benzenesulfonyl)-2-(3,3-difluoro-pyrrolidine-1-carbonyl)-cyclopentanecarboxylic acid (1-cyano-cyclopropyl)-amide;

(1R,2R,4R)-2-(3,3-Difluoro-pyrrolidine-1-carbonyl)-4-[3-(2-methyl-2H-pyrazol-3-yl)-benzenesulfonyl]-cyclopentanecarboxylic acid (1-cyano-cyclopropyl)-amide;

(1R,2R,4R)-2-(3,3-Difluoro-pyrrolidine-1-carbonyl)-4-[3-(1-methyl-1H-pyrazol-4-yl)-benzenesulfonyl]-cyclopentanecarboxylic acid (1-cyano-cyclopropyl)-amide;

(1R,2R,4R)-2-(3,3-Difluoro-pyrrolidine-1-carbonyl)-4-[3-(2-methyl-pyridin-4-yl)-benzenesulfonyl]-cyclopentanecarboxylic acid (1-cyano-cyclopropyl)-amide;

(1R,2R,4R)-4-[3-(2-Chloro-pyridin-4-yl)-benzenesulfonyl]-2-(3,3-difluoro-pyrrolidine-1-carbonyl)-cyclopentanecarboxylic acid (1-cyano-cyclopropyl)-amide;

(1R,2R,4R)-2-(3,3-Difluoro-pyrrolidine-1-carbonyl)-4-(toluene-3-sulfonyl)-cyclopentanecarboxylic acid (1-cyano-cyclopropyl)-amide;

(1R,2R,4R)-4-[4-(3,3-Difluoro-azetidin-1-yl)-2-trifluoromethyl-benzenesulfonyl]-2-methoxy-cyclopentanecarboxylic acid (1-cyano-cyclopropyl)-amide;

(1S,2S,4S)-4-[4-(3,3-Difluoro-azetidin-1-yl)-2-trifluoromethyl-benzenesulfonyl]-2-methoxy-cyclopentanecarboxylic acid (1-cyano-cyclopropyl)-amide;

(1R,2R,4R)-4-[4-(4-Hydroxy-piperidin-1-yl)-2-trifluoromethyl-benzenesulfonyl]-2-methoxy-cyclopentanecarboxylic acid (1-cyano-cyclopropyl)-amide;

(1S,2S,4S)-4-[4-(4-Hydroxy-piperidin-1-yl)-2-trifluoromethyl-benzenesulfonyl]-2-methoxy-cyclopentanecarboxylic acid (1-cyano-cyclopropyl)-amide;

(1R,2R,4R)-4-[4-(4-Acetyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide;

(1R,2R,4S)-4-[4-(4-Acetyl-piperazin-1-yl)-2-chloro-benzenesulfonyl]-2-(3,3-difluoro-pyrrolidine-1-carbonyl)-cyclopentanecarboxylic acid (1-cyano-cyclopropyl)-amide;

(1R,2R,4R)-2-Cyclobutoxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Cyclobutoxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Cyclobutoxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Cyclobutoxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-Cyclopentyloxy-4-[4-(2-methyl-pyridin-4-yl)-2-trifluoromethyl-benzenesulfonyl]-cyclopentanecarboxylic acid (1-cyano-cyclopropyl)-amide;

(1S,2S,4S)-2-Cyclopentyloxy-4-[4-(2-methyl-pyridin-4-yl)-2-trifluoromethyl-benzenesulfonyl]-cyclopentanecarboxylic acid (1-cyano-cyclopropyl)-amide;

(1R,2R,4R)-2-Cyclopentyloxy-4-[4-(1-methyl-1H-pyrazol-4-yl)-2-trifluoromethyl-benzenesulfonyl]-cyclopentanecarboxylic acid (1-cyano-cyclopropyl)-amide;

(1S,2S,4S)-2-Cyclopentyloxy-4-[4-(1-methyl-1H-pyrazol-4-yl)-2-trifluoromethyl-benzenesulfonyl]-cyclopentanecarboxylic acid (1-cyano-cyclopropyl)-amide;

(1R,2R,4R)-2-Methoxy-4-{4-[1-(3-methyl-oxetan-3-ylmethyl)-1H-pyrazol-4-yl]-2-trifluoromethyl-benzenesulfonyl}-cyclopentanecarboxylic acid (1-cyano-cyclopropyl)-amide;

(1S,2S,4S)-2-Methoxy-4-{4-[1-(3-methyl-oxetan-3-ylmethyl)-1H-pyrazol-4-yl]-2-trifluoromethyl-benzenesulfonyl}-cyclopentanecarboxylic acid (1-cyano-cyclopropyl)-amide;

(1R,2R,4R)-4-[4-(4-Cyclopropyl-piperazin-1-yl)-2-trifluoromethyl-benzenesulfonyl]-2-methoxy-cyclopentanecarboxylic acid (1-cyano-cyclopropyl)-amide;

(1S,2S,4S)-4-[4-(4-Cyclopropyl-piperazin-1-yl)-2-trifluoromethyl-benzenesulfonyl]-2-methoxy-cyclopentanecarboxylic acid (1-cyano-cyclopropyl)-amide;

(1R,2R,4R) and (1S,2S,4S)-2-Methoxy-4-[4-(1-methylcarbamoylmethyl-1H-pyrazol-4-yl)-2-trifluoromethyl-benzenesulfonyl]-cyclopentanecarboxylic acid (1-cyano-cyclopropyl)-amide;

(1R,2R,4R)-4-[4-(4-Acetyl-piperazin-1-yl)-2-trifluorom-ethyl-benzenesulfonyl]-2-methoxy-cyclopentanecar-boxylic acid (1-cyano-cyclopropyl)-amide;

(1S,2S,4S)-4-[4-(4-Acetyl-piperazin-1-yl)-2-trifluorom-ethyl-benzenesulfonyl]-2-methoxy-cyclopentanecar-boxylic acid (1-cyano-cyclopropyl)-amide;

(1R,2R,4R)-4-[4-(1-Dimethylcarbamoylmethyl-1H-pyra-zol-4-yl)-2-trifluoromethyl-benzenesulfonyl]-2-meth-oxy-cyclopentanecarboxylic acid (1-cyano-cyclopro-pyl)-amide;

(1S,2S,4S)-4-[4-(1-Dimethylcarbamoylmethyl-1H-pyra-zol-4-yl)-2-trifluoromethyl-benzenesulfonyl]-2-meth-oxy-cyclopentanecarboxylic acid (1-cyano-cyclopro-pyl)-amide;

(1R,2R,4R)-2-[(tetrahydro-1,1-dioxo-2H-thiopyran-4-yl) oxy]-4-(2-trifluoromethyl-benzenesulfonyl)-cyclopen-tanecarboxylic acid (1-cyano-cyclopropyl)-amide;

(1S,2S,4S)-2-[(tetrahydro-1,1-dioxo-2H-thiopyran-4-yl) oxy]-4-(2-trifluoromethyl-benzenesulfonyl)-cyclopen-tanecarboxylic acid (1-cyano-cyclopropyl)-amide;

(1R,2R,4R)-2-Cyclobutoxy-4-(2-trifluoromethyl-benze-nesulfonyl)-cyclopentanecarboxylic acid (1-cyano-cy-clopropyl)-amide;

(1S,2S,4S)-2-Cyclobutoxy-4-(2-trifluoromethyl-benze-nesulfonyl)-cyclopentanecarboxylic acid (1-cyano-cy-clopropyl)-amide;

(1R,2R,4R)-2-Cyclopentyloxy-4-(2-trifluoromethyl-ben-zenesulfonyl)-cyclopentanecarboxylic acid (1-cyano-cyclopropyl)-amide;

(1S,2S,4S)-2-Cyclopentyloxy-4-(2-trifluoromethyl-ben-zenesulfonyl)-cyclopentanecarboxylic acid (1-cyano-cyclopropyl)-amide;

(1R,2R,4R)-4-(2-Chloro-benzenesulfonyl)-2-(4-chloro-benzyloxy)-cyclopentanecarboxylic acid (1-cyano-cy-clopropyl)-amide;

(1S,2S,4S)-4-(2-Chloro-benzenesulfonyl)-2-(4-chloro-benzyloxy)-cyclopentanecarboxylic acid (1-cyano-cy-clopropyl)-amide;

(1R,2R,4R)-4-[4-(1-Ethylcarbamoylmethyl-1H-pyrazol-4-yl)-2-trifluoromethyl-benzenesulfonyl]-2-methoxy-cyclopentanecarboxylic acid (1-cyano-cyclopropyl)-amide;

(1S,2S,4S)-4-[4-(1-Ethylcarbamoylmethyl-1H-pyrazol-4-yl)-2-trifluoromethyl-benzenesulfonyl]-2-methoxy-cyclopentanecarboxylic acid (1-cyano-cyclopropyl)-amide;

(1R,2R)-2-(3,3-Difluoro-pyrrolidine-1-carbonyl)-4-(6-methyl-pyridazine-3-sulfonyl)-cyclopentanecarboxylic acid (1-cyano-cyclopropyl)-amide;

(1R,2R,4R)-4-(5-Chloro-pyridine-2-sulfonyl)-2-(3,3-dif-luoro-pyrrolidine-1-carbonyl)-cyclopentanecarboxylic acid (1-cyano-cyclopropyl)-amide;

(1R,2R,4S)-4-(5-Chloro-pyridine-2-sulfonyl)-2-(3,3-dif-luoro-pyrrolidine-1-carbonyl)-cyclopentanecarboxylic acid (1-cyano-cyclopropyl)-amide;

(1R,2R,4R)-2-(3,3-Difluoro-pyrrolidine-1-carbonyl)-4-(pyridine-2-sulfonyl)-cyclopentanecarboxylic acid (1-cyano-cyclopropyl)-amide;

(1R,2R,4S)-2-(3,3-Difluoro-pyrrolidine-1-carbonyl)-4-(pyridine-2-sulfonyl)-cyclopentanecarboxylic acid (1-cyano-cyclopropyl)-amide;

(1R,2R,4R)-2-Cyclopentyloxy-4-[4-(4-isopropyl-piper-azin-1-yl)-2-trifluoromethyl-benzenesulfonyl]-cyclo-pentanecarboxylic acid (1-cyano-cyclopropyl)-amide;

(1S,2S,4S)-2-Cyclopentyloxy-4-[4-(4-isopropyl-piper-azin-1-yl)-2-trifluoromethyl-benzenesulfonyl]-cyclo-pentanecarboxylic acid (1-cyano-cyclopropyl)-amide;

(1R,2R,4R)-2-Cyclopentyloxy-4-{4-[4-(2,2,2-trifluoro-ethyl)-piperazin-1-yl]-2-trifluoromethyl-benzenesulfo-nyl}-cyclopentanecarboxylic acid (1-cyano-cyclopro-pyl)-amide;

(1S,2S,4S)-2-Cyclopentyloxy-4-{4-[4-(2,2,2-trifluoro-ethyl)-piperazin-1-yl]-2-trifluoromethyl-benzenesulfo-nyl}-cyclopentanecarboxylic acid (1-cyano-cyclopro-pyl)-amide;

(1R,2R,4R)-2-Phenoxy-4-(2-trifluoromethyl-benzene-sulfonyl)-cyclopentanecarboxylic acid (1-cyano-cyclo-propyl)-amide;

(1S,2S,4S)-2-Phenoxy-4-(2-trifluoromethyl-benzene-sulfonyl)-cyclopentanecarboxylic acid (1-cyano-cyclo-propyl)-amide;

(1R,2R,4R)-2-(4-Chloro-benzyloxy)-4-(2-trifluorom-ethyl-benzenesulfonyl)-cyclopentanecarboxylic acid (1-cyano-cyclopropyl)-amide;

(1S,2S,4S)-2-(4-Chloro-benzyloxy)-4-(2-trifluorom-ethyl-benzenesulfonyl)-cyclopentanecarboxylic acid (1-cyano-cyclopropyl)-amide;

(1R,2R,4R)-2-(4-Chloro-benzyloxy)-4-(2,4-dichloro-benzenesulfonyl)-cyclopentanecarboxylic acid (1-cy-ano-cyclopropyl)-amide;

(1S,2S,4S)-2-(4-Chloro-benzyloxy)-4-(2,4-dichloro-ben-zenesulfonyl)-cyclopentanecarboxylic acid (1-cyano-cyclopropyl)-amide;

(1R,2R,4R)-2-(4-Chloro-benzyloxy)-4-(2,4-dichloro-benzenesulfonyl)-cyclopentanecarboxylic acid (4-cy-ano-1-methyl-piperidin-4-yl)-amide;

(1S,2S,4S)-2-(4-Chloro-benzyloxy)-4-(2,4-dichloro-ben-zenesulfonyl)-cyclopentanecarboxylic acid (4-cyano-1-methyl-piperidin-4-yl)-amide;

(1R,2R,4R)-2-(4-Chloro-benzyloxy)-4-(2-trifluorom-ethyl-benzenesulfonyl)-cyclopentanecarboxylic acid (4-cyano-1-methyl-piperidin-4-yl)-amide;

(1S,2S,4S)-2-(4-Chloro-benzyloxy)-4-(2-trifluorom-ethyl-benzenesulfonyl)-cyclopentanecarboxylic acid (4-cyano-1-methyl-piperidin-4-yl)-amide;

(1R,2R,4R)-2-Methoxy-4-[4-(1-methyl-1H-pyrazol-4-yl)-2-trifluoromethyl-benzenesulfonyl]-cyclopentan-ecarboxylic acid (4-cyano-1-methyl-piperidin-4-yl)-amide;

(1S,2S,4S)-2-Methoxy-4-[4-(1-methyl-1H-pyrazol-4-yl)-2-trifluoromethyl-benzenesulfonyl]-cyclopentanecar-boxylic acid (4-cyano-1-methyl-piperidin-4-yl)-amide;

4-Cyano-4-({(1R,2R,4R)-2-methoxy-4-[4-(1-methyl-1H-pyrazol-4-yl)-2-trifluoromethyl-benzenesulfonyl]-cy-clopentanecarbonyl}-amino)-piperidine-1-carboxylic acid ethyl ester;

4-Cyano-4-({(1S,2S,4S)-2-methoxy-4-[4-(1-methyl-1H-pyrazol-4-yl)-2-trifluoromethyl-benzenesulfonyl]-cy-clopentanecarbonyl}-amino)-piperidine-1-carboxylic acid ethyl ester;

(1R,2R,4R)-2-Methoxy-4-[4-(1-methyl-1H-pyrazol-4-yl)-2-trifluoromethyl-benzenesulfonyl]-cyclopentan-ecarboxylic acid (4-cyano-1-ethyl-piperidin-4-yl)-amide;

(1S,2S,4S)-2-Methoxy-4-[4-(1-methyl-1H-pyrazol-4-yl)-2-trifluoromethyl-benzenesulfonyl]-cyclopentanecar-boxylic acid (4-cyano-1-ethyl-piperidin-4-yl)-amide;

(1R,2R,4R)-2-(4-Chloro-benzyloxy)-4-(2-trifluorom-ethyl-benzenesulfonyl)-cyclopentanecarboxylic acid (4-cyano-1-ethyl-piperidin-4-yl)-amide;

(1S,2S,4S)-2-(4-Chloro-benzyloxy)-4-(2-trifluorom-ethyl-benzenesulfonyl)-cyclopentanecarboxylic acid (4-cyano-1-ethyl-piperidin-4-yl)-amide;

(1R,2R,4R)-2-(4-Chloro-benzyloxy)-4-(2,4-dichloro-benzenesulfonyl)-cyclopentanecarboxylic acid (4-cyano-1-ethyl-piperidin-4-yl)-amide;

(1S,2S,4S)-2-(4-Chloro-benzyloxy)-4-(2,4-dichloro-benzenesulfonyl)-cyclopentanecarboxylic acid (4-cyano-1-ethyl-piperidin-4-yl)-amide;

4-{[(1R,2R,4R)-2-(4-Chloro-benzyloxy)-4-(2-trifluoromethyl-benzenesulfonyl)-cyclopentanecarbonyl]-amino}-4-cyano-piperidine-1-carboxylic acid ethyl ester;

4-{[(1S,2S,4S)-2-(4-Chloro-benzyloxy)-4-(2-trifluoromethyl-benzenesulfonyl)-cyclopentanecarbonyl]-amino}-4-cyano-piperidine-1-carboxylic acid ethyl ester;

4-{[(1R,2R,4R)-2-(4-Chloro-benzyloxy)-4-(2,4-dichloro-benzenesulfonyl)-cyclopentanecarbonyl]-amino}-4-cyano-piperidine-1-carboxylic acid ethyl ester;

4-{[(1S,2S,4S)-2-(4-Chloro-benzyloxy)-4-(2,4-dichloro-benzenesulfonyl)-cyclopentanecarbonyl]-amino}-4-cyano-piperidine-1-carboxylic acid ethyl ester;

(1R,2R,4R)-4-(2-Chloro-benzenesulfonyl)-2-(4-chloro-phenoxy)-cyclopentanecarboxylic acid (1-cyano-cyclopropyl)-amide (1S,2S,4S)-4-(2-Chloro-benzenesulfonyl)-2-(4-chloro-phenoxy)-cyclopentanecarboxylic acid (1-cyano-cyclopropyl)-amide;

(1R,2R,4R)-2-(2-(4-chlorophenyl)propan-2-yloxy)-4-(2-chlorophenylsulfonyl)-N-(1-cyanocyclopropyl)cyclopentanecarboxamide;

(1S,2S,4S)-2-(2-(4-chlorophenyl)propan-2-yloxy)-4-(2-chlorophenylsulfonyl)-N-(1-cyanocyclopropyl)cyclopentanecarboxamide;

(1R,2R,4R)-4-(2-chlorophenylsulfonyl)-N-(1-cyanocyclopropyl)-2-(2-p-tolylpropan-2-yloxy)cyclopentanecarboxamide;

(1S,2S,4S)-4-(2-chlorophenylsulfonyl)-N-(1-cyanocyclopropyl)-2-(2-p-tolylpropan-2-yloxy)cyclopentanecarboxamide;

(1S,2S,4S)-2-Methoxy-4-[4-(4-methoxymethyl-[1,2,3]triazol-1-yl)-2-trifluoromethyl-benzenesulfonyl]-cyclopentanecarboxylic acid (1-cyano-cyclopropyl)-amide;

(1R,2R,4R)-2-Methoxy-4-[4-(4-methoxymethyl-[1,2,3]triazol-1-yl)-2-trifluoromethyl-benzenesulfonyl]-cyclopentanecarboxylic acid (1-cyano-cyclopropyl)-amide;

(1R,2R,4R)-4-(2-chlorophenylsulfonyl)-N-(1-cyanocyclopropyl)-2-(4-(trifluoromethyl)benzyloxy)cyclopentanecarboxamide;

(1S,2S,4S)-4-(2-chlorophenylsulfonyl)-N-(1-cyanocyclopropyl)-2-(4-(trifluoromethyl)benzyloxy)cyclopentanecarboxamide;

(1R,2R,4R)-4-(2-Chloro-benzenesulfonyl)-2-(4-chloro-2-methanesulfonyl-benzyloxy)-cyclopentanecarboxylic acid (1-cyano-cyclopropyl)-amide;

(1S,2S,4S)-4-(2-Chloro-benzenesulfonyl)-2-(4-chloro-2-methanesulfonyl-benzyloxy)-cyclopentanecarboxylic acid (1-cyano-cyclopropyl)-amide;

(1R,2R,4R)-4-(2-Chloro-benzenesulfonyl)-2-(4-chloro-3-fluoro-benzyloxy)-cyclopentanecarboxylic acid (1-cyano-cyclopropyl)-amide;

(1S,2S,4S)-4-(2-Chloro-benzenesulfonyl)-2-(4-chloro-3-fluoro-benzyloxy)-cyclopentanecarboxylic acid (1-cyano-cyclopropyl)-amide;

(1R,2R,4R)-4-(2-Chloro-benzenesulfonyl)-2-(3,4-dichloro-benzyloxy)-cyclopentanecarboxylic acid (1-cyano-cyclopropyl)-amide;

(1S,2S,4S)-4-(2-Chloro-benzenesulfonyl)-2-(3,4-dichloro-benzyloxy)-cyclopentanecarboxylic acid (1-cyano-cyclopropyl)-amide;

(1R,2R,4R)-4-(2-Chloro-benzenesulfonyl)-2-(4-chloro-2,6-difluoro-benzyloxy)-cyclopentanecarboxylic acid (1-cyano-cyclopropyl)-amide;

(1S,2S,4S)-4-(2-Chloro-benzenesulfonyl)-2-(4-chloro-2,6-difluoro-benzyloxy)-cyclopentanecarboxylic acid (1-cyano-cyclopropyl)-amide;

(1R,2R,4R)-4-(2-Chloro-benzenesulfonyl)-2-(4-chloro-2-fluoro-benzyloxy)-cyclopentanecarboxylic acid (1-cyano-cyclopropyl)-amide;

(1S,2S,4S)-4-(2-Chloro-benzenesulfonyl)-2-(4-chloro-2-fluoro-benzyloxy)-cyclopentanecarboxylic acid (1-cyano-cyclopropyl)-amide;

(1S,2S,4S)-4-{4-[4-(2-Hydroxy-ethyl)-[1,2,3]triazol-1-yl]-2-trifluoromethyl-benzenesulfonyl}-2-methoxy-cyclopentanecarboxylic acid (1-cyano-cyclopropyl)-amide; and (1R,2R,4R)-4-{4-[4-(2-Hydroxy-ethyl)-[1,2,3]triazol-1-yl]-2-trifluoromethyl-benzenesulfonyl}-2-methoxy-cyclopentanecarboxylic acid (1-cyano-cyclopropyl)-amide.

18. A compound according to claim 1 wherein said compound is (1R,2R,4R)-2-methoxy-4-[4-(1-methyl-1H-pyrazol-4-yl)-2-trifluoromethyl-benzenesulfonyl]-cyclopentanecarboxylic acid (1-cyano-cyclopropyl)-amide or a salt thereof.

19. A pharmaceutical composition comprising a compound in accordance with claim 1 and a therapeutically inert carrier.

* * * * *